(12) United States Patent
Sandanayaka et al.

(10) Patent No.: US 7,402,684 B2
(45) Date of Patent: Jul. 22, 2008

(54) BIARYL SUBSTITUTED HETEROCYCLE INHIBITORS OF LTA4H FOR TREATING INFLAMMATION

(75) Inventors: Vincent Sandanayaka, Northboro, MA (US); Jasbir Singh, Naperville, IL (US); Mark Gurney, Grand Rapids, MI (US); Bjorn Mamat, Reykjavik (IS); Peng Yu, Lisle, IL (US); Louis Bedell, Prospect Heights, IL (US); Lei Zhao, Naperville, IL (US); Rama K. Mishra, Chicago, IL (US)

(73) Assignee: deCODE genectics ehf., Reykjavik (IS)

( * ) Notice: Subject to any disclaimer, the term of this patent is extended or adjusted under 35 U.S.C. 154(b) by 0 days.

(21) Appl. No.: 11/426,287

(22) Filed: Jun. 23, 2006

(65) Prior Publication Data

US 2007/0066820 A1   Mar. 22, 2007

Related U.S. Application Data

(60) Provisional application No. 60/719,016, filed on Sep. 21, 2005.

(51) Int. Cl.
*C07D 207/08* (2006.01)
*A61K 31/40* (2006.01)

(52) U.S. Cl. .................... 548/574; 514/428
(58) Field of Classification Search ............. 548/574; 514/428
See application file for complete search history.

(56) References Cited

U.S. PATENT DOCUMENTS

2005/0043379 A1   2/2005   Axe et al.

FOREIGN PATENT DOCUMENTS

| EP | EP 0895989 A1 | 2/1999 |
| WO | WO 03/075921 | 2/2004 |
| WO | WO 2004/016609 | 2/2004 |

OTHER PUBLICATIONS

Penning, Thomas, "Inhibitors of Leukotriene A4 (LTA4) Hydrolase as Potential Anti-Inflammatory Agents," Current Pharmaceutical Design, 2001, pp. 163-179.
Penning, Thomas et al., "Synthesis of Imadazophyridines and Purines as Potent Inhibitors of Leukotriene A4 Hydrolase," Bioorganic & Medicinal Chemistry Letters 13, 2003, pp. 1137-1139.
PCT Search Report based International application No. PCT/2006/024393.

*Primary Examiner*—Rebecca Anderson
*Assistant Examiner*—Robert Havlin
(74) *Attorney, Agent, or Firm*—Heslin Rothenberg Farley & Mesiti P.C.; Philip E. Hansen; Charles E. Bell

(57) ABSTRACT

The present invention relates to a chemical genus of biaryl substituted heterocycle inhibitors of LTA4H (leukotriene A4 hydrolase) useful for the treatment and prevention and prophylaxis of inflammatory diseases and disorders. The compounds have general formula Ψ:

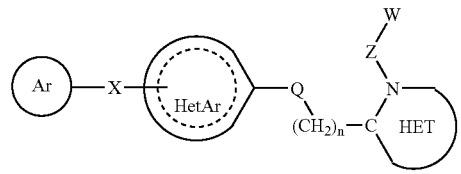

An example is

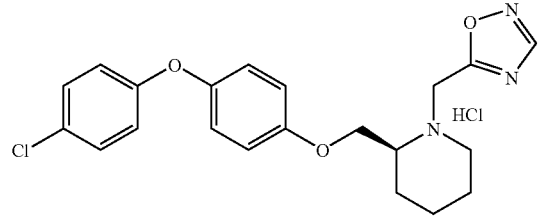

29 Claims, No Drawings

BIARYL SUBSTITUTED HETEROCYCLE INHIBITORS OF LTA4H FOR TREATING INFLAMMATION

CROSS REFERENCE TO RELATED APPLICATIONS

This application claims benefit from U.S. Provisional Application 60/719,016, filed Sep. 21, 2005, the entire contents of which are incorporated herein by reference.

FIELD OF THE INVENTION

The present invention relates to a chemical genus of biaryl substituted heterocycle inhibitors of LTA4H (leukotriene A4 hydrolase) useful for the treatment and prevention and prophylaxis of inflammatory diseases and disorders.

BACKGROUND OF THE INVENTION

The end products of the leukotriene pathway are potent inflammatory lipid mediators derived from arachidonic acid. They can potentially contribute to development of atherosclerosis and destabilization of atherosclerotic plaques through lipid oxidation and/or proinflammatory effects. As described elsewhere, a gene on chromosome 13q12 has been identified as playing a major role in myocardial infarction (MI), [Helgadottir et al., *Nature Genetics* doi:10.1038/ng1311, 8 Feb. 2004]. This gene (ALOX5AP), herein after referred to as an MI disease gene, comprises nucleic acid that encodes 5-lipoxygenase activating protein (FLAP), herein after referred to as FLAP. DNA variants in the FLAP gene increase risk for myocardial infarction by 1.8 fold and for stroke by 1.7 fold. The leukotriene pathway, through FLAP, leads to the production of leukotriene B4 by the enzyme leukotriene A4 hydrolase (LTA4H). Leukotriene B4 is one of the most potent chemokine mediators of arterial inflammation. Particular DNA variants in the gene encoding LTA4H also elevate risk for MI and stroke, as described elsewhere [Hakonarsson et al., *J. Am. Med. Assoc.* 293, 2245-2256 (2005)]. Individuals with a prior history of MI produce more leukotriene B4 when their isolated neutrophils are stimulated with ionomycin. Increased LTB4 production is particularly marked in male patients with a prior history of MI who carry risk variants in the FLAP gene [Helgadottir et al.] The treatment (prophylactic and/or therapeutic) of certain diseases and conditions (e.g., MI, acute coronary syndrome (ACS), stroke, atherosclerosis) associated with FLAP or with LTA4H can be accomplished by inhibiting LTA4H. Inhibiting LTA4H is advantageous for methods of treatment for MI or susceptibility to MI; for ACS (e.g., unstable angina, non-ST-elevation myocardial infarction (NSTEMI) or ST-elevation myocardial infarction (STEMI)); for decreasing risk of a second MI; for stroke (including transient ischemic attack) or susceptibility to stroke; for atherosclerosis, such as for patients requiring treatment (e.g., angioplasty, stents, coronary artery bypass graft) to restore blood flow in coronary arteries, such as patients requiring treatment for peripheral vascular disease including peripheral occlusive arterial disease, critical limb ischemia (e.g., gangrene, ulceration), and intermittent claudication to restore blood flow in the lower limbs; for atherosclerotic reno-vascular disease; for abdominal aortic aneurysm; and/or for decreasing leukotriene synthesis (e.g., for treatment of MI).

US Patent Application Publication No. 20050043378 and 20050043379, relate to benzooxazol-2-yl, benzothiazol-2-yl and 1H-benzoimidazol-2-yl compounds and derivatives thereof useful as leukotriene A4 hydrolase (LTA4H) inhibitors in treating inflammation and disorders associated with inflammation. These disclosures are incorporated herein by reference as they relate to utility.

SUMMARY OF THE INVENTION

The present invention relates to compounds exhibiting LTA4H enzyme inhibition, having general formula Ψ

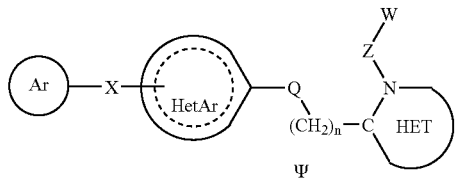

Ψ

In these compounds,

Ar is selected from the group consisting of
- aryl;
- heteroaryl;
- aryl substituted with from one to three substituents independently selected from the group consisting of halogen, loweralkyl, loweracyl, loweralkoxy, fluoroloweralkyl, fluoroloweralkoxy, hydroxy, hydroxy($C_1$-$C_4$) alkyl, formyl, formyl($C_1$-$C_4$)alkyl, cyano, cyano($C_1$-$C_4$) alkyl, benzyl, benzyloxy, phenyl, substituted phenyl, heteroaryl, heterocyclylalkyl, substituted heteroaryl, and nitro; and
- heteroaryl substituted with from one to three substituents independently selected from the group consisting of halogen, loweralkyl, loweracyl, loweralkoxy, fluoroloweralkyl, fluoroloweralkoxy, formyl, cyano, benzyl, benzyloxy, phenyl, heteroaryl, heterocyclylalkyl and nitro;

X is selected from the group consisting of direct bond, O, SO, $S(O_2)$, $NR^1$, $CH_2$, $CF_2$, $CH_2CH_2$, $CH_2NR^1$, $NR^1CH_2$, CH=CH, C=O, $CH_2$C=O, $CR^{1a}R^{1b}$, $OCR^{1a}R^{1b}CR^{1a}R^{1b}O$; $SO_2NR^1$, $NR^1SO_2$, C(=O)$NR^1$ and $NR^1$C(=O);

$R^1$ is selected separately in each occurrence from the group consisting of H and lower alkyl;

$R^{1a}$ is selected from the group consisting of H, OH and lower alkyl;

$R^{1b}$ is selected from the group consisting of H and lower alkyl, or $R^{1a}$ and $R^{1b}$ taken together may form a 3-6 membered ring, which may optionally contain a heteroatom chosen from O, S, and N;

HetAr is an aryl or heteroaryl ring attached via a ring carbon to Q, further characterized in that Q and X cannot be on adjacent positions in said aryl or heteroaryl ring;

Q is chosen from —O—, —$NR^1$— and $S(O)_p$;

Q and X cannot be on adjacent positions in said benzene or pyridine ring;

p is zero, 1 or 2;

n is an integer selected from 1-5;

HET is selected from the group consisting of
- 4-7-membered saturated nitrogenous heterocycle and
- 4-7-membered saturated nitrogenous heterocycle substituted with one or two substituents independently selected from the group consisting of halogen, hydroxyl, amino, carboxy, loweralkyl, loweracyl, loweralkoxy, N-oxide, fluoroloweralkyl, fluoroloweralkoxy, formyl, cyano, benzyl, benzyloxy, phenyl, heteroaryl and nitro; and taken together ZW is H or Z is $(CH_2)_{1-10}$, in which one or two $(CH_2)$ may optionally be replaced by —O—, —$NR^1$—, —SO—, —$S(O)_2$—, —C(=O)— or —C=O(NH)—, provided that said —O—, —$NR^1$—, —SO—, —$S(O)_2$—, —C(=O)— or —C=O(NH)— are not at the point of attachment to HET and are separated by at least one —$(CH_2)$—;

W is selected from the group consisting of acyl, hydroxyl, carboxyl, amino, —$C(O)NHR^4$, aminoacyl, —COOalkyl, —CHO, heterocyclyl, substituted aryl, substituted heterocyclyl, sulfonamide, —$C(O)$fluoroalkyl, —$C(O)CH_2C(O)$Oalkyl, —$C(O)CH_2C(O)$Ofluoroalkyl, —SH, —C(O)NH(OH), —$C(O)N(OH)R^4$, —N(OH)C(O)OH, —$N(OH)C(O)R^4$; and $R^4$ is selected from the group consisting of H, $(C_1$-$C_4)$ alkyl and phenyl$(C_1$-$C_4)$ alkyl.

A major subgenus is

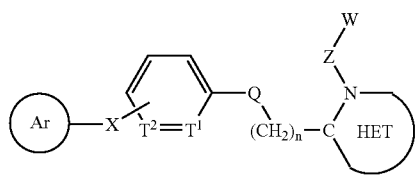

In these compounds, $T^1$ and $T^2$ are carbon, or one of $T^1$ and $T^2$ may be nitrogen. When $T^1$ and $T^2$ are carbon, a benzene ring is formed. When one of $T^1$ and $T^2$ is nitrogen, a pyridine ring is formed, and in the pyridines, X is at the para position relative to Q.

In a second aspect, the invention relates to a method for inhibiting leukotriene A4 hydrolase including contacting the LTA4H enzyme with a therapeutically effective amount of a compound of formula Ψ.

In a third aspect, the invention relates to a pharmaceutical composition comprising a pharmaceutically acceptable carrier and a therapeutically effective amount of a compound of formula Ψ.

In a fourth aspect, the invention relates to methods for the treatment and prevention or prophylaxis of a disease, condition or disorder associated with leukotriene A4 hydrolase. The methods comprise administering to a mammal a therapeutically effective amount of a compound described above. The disease or condition may be related to allergic, acute or chronic inflammation. The disease may be for example contact and atopic dermatitis, arthritis, allergic rhinitis, asthma or autoimmune diseases such as Crohn's disease, psoriasis, ulcerative colitis, inflammatory bowel disease, multiple sclerosis, ankylosing spondylitis, and the like. Similarly, the compounds defined above can be used in preventing recurring inflammatory attacks. The compounds are also useful for treating and preventing atherosclerosis, thrombosis, stroke, acute coronary syndrome, stable angina, peripheral vascular disease, critical leg ischemia, intermittent claudication, abdominal aortic aneurysm and myocardial infarction.

Compounds of the invention, which inhibit tumor growth and metastase find utility in the treatment and prevention of cancer, including esophageal cancer, brain cancer.

DETAILED DESCRIPTION OF THE INVENTION

Throughout this specification the substituents are defined when introduced and retain their definitions.

The invention relates to compounds of the general formula Ψ below.

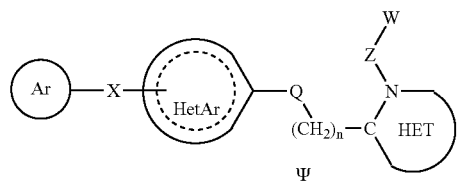

All of the compounds falling within the foregoing parent genus and its subgenera are useful as leukotriene A4 hydrolase inhibitors, but not all the compounds are novel. In particular, certain known species fall within the genus Ψ, although no utility in inhibiting LTA4H has been suggested for these species. It may be found upon examination that compounds that have been excluded from the claims to compounds are patentable to the inventors in this application; it may also be found that additional species and genera not presently excluded are not patentable to the inventors in this application. In either case, the exclusion of species and genera in applicants' claims are to be considered artifacts of patent prosecution and not reflective of the inventors' concept or description of their invention. The invention, in a composition aspect, is all compounds of formula Ψ except those that are in the public's possession. In particular, a search of the literature indicates that the following three subgenera encompass compounds that cannot be claimed:

(1) when Q is —O—, HET is (S)-pyrrolidine, rac-pyrrolidine or piperidine, Ar is phenyl or halo-substituted phenyl, HetAr is p-phenylene and the Z—W combination is H;

(2) when Q is $NR^1$, HET is thiazolidine, Ar is phenyl or substituted phenyl, HetAr is meta-phenylene and the ZW combination is H; and (3) when Q is —O—, HET is azetidine, Ar is phenyl, n is 1, HetAr is a 2,5-substituted pyridine and the Z—W combination is H.

The genus Ψ encompasses four subgenera, depending on the $T^1/T^2$ ring: 2,5-pyridinyl, reverse 2,5-pyridinyl, meta phenylene and para phenylene:

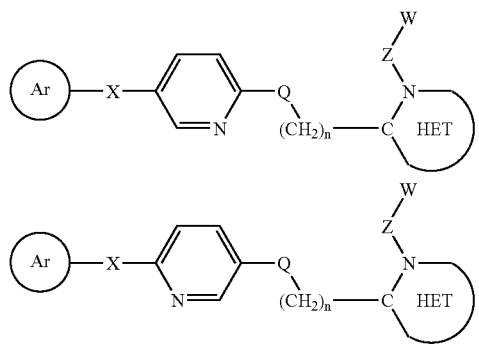

-continued

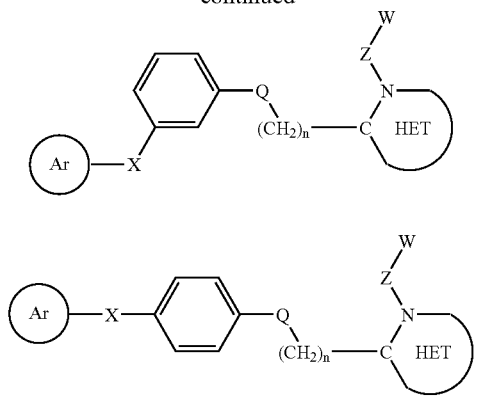

In one embodiment, the invention relates to biaryl heterocycles useful as LTA4H enzyme inhibitors, having the general formula:

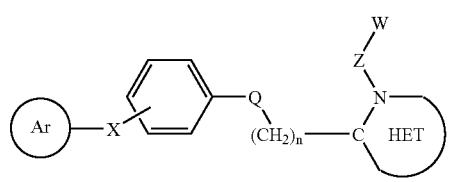

In some embodiments Q is selected from O, $S(O)_p$ and $NR^1$:

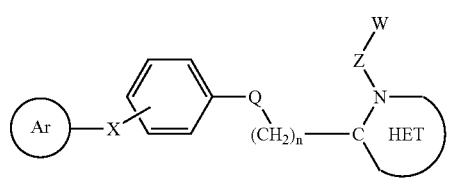

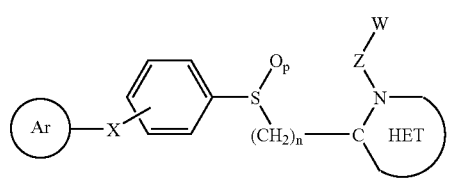

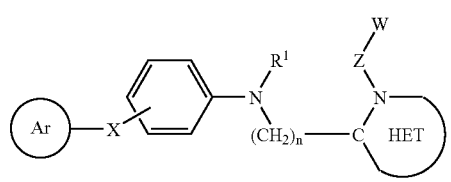

In some embodiments X is selected from $CH_2$, O and $NR^1$.
In some embodiments, the $T^1/T^2$ ring is para phenylene:

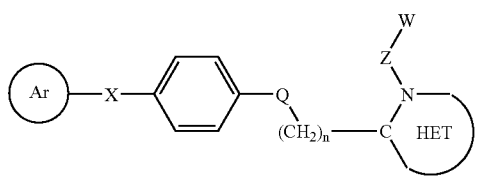

In some embodiments HET is selected from the group consisting of pyrrolidinone, pyrrolidine, piperidine, piperidinone, piperazine, morpholine, thiomorpholine, thiazolidine, thiazolidinone, oxazolidine and oxazolidinone and substituted pyrrolidinone, substituted pyrrolidine, substituted piperidine, substituted piperidinone, substituted piperazine, substituted morpholine, substituted thiomorpholine, substituted thiazolidine, substituted thiazolidinone, substituted oxazolidine and substituted oxazolidinone.

In some embodiments HET is pyrrolidine and the Z—W combination is other than hydrogen.

In some embodiments HET-Z-W is selected from pyridinylmethylpyrrolidine, oxadiazolylmethylpyrrolidine, carboxyalkylpyrrolidine and alkoxycarbonylalkylpyrrolidine.

In some embodiments HET-Z-W is carboxyalkyl pyrrolidine, having the chemical formula as shown below:

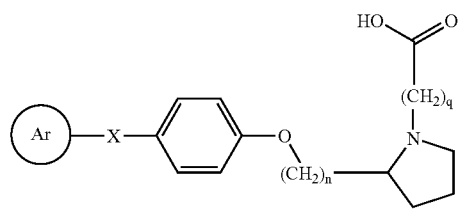

wherein q is an integer selected from 2-6.

In some embodiments HET is selected from the group consisting of unsubstituted pyrrolidine, pyrrolidinone, piperidine and piperidinone (i.e. Z—W is H).

In other embodiments HET-Z—W is carboxyalkyl (S) pyrrolidine, having the chemical formula as shown below:

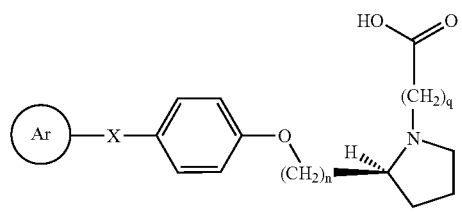

wherein q is an integer selected from 2-6.

In certain embodiments HET is (R) pyrrolidine having the chemical formula as shown below:

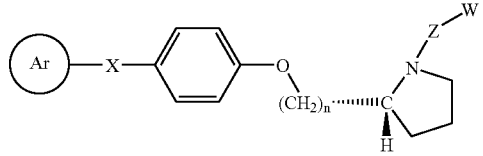

In some embodiments HET is (R) pyrrolidine and ZW is H, having chemical formula as shown below:

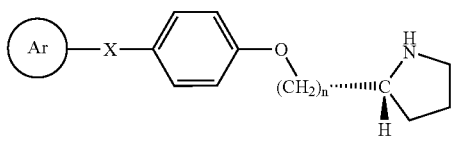

In certain embodiments HET is (R) pyrrolidine, X is selected from $CH_2$, O and $NR^1$. In certain embodiments HET is (R) pyrrolidine X is $CH_2$ or O, n is 1, and Ar is selected from phenyl and substituted phenyl, and X is selected from $CH_2$, O and $NR^1$. In further embodiments X is $CH_2$ or O, n is 1, and Ar is para-substituted phenyl. In other embodiments, Ar is heteroarylphenyl. In other embodiments, Ar is

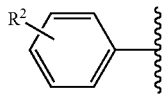

wherein the wavy line indicates the point of attachment to X and $R^2$ is chosen from hydrogen, halogen, trifluoromethyl, methyl, methoxy, thienyl, furanyl, and thienyl or furanyl substituted with halogen, trifluoromethyl, methyl or methoxy.

In some embodiments HET is (S) pyrrolidine, having chemical formula as shown below:

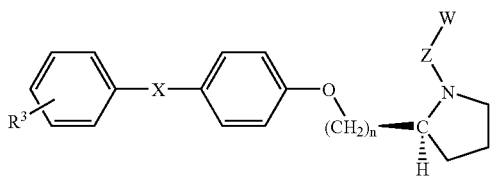

Where $R^3$ represents halogen, $CF^3$, methyl, methoxy, or $CF^3O$. X is O or $CH_2$, n is 1 or 2, Z is $C_1$-$C_4$ alkylene and W is COOH.

In some embodiments HET is (S) pyrrolidine, Q is oxygen and Ar is substituted phenyl, having chemical formula as shown below:

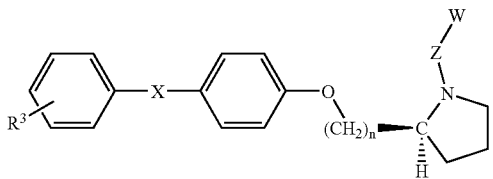

wherein $R^3$ represents one to three residues independently selected from the group consisting of benzyl, benzyloxy, phenyl and heteroaryl.

In some embodiments Ar is phenyl substituted with heteroaryl or heteroaryl substituted with a substituent selected from the group consisting of halogen, methyl, methoxy and trifluoromethoxy. Thienyl and furanyl are examples of heteroaryl.

In other embodiments, the $T^1/T^2$ ring is either pyridine and Q is oxygen or the $T^1/T$ ring is para phenylene, and Q is —$NR^1$— or —$S(O)_p$—. Exemplary generic formulae are:

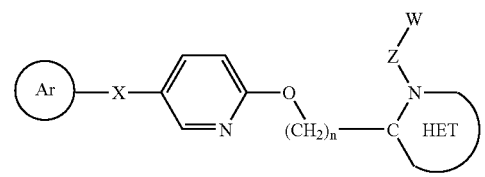

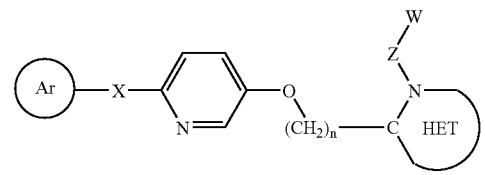

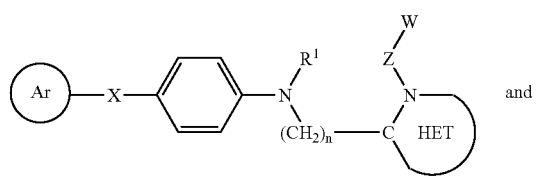

and

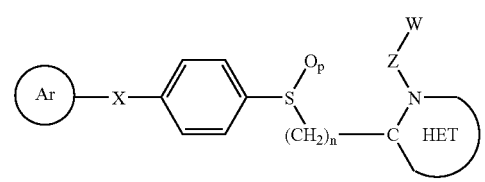

In these compounds, the variables may be as described above for the genus in which Q is —O— and the $T^1/T^2$ ring is p-phenylene.

In another aspect the present invention provides a pharmaceutical composition comprising a pharmaceutically acceptable carrier and a therapeutically effective amount of at least one compound as described above.

Methods of the invention parallel the compositions and formulations. The methods comprise administering to a patient in need of treatment a therapeutically effective amount of a compound according to the invention.

The present invention provides a method for inhibiting leukotriene A4 hydrolase comprising contacting the LTA4H enzyme with a therapeutically effective amount of a compound according to formula $\Psi$.

The method for inhibiting leukotriene A4 hydrolase includes contacting the LTA4H enzyme with a therapeutically effective amount of a compound of formula:

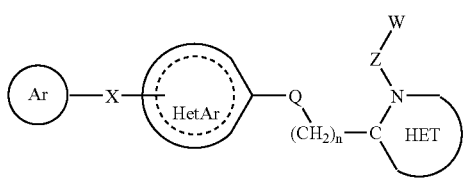

and any of its subgenera as described above. For example, the invention also relates to a method for inhibiting leukotriene A4 hydrolase comprising contacting the LTA4H enzyme with a therapeutically effective amount of a compound of formula:

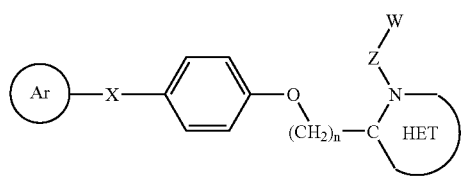

Furthermore, the present invention provides a method for inhibiting a disorder associated with leukotriene A4 hydrolase comprising administering to a mammal a therapeutically effective amount of a compound or a salt, hydrate or ester thereof according to formula $\Psi$. In some embodiments the disorder is associated with inflammation. In some embodiments the disorder is selected from allergic inflammation, acute inflammation and chronic inflammation.

The present invention also provides a method for treating inflammation comprising administering to a mammal a therapeutically effective amount of a compound according to formula $\Psi$ and an inhibitor of 5-lipoxygenase activating protein (FLAP) [e.g. MK-0591 (Merck), BAY-X1005 (Bayer), and R-(−)-2-[4-quinolin-2-yl-methoxy)phenyl]-2-cyclopentyl acetic acid] and/or a therapeutically effective amount of a compound of formula $\Psi$ and a leukotriene B4 (LTB4) antagonist [e.g. SC 41930 (Searle), SC 53228 (Searle), Accolate (zafirlukast; Zeneca), Singulair (montelukast; Merck), Ultair (pranlukast; Ono/Smith-Kline Beecham), ethyl [[4-[[3-[[4-[1-(4-hydroxyphenyl)-1-methylethyl]phenoxy]methyl]benzyl]oxy]phenyl]-(imino)methyl]carbamate (amelubant; Boehringer Ingelheim), 2-[3-[3-[(5-ethyl-4'-fluoro-2-hydroxybiphenyl-4-yl)oxy]propoxy]-2-propylphenoxy] benzoic acid (etalocib, Lilly) and CP-105696 (+)-1-(3S,4R)-[3-(4-phenyl-benzyl)-4-hydroxy-chroman-7-yl] cyclopentane carboxylic acid, *J. Pharmacol Exp Ther* 273: 176-184 (1995)].

Compounds of the genus represented by formula $\Psi$ above are inhibitors of LTA4H enzyme. As such they have utility in treating and preventing inflammatory diseases and disorders, as described above, particularly for such conditions as asthma, chronic obstructive pulmonary disease (COPD), atherosclerosis, rheumatoid arthritis, multiple sclerosis, inflammatory bowel diseases (IBD; including Crohn's disease and ulcerative colitis), or psoriasis, which are each characterized by excessive or prolonged inflammation at some stage of the disease.

Recent research indicates that the compounds are also useful for treating and preventing atherosclerosis, thrombosis, stroke, acute coronary syndrome, stable angina, peripheral vascular disease, critical leg ischemia, intermittent claudication, abdominal aortic aneurysm and myocardial infarction.

The compounds may be presented as salts. The term "pharmaceutically acceptable salt" refers to salts whose counter ion derives from pharmaceutically acceptable non-toxic acids and bases. Suitable pharmaceutically acceptable base addition salts for the compounds of the present invention include, but are not limited to, metallic salts made from aluminum, calcium, lithium, magnesium, potassium, sodium and zinc or organic salts made from lysine, N,N-dialkyl amino acid derivatives (e.g. N,N-dimethylglycine, piperidine-1-acetic acid and morpholine-4-acetic acid), N,N'-dibenzylethylenediamine, chloroprocaine, choline, diethanolamine, ethylenediamine, meglumine (N-methylglucamine) and procaine. When the compounds contain a basic residue, suitable pharmaceutically acceptable base addition salts for the compounds of the present invention include inorganic acids and organic acids. Examples include acetate, benzenesulfonate (besylate), benzoate, bicarbonate, bisulfate, carbonate, camphorsulfonate, citrate, ethanesulfonate, fumarate, gluconate, glutamate, bromide, chloride, isethionate, lactate, maleate, malate, mandelate, methanesulfonate, mucate, nitrate, pamoate, pantothenate, phosphate, succinate, sulfate, tartrate, p-toluenesulfonate, and the like.

For convenience and clarity certain terms employed in the specification, examples and claims are described herein.

Alkyl is intended to include linear, branched, or cyclic hydrocarbon structures and combinations thereof. Lower alkyl refers to alkyl groups of from 1 to 6 carbon atoms. Examples of lower alkyl groups include methyl, ethyl, propyl, isopropyl, butyl, s- and t-butyl and the like. Preferred alkyl groups are those of $C_{20}$ or below. Cycloalkyl is a subset of alkyl and includes cyclic hydrocarbon groups of from 3 to 8 carbon atoms. Examples of cycloalkyl groups include c-propyl, c-butyl, c-pentyl, norbornyl and the like.

$C_1$ to $C_{20}$ hydrocarbon includes alkyl, cycloalkyl, alkenyl, alkynyl, aryl, arylalkyl and combinations thereof. Examples include phenethyl, cyclohexylmethyl, camphoryl, adamantyl and naphthylethyl.

Alkoxy or alkoxyl refers to groups of from 1 to 8 carbon atoms of a straight, branched, cyclic configuration and combinations thereof attached to the parent structure through oxygen. Examples include methoxy, ethoxy, propoxy, isopropoxy, cyclopropyloxy, cyclohexyloxy and the like. Loweralkoxy refers to groups containing one to four carbons.

Alkoxyalkyl refers to ether groups of from 3 to 8 atoms of a straight, branched, cyclic configuration and combinations thereof attached to the parent structure through an alkyl. Examples include methoxymethyl, methoxyethyl, ethoxypropyl, and the like.

Alkoxyaryl refers to alkoxy substituents attached to an aryl, wherein the aryl is attached to the parent structure. Arylalkoxy refers to aryl substituents attached to an oxygen, wherein the oxygen is attached to the parent structure. Substituted arylalkoxy refers to a substituted aryl substituent attached to an oxygen, wherein the oxygen is attached to the parent structure.

Acyl refers to groups of from 1 to 8 carbon atoms of a straight, branched, cyclic configuration, saturated, unsaturated and aromatic and combinations thereof, attached to the parent structure through a carbonyl functionality. One or more carbons in the acyl residue may be replaced by nitrogen, oxygen or sulfur as long as the point of attachment to the parent remains at the carbonyl. Examples include acetyl, benzoyl, propionyl, isobutyryl, t-butoxycarbonyl, benzyloxycarbonyl and the like. Lower-acyl refers to groups containing one to four carbons.

Aryl and heteroaryl mean a 5- or 6-membered aromatic or heteroaromatic ring containing 0-3 heteroatoms selected from O, N, or S; a bicyclic 9- or 10-membered aromatic or heteroaromatic ring system containing 0-3 heteroatoms selected from O, N, or S; or a tricyclic 13- or 14-membered aromatic or heteroaromatic ring system containing 0-3 heteroatoms selected from O, N, or S. The aromatic 6- to 14-membered carbocyclic rings include, e.g., benzene and naphthalene, and according to the invention benzoxalane and residues in which one or more rings are aromatic, but not all need be. The 5- to 10-membered aromatic heterocyclic rings include, e.g., imidazole, pyridine, indole, thiophene, benzopyranone, thiazole, furan, benzimidazole, quinoline, isoquinoline, quinoxaline, pyrimidine, pyrazine, tetrazole and pyrazole.

Arylalkyl refers to a substituent in which an aryl residue is attached to the parent structure through alkyl. Examples are benzyl, phenethyl and the like. Heteroarylalkyl refers to a substituent in which a heteroaryl residue is attached to the parent structure through alkyl. Examples include, e.g., pyridinylmethyl, pyrimidinylethyl and the like. Heterocyclylalkyl refers to a substituent in which a heterocyclyl residue is attached to the parent structure through alkyl. Examples include morpholinoethyl and pyrrolidinylmethyl.

Heterocycle means a cycloalkyl or aryl residue in which from one to three carbons is replaced by a heteroatom selected from the group consisting of N, O and S. The nitrogen and sulfur heteroatoms may optionally be oxidized, and the nitrogen heteroatom may optionally be quaternized. Examples of heterocycles include pyrrolidine, pyrazole, pyrrole, indole, quinoline, isoquinoline, tetrahydroisoquinoline, benzofuran, benzodioxan, benzodioxole (commonly referred to as methylenedioxyphenyl, when occurring as a substituent), tetrazole, morpholine, thiazole, pyridine, pyridazine, pyrimidine, thiophene, furan, oxazole, oxazoline, isoxazole, dioxane, tetrahydrofuran and the like. It is to be noted that heteroaryl is a subset of heterocycle in which the heterocycle is aromatic. Examples of heterocyclyl residues additionally include piperazinyl, 2-oxopiperazinyl, 2-oxopiperidinyl, 2-oxo-pyrrolidinyl, 2-oxoazepinyl, azepinyl, 4-piperidinyl, pyrazolidinyl, imidazolyl, imidazolinyl, imidazolidinyl, pyrazinyl, oxazolidinyl, isoxazolidinyl, thiazolidinyl, isothiazolyl, quinuclidinyl, isothiazolidinyl, benzimidazolyl, thiadiazolyl, benzopyranyl, benzothiazolyl, tetrahydrofuryl, tetrahydropyranyl, thienyl, benzothienyl, thiamorpholinyl, thiamorpholinylsulfoxide, thiamorpholinylsulfone, oxadiazolyl, triazolyl and tetrahydroquinolinyl.

An oxygen heterocycle is a heterocycle containing at least one oxygen in the ring; it may contain additional oxygens, as well as other heteroatoms. A sulphur heterocycle is a heterocycle containing at least one sulphur in the ring; it may contain additional sulphurs, as well as other heteroatoms. A nitrogen heterocycle is a heterocycle containing at least one nitrogen in the ring; it may contain additional nitrogens, as well as other heteroatoms.

Oxygen heteroaryl is a subset of oxygen heterocycle; examples include furan and oxazole. Sulphur heteroaryl is a subset of sulphur heterocycle; examples include thiophene and thiazine. Nitrogen heteroaryl is a subset of nitrogen heterocycle; examples include pyrrole, pyridine and pyrazine.

A saturated nitrogenous heterocycle is a subset of nitrogen heterocycle. Saturated nitrogenous heterocycle contain at least one nitrogen and may contain additional nitrogens, as well as other heteroatoms. Examples include pyrrolidine, pyrazolidine, piperidine, morpholine, and thiomorpholine.

Substituted alkyl, aryl, cycloalkyl, heterocyclyl etc. refer to alkyl, aryl, cycloalkyl, or heterocyclyl wherein up to three H atoms in each residue are replaced with halogen, haloalkyl, hydroxy, loweralkoxy, carboxy, carboalkoxy (also referred to as alkoxycarbonyl), carboxamido (also referred to as alkylaminocarbonyl), cyano, carbonyl, nitro, amino, alkylamino, dialkylamino, mercapto, alkylthio, sulfoxide, sulfone, acylamino, amidino, phenyl, benzyl, heteroaryl, phenoxy, benzyloxy, or heteroaryloxy.

The terms "halogen" and "halo" refer to fluorine, chlorine, bromine or iodine.

It will be recognized that the compounds of this invention can exist in radiolabeled form, i.e., the compounds may contain one or more atoms containing an atomic mass or mass number different from the atomic mass or mass number usually found in nature. Radioisotopes of hydrogen, carbon, phosphorous, fluorine, and chlorine include $^{2}H$, $^{3}H$, $^{13}C$, $^{14}C$, $^{15}N$, $^{35}S$, $^{18}F$, and $^{36}Cl$, respectively. Compounds that contain those radioisotopes and/or other radioisotopes of other atoms are within the scope of this invention. Tritiated, i.e. 3H, and carbon-14, i.e., $^{14}C$, radioisotopes are particularly preferred for their ease in preparation and detectability. Radiolabeled compounds of formula Ψ of this invention and prodrugs thereof can generally be prepared by methods well known to those skilled in the art. Conveniently, such radiolabeled compounds can be prepared by carrying out the procedures disclosed in the Examples and Schemes by substituting a readily available radiolabeled reagent for a non-radiolabeled reagent.

As used herein, and as would be understood by the person of skill in the art, the recitation of "a compound" is intended to include salts, solvates, co-crystals and inclusion complexes of that compound. It also includes all polymorphs of the compound in crystalline form.

The term "solvate" refers to a compound of formula I in the solid state, wherein molecules of a suitable solvent are incorporated in the crystal lattice. A suitable solvent for therapeutic administration is physiologically tolerable at the dosage administered. Examples of suitable solvents for therapeutic administration are ethanol and water. When water is the solvent, the solvate is referred to as a hydrate. In general, solvates are formed by dissolving the compound in the appropriate solvent and isolating the solvate by cooling or using an antisolvent. The solvate is typically dried or azeotroped under ambient conditions. Co-crystals are combinations of two or more distinct molecules arranged to create a unique crystal form whose physical properties are different from those of its pure constituents. Pharmaceutical co-crystals have recently become of considerable interest for improving the solubility, formulation and bioavailability of such drugs as itraconazole [see Remenar et al. *J. Am. Chem. Soc.* 125, 8456-8457 (2003)] and fluoxetine. Inclusion complexes are described in Remington: The Science and Practice of Pharmacy 19$^{th}$ Ed.

(1995) volume 1, page 176-177. The most commonly employed inclusion complexes are those with cyclodextrins, and all cyclodextrin complexes, natural and synthetic, with or without added additives and polymer(s), as described in U.S. Pat. Nos. 5,324,718 and 5,472,954, are specifically encompassed within the claims. The disclosures of Remington and the '718 and '954 patents are incorporated herein by reference.

The compounds described herein may contain asymmetric centers and may thus give rise to enantiomers, diastereomers, and other stereoisomeric forms. Each chiral center may be defined, in terms of absolute stereochemistry, as (R)- or (S)-. The present invention is meant to include all such possible isomers, as well as, their racemic and optically pure forms. Optically active (R)- and (S)-isomers may be prepared using chiral synthons or chiral reagents, or resolved using conventional techniques. The prefix "rac" refers to a racemate. When the compounds described herein contain olefinic double bonds or other centers of geometric asymmetry, and unless specified otherwise, it is intended that the compounds include both E and Z geometric isomers. The representation of the configuration of any carbon-carbon double bond appearing herein is selected for convenience only, and unless explicitly stated, is not intended to designate a particular configuration. Thus a carbon-carbon double bond depicted arbitrarily as E may be Z, E, or a mixture of the two in any proportion. Likewise, all tautomeric forms are also intended to be included.

The graphic representations of racemic, ambiscalemic and scalemic or enantiomerically pure compounds used herein are taken from Maehr J. Chem. Ed. 62, 114-120 (1985): solid and broken wedges are used to denote the absolute configuration of a chiral element; wavy lines and single thin lines indicate disavowal of any stereochemical implication which the bond it represents could generate; solid and broken bold lines are geometric descriptors indicating the relative configuration shown but denoting racemic character; and wedge outlines and dotted or broken lines denote enantiomerically pure compounds of indeterminate absolute configuration.

Terminology related to "protecting", "deprotecting" and "protected" functionalities occurs throughout this application. Such terminology is well understood by persons of skill in the art and is used in the context of processes that involve sequential treatment with a series of reagents. In that context, a protecting group refers to a group, which is used to mask a functionality during a process step in which it would otherwise react, but in which reaction is undesirable. The protecting group prevents reaction at that step, but may be subsequently removed to expose the original functionality. The removal or "deprotection" occurs after the completion of the reaction or reactions in which the functionality would interfere. Thus, when a sequence of reagents is specified, as it is in the processes of the invention, the person of ordinary skill can readily envision those groups that would be suitable as "protecting groups". Suitable groups for that purpose are discussed in standard textbooks in the field of chemistry, such as Protective Groups in Organic Synthesis by T. W. Greene [John Wiley & Sons, New York, 1991], which is incorporated herein by reference.

A comprehensive list of abbreviations utilized by organic chemists appears in the first issue of each volume of the Journal of Organic Chemistry. The list, which is typically presented in a table entitled "Standard List of Abbreviations", is incorporated herein by reference.

In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants that are in themselves known, but are not mentioned here. The starting materials, for example in the case of suitably substituted benzimidazole ring compounds, are either commercially available, synthesized as described in the examples or may be obtained by the methods well known to persons of skill in the art.

LTA4H inhibitors have been shown to be effective anti-inflammatory agents in pre-clinical studies. For example, oral administration of LTA4H inhibitor SC57461 to rodents resulted in the inhibition of ionophore-induced LTB4 production m mouse blood ex vivo, and in rat peritoneum in vivo (Kachur et al., 2002, J. Pharm. Exp. Ther. 300(2), 583-587). Furthermore, eight weeks of treatment with the same inhibitor compound significantly improved colitis symptoms in a primate model (Penning, 2001, Curr. Pharm. Des. 7(3): 163-179). The spontaneous colitis that develops in these animals is very similar to human IBD. Therefore persons of skill in the art accept that positive results in LTA4H models are predictive of therapeutic utility in this and other human inflammatory diseases.

The inflammatory response is characterized by pain, increased temperature, redness, swelling, or reduced function, or by a combination of two or more of these symptoms. The terms inflammation, inflammatory diseases or inflammation-mediated diseases or conditions include, but are not limited to, acute inflammation, allergic inflammation, and chronic inflammation.

Autoimmune diseases are associated with chronic inflammation. There are about 75 different autoimmune disorders known that may be classified into two types, organ-specific (directed mainly at one organ) and non-organ-specific (affecting multiple organs).

Examples of organ-specific autoimmune disorders are insulin-dependent diabetes (Type I) which affects the pancreas, Hashimoto's thyroiditis and Graves' disease which affect the thyroid gland, pernicious anemia, which affects the stomach, Cushing's disease and Addison's disease, which affect the adrenal glands, chronic active hepatitis, which affects the liver; polycystic ovary syndrome (PCOS), celiac disease, psoriasis, inflammatory bowel disease (IBD) and ankylosing spondylitis.

Examples of non-organ-specific autoimmune disorders are rheumatoid arthritis, multiple sclerosis, systemic lupus and myasthenia gravis.

Furthermore, the compounds, compositions and methods of the present invention are useful in treating cancer. Leukotriene synthesis has been shown to be associated with different types of cancer including esophageal cancer, brain cancer, pancreatic cancer, colon cancer.

The terms "methods of treating or preventing" mean amelioration, prevention or relief from the symptoms and/or effects associated with lipid disorders. The term "preventing" as used herein refers to administering a medicament beforehand to forestall or obtund an acute episode. The person of ordinary skill in the medical art (to which the present method claims are directed) recognizes that the term "prevent" is not an absolute term. In the medical art it is understood to refer to the prophylactic administration of a drug to substantially diminish the likelihood or seriousness of a condition, and this is the sense intended in applicants' claims. As used herein, reference to "treatment" of a patient is intended to include prophylaxis. Throughout this application, various references are referred to. The disclosures of these publications in their entireties are hereby incorporated by reference as if written herein.

"Administering" the compound of the invention includes administering prodrug forms (e.g. esters) so as to provide effective levels of the compound in the subject. The term "prodrug" refers to a compound that is made more active in vivo. Activation in vivo may come about by chemical action or through the intermediacy of enzymes. Microflora in the GI tract may also contribute to activation in vivo. Common esters employed as prodrugs are methyl, ethyl and oxaalkyl esters. For example, under appropriate circumstances

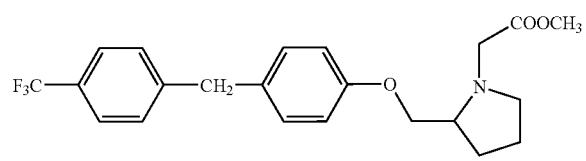

may be considered a prodrug of

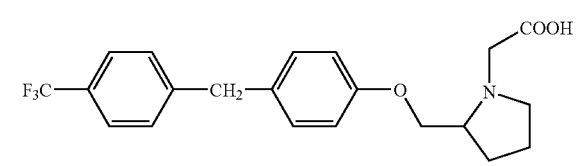

A variety of routes of administration are possible including, but not necessarily limited to parenteral (e.g., intravenous, intra-arterial, intramuscular, subcutaneous injection), oral (e.g., dietary or by inhalation), topical, nasal, rectal, or via slow releasing micro-carriers depending on the disease or condition to be treated. Oral, parenteral and intravenous administration are preferred modes of administration.

The term "mammal" is used in its dictionary sense. Humans are included in the group of mammals, and humans would be the preferred subjects.

While it may be possible for the compounds of formula Ψ to be administered as the raw chemical, it is preferable to present them as a pharmaceutical composition. According to a further aspect, the present invention provides a pharmaceutical composition comprising a compound of formula I, or a pharmaceutically acceptable salt or solvate thereof, together with one or more pharmaceutically carriers thereof and optionally one or more other therapeutic ingredients. The carrier(s) must be "acceptable" in the sense of being compatible with the other ingredients of the formulation and not deleterious to the recipient thereof.

The formulations include those suitable for oral, parenteral (including subcutaneous, intradermal, intramuscular, intravenous and intraarticular), rectal and topical (including dermal, buccal, sublingual and intraocular) administration. The most suitable route may depend upon the condition and disorder of the recipient. The formulations may conveniently be presented in unit dosage form and may be prepared by any of the methods well known in the art of pharmacy. All methods include the step of bringing into association a compound of formula Ψ or a pharmaceutically acceptable salt or solvate thereof ("active ingredient") with the carrier, which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder (including micronized and nanoparticulate powders) or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. The tablets may optionally be coated or scored and may be formulated so as to provide sustained, delayed or controlled release of the active ingredient therein.

The pharmaceutical compositions may include a "pharmaceutically acceptable inert carrier", and this expression is intended to include one or more inert excipients, which include starches, polyols, granulating agents, microcrystalline cellulose, diluents, lubricants, binders, disintegrating agents, and the like. If desired, tablet dosages of the disclosed compositions may be coated by standard aqueous or non-aqueous techniques, "Pharmaceutically acceptable carrier" also encompasses controlled release means.

Compositions of the present invention may also optionally include other therapeutic ingredients, anti-caking agents, preservatives, sweetening agents, colorants, flavors, desiccants, plasticizers, dyes, and the like. Any such optional ingredient must, of course, be compatible with the compound of the invention to insure the stability of the formulation. The dose range for adult humans is generally from 0.1 µg to 10 g/day orally. Tablets or other forms of presentation provided in discrete units may conveniently contain an amount of compound of the invention which is effective at such dosage or as a multiple of the same, for instance, units containing 0.1 mg to 500 mg, usually around 5 mg to 200 mg. The precise amount of compound administered to a patient will be the responsibility of the attendant physician. However, the dose employed will depend on a number of factors, including the age and sex of the patient, the precise disorder being treated, and its severity. The frequency of administration will depend on the pharmacodynamics of the individual compound and the formulation of the dosage form, which may be optimized by methods well known in the art (e.g. controlled or extended release tablets, enteric coating etc.).

Combination therapy can be achieved by administering two or more agents, each of which is formulated and administered separately, or by administering two or more agents in a single formulation. Other combinations are also encompassed by combination therapy. For example, two agents can be formulated together and administered in conjunction with a separate formulation containing a third agent. While the two or more agents in the combination therapy can be administered simultaneously, they need not be. For example, administration of a first agent (or combination of agents) can precede administration of a second agent (or combination of agents) by minutes, hours, days, or weeks. Thus, the two or more agents can be administered within minutes of each other or within any number of hours of each other or within any number or days or weeks of each other. In some cases even longer intervals are possible.

While in many cases it is desirable that the two or more agents used in a combination therapy be present in within the patient's body at the same time, this need not be so. Combination therapy can also include two or more administrations of one or more of the agents used in the combination. For example, if agent X and agent Y are used in a combination, one could administer them sequentially in any combination one or more times, e.g., in the order X-Y-X, X-X-Y, Y-X-Y, Y-Y-X, X-X-Y-Y, etc.

As LTA4H inhibitors, the compounds of formula Ψ have utility in treating and preventing inter alia inflammation. The compounds and compositions can be used advantageously in combination with other agents useful in treating and preventing inflammatory conditions and for treating and preventing atherosclerosis, thrombosis, stroke, acute coronary syndrome, stable angina, peripheral vascular disease, critical leg ischemia, intermittent claudication, abdominal aortic aneurysm and myocardial infarction. Such agents include FLAP inhibitors and LTB4 antagonists.

In general, the compounds of the present invention may be prepared by the methods illustrated in the general reaction schemes as, for example, described below, or by modifications thereof, using readily available starting materials, reagents and conventional synthesis procedures.

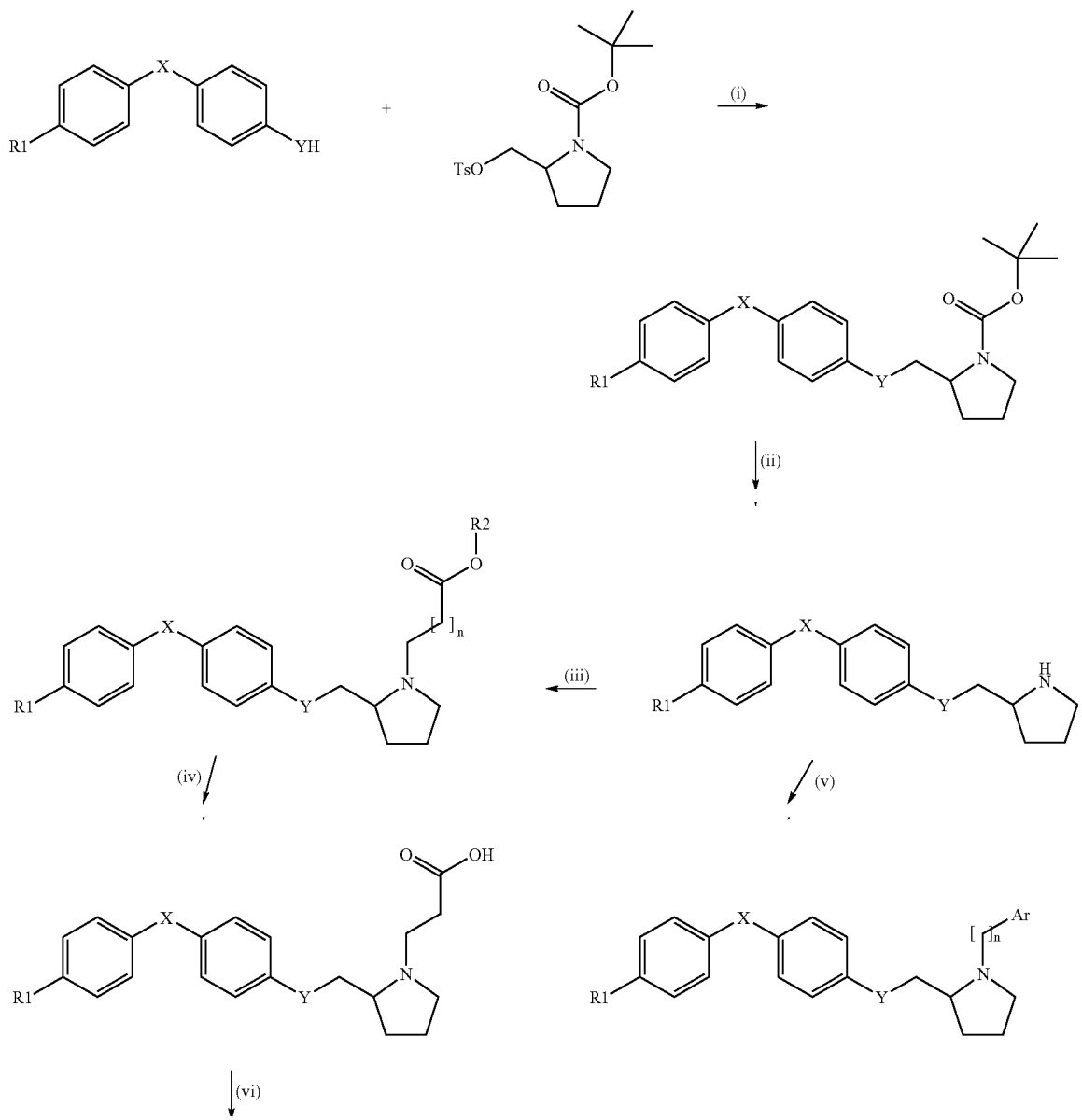

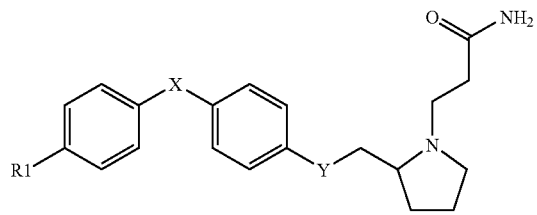
R1=H, OCF3, Ph, Cl, Me, CF3, F
X=C, O, CH2NH, CH3CO, CO, NH
Y=O, N, S
R2=H, Me, Et
Ar=pyridyl, oxadiazole
n=0, 1, 2
Scheme 1: (i) NaH/DMF or K2CO3/DMF (ii) HCl, ether or dioxane, (iii) Br(CH2)nCO2R2, Et3N, (iv) 2N NaOH or 2M HCl, (v) ArCH2Cl, Et3N, (vi) SOCl2, NH3/MeOH
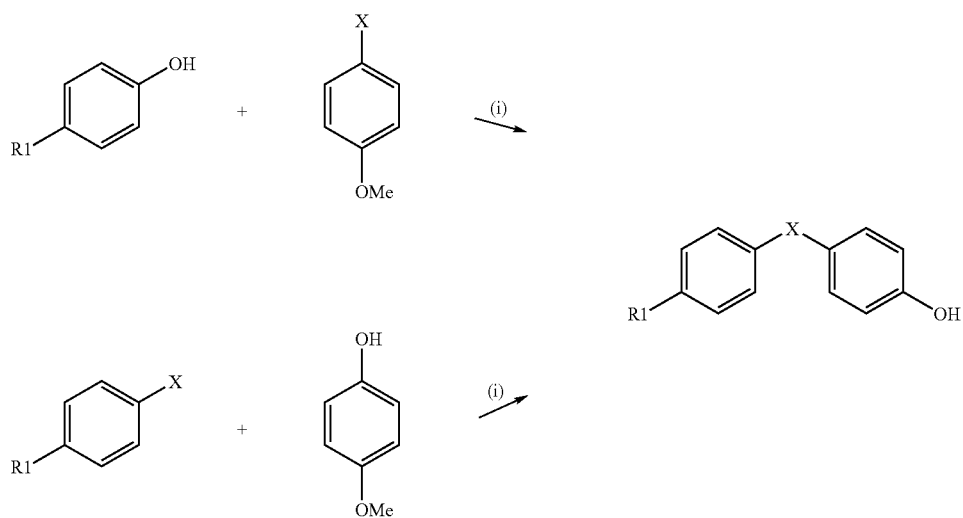
X=Br, I; R1=as defined in Scheme I
Scheme II: (i) (a) CuI, Cs2CO3, N,N-dimethylglycine, (b) BBr3, CH2Cl2
Scheme III
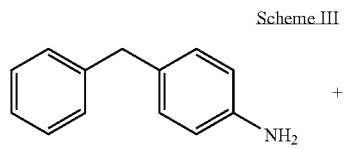
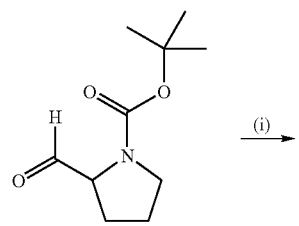

21
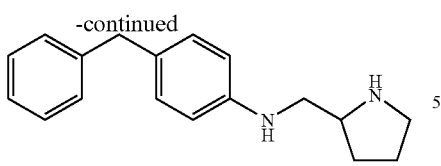
Scheme III: i) (a) Na(OAc)3, (b) 2M HCl
Scheme IV
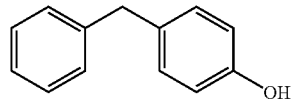
+
22
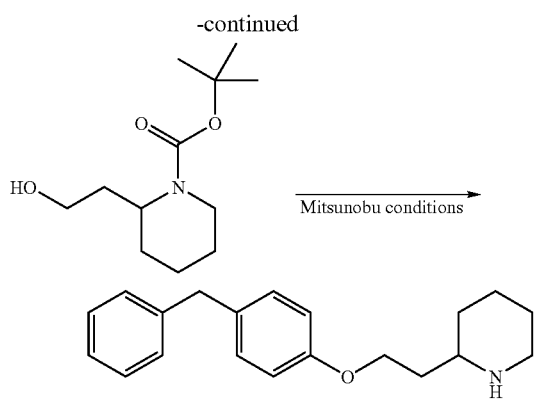
Scheme V
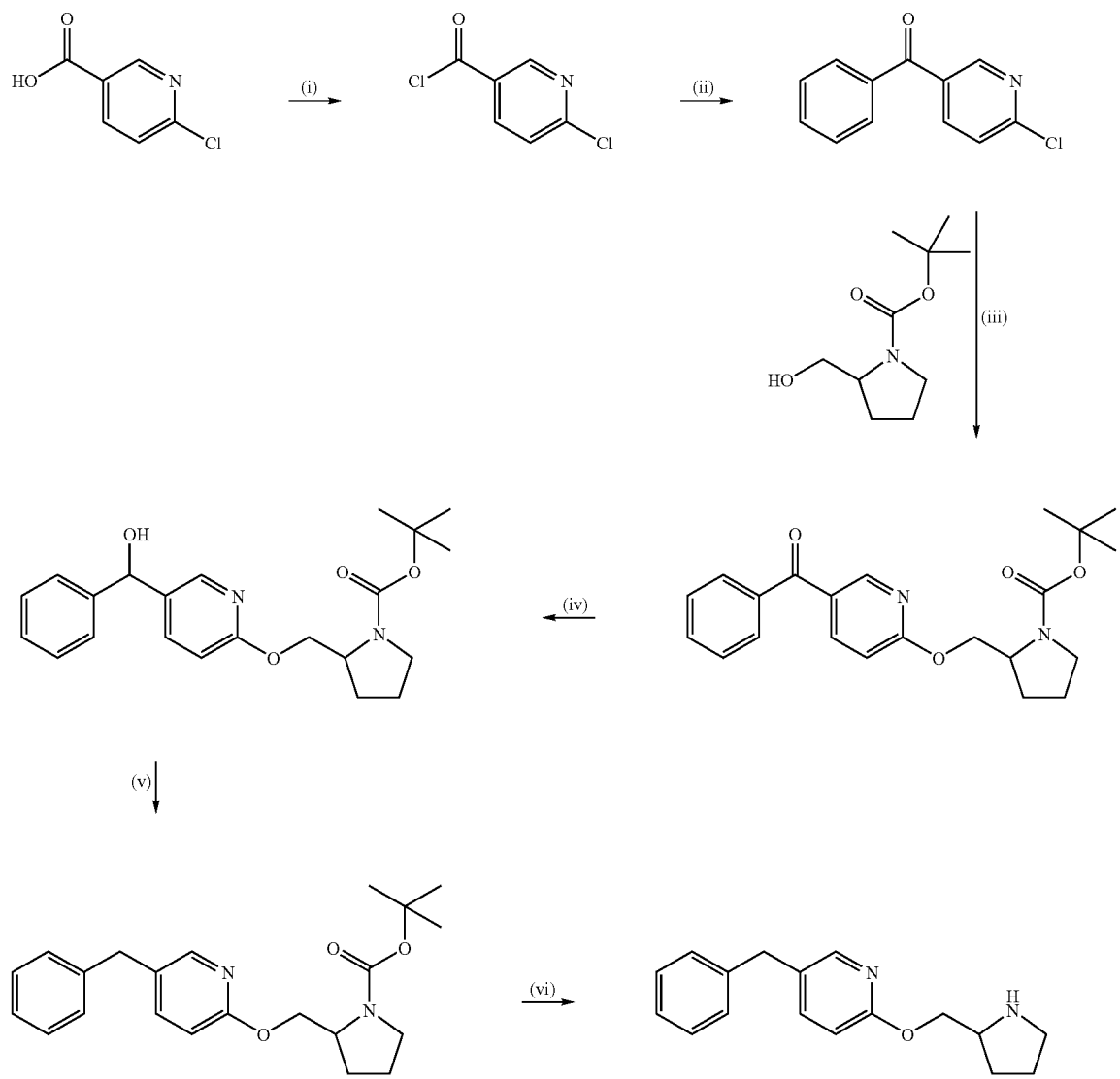

Scheme V: (i) SOCl2 (ii) benzene, AlCl3 (iii) 60% NaH,
(iv) NaBH4/EtOH, (v) H2, Pd/C (vi) 2M HCl ether
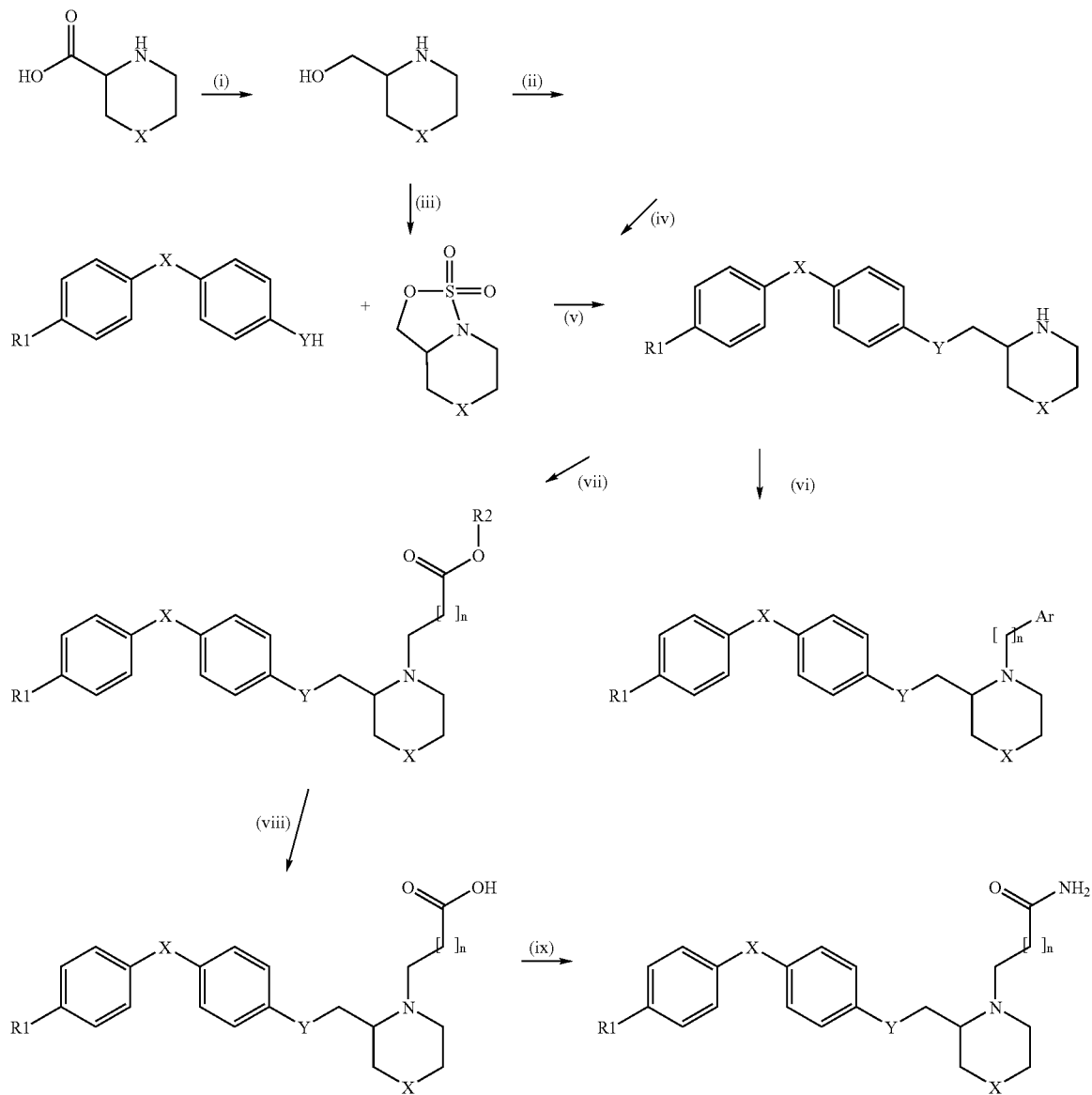
Scheme VI: (i) (a) BH3.THF, (b) 4M HCl, dioxane; (ii)
SOCl2, CH2Cl2; (iii) SO2Cl2, CH2Cl2; (iv) NaIO4,
RuCl3; (v) K2CO3, DMF; (vi) ArCH2Cl, Et3N; (vii)
Br(CH2)nCO2R2; (viii) 2N NaOH or 2M HCl; (ix) (a)
SOCl2, (b) NH3/MeOH
-continued
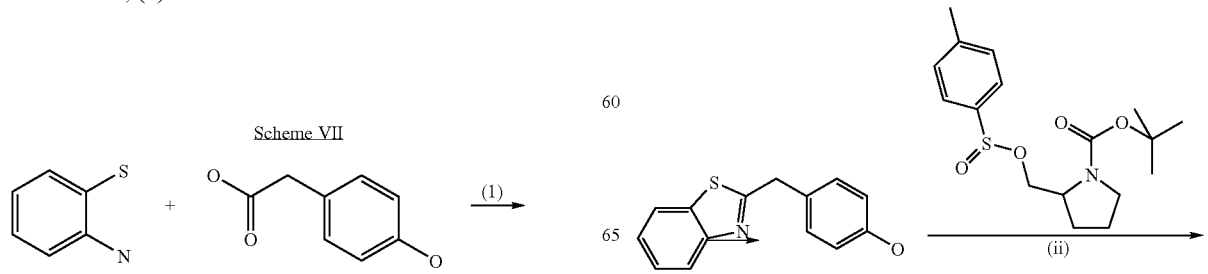
Scheme VII

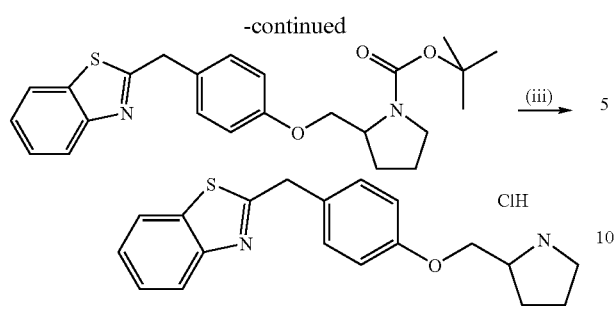
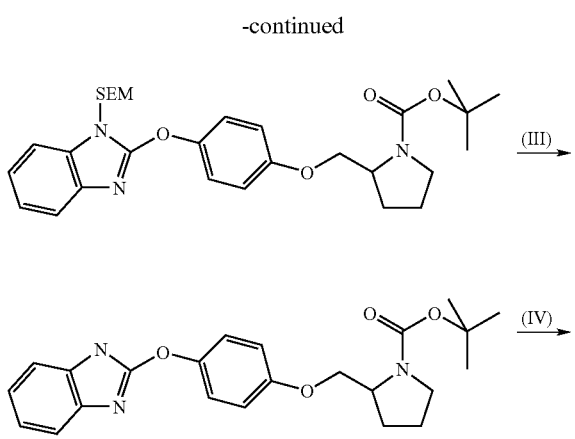
Scheme VII: (1) 150° C., (ii) NaH, DMF, (iii) HCl, dioxane
Scheme VIII
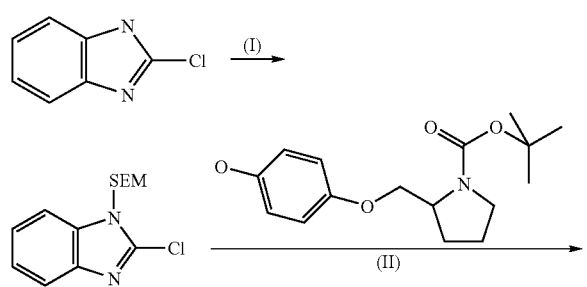
Scheme VIII: (i) NaH, SEMCl, DMF, (II) CsCO3, DMF, (III) TBAF THF (IV) HCl, dioxane
Scheme IX
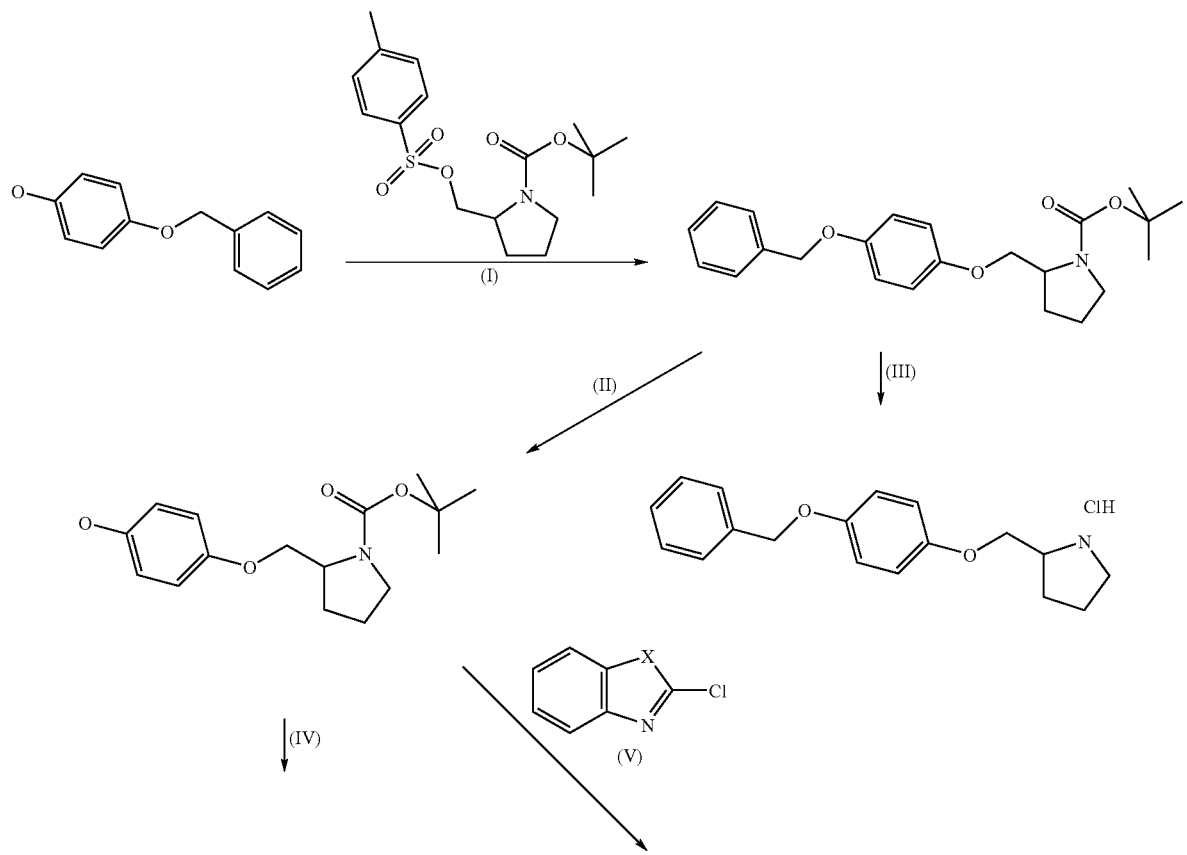

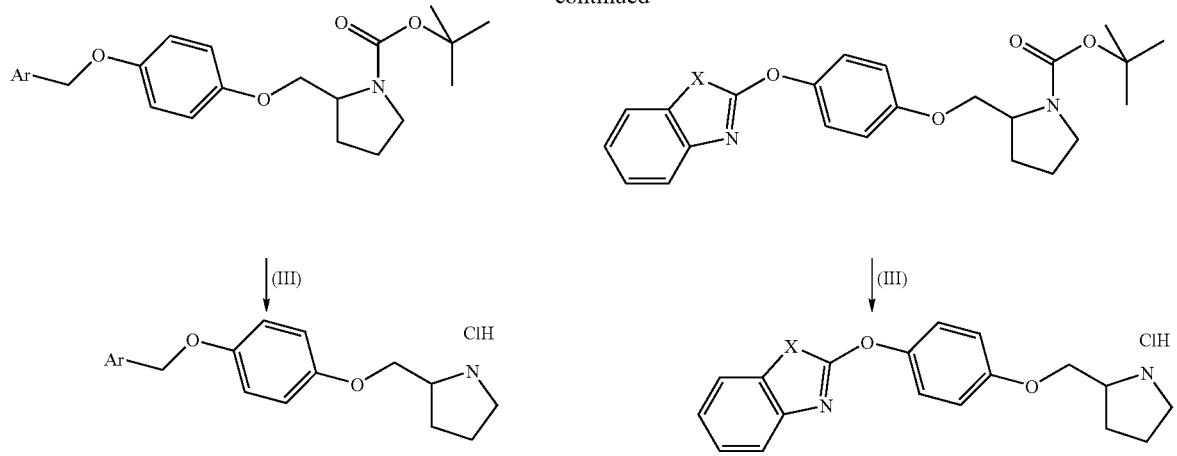
Scheme IX: (1) NaH, DMF, (II) H2, Pd/C, EtOH/THF, (III) HCl, dioxane, (IV) Cs2CO3, DMF, (V) Cs2CO3, acetone, MeCN
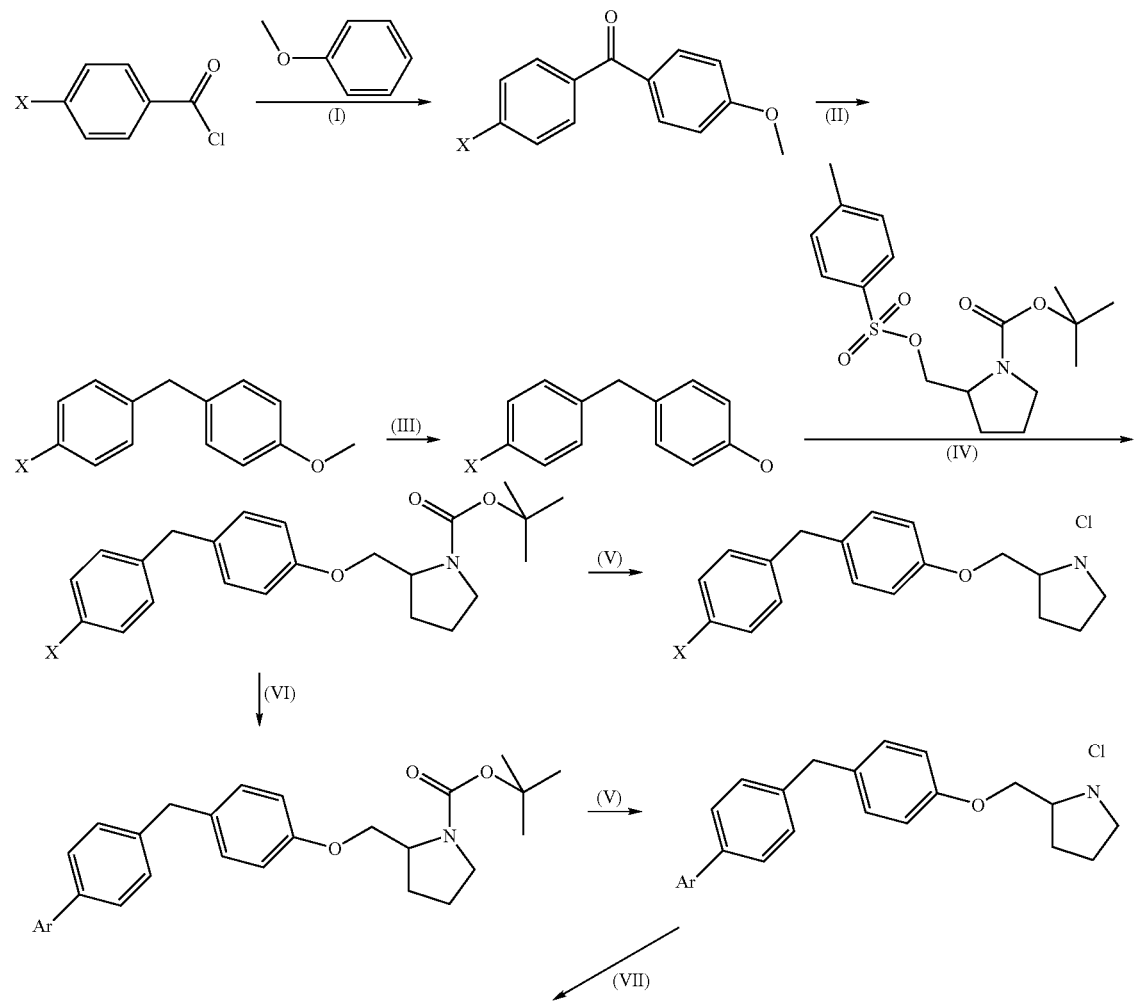

-continued
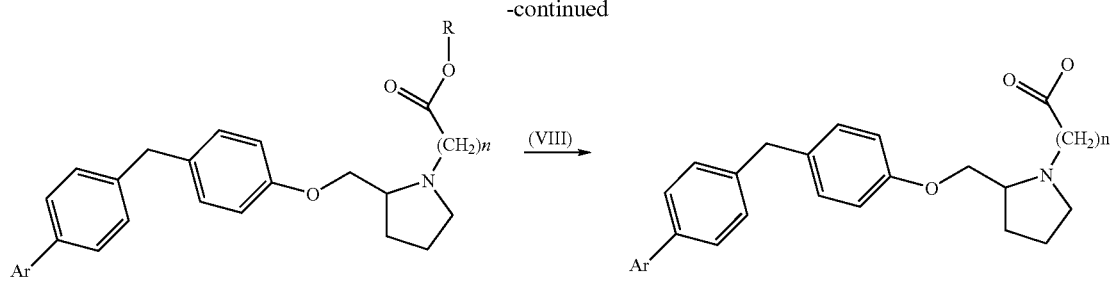
Scheme X: (I) AlCl3, nitrobenzene, (II) Et3SiH, TFA, (III) BBr3, CH2Cl2, (IV) NaH, DMF (V) HCl, dioxane, (VI) ArB(OH)2, Pd(OAc)2/PPh3/CsCO3, DME/EtOH/H2O, (VII) Br(CH2)nCO2R base, (VIII) NaOH or HCl.
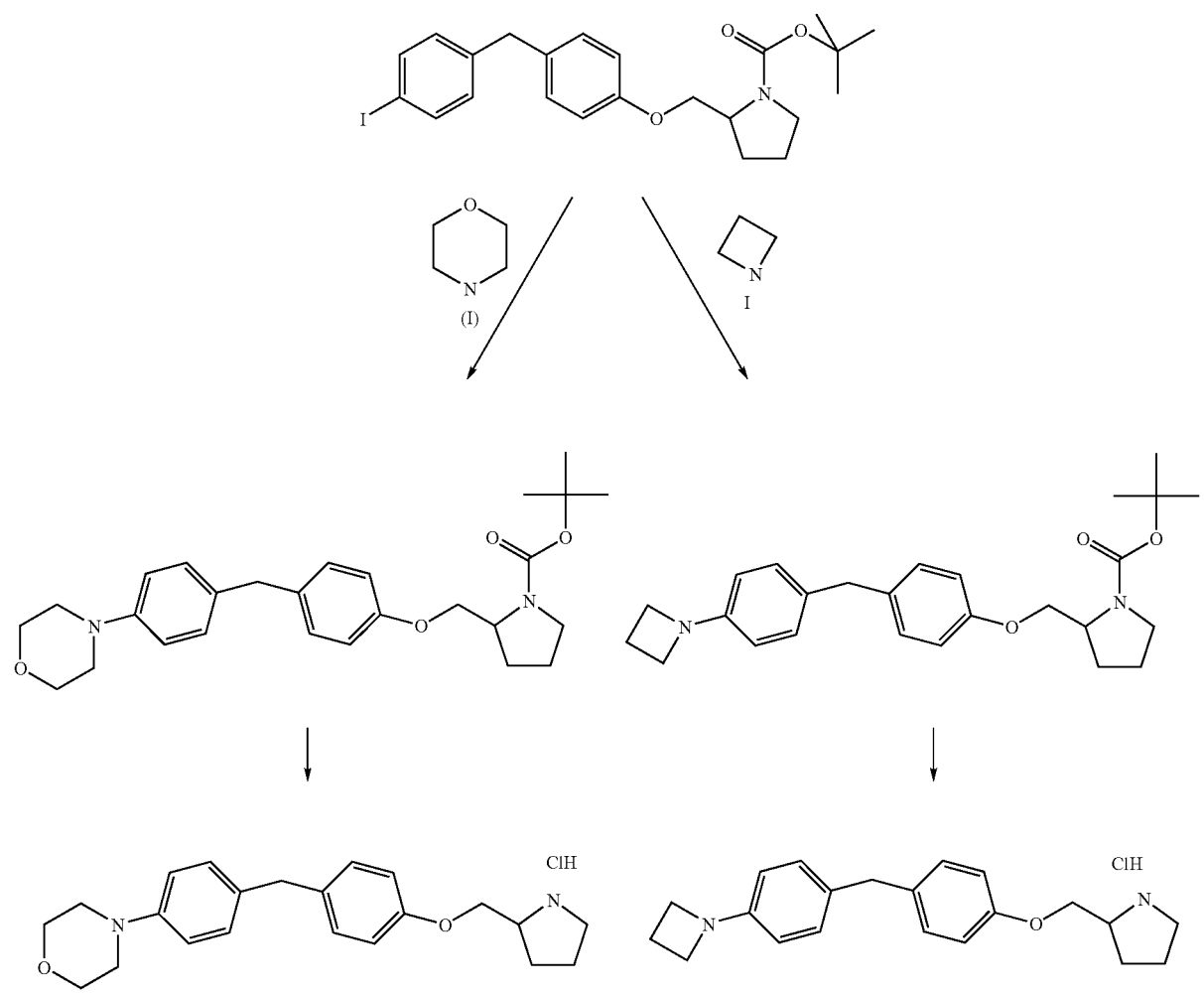

Scheme XI: (1) Pd2(dba)3/t-Bu3P, NaOtBu/toluene, (II) HCl, dioxane
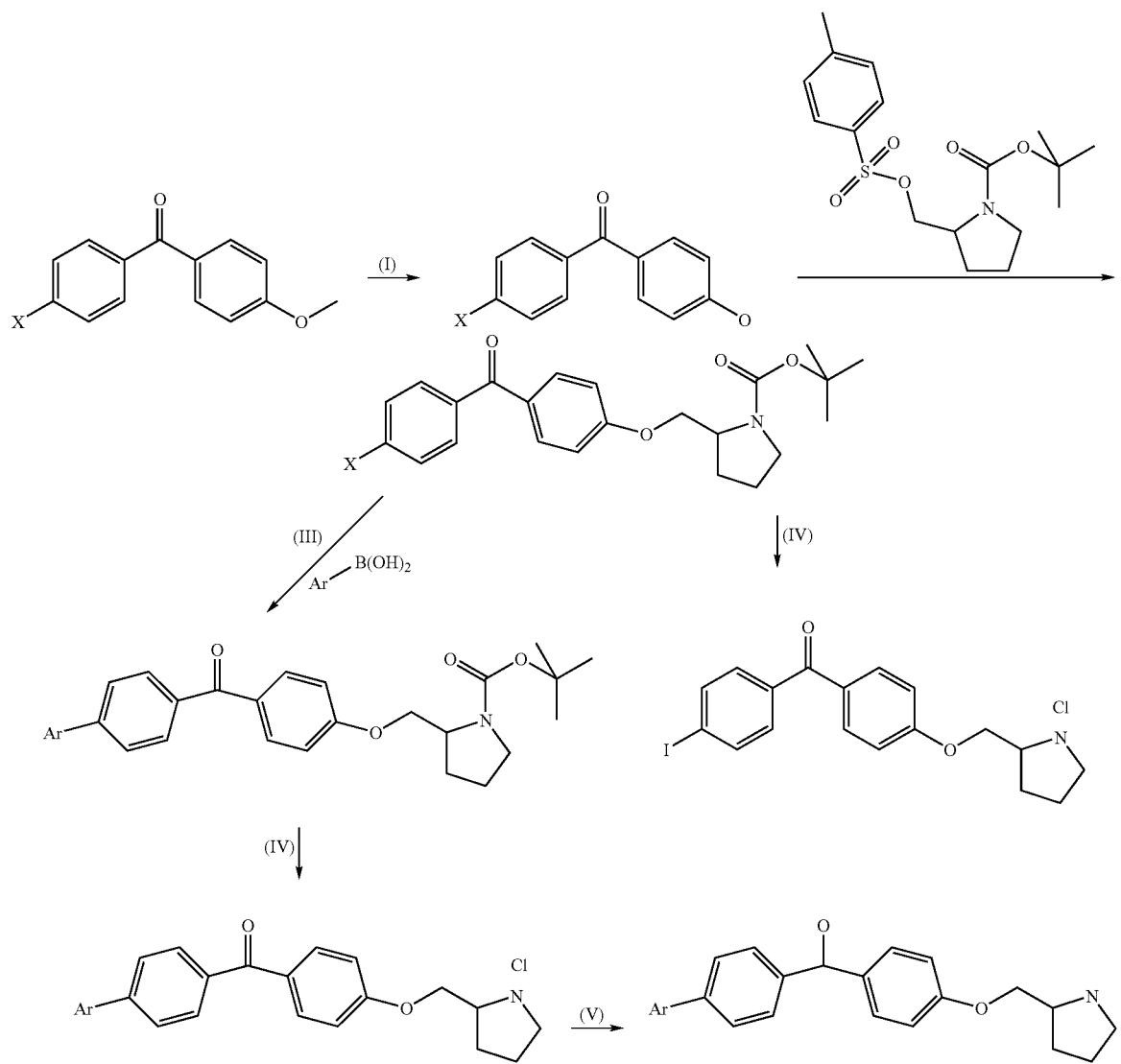
Scheme XII (I) BBr3, CH2Cl2, (II) NaH, DMF, (III) Pd(OAc)2/PPh3/CsCO3, DME/EtOH/H2O, (IV) HCl, dioxane, (V) NaBH4, EtOH
-continued
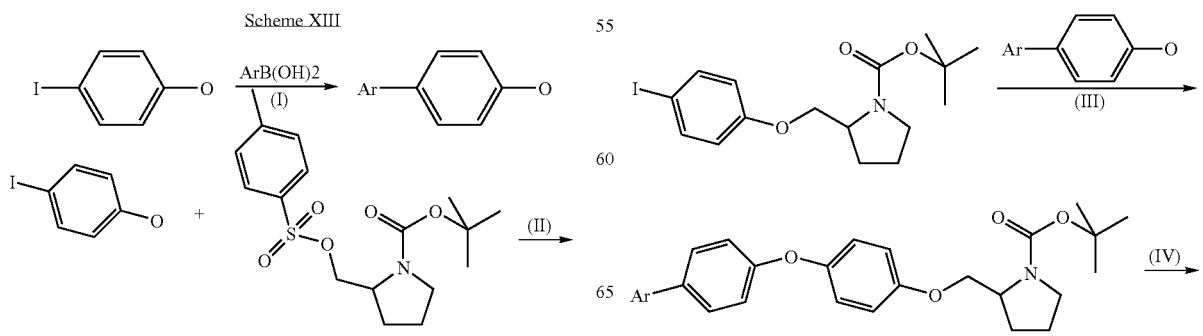

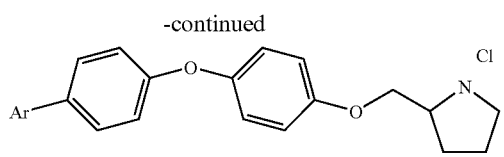
Scheme XIII: (I) Pd(OAc)2/PPh3/K2CO3, DME/EtOH/H2O, (II) NaH, DMF, (III) CS2CO3/(CH3)2NCH2CO2H, CuI/dioxane/98° C., (IV) HCl, dioxane
Scheme XIV
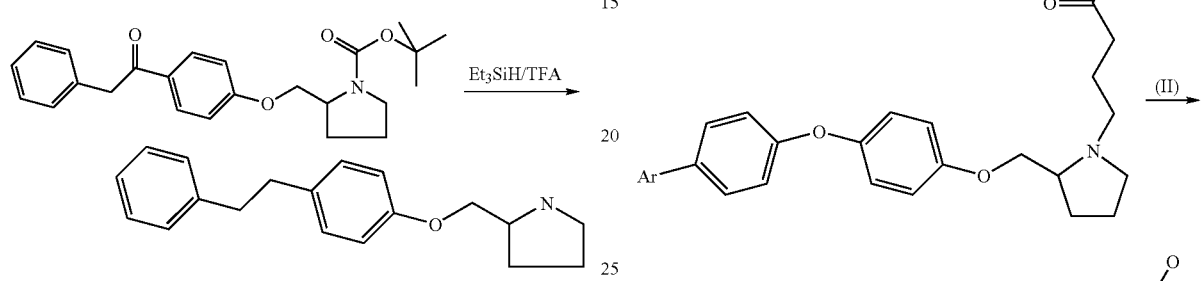
Scheme XV
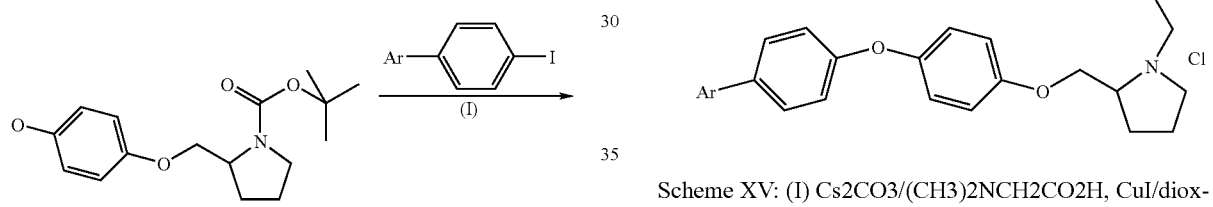
Scheme XV: (I) Cs2CO3/(CH3)2NCH2CO2H, CuI/dioxane/98° C., (II) HCl, dioxane, (III) K2CO3, DMF
Scheme XVI
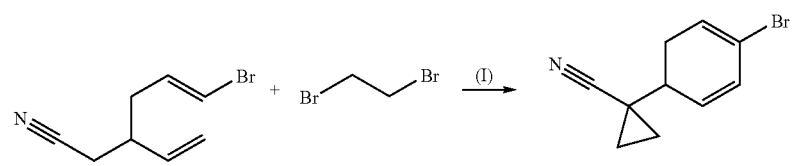
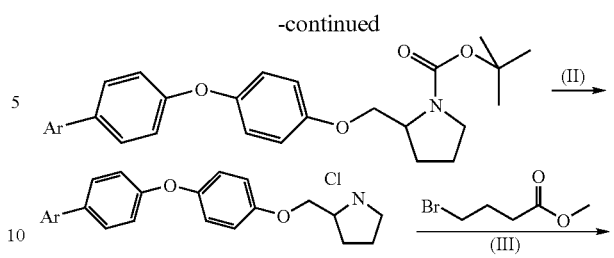

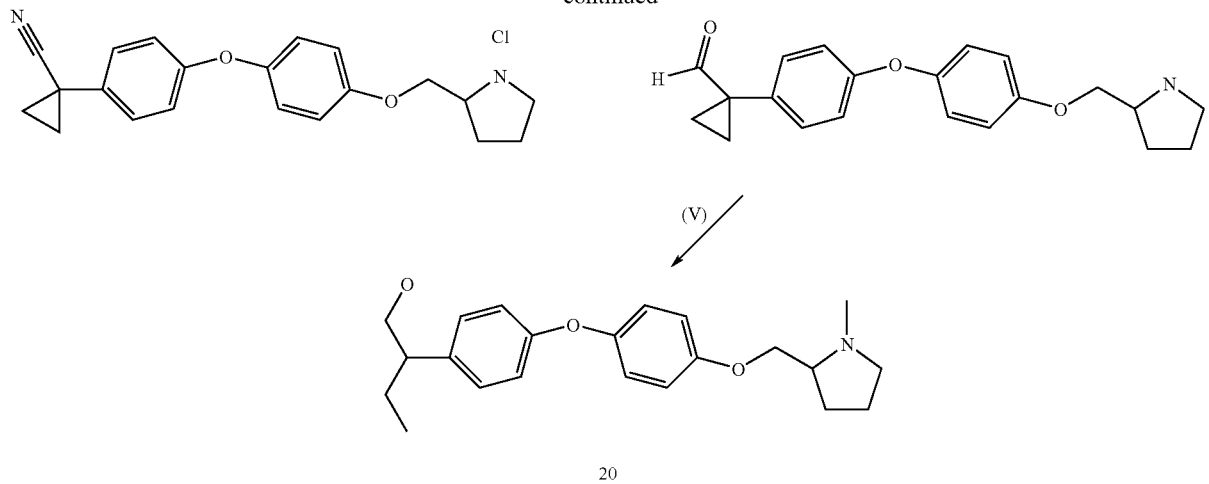
Scheme XVI: (I) TBAB/NaOH (50%), toluene, (II) CS2CO3/(CH3)2NCH2CO2H, CuI/dioxane/98° C., (III) HCl, dioxane, (IV) DIBAL, toluene, (V) NaBH4/EtOH
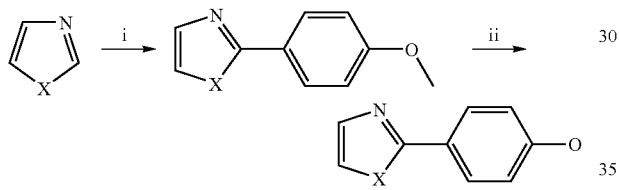
X=O, S
Scheme XVII: i) (a) n-BuLi, THF –78 C: (b) ZnCl₂, –78-65C (c)ArBr, (Ph₃P)₄Pd, rt-65C: ii) BBr₃, CH₂Cl₂, –78-rt, 16 h:
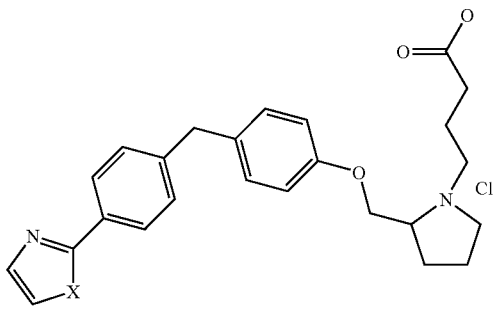
i) (a) n-BuLi, THF, –78C; (b) ZnCl₂, –78-65C; (c) ArBr, (Ph₃P)₄Pd, rt-65C; ii) HCl, dioxane; iii) bromoester, K₂CO₃, DMF; (b) NaOH/H₂O/THF, (c) HCl
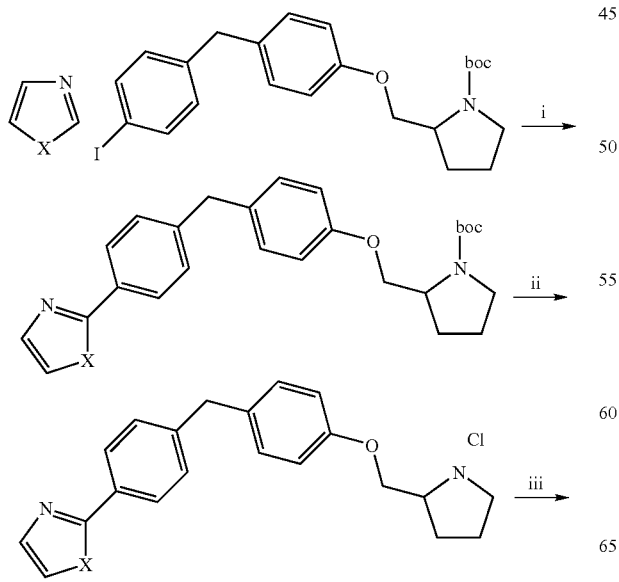
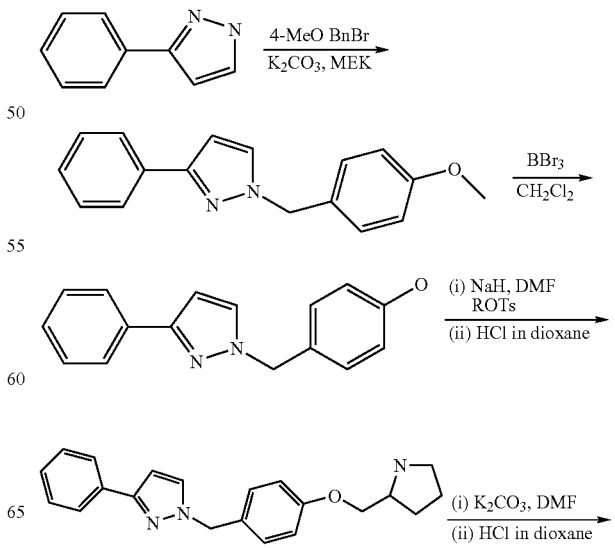

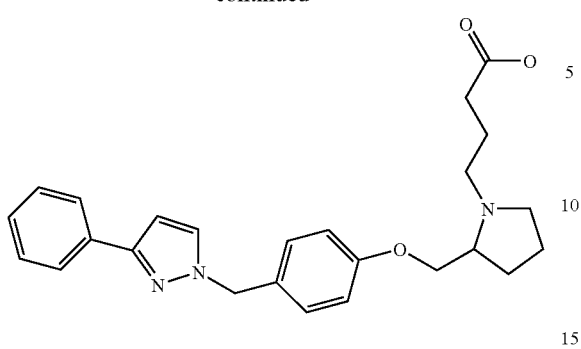
Scheme XIX: (I) 4-MeOBnBr, K2CO3, MEK, (II) BBr3, CH2CL2, (III) (a)NaH, DMF/HCl in dioxane, pyrrolidine tosylate (b) HCl in dioxane, (IV) (a) K2CO3, DMF, HCl, dioxane
Scheme XX
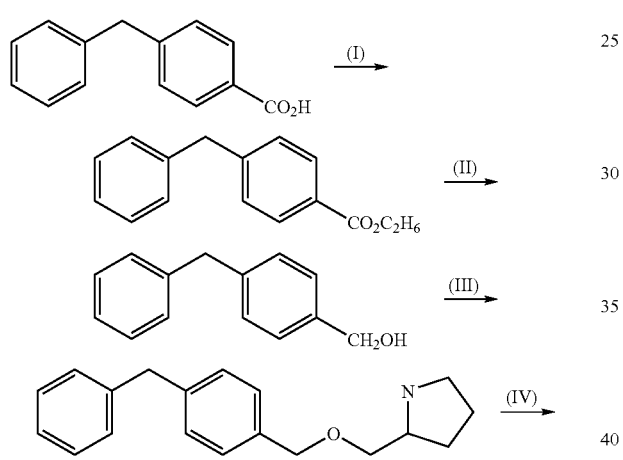
Scheme XX: (I) (a) (COCl)2, EtOH, Et3N, (II) LiAlH4, THF, (III) NaH, pyrrolidine tosylate, DMF, (IV) K2CO3, bromobutyryl acid
Scheme XXI
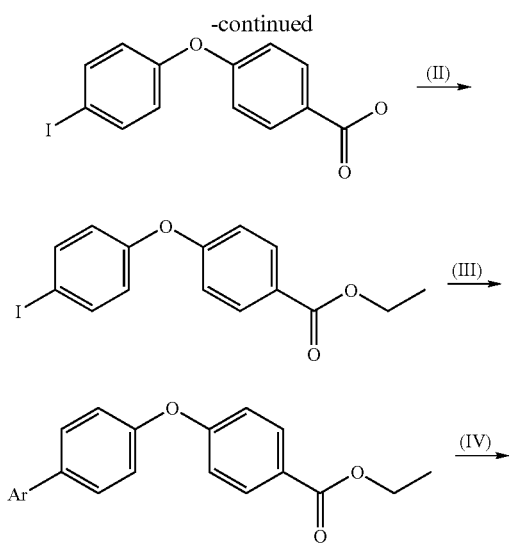
Scheme XXI: (I) n-BuLi, −78° C., CO2, (II) (COCl)2, EtOH, TEA, (III) ArB(OH)2, (Ph3 (IV) LiAlH4xane, (V) NaH, pyrrolidine tosylate, DMF
Scheme XXII
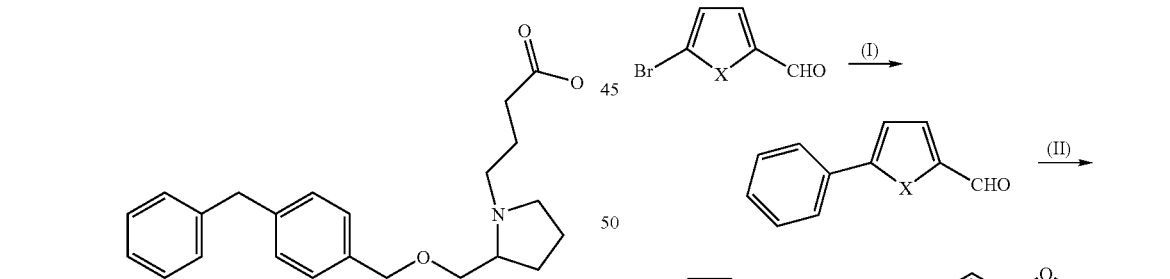

-continued

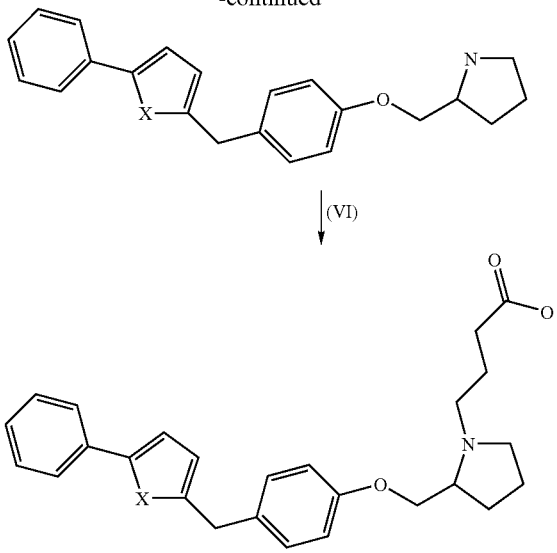

Scheme XXII: (I) ArB(OH)2, Pd/C, i-PrOH/H2O, reflux, (II) ArBr, n-BuLi, −78° C., THF, (III) Et3SiH, TFA, (IV) BBr3, CH2Cl2 (V) NaH, pyrrolidine tosylate, DMF, (VI) alkyl halide, K2CO3, DMF The following specific non-limiting examples are illustrative of the invention.

EXAMPLE 1

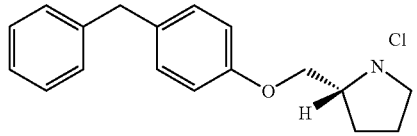

Step 1

(R)-2-(Toluene-4-sulfonyloxymethyl)-pyrrolidine-1-carboxylic acid tert-butyl ester: To a solution of (R)-Boc-prolinol (500 mg, 2.48 mmol) in pyridine (1.5 mL) was added tosyl chloride (565 mg, 2.96 mmol) in pyridine (1 mL) at 0° C., and the resulting mixture was stirred at 0° C. for 20 min. before allowing it to warm to rt. The mixture was stirred for 8 h at that temperature. The solvent was removed from the resulting suspension, and aq. 1N HCl was added to the crude product and extracted with EtOAc. Organic layer was washed with saturated aq. NaHCO₃ followed by water and brine. Organic layer was dried over anhy. Na₂SO₄ and the solvent was removed in vacuo to obtain the title product (800 mg, 91%) as a thick oil: MS; m/z 378 (M+Na); $^1$H NMR (400 MHz, CDCl₃); δ 1.38 (m, 9H), 1.79 (m, 2H), 1.93 (m, 2H), 2.44 (s, 3H), 3.26-3.32 (m, 3H), 3.88-3.97 (m, 2H), 4.07-4.14 (m, 2H), 7.34 (br s, 2H), 7.77 (d, 2H, J=8.0 Hz); HPLC (ELSD); 99%.

Step 2

(R)-2-(4-Benzyl-phenoxymethyl)-pyrrolidine-1-carboxylic acid tert-butyl ester: To a solution of 4-benzylphenol (103 mg, 0.56 mmol) in DMF (1 mL) was added 95% NaH (19 mg, 0.75 mmol) at 0° C., and the resulting mixture was stirred at 0° C. for 10 min. A solution of the tosylate (200 mg, 0.56 mmol) from Step 1 in DMF (2 mL) was added to the reaction mixture dropwise over 5 min., and the reaction was heated at 95° C. for 10 h. The mixture was concentrated and water was added, and extracted with EtOAc. The organic layer was washed with saturated aq. NaHCO₃ followed by water and brine. Organic layer was dried over anhy. Na₂SO₄ and the solvent was removed in vacuo to obtain the crude product, which was purified by silica gel flash chromatography to obtain the title product (150 mg, 73%) as a solid: MS; m/z 368 (M+H); $^1$H NMR (400 MHz, CDCl₃); δ 1.46 (m, 9H), 1.84-2.03 (m, 4H), 3.39 (m, 2H), 3.73-3.93 (m, 3H), 4.10 (m, 2H), 6.84 (m, 2H), 7.08 (m, 2H), 7.17 (m, 2H), 7.26 (m, 3H): HPLC (UV), 99.8%.

Step 3

(R)-2-(4-Benzylphenoxymethyl)pyrrolidine: To a solution of the product (4.5 g, 2.48 mmol) from Step 2 in dioxane (2 mL) was added 4M HCl in dioxane (8 mL) at rt and the resulting mixture was stirred for 1 h at that temperature. The solvent was removed in vacuo to obtain a thick oil. The oil was triturated with ether to obtain a white solid (2.5 g). The solid was recrystallized with toluene (20 mL) to obtain the title product (1.8 g, 53%) as a crystalline solid: MS; m/z 268 (M+H): $^1$H NMR (400 MHz, DMSO-d₆); δ 1.73 (m, 1H), 1.89 (m, 1H), 1.98 (m, 1H), 2.09 (m, 1H), 3.18 (m, 2H), 3.87 (m, 1H), 3.88 (s, 2H), 4.13 (dd, 1H, J1=7.2 Hz, J2=6.4 Hz), 4.19 (dd, 1H, J1=8.8, J2=3.2 Hz), 6.91 (d, 2H, J=6.8 Hz), 7.15-7.20 (m, 5H), 7.27 (m, 2H): HPLC (UV); 97.4%.

EXAMPLE 2

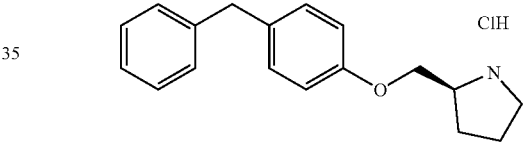

Step 1

(S)-2-(Toluene-4-sulfonyloxymethyl)-pyrrolidine-1-carboxylic acid tert-butyl ester: To a solution of S-(−)-1-Boc-2-pyrrolidine methanol (22 g, 110 mmol) in pyridine (56 mL) at 0° C. was added a solution of p-toluenesulfonyl chloride (22.9 g, 120 mmol) in pyridine (56 mL) portionwise over 5 min. The subsequent pale yellow reaction mixture was stirred at 0° C. for 2 h and then at ambient temperature overnight. Pyridine was removed in vacuo. The crude oil was extracted into ethyl acetate (400 mL) and sequentially washed with 0.5 M HCl (100 mL), saturated aq. NaHCO₃ (100 mL) and brine (100 mL). The combined organic layer was dried over anhydrous Na₂SO₄, filtered and concentrated in vacuo to give the title compound (39 g, >100%) as a yellow oil;

Step 2

(S)-2-(4-Benzyl-phenoxymethyl)-pyrrolidine-1-carboxylic acid tert-butyl ester: To a solution of 4-hydroxydiphenylmethane (0.77 g, 4.18 mmol) in anhydrous DMF (22.5 mL) at 0° C. was added a 60% dispersion of NaH in mineral oil (0.23 g, 5.75 mmol) portionwise over 5 min. The resulting slurry was stirred at 0° C. for 45 minutes before a solution of tosylate from step 1 (1.50 g, 4.22 mmol) in DMF (11 mL) was added dropwise over 5 min. The subsequent mixture was stirred at 60° C. overnight. The reaction mixture was poured over ice and then concentrated under reduced pressure. The crude residue was extracted into ethyl acetate and sequentially washed with water, saturated aq. NaHCO₃, water and brine. The combined organic layer was dried anhydrous Na$_2$SO$_4$, filtered and concentrated in vacuo to afford the title compound (1.8 g, >100%) as a tan oil;

Step 3

(S)-2-(4-Benzylphenoxymethyl)pyrrolidine: To a solution of the product from step 2 (2.9 g, 7.89 mmol) was added 4 M HCl in dioxane (15 mL) at ambient temperature. The resulting mixture was stirred overnight. The solvent was removed under reduced pressure to obtain an off-white solid. The solid was triturated with ether to afford Example 2 (2.0 g, 74%) as a white solid; MS; m/z 268 (M+H): $^1$H NMR (400 MHz, DMSO-d$_6$); δ 1.73 (m, 1H), 1.89 (m, 1H), 1.98 (m, 1H), 2.09 (m, 1H), 3.18 (m, 2H), 3.87 (m, 1H), 3.88 (s, 2H), 4.13 (dd, 1H, J1=7.2 Hz, J2=6.4 Hz), 4.19 (dd, 1H, J1=8.8, J2=3.2 Hz), 6.91 (d, 2H, J=6.8 Hz), 7.15-7.20 (m, 5H), 7.27 (m, 2H).

EXAMPLE 3

Step 1

4-[(S)-2-(4-benzyl-phenoxymethyl)-pyrrolidin-1-yl]-butyric acid methyl ester: To a solution of Example 2 (1.5 g, 4.94 mmol) in DMF (23 mL) was added potassium carbonate (1.4 g, 10.1 mmol) and methyl 4-bromobutyrate (0.72 mL, 6.26 mmol). The resulting slurry was stirred at ambient temperature overnight. The solvent was concentrated under reduced pressure and the crude product was taken up in ethyl acetate. The organic portion was washed with water, washed with brine, dried over Na$_2$SO$_4$, filtered and concentrated in vacuo. The crude product was purified by silica gel flash chromatography using hexane/EtOAc (gradient system) to give the title compound (0.73 g, 40%) as a yellow oil.

Step 2

4-[(S)-2-(4-benzyl-phenoxymethyl)-pyrrolidin-1-yl]-butylic acid To a solution of the product from step 1 (0.13 g, 0.35 mmol) was added 2N NaOH (0.29 mL, 0.58 mmol) and 80% MeOH/H$_2$O (4 mL). The resulting slurry was stirred at 50° C. for 67 h. The solvent was removed under reduced pressure and water was added to the residue. The pH was adjusted to 4 using 1 N HCl solution. The crude product was extracted with ethyl acetate. The combined organic layers were washed with water, washed with brine, dried over anhydrous Na$_2$SO$_4$ and concentrated in vacuo to afford the title compound (0.09 g, 77%) as a yellow semi-solid. $^1$H NMR (400 MHz, CDCl$_3$); δ 1.96-2.26 (m, 6H), 2.41 (t, J=6.6 Hz, 2H), 3.02 (m, 2H), 3.47 (m, 1H), 3.67 (m, 2H), 3.89 (s, 2H), 3.85 (dd, J1=4.0 Hz, J2=10.8 Hz, 1H), 4.50 (m, 1H), 6.84 (d, J=8.8 Hz, 2H), 7.09-7.19 (m, 5H), 7.25-7.28 (m, 2H); MS (m/z) 352.4 (M−1); LC (97.6%); HPLC (96.6%).

EXAMPLE 4

2-[(R)-2-(4-benzyl-phenoxymethyl)-pyrrolidin-1-ylmethyl]-pyridine: To a solution of Example 1 (0.20 g, 0.66 mmol) in DMF (5 mL) was added 2-picolyl chloride hydrochloride (0.10 g, 0.61 mmol) and triethylamine (0.24 mL, 1.72 mmol). The subsequent mixture was stirred at ambient temperature overnight. The reaction mixture was concentrated under reduced pressure. The crude residue was extracted into ethyl acetate (25 mL) and washed with water (25 mL) followed by brine (25 mL). The combined organic layers were dried over anhydrous Na$_2$SO$_4$, filtered and concentrated in vacuo. The crude product was purified by flash chromatography using hexane/EtOAc (gradient system) to give the title compound (0.07 g, 36%); $^1$H NMR (400 MHz, CDCl$_3$); δ 1.73-1.80 (m, 3H), 2.05 (m, 1H), 2.40 (m, 1H), 3.02-3.08 (m, 2H), 3.71 (d, J=13.6 Hz, 1H), 3.83 (m, 1H), 3.91 (s, 2H), 3.95 (m, 1H), 4.25 (d, J=13.6 Hz, 1H), 6.79 (d, J=8.8 Hz, 2H), 7.07 (d, J=8.8 Hz, 2H), 7.15-7.20 (m, 4H), 7.25-7.27 (m, 2H), 7.41 (m, 1H), 7.61 (m, 1H), 8.53 (m, 1H); MS (m/z) 359.2 (M+1); LC (100.0%).

EXAMPLE 5

3-[(R)-2-(4-benzyl-phenoxymethyl)-pyrrolidin-1-ylmethyl]-pyridine: Following the general procedure for Example 4, Example 1 (0.20 g, 0.66 mmol) in DMF (5 mL) was treated with 3-picolyl chloride hydrochloride (0.10 g, 0.61 mmol) and triethylamine (0.24 mL, 1.72 mmol) to afford the title compound (0.09 g, 46%); $^1$H NMR (400 MHz, CDCl$_3$); δ 1.71-1.78 (m, 3H), 2.04 (m, 1H), 2.29 (m, 1H), 2.94-3.03 (m, 2H), 3.51 (d, J=13.6 Hz, 1H), 3.86 (m, 1H), 3.92 (s, 2H), 3.95 (m, 1H), 4.18 (d, J=13.2 Hz, 1H), 6.81 (d, J=8.8 Hz, 2H), 7.09 (d, J=8.4 Hz, 2H), 7.16-7.30 (m, 5H), 7.67 (m, 2H), 8.48 (br s, 1H), 8.56 (br s, 1H); MS (m/z) 359.2 (M+1); LC (100.0%).

EXAMPLE 6

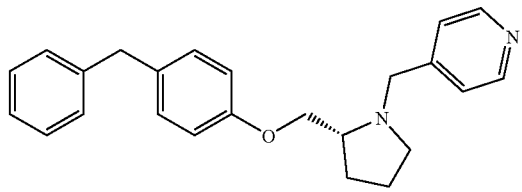

4-[(R)-2-(4-benzyl-phenoxymethyl)-pyrrolidin-1-ylmethyl]-pyridine: To a solution of Example 1 (0.25 g, 0.82 mmol) in dichloromethane (2 mL) was added 4-picolyl chloride hydrochloride (0.13 g, 0.79 mmol) and triethylamine (0.29 mL, 2.08 mmol). The resulting mixture was stirred at ambient temperature overnight. The crude product was extracted into dichloromethane and washed with water followed by brine. The combined organic layers were dried over anhydrous $Na_2SO_4$, filtered and concentrated in vacuo. The crude product was purified by flash chromatography using hexane/EtOAc (gradient system) to give the title compound (0.11 g, 45%); $^1$NMR (400 MHz, $CDCl_3$); δ 1.70-1.81 (m, 3H), 2.03 (m, 1H), 2.27 (m, 1H), 2.94-3.03 (m, 2H), 3.49 (d, J=14.4 Hz, 1H), 3.86 (m, 1H), 3.92 (s, 2H), 3.94 (m, 1H), 4.19 (d, J=14.4 Hz, 1H), 6.79 (d, J=8.8 Hz, 2H), 7.08 (d, J=8.8 Hz, 2H), 7.15-7.20 (m, 3H), 7.26-7.29 (m, 4H), 8.51 (m, 2H); MS (m/z) 359.5 (M+1); LC (99.7%); HPLC (91.6%)

EXAMPLE 7

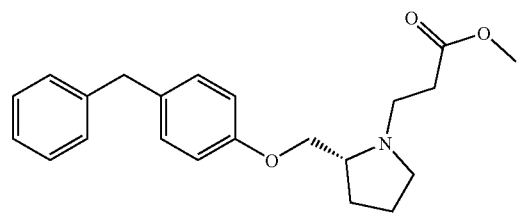

3-[(R)-2-(4-benzyl-phenoxymethyl)-pyrrolidin-1-yl]-propionic acid methyl ester: To a solution of Example 1 (0.2 g, 0.66 mmol) in DMF (5 mL) was added triethylamine (0.16 mL, 1.14 mmol) and methyl 3-bromopropionate (0.07 mL, 0.64 mmol). The resulting slurry was stirred at ambient temperature overnight. The solvent was removed under reduced pressure and the crude residue was extracted into ethyl acetate. The organic portion was washed with water, washed with brine, dried over anhydrous $Na_2SO_4$, filtered and concentrated in vacuo. The crude product was purified by silica gel flash chromatography using hexane/EtOAc (gradient system) to give the title compound (0.03 g, 13%); $^1$H NMR (400 MHz, $CDCl_3$); δ 1.68-1.80 (m, 3H), 1.93-2.04 (m, 1H), 2.29 (q, J=8.4 Hz, 1H), 2.53 (t, J=7.2 Hz, 2H), 2.70 (m, 1H), 2.87 (m, 1H), 3.13 (m, 1H), 3.24 (m, 1H), 3.66 (s, 3H), 3.75 (m, 1H), 3.92 (s, 2H), 3.93 (m, 1H), 6.82 (d, J=8.8 Hz, 2H), 7.08 (d, J=8.8 Hz, 2H), 7.16-7.20 (m, 3H), 7.27 (m, 2H); MS (m/z) 354.2 (M+1); LC (100.0%).

EXAMPLE 8

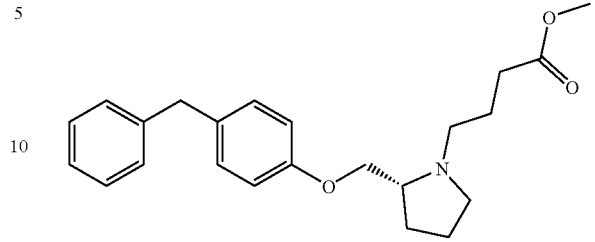

4-[(R)-2-(4-benzyl-phenoxymethyl)-pyrrolidin-1-yl]-butylic acid methyl ester: To a solution of Example 1 (0.5 g, 1.65 mmol) in dichloromethane (4.8 mL) was added triethylamine (0.46 mL, 3.30 mmol) and methyl 4-bromobutyrate (0.24 mL, 1.90 mmol). The resulting solution was stirred at ambient temperature for 16 hours. Water (25 mL) and dichloromethane (25 mL) were added to the reaction mixture and the crude residue was extracted into dichloromethane. The organic portion was washed with water (25 mL), washed with brine (25 mL), dried over anhydrous $Na_2SO_4$, filtered and concentrated in vacuo. The crude product was purified by silica gel flash chromatography using hexane/EtOAc (gradient system) to give the title compound (0.15 g, 24%); $^1$H NMR (400 MHz, $CDCl_3$); δ 1.66-1.86 (m, 5H), 1.96 (m, 1H), 2.20-2.45 (m, 4H), 2.86 (m, 2H), 3.14 (m, 1H), 3.63 (s, 3H), 3.74 (m, 1H), 3.89 (m, 1H), 3.92 (s, 2H), 6.82 (d, J=8.4 Hz, 2H), 7.08 (d, J=8.0 Hz, 2H), 7.16-7.20 (m, 3H), 7.27 (m, 2H); MS (m/z) 368.4 (M+1); LC (90.6%).

EXAMPLE 9

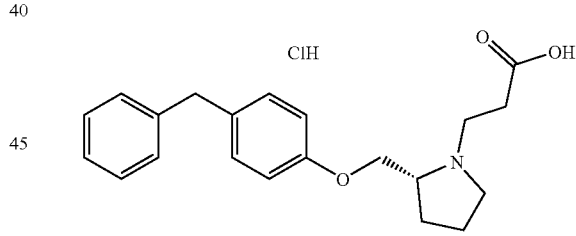

3-[(R)-2-(4-benzyl-phenoxymethyl)-pyrrolidin-1-yl]-propionic acid hydrochloride: To a solution of Example 7 (0.02 g, 0.05 mmol) was added 2N NaOH (0.04 mL, 0.08 mmol) and 80% MeOH/$H_2O$ (0.5 mL). The resulting slurry was stirred at 50° C. for 24 h. The solvent was removed under reduced pressure and water was added to the residue. The pH was adjusted to 4 using 1 N HCl solution. The crude product was extracted with ethyl acetate. The combined organic layers were washed with water, washed with brine, dried over anhydrous $Na_2SO_4$ and concentrated in vacuo to afford the title compound (12 mg, 67%); $^1$H NMR (400 MHz, $CDCl_3$); δ 1.41-1.63 (m, 2H), 1.92-2.22 (m, 2H), 2.75 (m, 3H), 3.02 (m, 1H), 3.50 (m, 3H), 3.90 (s, 2H), 4.09 (dd, J1=4.0 Hz, J2=10.4 Hz, 1H), 4.25 (m, 1H), 6.82 (d, J=8.4 Hz, 2H), 7.08-7.20 (m, 5H), 7.25-7.29 (m, 2H); MS (m/z) 340.7 (M+1); LC (100.0%).

EXAMPLE 10

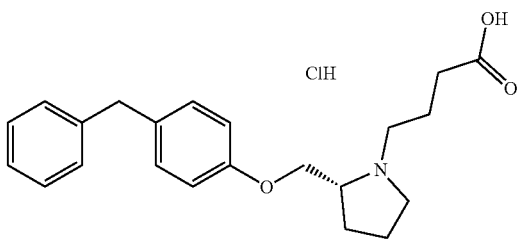

4-[(R)-2-(4-benzyl-phenoxymethyl)-pyrrolidin-1-yl]-butylic acid hydrochloride: Following the general procedure for Example 9, a solution of Example 8 (11 mg, 0.03 mmol) in 80% MeOH/$H_2O$ (0.4 mL) was treated with 2N NaOH (0.03 mL, 0.06 mmol) to afford the title compound (9 mg, 86%) as a yellow oil; $^1$H NMR (400 MHz, $CDCl_3$); δ 1.95-2.28 (m, 6H), 2.49 (m, 2H), 2.94 (m, 2H), 3.42-3.65 (m, 3H), 3.91 (s, 2H), 4.14 (dd, J1=3.6 Hz, J2=10.8 Hz, 1H), 4.42 (m, 1H), 6.83 (d, J=8.8 Hz, 2H), 7.10 (d, J=8.4 Hz, 2H), 7.15-7.20 (m, 3H), 7.27 (m, 2H); MS (m/z) 354.7 (M+1); LC (99.7%).

EXAMPLE 11

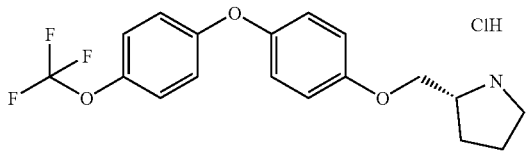

Step 1

To a solution of 4-(trifluoromethoxy)iodobenzene (0.54 mL, 3.45 mmol), 4-methoxyphenol (0.28 g, 2.26 mmol) and cesium carbonate (1.54 g, 4.73 mmol) in dioxane (10 mL) was added N,N-dimethylglycine hydrochloride (0.03 g, 0.22 mmol). The vessel was purged with nitrogen before Cu(I) iodide (0.02 g, 0.08 mmol) was added. The brownish-green reaction mixture was heated to 90° C. overnight. The reaction mixture was diluted with water and ethyl acetate. The organic portion was washed with brine, dried over anhydrous $Na_2SO_4$ and concentrated in vacuo to give the title compound (0.8 g, 100%) as brown oil.

Step 2

4-(4-trifluoromethoxy-phenoxy)-phenol: To a solution of the product from step 1 (0.5 g, 1.76 mmol) in dichloromethane (10 mL) at −78° C. was added boron tribromide (1.0 M solution in dichloromethane, 5.28 mL, 5.28 mmol) dropwise over 5 min. The subsequent mixture was stirred at −78° C. for 30 min followed by ambient temperature for 90 min. After cooling the reaction mixture to 0° C., it was slowly added to cold water/dichloromethane (50 mL/50 mL). The organic portion was washed with water, brine, dried over anhydrous $Na_2SO_4$ and concentrated in vacuo. The crude product was purified by silica gel flash chromatography using hexane/EtOAc (gradient system) to give the title compound (0.35 g, 74%) as a dark oil.

Step 3

(R)-2-[4-(4-trifluoromethoxy-phenoxy)-phenoxymethyl]-pyrrolidine-1-carboxylic acid tert-butyl ester: To a solution of the product from step 2 (0.2 g, 0.74 mmol) in anhydrous DMF (6 mL) at 0° C. was added a 60% dispersion of NaH in mineral oil (0.04 mg, 0.98 mmol) portionwise over 5 min. After the resulting slurry was stirred at 0° C. for 45 minutes, warmed to ambient temperature and then heated to 35° C. for 15 minutes, a solution of the tosyl intermediate (0.33 g, 0.93 mmol) in DMF (4 mL) was added dropwise over 5 min. The subsequent mixture was stirred at 75° C. overnight. The reaction mixture was poured over ice and then concentrated under reduced pressure. The crude residue was extracted into ethyl acetate and washed with water and brine. The combined organic portions were dried over anhydrous $Na_2SO_4$ and concentrated in vacuo. The crude product was purified by flash chromatography using hexane/EtOAc (gradient system) to afford the title compound (0.24 g, 70%) as a yellow oil.

Step 4

(R)-2-[4-(4-Trifluoromethoxy-phenoxy)-phenoxymethyl]-pyrrolidine hydrochloride: To the product from step 3 (0.23 g, 0.51 mmol) was added 4 M HCl in dioxane (5 mL). The resulting mixture was stirred at ambient temperature overnight. The solvent was removed in vacuo. The crude product was triturated with ether and dried under reduced pressure to afford the title product (0.12 g, 61%) as a light green oil; $^1$H NMR (400 MHz, DMSO-$d_6$) δ 1.74 (m, 1H), 1.94 (m, 2H), 2.12 (m, 1H), 3.22 (m, 2H), 3.89 (m, 1H), 4.15 (m, 1H), 4.25 (dd, J1=3.8 Hz, J2=10.8 Hz, 1H), 7.00-7.10 (m, 6H), 7.36 (d, J=8.4 Hz, 2H), 9.32 (br s, 1H); MS (m/z) 354.5 (M+1); LC (98.4%); HPLC (99.7%).

EXAMPLE 12

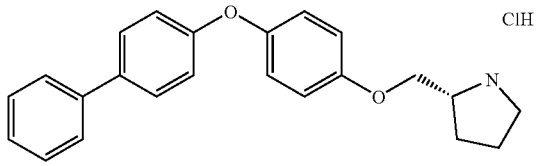

Step 1

4-(4-Methoxy-phenoxy)-biphenyl: To a solution of 4-bromo-biphenyl (1.00 g, 4.29 mmol), 4-methoxyphenol (0.35 g, 2.82 mmol) and cesium carbonate (1.85 g, 5.68 mmol) in dioxane (10 mL) was added N,N-dimethylglycine hydrochloride (0.04 g, 0.26 mmol). The vessel was purged with nitrogen before Cu(I) iodide (0.02 g, 0.11 mmol) was added. The reaction mixture was heated to 90° C. overnight. The reaction mixture was diluted with water and ethyl acetate. The organic portion was washed with brine, dried over anhydrous $Na_2SO_4$ and concentrated in vacuo to give the title compound (1.00 g, 100%) as a light green solid.

Step 2

4-(biphenyl-4-yloxy)-phenol: To a solution of the product from step 1 (0.5 g, 1.81 mmol) in dichloromethane (10 mL) at −78° C. was added boron tribromide (1.0 M solution in dichloromethane, 5.43 mL, 5.43 mmol) dropwise over 5-10 min. The subsequent mixture was stirred at −78° C. for an hour followed by ambient temperature for 1 h. After cooling the reaction mixture to 0° C., it was slowly added to cold water/dichloromethane (50 mL/50 mL). The organic portion was washed with water, brine, dried over anhydrous $Na_2SO_4$ and concentrated in vacuo. The crude product was purified by silica gel flash chromatography using hexane/EtOAc (gradient system) to give the title compound (0.24 g, 47%) as an off-white solid.

Step 3

(R)-2-[4-(biphenyl-4-yloxy)-phenoxymethyl]-pyrrolidine-1-carboxylic acid tert-butyl ester: To a solution of the product from step 2 (0.24 g, 0.91 mmol) in anhydrous DMF (4 mL) at 0° C. was added a 60% dispersion of NaH in mineral oil (0.05 g, 1.20 mmol) portionwise over 5 min. After the resulting slurry was stirred at 0° C. for 45 minutes, warmed to ambient temperature and then heated to 35° C. for 15 minutes, a solution of the tosyl intermediate (0.4 g, 1.13 mmol) in DMF (2 mL) was added dropwise over 5 min. The subsequent mixture was stirred at 75° C. for 60 h. The reaction mixture was poured over ice and then concentrated under reduced pressure. The crude residue was extracted into ethyl acetate and washed with water and brine. The combined organic portions were dried over anhydrous $Na_2SO_4$ and concentrated in vacuo. The crude product was purified by flash chromatography using hexane/EtOAc (gradient system) to afford the title compound (0.40 g, 98%) as a yellow oil.

Step 4

(R)-2-[4-(Biphenyl-4-yloxy)-phenoxymethyl]-pyrrolidine hydrochloride: Following the general procedure for Example 11 (step 4), the product from step 3 (0.2 g, 0.45 mmol) was treated with 4M HCl in dioxane (5 mL) to afford the title product (0.11 g, 62%) as a white solid; $^1$H NMR (400 MHz, DMSO-$d_6$) 1.75 (m, 1H), 1.88-2.02 (m, 2H), 2.12 (m 1H), 3.23 (m, 2H), 3.91 (m, 1H), 4.14 (m 1H), 4.26 (dd, J1=3.8 Hz, J2=10.4 Hz, 1H), 7.00 (d, J=8.8 Hz, 2H), 7.04-7.11 (m, 4H), 7.34 (m, 1H), 7.45 (m, 2H), 7.61-7.66 (m, 4H); MS (m/z) 346.7 (M+1); LC (98.9%); Elemental Analysis (Calc): C, 72.34; H, 6.33; N, 3.67. (Found): C, 71.72; H, 6.29; N, 3.66.

EXAMPLE 13

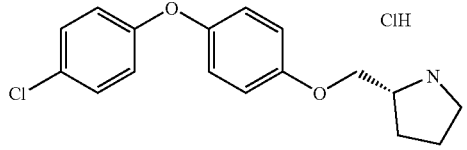

Step 1

1-Methoxy-4-(4-chlorophenoxy)benzene Following the general procedure for Example 12 (step 1), N,N-dimethylglycine hydrochloride (0.04 g, 0.26 mmol), cesium carbonate (1.85 g, 5.68 mmol), and Cu(I) iodide (0.02 g, 0.11 mmol) were added to a solution of 4-bromochlorobenzene (0.82 g, 4.28 mmol) and 4-methoxyphenol (0.35 g, 2.82 mmol) in dioxane (10 mL) to afford the title compound (0.76 g, 100%) as a brown oil.

Step 2

4-(4-chloro-phenoxy)-phenol: Following the general procedure for Example 12 (step 2), boron tribromide (1.0 M solution in dichloromethane, 9.66 mL, 9.66 mmol) was added to the product from step 1 (0.76 g, 3.22 mmol) in dichloromethane (15 mL) to afford the title compound (0.37 g, 52%) as a light-green solid.

Step 3

(R)-2-[4-(4-chloro-phenoxy)-phenoxymethyl]-pyrrolidine-1-carboxylic acid tert-butyl ester: To a solution of the product from step 2 (0.25 g, 1.13 mmol) in anhydrous DMF (6 mL) at 0° C. was added a 60% dispersion of NaH in mineral oil (0.06 g, 1.50 mmol) portionwise over 5 min. After the resulting slurry was stirred at 0° C. for 45 minutes, warmed to ambient temperature and then heated to 35° C. for 15 minutes, a solution of the tosyl intermediate (0.49 g, 1.38 mmol) in DMF (4 mL) was added dropwise over 5 min. The subsequent mixture was stirred at 75° C. for 16 h. The reaction mixture was poured over ice and then concentrated under reduced pressure. The crude residue was extracted into ethyl acetate and washed with water and brine. The combined organic portions were dried over anhydrous $Na_2SO_4$ and concentrated in vacuo. The crude product was purified by flash chromatography using hexane/EtOAc (gradient system) to afford the title compound (0.37 g, 81%) as a yellow oil.

Step 4

(R)-2-[4-(4-Chloro-phenoxy)-phenoxymethyl]-pyrrolidine hydrochloride: To the product from step 3 (0.36 g, 0.89 mmol) was added 4 M HCl in dioxane (5 mL). The resulting mixture was stirred at ambient temperature for 2 h. The solvent was removed in vacuo. The crude product was triturated with ether and dried under reduced pressure to afford the title compound (0.19 g, 70%) as a light yellow solid; $^1$H NMR (400 MHz, DMSO-$d_6$) 1.75 (m, 1H), 1.87-2.01 (m, 2H), 2.12 (m, 1H), 3.21 (m, 2H), 3.89 (m, 1H), 4.17 (m, 1H), 4.24 (dd, J1=4.0 Hz, J2=10.8 Hz, 1H), 6.94 (d, J=9.2 Hz, 2H), 7.05 (s, 4H), 7.40 (d, J=8.8 Hz, 2H); MS (m/z) 304.2 (M+1); LC (97.1%);

HPLC (99.1%); Elemental Analysis (Calc): C, 60.01; H, 5.63; N, 4.12. (Found): C, 59.81, H, 5.63, N, 4.11.

EXAMPLE 14

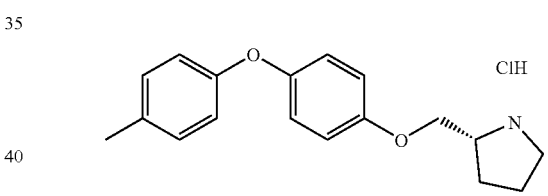

Step 1

1-Methoxy-4-(4-methylphenoxy)benzene Following the general procedure for Example 11 (step 1), N,N-dimethylglycine hydrochloride (0.03 g, 0.22 mmol), cesium carbonate (1.59 g, 4.88 mmol) and Cu(I) iodide (0.02 g, 0.09 mmol) were added to a solution of 4-iodotoluene (0.8 g, 3.67 mmol) and 4-methoxyphenol (0.3 g, 2.42 mmol) in dioxane (10 mL) to afford the title compound (0.92 g, 100%) as a brown oil.

Step 2

4-p-tolyloxy-phenol: Following the general procedure for Example 12 (step 2), boron tribromide (1.0 M solution in dichloromethane, 7.75 mL, 7.75 mmol) was added to the product from step 1 (0.75 g, 3.50 mmol) in dichloromethane (10 mL) to afford the title compound was obtained (0.26 g, 36%) as a yellow solid.

Step 3

(R)-2-(4-p-tolyloxy-phenoxymethyl)-pyrrolidine-1-carboxylic acid tert-butyl ester: To a solution of the product from step 2 (0.25 g, 1.25 mmol) in anhydrous DMF (6 mL) at 0° C. was added a 60% dispersion of NaH in mineral oil (0.06 g, 1.43 mmol) portionwise over 5 min. After the resulting slurry was stirred at 0° C. for 45 minutes, warmed to ambient temperature and then heated to 35° C. for 15 minutes, a solution of the tosyl intermediate (0.47 g, 1.32 mmol) in DMF (4 mL) was added dropwise over 5 min. The subsequent mixture was stirred at 75° C. for 16 h. The reaction mixture was poured over ice and then concentrated under reduced pressure. The crude residue was extracted into ethyl acetate and washed with water and brine. The combined organic portions were dried over anhydrous $Na_2SO_4$ and concentrated in vacuo. The crude product was purified by flash chromatography using hexane/EtOAc (gradient system) to afford the title compound (0.42 g, 88%) as a yellow solid.

Step 4

(R)-2-(4-p-Tolyloxy-phenoxymethyl)-pyrrolidine hydrochloride: Following the general procedure for Example 13 (step 4), the product from step 3 (0.39 g, 1.02 mmol) was treated with 4M HCl in dioxane (6 mL) to afford the title compound (0.12 g, 67%) as an off-white solid; $^1$H NMR (400 MHz, DMSO-$d_6$) 1.74 (m, 1H), 1.94 (m, 2H), 2.11 (m, 1H), 2.27 (s, 3H), 3.21 (m, 2H), 3.88 (m, 1H), 4.13 (m, 1H), 4.22 (dd, J1=3.8 Hz, J2=10.8 Hz, 1H), 6.83 (d, J=8.4 Hz, 2H), 6.98 (m, 4H), 7.16 (d, J=8.4 Hz, 2H), 9.11 (br s, 1H), 9.67 (br s, 1H); MS (m/z) 284.4 (M+1); LC (98.8%); HPLC (99.3%).

EXAMPLE 15

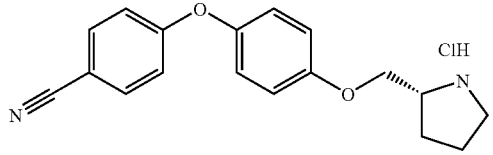

Step 1

4-(4-Methoxy-phenoxy)-benzonitrile: To a solution of 4-iodobenzonitrile (0.458 g, 2 mmol), 4-methoxyphenol (0.372 g, 3 mmol) and cesium carbonate (1.30 g, 4 mmol) in dioxane (4 mL) was added N,N-dimethylglycine hydrochloride (0.025 g, 0.18 mmol). The vessel was purged with nitrogen before Cu(I) iodide (0.014 g, 0.07 mmol) was added. The reaction mixture was heated to 90° C. overnight. The reaction mixture was diluted with water and ethyl acetate. The organic portion was washed with brine, dried over anhydrous $Na_2SO_4$ and concentrated in vacuo to give the title compound (0.51 g, 100%); $^1$H NMR (400 MHz, CDCl$_3$); δ 3.83 (s, 3H), 6.92-7.02 (m, 6H), 7.56-7.58 (m, 2H).

Step 2

4-(4-Hydroxy-phenoxy)-benzonitrile: Following the general procedure for Example 11 (step 2), boron tribromide (1.0 M solution in dichloromethane, 5.73 mL, 5.73 mmol) was added to the product from step 1 (0.43 g, 1.91 mmol) in dichloromethane (10 mL) to afford the title compound (0.30 g, 74%) as an off-white solid.

Step 3

2-[4-(4-Cyano-phenoxy)-phenoxymethyl]-pyrrolidine-1-carboxylic acid tert-butyl ester: Following the general procedure for Example 12 (step 3), a 60% dispersion of NaH in mineral oil (0.05 g, 1.25 mmol) and the tosyl intermediate (0.41 g, 1.15 mmol) were added to a solution of the product from step 2 (0.2 g, 0.95 mmol) in anhydrous DMF (10 mL) to afford the title compound (0.30 g, 81%) as a yellow oil.

Step 4

4-[4-((R)-1-Pyrrolidin-2-ylmethoxy)-phenoxy]-benzonitrile hydrochloride: Following the general procedure for Example 11 (step 4), the product from step 3 (0.3 g, 0.76 mmol) was treated with 4M HCl in dioxane (5 mL) to afford the title compound (0.21 g, 85%) as a white solid; $^1$H NMR (400 MHz, DMSO-$d_6$) 1.75 (m, 1H), 1.88-2.02 (m, 2H), 2.12 (m, 1H), 3.22 (m, 2H), 3.90 (m, 1H), 4.17 (m, 1H), 4.27 (dd, J1=3.8 Hz, J2=10.8 Hz, 1H), 7.03 (d, J=9.2 Hz, 2H), 7.09 (m, 2H), 7.15 (m, 2H), 7.82 (d, J=8.8 Hz, 2H), 9.10 (br s, 1H), 9.65 (br s, 1H); MS (m/z) 295.5 (M+1); LC (95.1%),

EXAMPLE 16

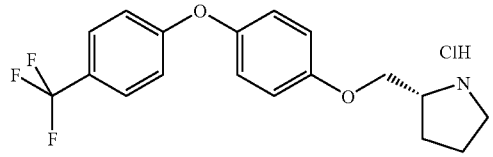

Step 1

(R)-2-[4-(4-Trifluoromethyl-phenoxy)-phenoxymethyl]-pyrrolidine-1-carboxylic acid tert-butyl ester: Following the general procedure for Example 12 (step 3), a 60% dispersion of NaH in mineral oil (0.06 g, 1.58 mmol) and the tosyl intermediate (0.51 g, 1.43 mmol) were added to a solution of 4-[(4-trifluoromethyl)phenoxy]phenol (0.3 g, 1.18 mmol) in anhydrous DMF (10 mL) to afford the title compound (0.41 g, 79%) as a yellow oil; MS, m/z 437 (M+1).

Step 2

(R)-2-[4-(4-Trifluoromethyl-phenoxy)-phenoxymethyl]-pyrrolidine hydrochloride: Following the general procedure for Example 11 (step 4), the product from step 1 (0.41 g, 0.94 mmol) was treated with 4M HCl in dioxane (5 mL) to afford the title compound (0.22 g, 70%); $^1$H NMR (400 MHz, DMSO-$d_6$) δ 1.76 (m, 1H), 1.95 (m, 2H), 2.13 (m, 1H), 3.23 (m, 2H), 3.90 (m, 1H), 4.17 (m, 1H), 4.26 (dd, J1=3.6 Hz, J2=10.4 Hz, 1H), 7.05-7.16 (m, 6H), 7.72 (d, J=8.4 Hz, 2H); MS (m/z) 338.5 (M+1); LC (99.1%); HPLC (99.4%).

EXAMPLE 17

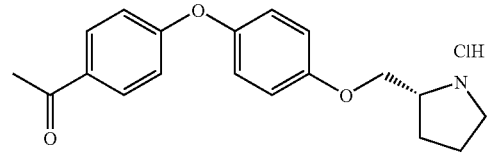

Step 1

1-[4-(4-Hydroxy-phenoxy)-phenyl]-ethanone: To a solution of 4-acetyl-4-methoxydiphenyl ether (0.5 g, 2.1 mmol) in dichloromethane (10 mL) at −78° C. was added boron tribromide (1.0 M solution in dichloromethane, 6.2 mL, 6.2 mmol) dropwise over 5 min. The subsequent mixture was stirred at −78° C. for an hour followed by ambient temperature for an hour. After cooling the reaction mixture to 0° C., it was slowly added to cold water/dichloromethane (50 mL/50 mL). The organic portion was washed with water, brine, dried over anhydrous $Na_2SO_4$ and concentrated in vacuo. The crude product was purified by silica gel flash chromatography using hexane/EtOAc (gradient system) to give the title compound (210 mg, 45%); $^1$H NMR (400 MHz, CDCl$_3$); δ 2.57 (s, 3H), 6.86-6.88 (d, 2H, J=8.0 Hz), 6.93-6.98 (m, 4H), 7.91-7.93 (d, 2H, J=8.0 Hz), Step 2

(R)-2-[4-(4-Acetyl-phenoxy)-phenoxymethyl]-pyrrolidine-1-carboxylic acid tert-butyl ester: To a solution of the product from step 2 (0.11 g, 0.48 mmol) in anhydrous DMF (3 mL) at 0° C. was added a 60% dispersion of NaH in mineral oil (0.03 g, 0.65 mmol) portionwise over 5 min. After the resulting slurry was stirred at 0° C. for 45 minutes, warmed to ambient temperature and stirred for 45 minutes, a solution of the tosyl intermediate (0.21 g, 0.59 mmol) in DMF (2 mL) was added dropwise over 5 min. The subsequent mixture was stirred at 80° C. for 16 h. The reaction mixture was poured over ice and then concentrated under reduced pressure. The crude residue was extracted into ethyl acetate and washed with water and brine. The combined organic portions were dried over anhydrous Na$_2$SO$_4$ and concentrated in vacuo. The crude product was purified by flash chromatography using hexane/EtOAc (gradient system) to afford the title compound (0.13 g, 67%) as a yellow oil.

Step 3

1-{4-[4-((R)-1-Pyrrolidin-2-ylmethoxy)-phenoxy]-phenyl}-ethanone hydrochloride: Following the general procedure for Example 13 (step 4), the product from step 3 (0.13 g, 0.30 mmol) was treated with 4M HCl in dioxane (5 mL) to afford the title compound (0.08 g, 80%) as a tan solid, $^1$H NMR (400 MHz, CD$_3$OD) δ 1.93 (m, 1H), 2.09-2.19 (m, 2H), 2.29 (m, 1H), 2.56 (s, 3H), 3.37 (m, 2H), 4.05 (m, 1H), 4.13 (t, J=18.8 Hz, 1H), 4.35 (d, J=8.8 Hz, 1H), 6.96 (d, J=8.8 Hz, 2H), 7.08 (s, 4H), 7.97 (d, J=8.8 Hz, 2H); MS (m/z) 312.3 (M+1); LC (100.0%); HPLC (98.9%).

EXAMPLE 18

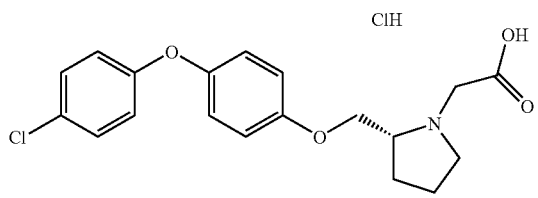

Step 1

1-Methoxy-4-(4-chlorophenoxy)benzene To a solution of 1-chloro-4-iodobenzene (15 g, 62.9 mmol), 4-methoxyphenol (11.7 g, 94 mmol) and cesium carbonate (40.8 g, 126 mmol) in dioxane (125 mL) was added N,N-dimethylglycine hydrochloride (0.790 g, 5.661 mmol). The vessel was purged with nitrogen before Cu(I) iodide (0.431 g, 2.3 mmol) was added. The reaction mixture was heated to 90° C. overnight. The reaction mixture was diluted with water and ethyl acetate. The organic portion was washed with brine, dried over anhydrous Na$_2$SO$_4$ and concentrated in vacuo to give the title compound (14.76 g, 100%); $^1$H NMR (400 MHz, CDCl$_3$); δ 3.81 (s, 3H), 6.77-6.78 (m, 2H), 6.87-6.90 (m, 2H), 6.95-6.97 (m, 2H), 7.23-7.26 (m, 2H).

Step 2

4-(4-Chloro-phenoxy)-phenol: To a solution of the product from step 1 (2.86 g, 12.18 mmol) in dichloromethane (50 mL) at −78° C. was added boron tribromide (1.0 M solution in dichloromethane, 30 mL, 30.5 mmol) dropwise over 5 min. The subsequent mixture was stirred at −78° C. for an hour followed by ambient temperature for an hour. After cooling the reaction mixture to 0° C., it was slowly added to cold water/dichloromethane (50 mL/50 mL). The organic portion was washed with water, brine, dried over anhydrous Na$_2$SO$_4$ and concentrated in vacuo. The crude product was purified by silica gel flash chromatography using hexane/EtOAc (gradient system) to give the title compound (2 g, 75%); $^1$H NMR (400 MHz, CDCl$_3$); δ 4.8 (s, 1H), 7.23-7.26 (m, 2H), 6.81-6.92 (m, 6H).

Step 3

(R)-2-[4-(4-chloro-phenoxy)-phenoxymethyl]-pyrrolidine-1-carboxylic acid tert-butyl ester: Following the general procedure for Example 12 (step 3), a 60% dispersion of NaH in mineral oil (0.48 g, 12.0 mmol) and the tosyl intermediate (3.90 g, 11.0 mmol) were added to a solution of 4-(4-Chloro-phenoxy)-phenol (2.00 g, 9.06 mmol) in anhydrous DMF (38 mL) to afford the title compound (3.6 g, 98%) as a white solid.

Step 4

(R)-2-[4-(4-Chloro-phenoxy)-phenoxymethyl]-pyrrolidine: Following the general procedure for Example 11 (step 4), the product from step 3 (3.60 g, 8.91 mmol) was treated with 4M HCl in dioxane (6 mL) to afford the title compound (2.56 g, 84%) as a white solid.

Step 5

{(R)-2-[4-(4-Chloro-phenoxy)-phenoxymethyl]-pyrrolidin-1-yl}-acetic acid tert-butyl ester: To a solution of the product from step 4 (0.8 g, 2.63 mmol) in dichloromethane (7.6 mL) was added triethylamine (0.78 mL, 5.60 mmol) and t-butyl bromoacetate (0.45 mL, 3.05 mmol). The resulting solution was stirred at 30° C. overnight. The reaction mixture was poured into water/dichloromethane (50 mL/50 mL). The crude residue was extracted into dichloromethane. The organic portion was washed with water (50 mL), washed with brine (50 mL), dried over anhydrous Na$_2$SO$_4$, filtered and concentrated in vacuo. The crude product was purified by silica gel flash chromatography using hexane/EtOAc (gradient system) to give the title compound (0.83 g, 75%);

Step 6

{(R)-2-[4-(4-Chloro-phenoxy)-phenoxymethyl]-pyrrolidin-1-yl}-acetic acid hydrochloride: To the product from step 5 (0.60 g, 1.42 mmol) was added a 1:1 mixture of concentrated HCl/dioxane (28 mL). The resulting solution was stirred at 60° C. for 4 h. The solvent was removed in vacuo. The crude product was triturated with ether and dried under reduced pressure to afford the title compound (0.49 g, 52%) as a white solid.

$^1$H NMR (400 MHz, DMSO-d$_6$); δ 1.83 (m, 1H), 2.03 (m, 2H), 2.24 (m, 1H), 3.30 (m, 1H), 3.70 (m, 1H), 4.02 (m, 1H), 4.20-4.39 (m, 4H), 6.94 (d, J=9.2 Hz, 2H), 7.02-7.07 (m, 4H), 7.40 (d, J=9.2 Hz, 2H); MS (m/z) 360.4 (M−1); LC (98.8%).

EXAMPLE 19

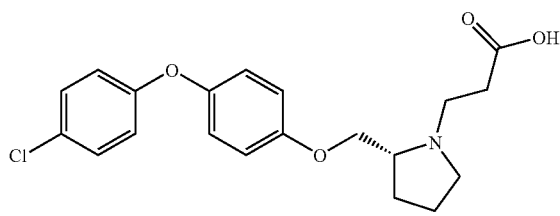

Step 1

3-{(R)-2-[4-(4-Chloro-phenoxy)-phenoxymethyl]-pyrrolidin-1-yl}-propionic acid methyl ester: To a solution of Example 18 (step 4) (0.8 g, 2.63 mmol) in dichloromethane (7.6 mL) was added triethylamine (0.78 mL, 5.60 mmol) and methyl 3-bromopropionate (0.32 mL, 2.93 mmol). The resulting solution was stirred at 30° C. overnight. The reaction mixture was poured into water/dichloromethane (50 mL/50 mL). The crude residue was extracted into dichloromethane. The organic portion was washed with water (50 mL), washed with brine (50 mL), dried over anhydrous Na$_2$SO$_4$, filtered and concentrated in vacuo. The crude product was purified by silica gel flash chromatography using hexane/EtOAc (gradient system) to give the title compound (0.79 g, 77%).

Step 2

3-{(R)-2-[4-(4-Chloro-phenoxy)-phenoxymethyl]-pyrrolidin-1-yl}-propionic acid hydrochloride: Following the general procedure for Example 18, the product from step 1 (0.62 g, 1.59 mmol) was treated with a 1:1 mixture of concentrated HCl/dioxane (28 mL) to afford the title compound (0.40 g, 68%) as a white solid.

$^1$H NMR (400 MHz, DMSO-d$_6$); δ 1.83 (m, 1H), 2.00 (m, 2H), 2.24 (m, 1H), 2.86 (m, 2H), 3.18 (m, 1H), 3.38 (m, 1H), 3.63 (m, 2H), 3.96 (m, 1H), 4.28-4.37 (m, 2H), 6.94 (d, J=9.2 Hz, 2H), 7.06 (s, 4H), 7.39 (d, J=8.8 Hz, 2H); MS (m/z) 374.5 (M−1); LC (98.0%).

EXAMPLE 20

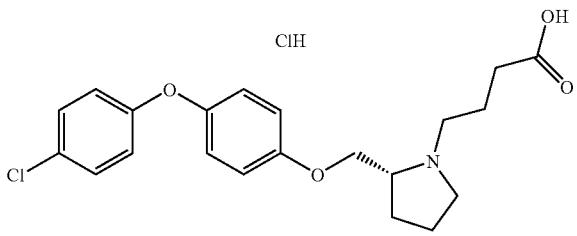

Step 1

4-{(R)-2-[4-(4-Chloro-phenoxy)-phenoxymethyl]-pyrrolidin-1-yl}-butyric acid methyl ester: To a solution of Example 18 (step 4) (0.8 g, 2.63 mmol) in dichloromethane (7.6 mL) was added triethylamine (0.78 mL, 5.60 mmol) and methyl 4-bromobutyrate (0.35 mL, 3.04 mmol). The resulting solution was stirred at 30° C. overnight. The reaction mixture was poured into water/dichloromethane (50 mL/50 mL). The crude residue was extracted into dichloromethane. The organic portion was washed with water (50 mL), washed with brine (50 mL), dried over anhydrous Na$_2$SO$_4$, filtered and concentrated in vacuo. The crude product was purified by silica gel flash chromatography using hexane/EtOAc (gradient system) to give the title compound (0.60 g, 57%).

Step 2

4-{(R)-2-[4-(4-Chloro-phenoxy)-phenoxymethyl]-pyrrolidin-1-yl}-butyric acid hydrochloride: Following the general procedure for Example 18, the product from step 1 (0.80 g 1.99 mmol) was treated with a 1:1 mixture of concentrated HCl dioxane (36 mL) to afford the title compound (0.21 g, 26%) as a white solid.

$^1$H NMR (400 MHz, DMSO-d$_6$); δ 1.82-2.03 (m, 5H), 2.24 (m, 1H), 2.38 (t, J=7.2 Hz, 2H), 3.15 (m, 2H), 3.49 (m, 1H), 3.64 (m, 1H), 3.90 (m, 1H), 4.28-4.34 (m, 2H), 6.94 (d, J=9.2 Hz, 2H), 7.06 (s, 4H), 7.40 (d, J=8.8 Hz, 2H); MS (m/z) 388.5 (M−1); LC (96.2%); HPLC (94.1%).

EXAMPLE 21

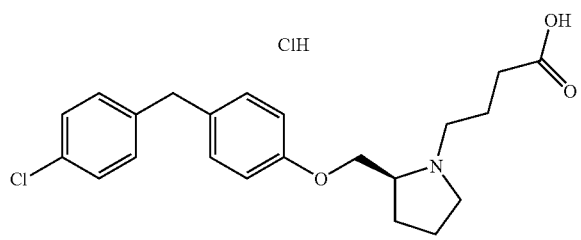

Step 1

(S)-2-[4-(4-Chloro-benzyl)-phenoxymethyl]-pyrrolidine-1-carboxylic acid tert-butyl ester: To a solution of 4-(4-chlorobenzyl)-phenol (2.20 g, 10.1 mmol) in anhydrous DMF (30 mL) at 0° C. was added a 60% dispersion of NaH in mineral oil (0.75 g, 18.8 mmol) portionwise over 10 min. After the resulting slurry was stirred at 0° C. for 45 minutes, warmed to ambient temperature and stirred for 90 minutes, a solution of the tosyl intermediate (3.94 g, 11.1 mmol) in DMF (9.4 mL) was added dropwise over 5 min. The subsequent mixture was stirred at 90° C. overnight. The reaction mixture was poured over ice and then concentrated under reduced pressure. The crude residue was extracted into ethyl acetate and washed with water and brine. The combined organic portions were dried over anhydrous Na$_2$SO$_4$ and concentrated in vacuo. The crude product was purified by flash chromatography using hexane/EtOAc (gradient system) to afford the title compound (3.55 g, 88%).

Step 2

(S)-2-[4-(4-Chloro-benzyl)-phenoxymethyl]-pyrrolidine hydrochloride: To the product from step 1 (3.55 g, 8.83 mmol) was added 4M HCl in dioxane (35 mL). The resulting mixture was stirred at ambient temperature overnight. The solvent was removed in vacuo. The crude product was triturated with ether and dried under reduced pressure to afford the title product (2.00 g, 67%) as a white solid.

Step 3

4-{(S)-2-[4-(4-Chloro-benzyl)-phenoxymethyl]-pyrrolidin-1-yl}-butyric acid methyl ester: To a solution of the product from step 2 (1.50 g, 4.43 mmol) in DMF (20 mL) was added potassium carbonate (1.23 g, 8.90 mmol) and methyl 4-bromobutyrate (0.64 mL, 5.56 mmol). The resulting suspension was stirred at ambient temperature overnight. The reaction mixture diluted with water and ethyl acetate. The crude residue was extracted into ethyl acetate. The organic portion was washed with water, washed with brine, dried over anhydrous Na$_2$SO$_4$, filtered and concentrated in vacuo. The crude product was purified by silica gel flash chromatography using hexane/EtOAc (gradient system) to give the title compound (1.22 g, 69%) as a yellow oil.

Step 4

4-{(S)-2-[4-(4-Chloro-benzyl)-phenoxymethyl]-pyrrolidin-1-yl}-butylic acid hydrochloride: To a solution of the product from step 3 (1.00 g, 2.49 mmol) in MeOH (10 mL) was added 2N NaOH (3.30 mL, 6.60 mmol). The resulting pink solution was stirred at ambient temperature overnight. The solvent was removed in vacuo. The crude oil was dissolved in water (20 mL) and the pH was adjusted to 7 with 2N HCl solution. The crude residue was extracted into ethyl acetate. The combined organic portions were washed with brine, dried over anhydrous Na$_2$SO$_4$, filtered and concentrated in vacuo. The crude product was purified by silica gel flash chromatography using MeOH/dichloromethane (gradient system) to give the free base of the title compound as a yellowish-brown oil. To the subsequent oil was added 2M HCl in diethyl ether (20 mL). The resulting mixture was stirred at ambient temperature for 6 hours. The solvents were decanted. The remaining off-white solid was triturated in diethyl ether (30 mL) overnight. The slurry was filtered, washed with diethyl ether (10 mL×3) and dried in vacuo at 45° C. overnight to afford the title compound as a white solid (0.61 g, 58%). $^1$H NMR (400 MHz, DMSO-d$_6$); δ 1.72-2.02 (m, 5H), 2.22 (m, 1H), 2.37 (m, 2H), 3.13 (m, 2H), 3.46 (m, 1H), 3.61 (m, 1H), 3.85 (m, 1H), 3.88 (s, 2H), 4.27 (m, 2H), 6.92 (d, J=8.4 Hz, 2H), 7.17 (d, J=8.8 Hz, 2H), 7.22 (d, J=8.4 Hz, 2H), 7.33 (d, J=8.8 Hz, 2H), 10.47 (br s, 1H), 12.33 (br s, 1H); MS (m/z) 388.4 (M+1); LC (100.0%); HPLC (99.5%); Elemental Analysis (Calc) C, 62.27; H, 6.41; N, 3.30. (Found) C, 62.46; H, 6.47; N, 3.26.

EXAMPLE 22

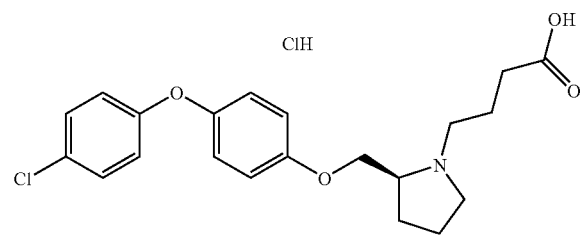

Step 1

(4-Chloro-phenoxy)methoxy benzene: Following the general procedure for Example 11 (step 1), N,N-dimethylglycine hydrochloride (0.51 g, 3.65 mmol), cesium carbonate (26 g, 79.8 mmol) and Cu(I) iodide (0.29 g, 1.52 mmol) were added to a solution of 4-chloroiodobenzene (6.4 g, 26.8 mmol) and 4-methoxyphenol (5.00 g, 40.3 mmol) in dioxane (10 mL) to afford the title compound (8.2 g, 100%) as a brown oil.

Step 2

4-(4-Chloro-phenoxy)-phenol: To a solution of the product from step 1 (6.3 g, 26.8 mmol) in dichloromethane (72 mL) at −78° C. was added boron tribromide (7.6 mL, 80.3 mmol) dropwise over 5 min. The subsequent mixture was stirred at −78° C. for an hour, warmed to ambient temperature and stirred for 1 hour. After cooling the reaction mixture to 0° C., it was slowly added to cold water/dichloromethane. The organic portion was washed with water, brine, dried over anhydrous Na$_2$SO$_4$ and concentrated in vacuo. The crude product was purified by silica gel flash chromatography using EtOAc/hexane (gradient system) to give the title compound (4.50 g, 76%).

Step 3

(S)-2-[4-(4-Chloro-phenoxy)-phenoxymethyl]-pyrrolidine-1-carboxylic acid tert-butyl ester: To a solution of 4-(4-Chloro-phenoxy)phenol (4.00 g, 18.1 mmol) in anhydrous DMF (65 mL) at 0° C. was added a 60% dispersion of NaH in mineral oil (0.96 g, 24.0 mmol) portionwise over 10 min. After the resulting slurry was stirred at 0° C. for 45 minutes, warmed to ambient temperature and stirred for 90 minutes, a solution of the tosyl intermediate (7.20 g, 20.3 mmol) in DMF (11 mL) was added dropwise over 5 min. The subsequent mixture was stirred at 90° C. overnight. The reaction mixture was poured over ice and then concentrated under reduced pressure. The crude residue was extracted into ethyl acetate and washed with water and brine. The combined organic portions were dried over anhydrous Na$_2$SO$_4$ and concentrated in vacuo. The crude product was purified by flash chromatography using hexane/EtOAc (gradient system) to afford the title compound (6.30 g, 86%) as an off-white solid.

Step 4

(S)-2-[4-(4-Chloro-phenoxy)-phenoxymethyl]-pyrrolidine hydrochloride: To the product from step 3 (6.30 g, 15.6 mmol) was added 4 M HCl in dioxane (62 mL). The resulting mixture was stirred at ambient temperature overnight. The solvent was removed in vacuo. The crude product was triturated with ether and dried under reduced pressure to afford the title product (3.47 g, 65%) as an off-white solid.

Step 5

4-{(S)-2-[4-(4-Chloro-phenoxy)-phenoxymethyl]-pyrrolidin-1-yl}-butyric acid methyl ester: To a solution of the product from step 4 (3.47 g, 10.2 mmol) in DMF (46.0 mL) was added potassium carbonate (2.85 g, 20.6 mmol) and methyl 4-bromobutyrate (1.48 mL, 12.9 mmol). The resulting suspension was stirred at ambient temperature overnight. The reaction mixture was diluted with water and ethyl acetate. The crude residue was extracted into ethyl acetate. The organic portion was washed with water, washed with brine, dried over anhydrous Na$_2$SO$_4$, filtered and concentrated in vacuo. The crude product was purified by silica gel flash chromatography using hexane/EtOAc (gradient system) to give the title compound (2.30 g, 63%) as a yellow oil.

Step 6

4-{(S)-2-[4-(4-Chloro-phenoxy)-phenoxymethyl]-pyrrolidin-1-yl}-butyric acid hydrochloride: To a solution of the product from step 5 (2.20 g, 5.45 mmol) in MeOH (22 mL) was added 2N NaOH (7.23 mL, 14.5 mmol). The resulting purplish-pink solution was stirred at ambient temperature overnight. The solvent was removed in vacuo. The crude oil was dissolved in water (45 mL) and the pH was adjusted to 7 with 2N HCl solution. The crude residue was extracted into ethyl acetate. The combined organic portions were washed with brine, dried over anhydrous Na$_2$SO$_4$, filtered and concentrated in vacuo. The crude product was purified by silica gel flash chromatography using MeOH/dichloromethane (gradient system) to give the free base of the title compound as a yellow oil. To the subsequent oil was added 2M HCl in diethyl ether (35 mL). The resulting mixture was stirred at ambient temperature for 2 hours. The solvents were decanted. The remaining white solid was triturated in diethyl ether (50 mL) for 1 hour. The slurry was filtered, washed with diethyl ether (25 mL×3) and dried in vacuo at 45° C. for 48 hours to afford the title compound as a white solid (0.84 g, 36%).

$^1$H NMR (400 MHz, DMSO-d$_6$); δ 1.82-2.03 (m, 5H), 2.23 (m, 1H), 2.38 (t, J=7.2 Hz, 2H), 3.14 (m, 2H), 3.48 (m, 1H), 3.63 (m, 1H), 3.90 (m, 1H), 4.28-4.37 (m, 2H), 6.94 (d, J=8.8 Hz, 2H), 7.06 (s, 4H), 7.40 (d, J=8.8 Hz, 2H), 10.55 (br s, 1H), 12.30 (br s, 1H); HPLC (99.5%); Elemental Analysis (Calc) C, 59.16; H, 5.91; N, 3.29. (Found) C, 59.07, H, 5.88, N, 3.21.

EXAMPLE 23

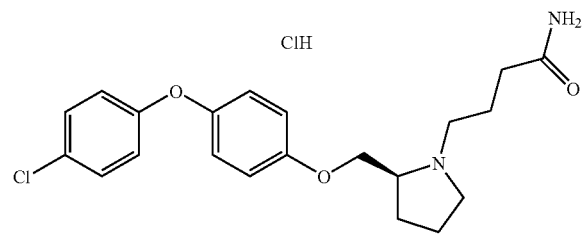

Step 1

4-{(S)-2-[4-(4-Chloro-phenoxy)-phenoxymethyl]-pyrrolidin-1-yl}-butyramide: After stirring at ambient temperature for 60 h, TLC showed starting material plus desired compound. The reaction mixture was poured into a Parr reactor and heated to 100° C. for 16 h. (A large pressure build-up of 95-100 psi was observed). Nitrogen was bubbled through the reaction mixture to remove the ammonia. The solvent was removed in vacuo. The crude residue was purified by silica gel flash chromatography using MeOH/dichloromethane (gradient system) to give the free base of the title compound as a sticky, yellow solid. To this solid was added 2N HCl in ether (14 mL). The resulting mixture was stirred at ambient temperature for 16 h. The solvent was removed under reduced pressure to obtain crude product. The residue was triturated with ether to afford the title compound (0.58 g) as a tan powder; $^1$H NMR (400 MHz, DMSO-d$_6$); 1.78-2.05 (m, 5H), 2.23 (m, 3H), 3.14 (m, 2H), 3.46 (m, 1H), 3.63 (m, 1H), 3.88 (m, 1H), 4.33 (m, 1H), 6.94 (d, J=8.8 Hz, 3H), 7.06 (s, 4H), 7.40 (d, J=8.8 Hz, 2H), 7.45 (br s, 1H) 10.6 (br s, 1H); MS (m/z) 391.4 (M+1); LC (94.3%); HPLC (93.8%).

EXAMPLE 24

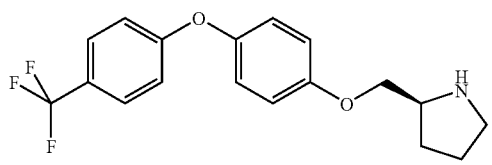

(S)-2-[4-(4-trifluoromethyl-phenoxy)-phenoxymethyl]-pyrrolidine To a solution of 4-(4-trifluoromethyl-phenoxy)-phenol (1.25 g, 5.0 mmol) in DMF (13 mL) was added 60% NaH (5.0 mmol) at 0° C. and the resulting mixture was stirred at rt for one hour. This was followed by addition of (S)-2-(toluene-4-sulfonyloxymethyl)-pyrrolidine-1-carboxylic acid tert-butyl ester (1.78 g, 5.0 mmol) in one portion to above reaction and the reaction was heated at 60° C. for 16 h. The mixture was partitioned between water and diethyl ether. The organic layer was washed with brine, dried over anhy. Na$_2$SO$_4$, and concentrated in vacuo to obtain an oil as (S)—N-Boc-2-[4-(4-trifluoromethyl-phenoxy)-phenoxymethyl]-pyrrolidine, which was dissolved in 20 ml of DCM and treated with trifluoroacetic acid (5 mL) at if for one hour. The reaction was evaporated in vacuo to give a tan oil. Water was added and pH was adjusted to 10 with aqueous saturated Na$_2$CO$_3$ solution. The aqueous phase was extracted with EtOAc and the organic layer was washed with brine, dried over anhy. Na$_2$SO$_4$, and concentrated in vacuo to obtain an oil, which was purified by flash chromatography eluting with 2-5% hexane/EtOAc to afford the title compound (1.45 g, 86%) as a light tan solid: MS; m/z 338 (M+1).

$^1$H NMR (400 HMz, CDCl$_3$) δ 1.56 (m, 1H), 1.81 (m, 2H), 1.95 (m, 1H), 2.92-3.07 (m, 2H), 3.52 (m, 1H), 3.85 (dd, J1=6.8 Hz, J2=8.8 Hz, 1H), 3.92 (dd, J=4.8, 9.2 Hz, 1H), 6.91-6.99 (m, 6H), 7.53 (d, J=8.4 Hz, 2H).

EXAMPLE 25

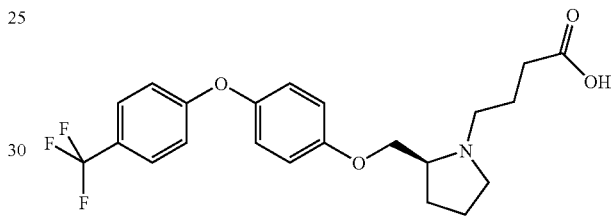

Step 1.

(S)-2-[4-(4-trifluoromethyl-phenoxy)-phenoxymethyl]-pyrrolidine-1-yl} butyric ethyl ester: (S)-2-[4-(4-trifluoromethyl-phenoxy)-phenoxymethyl]-pyrrolidine (340 mg, 1 mmol) was taken into DMF (4 mL), and 4-bromo-butylic acid ethyl ester (195 mg, 1.0 mmol) was added, followed by potassium carbonate (138 mg, 1.0 mmol). The mixture was heated to 60° C. overnight and then diluted with water, and extracted with EtOAc. The combined organic was washed with brine, dried over anhy. Na$_2$SO$_4$, and concentrated in vacuo to dryness. The compound was then purified by flash chromatography, eluting with 1% methanol in dichloromethane. The product (210 mg, 46% yield) was confirmed by LCMS; m/z 452 (M+1).

Step 2:

(S)-2-[4-(4-trifluoromethyl-phenoxy)-phenoxymethyl]-pyrrolidine-1-yl} butyric acid: To a solution of (S)-2-[4-(4-trifluoromethyl-phenoxy)-phenoxymethyl]-pyrrolidine-1-yl} butyric acid ethyl ester (210 mg, 0.46 mmol) in methanol (4 mL) was added 1N NaOH (0.46 mL, 0.46 mmol) and the mixture was stirred at 60° C. for three hours. Water was added and the pH was adjusted to 5 using 1 N HCl. The desired product was extracted with EtOAc. The organic portion was washed with brine, dried (anhydrous Na$_2$SO$_4$) and concentrated in vacuo to afford the title compound (60 mg, 30%) as a white solid: MS; m/z 424 (M+1). $^1$H NMR (400 HMz, DMSO-d$_6$) δ 1.52-1.72 (m, 5H), 1.77-1.94 (m, 3H), 2.18 (m, 1H), 2.28 (m, 1H), 2.77 (m, 2H), 3.02 (m, 1H), 3.72 (dd, J1=7.2 Hz, J2=9.2 Hz, 1H), 3.93 (dd, J1=4.8 Hz, J2=9.2 Hz, 1H), 7.00-7.08 (m, 6H), 7.69 (d, J=9.2 Hz, 2H).

EXAMPLE 26

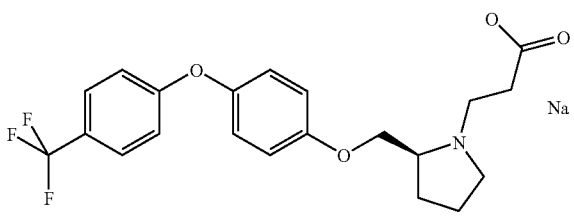

Step 1.

(S)-2-[4-(4-trifluoromethyl-phenoxy)-phenoxymethyl]-pyrrolidine-1-yl} propionic acid methyl ester. The title compound (129 mg, 29%) was prepared from 1-(4-Phenoxy-phenyl)-piperazine (337 mg, 1 mmol) by a similar procedure as that described for the synthesis of (S)-2-[4-(4-trifluoromethyl-phenoxy)-phenoxymethyl]-pyrrolidine butyric acid ethyl ester: MS, m/z 424 (M+1).

Step 2.

(S)-2-[4-(4-trifluoromethyl-phenoxy)-phenoxymethyl]-pyrrolidine-1-yl} propionic acid sodium salt: (S)-2-[4-(4-trifluoromethyl-phenoxy)-phenoxymethyl]-pyrrolidine-1-yl} propionic acid methyl ester (129 mg, 0.29 mmol) was dissolved in methanol (4 mL) followed by addition of 1N NaOH aqueous solution (0.29, 0.29 mmol). The reaction solution was stirred at 60° C. for 3 hrs and then evaporated in vacuo to dryness. The residue was stirred with diethyl ethyl and hexane. The supernatant was removed to give a white solid as the title compound (80 mg, 63%): MS; m/z 408 (M−1)-0.1H NMR (400 MHz, DMSO-$d_6$) δ 1.60-1.70 (m, 3H), 1.88-2.11 (m, 3H), 2.15 (m, 1H), 2.46 (m, 1H), 2.74 (m, 1H), 3.00 (m, 2H), 3.72 (dd, J1=7.2 Hz, J2=9.6 Hz, 1H), 3.96 (dd, J1=4.0 Hz J2=9.2 Hz, 1H), 6.99-7.08 (m, 6H), 7.69 (d, J=8.4 Hz, 2H).

EXAMPLE 27

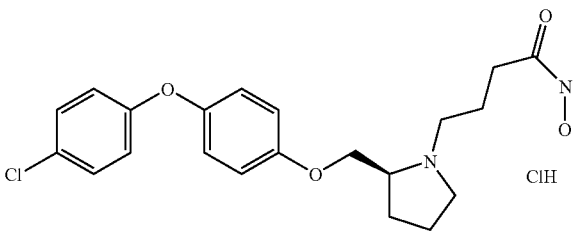

Step 1:

4-{(S)-2-[4-(4-Chloro-phenoxy)-phenoxymethyl]-pyrrolidin-1-yl}-N-(tetrahydro-pyran-2-yloxy)-butyramide: To solution of the Example 22 (0.500 g, 158 mmol) in, Hydroxybenzotriazole hydrate (0.191 g, 1.41 mmol), and N-Methyl-Morpholine (0.42 mL, 3.85 mmol) in anhydrous N,N-Dimethylformamide (DMF) at room temperature under an atmosphere of nitrogen was added 1-[3-(Dimethylamino)propyl]-3-ethylcarbodiimide hydrochloride (0.295 g, 1.54 mmol), and the resulting mixture was stirred at room temperature for about 30 minutes. After 30 minutes, O-(Tetrahydro-2H-pyran-2-yl)hydroxylamine (0.225 g, 1.92 mmol) was added to the reaction mixture was stirred for 18 h under an atmosphere of nitrogen. The mixture was poured into 30 mL water solution and extracted with ethyl acetate (EtOAc) (3×10 mL). The combined organic layers were washed with brine (40 mL) and dried over anhydrous $Na_2SO_4$. The organic layer was concentrated in vacuo to obtain the crude mixture, which was purified by of silica gel flash chromatography, using methanol/dichloromethane (DCM) (gradient system), to obtain the product (0.260 g, 24%).

Step 2:

4-({(S)-1-[4-(4-Chloro-phenoxy)-phenoxymethyl]-propyl}-ethyl-amino)-N-hydroxy-butyramide hydrochloride: To solution of the product (0.260 g, 0.532 mmol) in step 2, in 4N HCl in dioxane (0.203 mL, 10.6 mmol) was stirred at ambient temperature for about 2 h and then concentrated in vacuo. The residue was triturated with diethyl ether to afford the desired product as a red solid (0.100 g, 43%): $^1$H NMR (400 MHz, CD$_3$OD): ▢2.01-2.406 (m 7H), 3.24-3.28 (m 3H), 3.56-3.79 (m, 2H), 3.97-3.98 (m, 1H), 4.20-4.25 (m, 1H), 4.36-4.39 (m, 1H), 6.90 (d, 2H, J=8.8 Hz), 7.03 (dd, 4H, J=9 Hz, J=27.6 Hz), 7.30 (d, 2H, J=8.8 Hz); MS: m/z 403 (MH)$^-$; LCMS (UV) 90%.

EXAMPLE 28

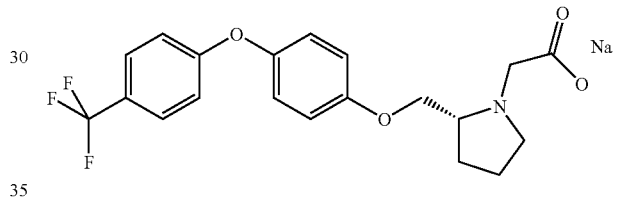

Step 1.

(R)-2-[4-(4-trifluoromethyl-phenoxy)-phenoxymethyl]-pyrrolidine-1-yl} acetic acid methyl ester: (R)-2-[4-(4-trifluoromethyl-phenoxy)-phenoxymethyl]-pyrrolidine hydrochloride (372 mg, 1.0 mmol) was taken into DMF (5 mL), and 2-bromo-acetic acid methyl ester (153 mg, 11.0 mmol) and potassium carbonate (260 mg, 2.0 mmol) were added. The mixture was stirred at rt overnight and then diluted with water and extracted with diethyl ether. The combined organic was washed with brine, dried over anhy. $Na_2SO_4$, and concentrated in vacuo to dryness. The compound was then purified by silica gel flash chromatography, eluting with 1-3% methanol in dichloromethane. The product (276 mg, 67% yield) was confirmed by LCMS; m/z 410 (M+1).

Step 2.

(R)-2-[4-(4-trifluoromethyl-phenoxy)-phenoxymethyl]-pyrrolidine-1-yl} acetic acid sodium salt: The title compound (250 mg, 89%) was prepared from (R)-2-[4-(4-trifluoromethyl-phenoxy)-phenoxymethyl]-pyrrolidine-1-yl} acetic acid methyl ester (276 mg, 0.67 mmol) by a similar procedure as that described for the synthesis of (S)-2-[4-(4-trifluoromethyl-phenoxy)-phenoxymethyl]-pyrrolidine-1-yl} propionic acid sodium salt MS; m/z 394 (M−1)$^-$.

$^1$H NMR (400 HMz, DMSO-$d_6$) δ 1.59-1.68 (m, 3H), 1.93 (m, 1H), 2.51 (m, 1H), 2.91 (d, J=15.6 Hz, 1H), 3.02-3.11 (m, 2H), 3.15 (d, J=15.6 Hz, 1H), 3.71 (dd, J1=7.2 Hz, J2=9.2 Hz, 1H), 3.99 (dd, J1=3.6 Hz, J2=9.2, 1H), 4.33 (m, 2H), 7.99-7.08 (m, 6H), 7.82 (d, J=8.4 Hz, 2H).

EXAMPLE 29

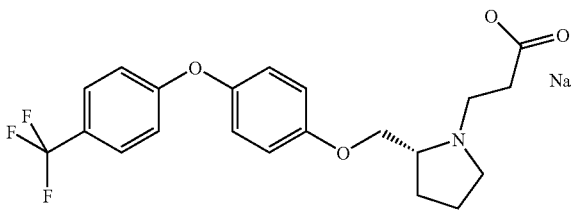

Step 1.

(R)-2-[4-(4-trifluoromethyl-phenoxy)-phenoxymethyl]-pyrrolidine-1-yl} propionic acid methyl ester: The title compound (251 mg, 59%) was prepared from 1-(4-Phenoxy-phenyl)-piperazine (373 mg, 1 mmol) by a similar procedure as that described for the synthesis of (S)-2-[4-(4-trifluoromethyl-phenoxy)-phenoxymethyl]-pyrrolidine: MS; m/z 424 (M+1).

Step 2.

(R)-2-[4-(4-trifluoromethyl-phenoxy)-phenoxymethyl]-pyrrolidine-1-yl} propionic acid sodium salt: The title compound (200 mg, 90%) was prepared from (R)-2-[4-(4-trifluoromethyl-phenoxy)-phenoxymethyl]-pyrrolidine-1-yl} acetic acid methyl ester (251 mg, 0.51 mmol) by a similar procedure as that described for the synthesis of (S)-2-[4-(4-trifluoromethyl-phenoxy)-phenoxymethyl]-pyrrolidine-1-yl} propionic acid sodium salt MS; m/z 408 (M−1)⁻. $^1$H NMR (400 HMz, DMSO-$d_6$) δ 1.60-1.70 (m, 3H), 1.88-2.11 (m, 3H), 2.15 (m, 1H), 2.46 (m, 1H), 2.74 (m, 1H), 3.00 (m, 2H), 3.72 (dd, J1=7.2 Hz, J2=9.6 Hz, 1H), 3.96 (dd, J1=4.0 Hz, J2=9.2 Hz, 1H), 6.99-7.08 (m, 6H), 7.69 (d, J=8.4 Hz, 2H).

EXAMPLE 30

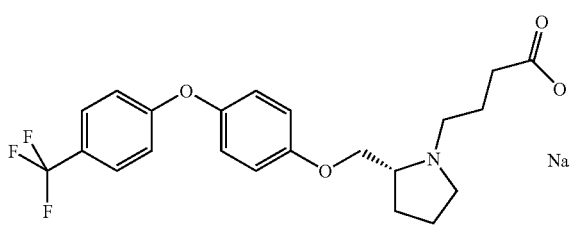

Step 1.

(R)-2-[4-(4-trifluoromethyl-phenoxy)-phenoxymethyl]-pyrrolidine-1-yl} butyric acid ethyl ester. The title compound (268 mg, 59%) was prepared from 1-(4-Phenoxy-phenyl)-piperazine (373 mg, 1 mmol) by a similar procedure as that described for the synthesis of (S)-2-[4-(4-trifluoromethyl-phenoxy)-phenoxymethyl]-pyrrolidine: MS; m/z 452 (M+1).

Step 2.

(R)-2-[4-(4-trifluoromethyl-phenoxy)-phenoxymethyl]-pyrrolidine-1-yl} butyric acid sodium salt: The title compound (240 mg, 91%) was prepared from (R)-2-[4-(4-trifluoromethyl-phenoxy)-phenoxymethyl]-pyrrolidine-1-yl} butyric acid ethyl ester (268 mg, 0.59 mmol by a similar procedure as that described for the synthesis of(S)-2-[4-(4-trifluoromethyl-phenoxy)-phenoxymethyl]-pyrrolidine-1-yl} propionic acid sodium salt MS: m/z 422 (M−1)⁻; $^1$H NMR (400 HMz, DMSO-$d_6$) δ 1.52-1.72 (m, 5H), 1.77-1.94 (m, 3H), 2.18 (m 1H), 2.28 (m, 1H), 2.77 (m, 2H), 3.02 (m, 1H), 3.72 (dd, J1=7.2 Hz, J2=9.2 Hz, 1H), 3.93 (dd, J1=4.8 Hz, J2=9.2 Hz, 1H), 7.00-7.08 (m, 6H), 7.69 (d, J=9.2 Hz, 2H).

EXAMPLE 31

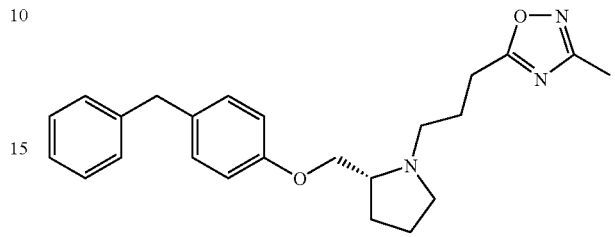

5-{3-[(R)-2-(4-benzyl-phenoxymethyl)-pyrrolidin-1-yl]-propyl}-3-methyl-[1,2,3]oxadiazole: To a suspension of acetamide oxime (0.40 g, 5.4 mmol) in THF (30 mL) was added NaH (0.24 g of a 60% suspension in oil, 6.0 mmol) at RT in the presence of 4 Å molecular sieves (0.6 g) and the mixture was heated at 50° C. for 20 min. 4-[(R)-2-(4-benzyl-phenoxymethyl)-pyrrolidin-1-yl]-butyric acid methyl ester was added and the reaction was stirred at 60° C. for 2 h. After cooling the reaction was filtered and partitioned between water and dichloromethane. The extracts were washed with brine, dried over anhy. $Na_2SO_4$, and concentrated in vacuo to dryness. The crude compound was then purified by flash chromatography, eluting with 1-5% methanol in dichloromethane. The product (310 mg, 58% yield) was confirmed by LCMS: m/z 392 (M+1). $^1$H NMR (400 HMz, CDCl$_3$) δ 1.62-1.79 (m, 3H), 1.92-2.03 (m, 3H), 2.23 (m, 1H), 2.33 (s, 3H), 2.49 (m, 1H), 2.81-2.99 (m, 4H), 3.14 (m, 1H), 3.73 (dd, J1=6.4 Hz, J2=9.2 Hz, 1H), 3.86 (dd, J1=4.8 Hz, J2=9.6 Hz, 1H), 3.92 (s, 2H), 6.81 (dd, J1=2.0 Hz, J2=6.8 Hz, 2H), 7.08 (d, J=8.0 Hz, 2H), 7.16-7.29 (m, 5H).

EXAMPLE 32

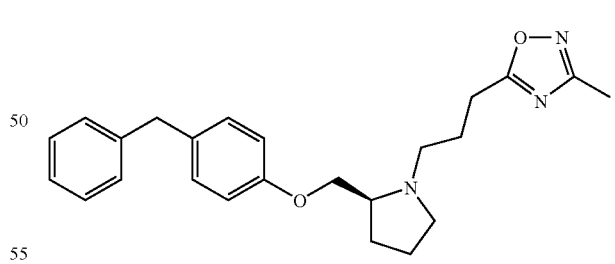

5-{3-[(S)-2-(4-benzyl-phenoxymethyl)-pyrrolidin-1-yl]-propyl}-3-methyl-[1,2,3]oxadiazole: The title compound (0.210 mg, 40%) was prepared from 4-[(S)-2-(4-benzyl-phenoxymethyl)-pyrrolidin-1-yl]-butyric acid methyl ester (337 mg, 1 mmol) by a similar procedure as that described for the synthesis of 5-{3-[(R)-2-(4-benzyl-phenoxymethyl)-pyrrolidin-1-yl]-propyl}-3-methyl-[1,2,3]oxadiazole: MS; m/z 392 (M+1). $^1$H NMR (400 HMz, CDCl$_3$) δ 1.62-1.79 (m, 3H), 1.92-2.03 (m, 3H), 2.23 (m, 1H), 2.33 (s, 3H), 2.49 (m, 1H), 2.81-2.99 (m, 4H), 3.14 (m, 1H), 3.73 (dd, J1=6.4 Hz, J2=9.2

Hz, 1H), 3.86 (dd, J1=4.8 Hz, J2=9.6 Hz, 1H), 3.92 (s, 2H), 6.81 (dd, J1=2.0 Hz, J2=6.8 Hz, 2H), 7.08 (d, J=8.0 Hz, 2H), 7.16-7.29 (m, 5H).

EXAMPLE 33

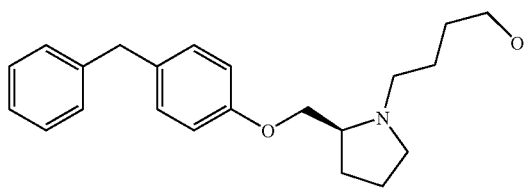

4-[(S)-2-(4-Benzyl-phenoxymethyl)-pyrrolidin-1-yl]-butan-1-ol: To a solution of 4-[(S)-2-(4-benzyl-phenoxymethyl)-pyrrolidin-1-yl]-butyric acid methyl ester (0.37 g, 1 mmol) in toluene (2 mL) was added 1.5M diisobutylaluminum hrdride in toluene (2 mL, 3 mmol) at −60° C. and then stirred the reaction at −30 to −20° C. for 2 h, followed by addition of 15% AcOH dropwise. The reaction was stirred at room temperature for 30 minutes and formed white solid was filtered and washed with acetone. The filtrate was concentrated in vacuo to yield the title compound as a white solid (0.22 g, 79%); MS; m/z 340.8 (M+H). $^1$H NMR (400 HMz, CDCl$_3$) δ 1.61-2.26 (m, 8H), 2.79 (m, 1H), 2.85 (m, 1H), 3.25 (m, 2H), 3.42 (m, 2H), 3.54 (m, 1H), 3.68 (m, 1H), 3.75 (m, 1H), 3.92 (s, 2H), 6.82 (d, J=8.8 Hz, 2H), 7.09-7.21 (m, 5H), 7.28 (m, 2H).

EXAMPLE 34

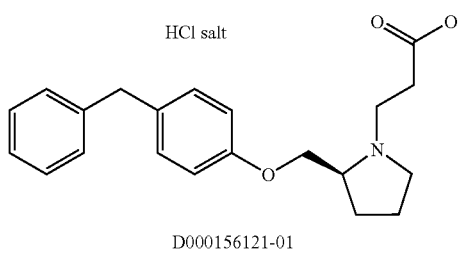

HCl salt

D000156121-01

Step 1:

3-[(S)-2-(4-Benzyl-phenoxymethyl)-pyrrolidin-1-yl]-propionic acid methyl ester: (S)-2-(4-Benzyl-phenoxymethyl)-pyrrolidine (200 mg, 0.658 mmol) was taken into DMF (2 mL), and methyl 3-bromopropionate (121 mg, 0.724 mmol) was added, followed by potassium carbonate (182 mg, 1.317 mmol). The mixture was heated to 60° C. and left to react overnight. The mixture was diluted with water, and extracted with ethyl acetate (3×). The combined ethyl acetate layers were washed with brine, dried over anhydrous sodium sulfate, and concentrated to dryness. The compound was then purified by flash chromatography (eluted with 1% methanol in dichloromethane with a 30:1 silica ratio) to obtain the title product (32.6 mg, 0.092 mmol, 14% yield); LCMS; m/z 353.47. found 354.3 (M+1). $^1$H NMR (400 MHz, CDCl$_3$) δ 3.92 (s, 1H), 1.59 (s, 2H), 1.76-1.78 (m, 1H), 1.93-2.00 (m, 1H), 2.28-2.30 (m, 1H), 2.52-2.55 (m, 2H), 2.67-2.74 (m, 1H), 2.84-2.91 (m, 1H), 3.11-3.15 (m, 1H), 3.20-3.27 (m, 1H), 3.66 (s, 3H), 3.73-3.77 (m, 1H), 3.91-3.92 (m, 2H), 6.81-6.84 (m, 2H), 7.07-7.09 (m, 2H), 7.16-7.29 (m, 5H).

Step 2:

3-[(S)-2-(4-Benzyl-phenoxymethyl)-pyrrolidin-1-yl]-propionic acid HCl salt: 3-[(S)-2-(4-Benzyl-phenoxymethyl)-pyrrolidin-1-yl]-propionic acid methyl ester (32.6 mg, 0.092 mmol) was added to a solution of HCl (conc.) in Dioxane (1:3, 2 mL). The reaction was run a 60° C. for 4 h. The Mixture was concentrated to dryness and dried in a vacuum over at 50° C. The residue was triturated with diethyl ether and dried to provide the title product (19 mg, 0.056 mmol, 60% yield); LCMS: m/z 339.44 (free amine). found 340 (M+1). $^1$H NMR (400 MHz, DMSO-d$_6$) δ 1.77 1.837 (m, 1H), 1.93-1.96 (m, 1H), 1.99-2.04 (m, 1H), 2.20-2.25 (m, 1H), 2.80-2.85 (m, 1H), 3.16-3.18 (m, 1H), 3.31-3.41 (m, 1H), 3.56-3.88 (m, 6H), 4.25-4.32 (m, 2H), 6.90-6.92 (d, J=8.4, 2H), 7.16-7.21 (m, 5H), 7.26-7.29 (m, 2H), 10.34 (s, 1H).

EXAMPLE 35

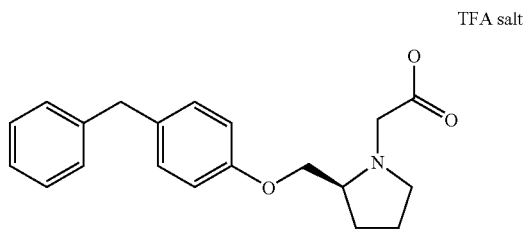

TFA salt

Step 1:

[(S)-2-(4-Benzyl-phenoxymethyl)-pyrrolidin-1-yl]-acetic acid tert-butyl ester: (S)-2-(4-Benzyl-phenoxymethyl)-pyrrolidine (200 mg, 0.658 mmol) was taken into DMF (2 mL), and t-butylbromoacetate (141 mg, 0.724 mmol) was added, followed by potassium carbonate (182 mg, 1.317 mmol). The mixture was heated to 60° C. and left to react overnight. The mixture was diluted with water, and extracted with ethyl acetate (3×). The combined ethyl acetate layers were washed with brine, dried over sodium sulfate, and concentrated to dryness. The compound was then purified by flash chromatography (eluted with 0.5% methanol in dichloromethane with a 40:1 silica ratio) to obtain the title product (161 mg, 0.423 mmol, 64% yield); LCMS; m/z 381.52. found 381 (M). $^1$H NMR (400 MHz, CDCl$_3$) δ 1.45 (s, 9H), 1.66-1.73 (m, 2H), 1.79-1.85 (m, 2H), 1.99-2.06 (m, 1H), 2.63-2.69 (m, 1H), 3.18-3.22 (m, 2H), 3.40 (d, J=17.2, 1H), 3.59 (d, J=16.8, 1H), 3.79-3.83 (m, 1H), 3.91-3.95 (m, 2H), 6.82 (d, J=8.88, 2H), 7.08 (d, J=8.8, 2H), 7.15-7.27 (m, 5H).

Step 2

[(S)-2-(4-Benzyl-phenoxymethyl)-pyrrolidin-1-yl]-acetic acid TFA salt: [(S)-2-(4-Benzyl-phenoxymethyl)-pyrrolidin-1-yl]-acetic acid tert-butyl ester (30 mg, 0.079 mmol) was added to a solution of trifluoroacetic acid and dichloromethane (1:3, 4 mL). The reaction was run at room temperature for 4 h. The Mixture was concentrated to dryness and dried in a vacuum over at 50° C. The residue was triturated with diethyl ether and dried to obtain the title product (24.1 mg, 0.074 mmol, 94% yield) was confirmed by LCMS: m/z 325.41 (free amine). found 325 (M); $^1$H NMR (400 MHz, DMSO-d6) δ 1.78-1.83 (m, 1H), 1.96-2.05 (m, 1H), 2.19-2.25 (m, 1H), 3.31 (s, 1H), 3.68 (s, 1H), 3.88 (s, 2H), 3.98 (s, 1H), 4.18-4.34 (m, 4H), 6.88-6.90 (d, J=8.8, 2H), 7.17-7.21 (m, 5H), 7.26-7.29 (m, 2H).

EXAMPLE 36

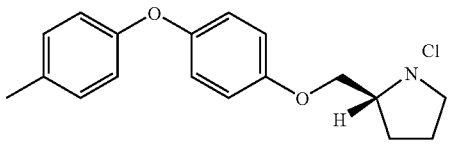

Step 1

1-methoxy-4-(4-methylphenoxy)benzene: 4-methoxy phenol (18 g, 0.145 mol) was taken into anhydrous dioxane (250 mL). 4-iodotoluene (47.42 g, 0.217 mol), cesium carbonate (94.49 g, 0.29 mol), N,N-dimethylglycine HCl (1.97 g, 0.014 mol), and copper iodide (0.966 g, 0.005 mol) were added to the solution. The reaction was heated to 90° C. for 12 h under nitrogen, with mechanical stirring. The reaction was concentrated to dryness and the residue was partitioned between water and ethyl acetate. The aqueous layer was washed with ethyl acetate (4×). The ethyl acetate was washed with brine, dried over sodium sulfate and concentrated to dryness. The crude product was purified by flash chromatography (10:1 silica ratio, eluted with 3% ethyl acetate in hexane) to obtain the title product (23.50 g, 0.1097 moles, 76% yield). $^1$H NMR (400 MHz, DMSO-d$_6$); δ 2.26 (s, 3H), 3.73 (s, 3H), 6.82 (d, J=8.8, 2H), 6.94 (s, 4H), 7.14 (d, J=8, 2H).

Step 2

4-p-Tolyloxy-phenol: 1-methoxy-4-(4-methylphenoxy)benzene (23.50 g, 0.110 mol) was taken into anhydrous dichloromethane (100 mL). The mixture was cooled to −78° C. Boron tribromide (82.43 g, 0.329 mol) in anhydrous dichloromethane (100 mL) was added to the reaction dropwise over 10 min. The reaction was kept at −78° C. for 2 h. and was then allowed to warm to room temperature overnight. The reaction was then cooled to 0° C. and quenched with methanol. The mixture was concentrated to dryness and the residue taken into dichloromethane. The pH was adjusted to ~8 with sodium bicarbonate (aq). The mixture was partitioned and the aqueous layer was washed with dicholoromethane (3×). The combined organic layers were washed with water (2×), brine (1×) and concentrated to dryness to obtain the title product (18.29 g, 0.091 mol, 83% yield); LCMS, m/z 200. found 199 (M−H). $^1$H NMR (400 MHz, DMSO-d$_6$) δ 2.25 (s, 3H), 6.74-6.85 (m, 6H), 7.10-7.13 (m, 2H), 9.28 (s, 1H).

Step 3

(S)-2-(Toluene-4-sulfonyloxymethyl)-pyrrolidine-1-carboxylic acid tert-butyl ester: (S)-2-Hydroxymethyl-pyrrolidine-1-carboxylic acid tert-butyl ester (10 g, 0.05 mol) was taken into anhydrous pyridine (51 mL). The reaction was cooled to 0° C. and p-toluenesulfonyl chloride (10.42 g, 0.055 mol) in anhydrous pyridine (25 mL) was added dropwise over 10 min. The reaction ran at 0° C. for 2 h. and then allowed to warm to room temperature overnight. The mixture was concentrated to dryness and the residue was taken into ethyl acetate (200 mL) and washed with 0.5N HCl (50 mL). The ethyl acetate was then washed with aqueous sodium bicarbonate (100 mL), brine, dried over sodium sulfate and concentrated to dryness to obtain the title product (17.55 g, 0.049 mol, 99% yield); MS; m/z 355. found 356 (M+H). $^1$H NMR (400 MHz, DMSO-d6) δ 1.28 (s, 9H), 1.72 (s, 1H), 1.90 (s, 1H), 2.42 (s, 3H), 3.14-3.23 (m, 2H), 3.84 (s, 1H), 3.97-4.06 (m, 2H), 7.49 (d, J=8.0, 2H), 7.78 (d, J=8.0, 2H).

Step 4

(S)-2-(4-p-Tolyloxy-phenoxymethyl)-pyrrolidine-1-carboxylic acid tert-butyl ester: 4-p-Tolyloxy-phenol (2 g, 9.98 mmol) was taken into anhydrous dimethylformamide (40 mL) and cooled to 0° C. A 60% dispersion of Sodium hydride (0.52 g, 13 mmol) was added portionwise over 10 min. The reaction was kept at 0° C. for 45 min. and then heated to 35° C. for 15 min. (S)-2-(Toluene-4-sulfonyloxymethyl)-pyrrolidine-1-carboxylic acid tert-butyl ester (4.26 g, 11.9 mmol) was taken into anhydrous dimethylformamide (20 mL) and added to the reaction dropwise over 5 min. The reaction was heated at 75° C. for 12 h. The reaction was quenched with water under nitrogen atmosphere. The mixture was extracted with ethyl acetate (3×). The ethyl acetate was washed with brine, dried over sodium sulfate, and concentrated to dryness. The crude product was purified by flash chromatography (20:1 silica ratio, eluted with 10% ethyl acetate in hexane) to obtain the title product (3.02 g, 7.88 mmol, 79% yield); MS; m/z 383. found 384 (M+H); $^1$H NMR (400 MHz, DMSO-d6) δ 1.40 (s, 9H), 1.80 (s, 1H), 1.89-1.92 (m, 3H), 2.26 (s, 3H), 3.27 (s, 2H), 3.86 (s, 1H), 4.00-4.06 (m, 2H), 6.81-6.83 (m, 2H), 6.91-6.98 (m, 4H), 7.13-7.15 (m, 2H).

Step 5

(S)-2-(4-p-Tolyloxy-phenoxymethyl)-pyrrolidine (S)-2-(4-p-tolyloxyphenoxymethyl)-pyrrolidine HCl: (S)-2-(4-p-Tolyloxy-phenoxymethyl)-pyrrolidine-1-carboxylic acid tert-butyl ester (3.02 g, 7.88 mmol) was taken into 4M HCl in dioxane (10 mL) and reacted at room temperature for 12 h. The mixture was concentrated to dryness to obtain the title product (2.35 g, 7.35 mmol, 93% yield); MS; m/z 320. found 284 (M-36 HCl). $^1$H NMR (400 MHz, DMSO-d6) δ 1.70-1.78 (m, 1H), 1.87-1.94 (m, 1H), 1.96-2.01 (m, 1H), 2.08-2.14 (m, 1H), 2.27 (s, 3H), 3.17-3.24 (m, 2H), 3.86-3.92 (m, 1H), 4.10-4.15 (m, 1H), 4.20-4.24 (m, 1H), 6.82-6.84 (d, J=8.0, 2H), 6.99-7.0 (m, 4H), 7.15-7.17 (d, J=8.0, 2H), 9.34 (s, 1H).

EXAMPLE 37

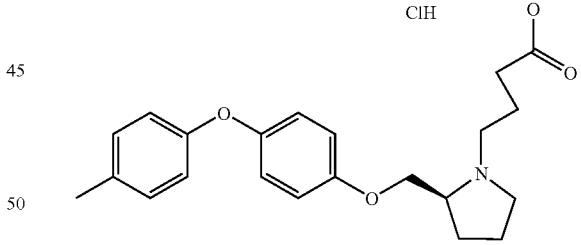

Step 1

4-[(S)-2-(4-p-Tolyloxy-phenoxymethyl)-pyrrolidin-1-yl]-butyric acid ethyl ester (S)-2-(4-p-Tolyloxy-phenoxymethyl)-pyrrolidine (S)-2-(4-p-Tolyloxyphenoxymethyl)-pyrrolidine HCl (400 mg, 1.25 mmol), was taken into dimethylformamide (4 mL). Ethyl-4-bromobutyrate (269 mg, 1.38 mmol) was added followed by potassium carbonate (346 mg, 2.5 mmol). The reaction was heated at 60° C. for 12 h. The reaction was then cooled to room temperature and partitioned between water and ethyl acetate. The aqueous layer was washed with ethyl acetate (3×). The ethyl acetate was washed with brine, dried over anhydrous sodium sulfate, and concentrated to dryness. The crude product was purified by flash chromatography (20:1 silica ratio, eluted with 5% methanol in dichloromethane) to obtain the title product (348 mg, 0.875 mmol, 70% yield); MS; m/z 397. found 398 (M+1). $^1$H NMR (400 MHz, DMSO-d6) δ 1.13-1.16 (m, 3H), 1.58-1.71 (m, 5H), 1.89-1.94 (m, 1H), 2.15-2.36 (m, 7H), 2.76-2.85 (m, 2H), 3.03-3.04 (m, 1H), 3.70-3.74 (m, 1H), 3.84-3.88 (m, 1H), 3.98-4.03 (m, 2H), 6.82 (d, J=8.4, 2H), 6.92 (s, 4H), 7.14 (d, J=8.6, 2H).

Step 2

4-[(S)-2-(4-p-Tolyloxy-phenoxymethyl)-pyrrolidin-1-yl]-butylic acid HCl: 4-[(S)-2-(4-p-Tolyloxy-phenoxymethyl)-pyrrolidin-1-yl]-butyric acid ethyl ester (348 mg, 0.875 mmol) was taken into a mixture of concentrated HCl and Dioxane (1:1, 3 mL). The reaction was heated at 60° C. for 5 h. The reaction was concentrated to dryness under vacuum, and then dried in a vacuum oven at 50° C. for 12 h. The title product (346 mg, 0.853, 97% yield) MS; m/z 405.92. found 370 (M-35HCl). $^1$H NMR (400 MHz, DMSO-d6) δ1.78-1.8 (m, 2H), 1.90-2.05 (m, 3H), 2.21-2.26 (m, 1H), 2.27 (s, 3H), 2.36-2.40 (m, 1H), 3.10-3.16 (m, 2H), 3.47-3.49 (m, 1H), 3.61-3.70 (m, 1H), 3.86-3.10 (2H), 4.27-4.37 (m, 2H), 6.83-6.49 (m, 2H), 6.96-7.04 (m, 4H), 7.14-7.17 (m, 2H), 10.55 (s, 1H).

EXAMPLE 38

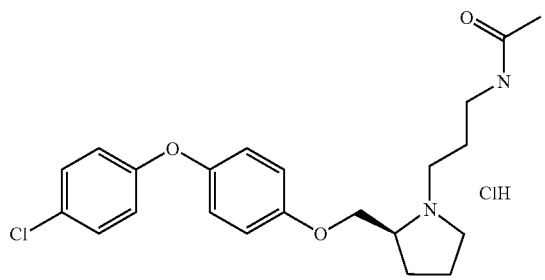

Step 1

2-(3-{(S)-2-[4-(4-Chloro-phenoxy)-phenoxymethyl]-pyrrolidin-1-yl}-propyl)-isoindole-1,3-dione: (S)-2-[4-(4-Chloro-phenoxy)-phenoxymethyl]-pyrrolidine (200 mg, 0.658 mmol) was taken into anhydrous DMF (2 mL) in a nitrogen flushed 20 mL vial. N-(3-Bromopropyl)phthalimide (194 mg, 0.724 mmol) was added to the mixture followed by potassium carbonate (364 mg, 2.43 mmol). The reaction was sealed and heated at 60° C. for 24 h. The mixture was then cooled to room temperature and partitioned between ethyl acetate and water. The water layer was washed with ethyl acetate (3×). The combined ethyl acetate layers were then washed with brine, dried over anhydrous sodium sulfate, filtered, and concentrated to dryness. The resulting residue was then purified by silica gel flash chromatography (20:1 silica ratio, eluted with 40% methanol in dichloromethane). The overlap from the purification was repurified by silica gel flash chromatography (20:1 silica ratio, eluted with 1% methanol in dichloromethane followed by 5% methanol in dichloromethane) to obtain the title product (198 mg, 403 mmol, 61%); MS; m/z 491 (M); $^1$H NMR (400 MHz, DMSO-d6) δ 1.5-1.67 (m, 3H), 1.75-1.82 (m, 2H), 1.86-1.91 (m, 1H), 2.13-2.14 (m, 1H), 2.34-2.37 (m, 1H), 2.72-2.73 (m, 1H), 2.89-2.94 (m, 1H), 3.02-3.06 (m, 1H), 3.60-3.70 (m, 3H), 3.88-3.91 (m, 1H), 6.89-6.98 (m, 6H), 7.38 (d, J=9.2, 2H), 7.82-7.85 (m, 4H).

Step 2

3-{(S)-2-[4-(4-Chloro-phenoxy)-phenoxymethyl]-pyrrolidin-1-yl}-propylamine 2-(3-{(S)-2-[4-(4-Chloro-phenoxy)-phenoxymethyl]-pyrrolidin-1-yl}-propyl)-isoindole-1,3-dione (197 mg, 0.403 mmol), was taken into methanol (2 mL), and hydrazine hydrate (25 mg, 0.504 mmol) was added. The reaction ran at room temperature for 24 h. The reaction mixture was filtered and concentrated to dryness under vacuum. The crude product was purified by flash silica chromatography (40:1 silica ration, eluted with 20% methanol in dichloromethane, with a wash consisting of 20% methanol, 1% ammonium hydroxide in dichloromethane) to obtain the title product (104 mg, 0.287 mmol, 71%); MS; m/z 361 (M); $^1$H NMR (400 MHz, DMSO-d6) δ 1.5-1.54 (m, 1H), 1.58-1.72 (m, 3H), 1.88-1.94 (m, 1H), 2.14-2.19 (m, 1H), 2.29-2.36 (m, 1H), 2.50-2.52 (m, 1H), 2.57-2.77 (m, 1H), 2.89-2.91 (m, 1H), 3.03-3.07 (m, 1H), 3.17 (s, 2H), 3.73-3.76 (m, 1H), 3.91-3.94 (m, 1H), 4.08 (s, 1H), 6.92-6.94 (m, 2H), 6.98-6.99 (m, 4H), 7.37-7.39 (m, 2H).

Step 3

N-(3-{(S)-2-[4-(4-Chloro-phenoxy)-phenoxymethyl]-pyrrolidin-1-yl}-propyl)-acetamide HCl: 3-{(S)-2-[4-(4-Chloro-phenoxy)-phenoxymethyl]-pyrrolidin-1-yl}-propylamine (50 mg, 0.139 mmol) and Diisopropylethyl amine (26.9 mg, 0.208 mmol) were taken into dichloromethane (2 ml). Acetic Anhydride (0.016 mL, 0.166 mmol) was then added to the reaction mixture. The reaction was left at room temperature for 24 h. The mixture was then partitioned between sodium bicarbonate (aq) and dichloromethane. The aqueous layer was washed with dichloromethane (3×). The combined organic layers were washed with brine, dried over sodium sulfate, and concentrated to dryness. The crude compound was purified by flash silica chromatography (40:1 silica ratio, eluted with 5% methanol in dichloromethane, followed by 10% methanol in dichloromethane). The pure product was then taken into 4M HCl in dioxane and left at room temperature for 3 h. The mixture was concentrated to dryness under vacuum to yield the title product (22 mg, 0.05 mmol, 36%); LCMS; m/z 404 (m+1 of free amine); $^1$H NMR (400 MHz, DMSO-d6) δ 1.8-2.05 (m, 7H), 2.20-2.27 (m, 1H), 3.07-3.18 (m, 3H), 3.43-3.52 (m, 1H), 3.54-3.57 (m, 1H), 4.28-4.38 (m, 2H), 4.88 (s, 3H), 6.93-6.96 (m, 2H), 7.06 (s, 4H), 7.39-7.41 (m, 2H), 8.06 (m, 1H)

EXAMPLE 39

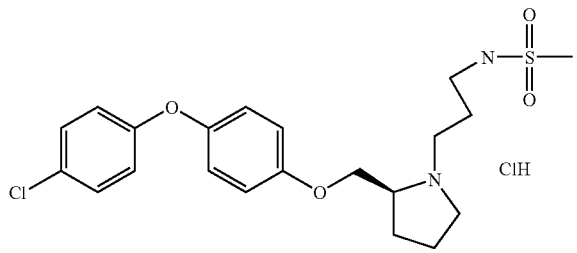

Step 1

2-(3-{(S)-2-[4-(4-Chloro-phenoxy)-phenoxymethyl]-pyrrolidin-1-yl}-propyl)-isoindole-1,3-dione: (S)-2-[4-(4-Chloro-phenoxy)-phenoxymethyl]-pyrrolidine (200 mg, 0.658 mmol) was taken into anhydrous DMF (2 mL) in a nitrogen flushed 20 mL vial. N-(3-Bromopropyl)phthalimide (194 mg, 0.724 mmol) was added to the mixture followed by potassium carbonate (364 mg, 2.43 mmol). The reaction was sealed and heated at 60° C. for 24 h. The mixture was then cooled to room temperature and partitioned between ethyl acetate and water. The water layer was washed with ethyl acetate (3×). The combined ethyl acetate layers were then washed with brine, dried over anhydrous sodium sulfate, filtered, and concentrated to dryness. The resulting residue was then purified by silica gel flash chromatography (20:1 silica ratio, eluted with 40% Methanol in dichloromethane). The overlap from the purification was repurified by silica gel flash chromatography (20:1 silica ratio, eluted with 1% methanol in dichloromethane followed by 5% methanol in dichloromethane) to obtain the title product (198 mg, 403 mmol, 61%); MS; m/z 491 (M); $^1$H NMR (400 MHz, DMSO-d6) δ 1.5-1.67 (m, 3H), 1.75-1.82 (m, 2H), 1.86-1.91 (m, 1H), 2.13-2.14 (m, 1H), 2.34-2.37 (m, 1H), 2.72-2.73 (m, 1H), 2.89-2.94 (m, 1H), 3.02-3.06 (m, 1H), 3.60-3.70 (m, 3H), 3.88-3.91 (m, 1H), 6.89-6.98 (m, 6H), 7.38 (d, J=9.2, 2H), 7.82-7.85 (m, 4H).

Step 2

3-{(S)-2-[4-(4-Chloro-phenoxy)-phenoxymethyl]-pyrrolidin-1-yl}-propylamine 2-(3-{(S)-2-[4-(4-Chloro-phenoxy)-phenoxymethyl]-pyrrolidin-1-yl}-propyl)-isoindole-1,3-dione (197 mg, 0.403 mmol), was taken into methanol (2 mL), and hydrazine hydrate (25 mg, 0.504 mmol) was added. The reaction ran at room temperature for 24 h. The reaction mixture was filtered and concentrated to dryness under vacuum. The crude product was purified by flash silica chromatography (40:1 silica ration, eluted with 20% methanol in dichloromethane, with a wash consisting of 20% methanol, 1% ammonium hydroxide in dichloromethane.) to obtain the title product (104 mg, 0.287 mmol, 71%). MS; m/z 361 (M); $^1$H NMR (400 MHz, DMSO-d6) δ 1.5-1.54 (m, 1H), 1.58-1.72 (m, 3H), 1.88-1.94 (m, 1H), 2.14-2.19 (m, 1H), 2.29-2.36 (m, 1H), 2.50-2.52 (m, 1H), 2.57-2.77 (m, 1H), 2.89-2.91 (m, 1H), 3.03-3.07 (m, 1H), 3.17 (s, 2H), 3.73-3.76 (m, 1H), 3.91-3.94 (m, 1H), 4.08 (s, 1H), 6.92-6.94 (m, 2H), 6.98-6.99 (m, 4H), 7.37-7.39 (m, 2H).

Step 3

N-(3-{(S)-2-[4-(4-Chloro-phenoxy)-phenoxymethyl]-pyrrolidin-1-yl}-propyl)-methanesulfonamide HCl: 3-{(S)-2-[4-(4-Chloro-phenoxy)-phenoxymethyl]-pyrrolidin-1-yl}-propylamine (50 mg, 0.139 mmol) and Diisopropylethyl amine (26.9 mg, 0.208 mmol) were taken into dichloromethane (2 ml). The reaction was cooled to −10° C. and the sulfonyl chloride (0.013 mL, 0.166 mmol) was added dropwise over 5 minutes. The reaction was left to slowly warm to room temperature for 24 h. The mixture was then partitioned between sodium bicarbonate (aq) and dichloromethane. The aqueous layer was washed with dichloromethane (3×). The combined organic layers were washed with brine, dried over sodium sulfate, and concentrated to dryness. The crude compound was purified by flash silica chromatography (40:1 silica ratio, eluted with 2% methanol in dichloromethane, 5% methanol in dichloromethane, and 10% methanol in dichloromethane). The pure product was then taken into 4M HCl in dioxane and left to react at room temperature for 3 h. The mixture was concentrated to dryness under vacuum to yield the title product (5.2 mg, 0.01 mmol, 7.8%); LCMS; m/z 439 (m of free amine); $^1$H NMR (400 MHz, DMSO-d6) 1.80-1.88 (m, 1H), 1.92-1.97 (m, 3H), 2.02-2.10 (m, 1H), 2.20-2.27 (m, 1H), 3.03 (s, 3H), 3.05-3.14 (m, 2H), 3.15-3.32 (m, 2H), 3.45-3.51 (m, 2H), 3.64-3.72 (m, 1H), 4.205-4.33 (m, 2H), 6.93-6.95 (m, 2H), 7.07 (s, 4H), 7.39-7.41 (m, 2H).

EXAMPLE 40

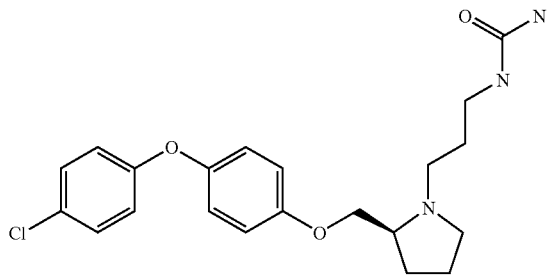

Step 1

(3-{(S)-2-[4-(4-Chloro-phenoxy)-phenoxymethyl]-pyrrolidin-1-yl}-propyl)-urea 3-{(S)-2-[4-(4-Chloro-phenoxy)-phenoxymethyl]-pyrrolidin-1-yl}-propylamine (196 mg, 0.543 mmol) was taken into acetic acid (2 mL), and sodium cyonate (49 mg, 0.760 mg) was added. The reaction was run at room temperature for 24 h. The mixture was quenched with sodium bicarbonate solution and extracted with ethyl acetate three times. The combined organic layers were washed with brine, dried over sodium sulfate, and concentrated to dryness. The resulting residue was then purified by silica gel flash chromatography (20:1 silica ratio, eluted with a gradient of 1% methanol in dichloromethane to 10% methanol in dichloromethane) to obtain the title product (101 mg, 46%); LCMS; m/z 405 (M+1); $^1$H NMR (400 MHz, DMSO-d6) δ 1>51-1.66 (m, 3H), 1.68-1.74 (m, 2H), 1.76 (s, 3H), 1.88-1.95 (m, 1H), 2.14-2.21 (m, 1H), 2.29-2.35 (m, 1H), 2.76 (m, 1H), 2.82-2.89 (m, 1H), 3.03-3.08 (m, 3H), 3.72-3.77 (m, 1H), 3.90-3.94 (m, 1H), 6.93 (d, J=8.8, 2H), 6.99 (s, 4H), 7.38 (d, J=9.2, 2H), 7.77 (s, 1H).

EXAMPLE 41

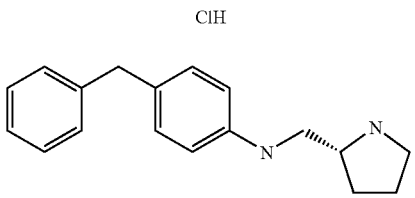

Step 1

(R)-2-[(4-Benzyl-phenylamino)-methyl]-pyrrolidine-1-carboxylic acid tert-butyl ester: To a solution of 4-benzyl aniline (200 mg, 1.1 mmol) in dichloroethane (1.5 mL) was added a solution of N-(t-butoxycarbonyl)-D-prolinal (239 mg, 1.2 mmol) in dichloroethane (1.5 mL) at 0-5° C. Sodium triacetoxyborohydride (393 mg, 1.85 mmol) was added to the above solution. Acetic acid (65 mg, 1.1 mmol) in dichloroethane (1 mL) was added dropwise, over a period of 5 min at 0-5° C. The reaction mixture was stirred at 0-10° C. for 3 h. The mixture was diluted with saturated aq NaHCO$_3$ and extracted with dichloromethane. Organic layer was dried over anhy. MgSO$_4$ and the solvent was removed in vacuo to obtain the crude mixture, which was purified by silica gel flash chromatography to obtain the title product (340 mg, 85%).

Step 2

(4-Benzyl-phenyl)-(R)-1-pyrrolidin-2-ylmethyl-amine: To the product from step 1 (340 mg, 0.927 mmol) was added 4M HCl in dioxane (6 mL) and the resulting mixture was stirred at rt for 3 h. The solvent was removed in vacuo to obtain the title product as a white solid (264 mg, 84%). The solid was dried under vacuum oven at 50° C. for 15 h: MS; m/z 267 (M+H); LCMS (UV) 99%: HPLC 98.8%. $^1$H NMR (400 MHz, DMSO-$d_6$) δ 1.61-1.66 (m, 1H), 1.84-1.94 (m, 2H), 2.04-2.09 (m, 1H), 3.13-3.18 (m, 2H), 3.30-3.37 (m, 2H), 3.57 (s, 1H), 3.62-3.67 (m, 1H), 3.79 (s, 2H), 6.63 (d, 2H, J=8.4 Hz), 7.0 (d, 2H, J=8.4 Hz), 7.13-7.19 (m, 3H), 7.24-7.28 (m, 2H), 8.9 (s, 1H), 9.4 (s, 1H).

EXAMPLE 42

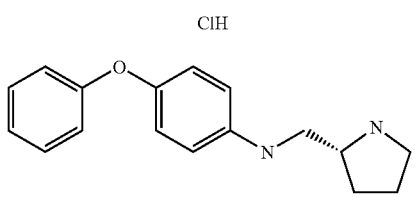

Step 1

(R)-2-[(4-Phenoxy-phenylamino)-methyl]-pyrrolidine-1-carboxylic acid tert-butyl ester: To a solution of 4-phenoxy aniline (100 mg, 0.54 mmol) in dichloroethane (1.5 mL) was added a solution of N-(t-butoxycarbonyl)-D-prolinal (118 mg, 0.594 mmol) in dichloroethane (1.5 mL) at 0-5° C. Sodium triacetoxyborohydride (194 mg, 0.92 mmol) was added to the above solution. Acetic acid (32 mg, 0.54 mmol) in dichloroethane (1 mL) was added dropwise, over a period of 5 min at 0-5° C. The reaction mixture was stirred at 0-10° C. for 3 h. The mixture was diluted with saturated aq NaHCO$_3$ and extracted with dichoromethane. Organic layer was dried over anhy. MgSO$_4$ and the solvent was removed in vacuo to obtain the crude mixture, which was purified by silica gel flash chromatography to obtain the title product (155 mg, 78%); MS; m/z 369 (M+H).

Step 2

(4-Phenoxy-phenyl)-(R)-1-pyrrolidin-2-ylmethyl-amine: To the product from step 1 (155 mg, 0.42 mmol) was added 4M HCl in dioxane (6 mL) and the resulting mixture was stirred at rt for 3 h. The solvent was removed in vacuo to obtain the product as a solid (135 mg, 94%). The solid was dried under vacuum oven at 50° C. for 15 h: MS; m/z 269 (M+H): LCMS (UV) 99.6%: Elemental analysis: Calc C, 59.83H, 6.50 N, 8.21. Found C, 59.69H, 6.55 N, 7.97. $^1$H NMR (400 MHz, DMSO-$d_6$) δ 1.64-1.70 (m, 1H), 1.88-1.98 (m, 2H), 2.07-2.12 (m, 1H), 3.16-3.20 (m, 2H), 3.30-3.37 (m, 2H), 3.57 (s, 1H), 3.66-374 (m, 1H), 6.76 (d, 2H, J=8.8 Hz), 6.88 (t, 4H, J=18 Hz), 7.03 (t, 1H, J=16 Hz), 7.30-7.34 (m, 2H), 9.0 (s, 1H), 9.4 (s, 1H).

EXAMPLE 43

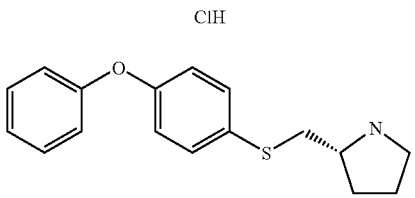

Step 1

(R)-2-(4-Phenoxy-phenylsulfanylmethyl)-pyrrolidine-1-carboxylic acid tert-butyl ester: To a solution of 4-phenoxy benzenethiol (200 mg, 0.988 mmol) in DMF (3 mL) at 0-5° C. was added 60% NaH (73 mg, 1.83 mmol) at 0-5° C. The reaction mixture was stirred at rt for 15 min at 0-5° C. A solution of (R)-2-(Toluene-4-sulfonyloxymethyl)-pyrrolidine-1-carboxylic acid tert-butyl ester (357 mg, 1 mmol) in DMF (2 mL) was added to the above mixture at 0-5° C. The reaction mixture was warmed to it and then heated at 90° C. for 15 h. The mixture was concentrated, diluted with saturated aq NaHCO$_3$ and extracted with ethyl acetate. The aqueous layer was re-extracted with ethylacetate. The combined organic layers were dried over anhy. MgSO$_4$ and the solvent was removed in vacuo to obtain the crude mixture, which was purified by silica gel flash chromatography to obtain the title product (272 mg, 71%).

Step 2

(R)-2-(4-Phenoxy-phenylsulfanylmethyl)-pyrrolidine: To the product from step 1 (272 mg, 0.705 mmol) in methanol (3 mL) was added 2M HCl in diethyl ether (12 mL) and the resulting mixture was stirred at rt for 6 h. The solvent was removed in vacuo to obtain the title product as a solid (135 mg, 94%); MS; m/z 286 (M+H); LCMS (UV) 99%. $^1$H NMR (400 MHz, CD$_3$OD) δ 1.73-1.81 (m, 1H), 2.0-2.11 (m, 2H), 2.21-2.27 (m, 1H), 3.08-3.13 (m, 2H), 3.26-3.36 (m, 2H), 3.61-3.64 (m, 1H), 7.50 (d, 2H, J=11.6 Hz), 7.35-7.39 (m, 2H), 7.15 (t, 1H, J=16 Hz); 6.96-7.01 (m, 4H)

EXAMPLE 44

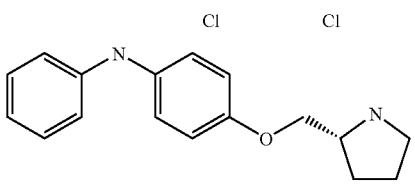

Step 1

(R)-2-(4-Phenylamino-phenoxymethyl)-pyrrolidine-1-carboxylic acid tert-butyl ester: To a solution of 4-hydroxydiphenylamine (200 mg, 1.08 mmol) in DMF (3 mL) at 0-5° C. was added 60% NaH (80 mg, 2 mmol) at 0-5° C. The reaction mixture was stirred at rt for 15 min at 0-5° C. A solution of (R)-2-(Toluene-4-sulfonyloxymethyl)-pyrrolidine-1-carboxylic acid tert-butyl ester (387 mg, 1.09 mmol) in DMF (2 mL) was added to the above mixture at 0-5° C. The reaction mixture was warmed to it and then heated at 90° C. for 15 h. The mixture was concentrated, diluted with saturated aq NaHCO₃ and extracted with ethyl acetate. The aqueous layer was re-extracted with ethylacetate. The combined organic layers were dried over anhy. MgSO₄ and the solvent was removed in vacuo to obtain the crude mixture, which was purified by silica gel flash chromatography to obtain the title product (289 mg, 73%).

Step 2

Phenyl-[4-((R)-1-pyrrolidin-2-ylmethoxy)-phenyl]-anine: To the product from step 1 (155 mg, 0.421 mmol) was added 4M HCl in dioxane (6 mL) and the resulting mixture was stirred at rt for 2 h. The solvent was removed in vacuo to obtain the title product as a solid (104 mg, 72%); MS; m/z 268 (M+H): LCMS (UV) 99%; ¹H NMR (400 MHz, CD₃OD) δ 1.86-1.96 (m, 1H), 2.06-2.18 (m, 2H), 2.23-2.31 (m, 1H), 3.32-3.39 (m, 2H), 3.99-4.12 (m, 2H), 4.30-4.33 (m, 1H), 6.92-7.01 (m, 3H), 7.07 (d, 2H, J=7.6 Hz), 7.16 (d, 2H, J=8.4 Hz); 7.26 (t, 2H, J=15.2 Hz)

EXAMPLE 45

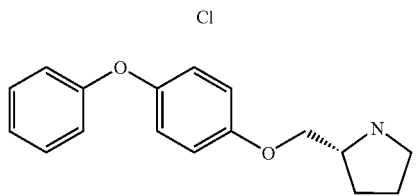

Step 1

(R)-2-(4-Phenoxy-phenoxymethyl)-pyrrolidine-1-carboxylic acid tert-butyl ester: To a solution of 4-phenoxyphenol (200 mg, 1.07 mmol) m DMF (3 mL) at 0-5° C. was added 60% NaH (75 mg, 1.875 mmol) at 0-5° C. The reaction mixture was stirred at rt for 15 min at 0-5° C. A solution of (R)-2-(Toluene-4-sulfonyloxymethyl)-pyrrolidine-1-carboxylic acid tert-butyl ester (382 mg, 1.074 mmol) in DMF (2 mL) was added to the above mixture at 0-5° C. The reaction mixture was warmed to it and then heated at 90° C. for 15 h. The mixture was concentrated, diluted with saturated aq NaHCO₃ and extracted with ethyl acetate. The aqueous layer was re-extracted with ethylacetate. The combined organic layers were dried over anhy. MgSO₄ and the solvent was removed in vacuo to obtain the crude mixture, which was purified by silica gel flash chromatography to obtain the title product (256 mg, 64%); MS; m/z 370 (M+H) LCMS (UV) >90%.

Step 2

(R)-2-(4-Phenoxy-phenoxymethyl)-pyrrolidine: To the product from step 1 (91 mg, 0.246 mmol) was added 4M HCl in dioxane (6 mL) and the resulting mixture was stirred at rt for 3 h. The solvent was removed in vacuo to obtain the product as a oil (63 mg, 95%); MS; m/z 270 (M+H): LCMS (UV) 99%; ¹H NMR (400 MHz, DMSO-d₆) δ 1.71-1.78 (m, 1H), 1.89-2.0 (m, 2H), 2.1-2.15 (m, 1H), 3.16-3.24 (m, 2H), 3.88-3.93 (m, 1H), 4.11-4.15 (dd, 1H J1=8.4 Hz, J2=10.8 Hz), 4.22-4.26 (dd, 1H J1=3.6 Hz, J2=10.8 Hz), 6.91-6.94 (m, 2H), 7.03 (s, 3H), 7.06-7.1 (m, 1H), 7.34-7.38 (m, 2H)

EXAMPLE 46

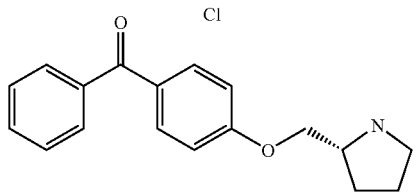

Step 1

(R)-2-(4-Benzoyl-phenoxymethyl)-pyrrolidine-1-carboxylic acid tert-butyl ester: To a solution of 4-hydroxybenzophenone (200 mg, 1 mmol) in DMF (3 mL) at 0-5° C. was added 60% NaH (70 mg, 1.75 mmol) at 0-5° C. The reaction mixture was stirred at rt for 15 min at 0-5° C. A solution of (R)-2-(Toluene-4-sulfonyloxymethyl)-pyrrolidine-1-carboxylic acid tert-butyl ester (358 mg, 1 mmol) in DMF (2 mL) was added to the above mixture at 0-5° C. The reaction mixture was warmed to rt and then heated at 90° C. for 15 h. The mixture was concentrated, diluted with saturated aq NaHCO₃ and extracted with ethyl acetate. The aqueous layer was re-extracted with ethylacetate. The combined organic layers were dried over anhy. MgSO₄ and the solvent was removed in vacuo to obtain the crude mixture, which was purified by silica gel flash chromatography to obtain the title product (210 mg, 54%).

Step 2

Phenyl-[4-((R)-1-pyrrolidin-2-ylmethoxy)-phenyl]-methanone: To the product from step 1 (70 mg, 0.183 mmol) was added 4M HCl in dioxane (6 mL) and the resulting mixture was stirred at rt for 3 h. The solvent was removed in vacuo to obtain the product as a brown solid, (51 mg, 99%): MS, m/z 282 (M+H): LCMS (UV) 99%: HPLC 98.3%; ¹H NMR (400 MHz, DMSO-d₆) δ 1.72-1.81 (m, 1H), 1.89-2.00 (m, 2H), 2.02-2.19 (m, 1H), 3.19-3.26 (m, 2H), 3.91-3.98 (m, 1H), 4.25-4.30 (dd, 1H J1=8.4 Hz, J2=10.8 Hz), 4.36-4.40 (dd, 1H J1=3.6 Hz, J2=10.8 Hz), 7.15 (d, 2H, J=9.2 Hz), 7.54-7.59 (m, 2H), 7.65-7.71 (m, 3H); 7.785 (d, 2H, J=8.8 Hz), 9.4 (s, 2H)

EXAMPLE 47

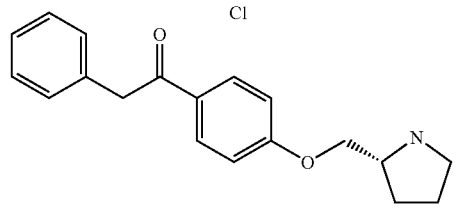

Step 1

(R)-2-(4-Phenylacetyl-phenoxymethyl)-pyrrolidine-1-carboxylic acid tert-butyl ester: To a solution of benzyl 4-hydroxyphenylketone (200 mg, 0.94 mmol) in DMF (3 mL) at 0-5° C. was added 60% NaH (65 mg, 1.625 mmol) at 0-5° C. The reaction mixture was stirred at rt for 15 min at 0-5° C. A solution of (R)-2-(Toluene-4-sulfonyloxymethyl)-pyrrolidine-1-carboxylic acid tert-butyl ester (334 mg, 1 mmol) in DMF (2 mL) was added to the above mixture at 0-5° C. The reaction mixture was warmed to rt and then heated at 90° C. for 15 h. The mixture was concentrated, diluted with saturated aq NaHCO₃ and extracted with ethyl acetate. The aqueous layer was re-extracted with ethylacetate. The combined organic layers were dried over anhy. MgSO₄ and the solvent was removed in vacuo to obtain the crude mixture, which was purified by silica gel flash chromatography to obtain the title product (150 mg, 40%): MS; m/z 396 (M+H): LCMS (UV) 94%.

Step 2

2-Phenyl-1-[4-((R)-1-pyrrolidin-2-ylmethoxy)-phenyl]-ethanone: To the product from step 1 (51 mg, 0.129 mmol) was added 4M HCl in dioxane (6 mL) and the resulting mixture was stirred at rt for 3 h. The solvent was removed in vacuo to obtain the title product as a yellow solid (43 mg, 99%): MS; m/z 296 (M+H): LCMS (UV) 99%. $^1$H NMR (400 MHz, DMSO-$d_6$) δ 1.72-1.77 (m, 1H), 1.87-2.01 (m, 2H), 2.11-2.15 (m, 1H), 3.21-3.23 (m, 2H), 3.91-3.93 (m, 1H), 4.22-4.27 (dd, 1H J1=8, J2=10.8 Hz), 4.33-4.37 (dd, 1H J1=4 Hz, J2=10.8 Hz), 4.33 (s, 2H), 7.09 (d, 2H, J=9.2 Hz), 7.20-7.33 (m, 4H); 8.05 (d, 2H, J=9.2 Hz), 9.1 (s, 1H), 9.6 (s, 1H).

EXAMPLE 48

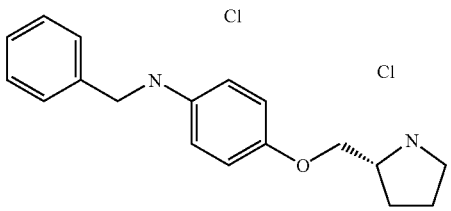

Step 1

(R)-2-(4-Benzylamino-phenoxymethyl)-pyrrolidine-1-carboxylic acid tert-butyl ester: To a solution of 4-(benzylamino) phenol (200 mg, 1 mmol) in DMF (3 mL) at 0-5° C. was added 60% NaH (48 mg, 1.2 mmol) at 0-5° C. The reaction mixture was stirred at rt for 15 min at 0-5° C. A solution of (R)-2-(Toluene-4-sulfonyloxymethyl)-pyrrolidine-1-carboxylic acid tert-butyl ester (356 mg, 1 mmol) in DMF (2 mL) was added to the above mixture at 0-5° C. The reaction mixture was warmed to rt and then heated at 90° C. for 15 h. The mixture was concentrated, diluted with saturated aq NaHCO₃ and extracted with ethyl acetate. The aqueous layer was re-extracted with ethylacetate. The combined organic layers were dried over anhy. MgSO₄ and the solvent was removed in vacuo to obtain the crude mixture, which was purified by silica gel flash chromatography to obtain the title product (169 mg, 44%).

Step 2

Benzyl-[4-((R)-1-pyrrolidin-2-ylmethoxy)-phenyl]-anine: To the product from step 1 (148 mg, 0.387 mmol) in methanol (3 mL) was added 1M HCl in diethyl ether (6 mL) and the resulting mixture was stirred at rt for 3 h. The solvent was removed in vacuo to obtain the title product as a solid (128 mg, 93%); MS; m/z 283 (M+H): LCMS (UV) 97%: Elemental analysis Calc C, 60.85 H, 6.81 N, 7.88. Found C, 57.26 H, 7.21 N, 7.24. $^1$H NMR (400 MHz, DMSO-$d_6$) δ 1.60-1.73 (m, 1H), 1.87-2.12 (m, 3H), 3.17-3.21 (m, 2H), 3.84-3.87 (m, 2H), 4.19-4.23 (dd, 1H J1=3.6 Hz, J2=10.8 Hz), 4.11-4.16 (m, 1H), 4.44 (s, 2H), 7.0 (d, 2H J=8.8 Hz), 7.29-7.38 (m, 5H); 7.48-7.49 (m, 2H) 9.1 (s, 1H), 9.8 (s, 1H).

EXAMPLE 49

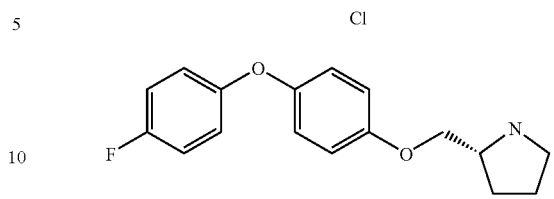

Step 1

(R)-2-[4-(4-Fluoro-phenoxy)-phenoxymethyl]-pyrrolidine-1-carboxylic acid tert-butyl ester: To a solution of 4-(4-Fluoro-phenoxy)-phenol (200 mg, 0.979 mmol) in DMF (3 mL) at 0-5° C. was added 60% NaH (70 mg, 1.76 mmol) at 0-5° C. The reaction mixture was stirred at rt for 15 min at 0-5° C. A solution of (R)-2-(Toluene-4-sulfonyloxymethyl)-pyrrolidine-1-carboxylic acid tert-butyl ester (348 mg, 0.979 mmol) in DMF (2 mL) was added to the above mixture at 0-5° C. The reaction mixture was warmed to rt and then heated at 90° C. for 15 h. The mixture was concentrated, diluted with saturated aq NaHCO₃ and extracted with ethyl acetate. The aqueous layer was re-extracted with ethylacetate. The combined organic layers were dried over anhy. MgSO₄ and the solvent was removed in vacuo to obtain the crude mixture, which was purified by silica gel flash chromatography to obtain title the product (280 mg, 74%).

Step 2

(R)-2-[4-(4-Fluoro-phenoxy)-phenoxymethyl]-pyrrolidine: To the product from step 1 (271 mg, 0.699 mmol) in methanol (3 mL) was added 1M HCl in diethyl ether (15 mL) and the resulting mixture was stirred at rt for 7 h. The solvent was removed in vacuo to obtain the product as a solid (228 mg, 99%): MS; m/z 288 (M+H): LCMS (UV) 98%. $^1$H NMR (400 MHz, DMSO-$d_6$) δ 1.70-1.76 (m, 1H), 1.89-1.99 (m, 2H), 2.01-2.14 (m, 1H), 3.18-3.23 (m, 2H), 3.87-3.90 (m, 1H), 4.12-4.16 (dd, 1H J1=8.4 Hz, J2=10.8 Hz), 4.21-4.25 (dd, 1H J1=4 Hz, J2=10.8 Hz), 6.96-6.99 (m, 2H), 7.014-7.016 (m, 4H), 7.17-7.22 (m, 2H), 9.1 (s, 1H), 9.7 (s, 1H)

EXAMPLE 50(a)

Starting Material for Examples 52 et seq.

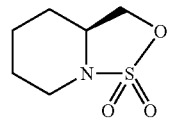

Step 1

(S)-2-Hydroxymethyl-piperidine-1-carboxylic acid tert-butyl ester: To a solution of (S)-Piperidine-1,2-dicarboxylic acid 1-tert-butyl ester (5 g, 21.8 mmol) in anhydrous THF (32 mL) at 0-5° C. was added borane-tetrahydrofuran complex (1M solution in THF) (3.6 g, 41.84 mmol) over a period of 15 min. The mixture was stirred at 0-5° C. for 2 h and then at rt for 2 h. The mixture was added over a period of 10 min to cold water (75 mL) and extracted with EtOAc (300 mL). The aqueous layer was re-extracted with EtOAc (2×150 mL). The organic layers were combined, dried over anhydrous Na$_2$SO$_4$ and concentrated to obtain the title product as a colorless oil (4.72 g).

Step 2

(S)-1-Piperidin-2-yl-methanol hydrochloride: A 4M HCl solution in dioxane (30 mL) was added to (S)-2-Hydroxymethyl-piperidine-1-carboxylic acid tert-butyl ester (5.12 g, 23.78 mmol). The mixture was stirred at rt for 3 h. The solvent was removed in vacuo to yield the title product as a hydrochloride salt (3.43 g, 95%).

Step 3

(S)-Hexahydro-[1,2,3]oxathiazolo[3,4-a]pyridine 1-oxide: To a solution of (S)-1-Piperidin-2-yl-methanol hydrochloride (3.43 g, 22.63 mmol), imidazole (6.1 g, 88.72 mmol) and triethylamine (7.33 g, 72.42 mmol) in anhydrous dichloromethane (120 mL) at 0-5° C. was added a solution of thionyl chloride (3.2 g, 25.86 mmol) in anhydrous dichloromethane (10 mL) over a period of 45 min. The reaction mixture was stirred at 0-5° C. for 45 min, partitioned with H$_2$O and the aqueous layer was extracted with dichloromethane (2×150 mL). The combined organic layer was washed with H$_2$O, dried over Na$_2$SO$_4$, and concentrated in vacuo to give an orange liquid. Flash column chromatography purification (silica gel, 2% EtOAc in dichloromethane) afforded the title product as a clear, colorless liquid (1.31 g, 36%).

Step 4

(S)—Hexahydro-[1,2,3]oxathiazolo[3,4-a]pyridine 1,1-dioxide: To a solution of (S)-Hexahydro-[1,2,3]oxathiazolo[3,4-a]pyridine 1-oxide (1.31 g, 8.125 mmol) in anhydrous acetonitrile (10 mL) was added sodium (meta)periodate (1.91 g, 8.9375 mmol), followed by ruthenium(III) chloride hydrate (17 mg, 0.08125 mmol), and then H$_2$O (10 mL). The mixture was stirred at 0° C. for 10 min and at rt for 20 min, then diluted with saturated NaHCO3 (30 mL) and EtOAc (100 mL). The aqueous layer was extracted with EtOAc (80 mL) and DCM (80 mL). The combined organic layer was dried over Na$_2$SO$_4$, concentrated in vacuo, and purified by flash column chromatography (silica gel, 2% EtOAc in DCM) to afforded the title product as a clear, colorless oil (1.1 g, 76%).

EXAMPLE 50(b)

Starting Material for Examples 50 et seq.

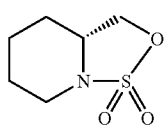

Step 1

(R)-2-Hydroxymethyl-piperidine-1-carboxylic acid tert-butyl ester: To a solution of (R)-Piperidine-1,2-dicarboxylic acid 1-tert-butyl ester (5 g, 21.8 mmol) in anhydrous THF (32 mL) at 0-5° C. was added borane-tetrahydrofuran complex (1M solution in THF) (3.6 g, 41.84 mmol) over a period of 15 min. The mixture was stirred at 0-5° C. for 2 h and then at rt for 2 h. The mixture was added over a period of 10 min to cold water (75 mL) and extracted with EtOAc (300 mL). The aqueous layer was re-extracted with EtOAc (2×150 mL). The organic layers were combined, dried over anhydrous Na$_2$SO$_4$ and concentrated to obtain the title product as a colorless oil (4.65 g., 99%).

Step 2

(R)-1-Piperidin-2-yl-methanol hydrochloride: A 4M HCl solution in dioxane (30 mL) was added to (R)-2-Hydroxymethyl-piperidine-1-carboxylic acid tert-butyl ester (4.65 g, 21.6 mmol). The mixture was stirred at rt for 3 h. The solvent was removed in vacuo to yield the title product as a hydrochloride salt (3.47 g).

Step 3

(R)-Hexahydro-[1,2,3]oxathiazolo[3,4-a]pyridine 1-oxide: To a solution of (R)-1-Piperidin-2-yl-methanol hydrochloride (3.47 g, 22.89 mmol), imidazole (6.1 g, 89.72 mmol) and triethylamine (7.41 g, 73.25 mmol) in anhydrous dichloromethane (100 mL) at 0-5° C. was added a solution of thionyl chloride (3.2 g, 25.86 mmol) in anhydrous dichloromethane (10 mL) over a period of 45 min. The reaction mixture was stirred at 0-5° C. for 45 min, partitioned with H$_2$O and the aqueous layer was extracted with dichloromethane (2×150 mL). The combined organic layer was washed with H$_2$O, dried over Na$_2$SO$_4$, and concentrated in vacuo to give an orange liquid. Flash column chromatography purification (silica gel, 2% EtOAc in dichloromethane) afforded the oxide as a clear, colorless liquid (1.08 g, 30%).

Step 4

(R) —Hexahydro-[1,2,3]oxathiazolo[3,4-a]pyridine 1,1-dioxide: To a solution of (R)-hexahydro-[1,2,3]oxathiazolo[3,4-a]pyridine 1-oxide (1.09 g, 6.76 mmol) in anhydrous acetonitrile (10 mL) was added sodium (meta)periodate (1.6 g, 7.436 mmol), followed by ruthenium(III) chloride hydrate (14 mg, 0.0676 mmol), and then H$_2$O (10 mL). The mixture was stirred at 0° C. for 10 min and at rt for 20 min, then diluted with saturated NaHCO$_3$ (30 mL) and EtOAc (100 mL). The aqueous layer was extracted with EtOAc (80 mL) and dichloromethane (80 mL). The combined organic layer was dried over Na$_2$SO$_4$, concentrated in vacuo, and purified by flash column chromatography (silica gel, 2% EtOAc in dichloromethane) to afforded the title product as a clear, colorless oil (0.890 g, 69%).

EXAMPLE 50

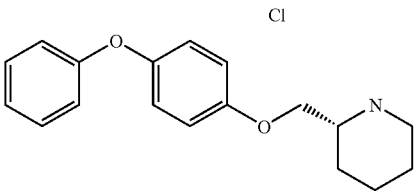

Step 1

(R)-2-(4-Phenoxy-phenoxymethyl)-piperidine hydrochloride: A mixture of (R)-Hexahydro-[1,2,3]oxathiazolo[3,4-a]pyridine 1,1-dioxide (198 mg, 1.12 mmol), 4-phenoxyphenol (160 mg, 0.859 mmol), and potassium carbonate (237 mg, 1.72 mmol) in DMF (2 mL) at 50° C. was heated for 18 h and then at 65° C. for 7 h. The ambient mixture's pH was adjusted to 1 with an aqueous 20% H$_2$SO$_4$ solution and stirred at ambient temperature for about 20 h. The reaction solution's pH was adjusted to 12-14 with 5N NaOH, and extracted with EtOAc (20 mL). Aqueous layer was re-extracted with ethylacetate (10 mL). The organic layers were combined, dried over anhydrous $Na_2SO_4$, and concentrated to an oil. The oil was treated with 2M HCl in ether to give the title product as a solid (123 mg, 45%): MS; m/z 284 (MH)$^+$; LCMS (UV) 99%: Elemental analysis Calc C, 67.60 H, 6.93 N, 4.38. Found C, 61.20H, 6.67 N, 4.71. $^1$H NMR (400 MHz, DMSO-d$_6$) δ 1.60-1.85 (m, 6H), 2.89-2.94 (m, 1H), 3.25 (d, 1H, J=12 Hz), 3.33-3.47 (m, 1H), 4.09-4.14 (dd, 1H J1=7.2 Hz, J2=10.4 Hz), 4.17-4.21 (dd, 1H J1=4 Hz, J2=10.8 Hz)), 6.92-6.94 (m, 2H), 7.0-7.1 (m, 5H); 7.33-7.37 (m, 2H,) 9.19 (s, 1H,)

EXAMPLE 51

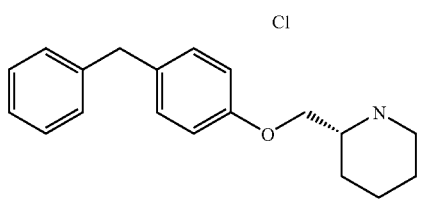

Step 1

(R)-2-(4-Benzyl-phenoxymethyl)-piperidine hydrochloride: A mixture of (R)-Hexahydro-[1,2,3]oxathiazolo[3,4-a]pyridine 1,1-dioxide (200 mg, 1.13 mmol), 4-hydroxydiphenyl methane (160 mg, 0.868 mmol), and potassium carbonate (240 mg, 1.74 mmol) in DMF (2 mL) at 50° C. was heated for 18 h and then at 65° C. for 7 h. The ambient mixture's pH was adjusted to 1 with an aqueous 20% $H_2SO_4$ solution and stirred at ambient temperature for about 20 h. The reaction solution's pH was adjusted to 12-14 with 5N NaOH, and extracted with EtOAc (20 mL). Aqueous layer was re-extracted with ethylacetate (10 mL). The organic layers were combined, dried over anhydrous $Na_2SO_4$, and concentrated to an oil. The oil was treated with 2M HCl in ether to give the title product as a solid (50 mg, 18%): MS; m/z 282 (MH)$^+$; LCMS (UV) 86%; $^1$H NMR (400 MHz, DMSO-d$_6$) δ 1.54-1.92 (m, 6H), 2.83-2.92 (m, 1H), 3.24 (d, 1H, J=12.4 Hz), 3.37-3.43 (m, 1H), 3.88 (s, 2H), 4.04-4.09 (dd, 1H J1=6.8 Hz, J2=10.4 Hz), 4.12-4.16 (dd, 1H J1=3.6 Hz, J2=10.8 Hz)), 6.92-6.94 (m, 2H), 7.16-7.29 (m, 7H), 9.0-9.15 (m, 1H,)

EXAMPLE 52

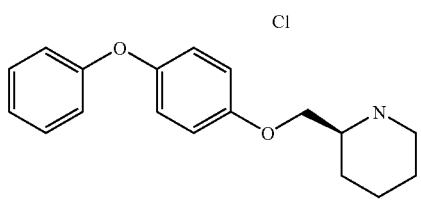

Step 1

(S)-2-(4-Phenoxy-phenoxymethyl)-piperidine hydrochloride: A mixture of (S)-Hexahydro-[1,2,3]oxathiazolo[3,4-a]pyridine 1,1-dioxide (198 mg, 1.12 mmol), 4-phenoxyphenol (160 mg, 0.86 mmol), and potassium carbonate (237 mg, 1.72 mmol) in DMF (2.5 mL) was heated for 18 h at 65° C. The ambient mixture's pH was adjusted to 1 with an aqueous 20% $H_2SO_4$ solution and stirred at ambient temperature for about 20 h. The reaction solution's pH was adjusted to 12-14 with 5N NaOH, and extracted with EtOAc (2×18 mL). The organic layers were combined, washed with water (30 mL), dried over anhydrous $Na_2SO_4$, and concentrated to an oil. The oil was treated with 2M HCl in ether to give the title product as a white solid (116 mg, 42%): MS; m/z 284 (MH)$^+$; LCMS (UV) 93% HPLC 99.4%; $^1$H NMR (400 MHz, DMSO-d$_6$) δ 1.5-1.88 (m, 6H), 2.90-2.95 (m, 1H), 3.25 (d, 1H, J=13.2 Hz), 3.44-3.49 (m, 1H), 4.08-4.13 (dd, 1H J1=7.2 Hz, J2=10.4 Hz), 4.17-4.20 (dd, 1H J1=4 Hz, J2=10.8 Hz)), 6.92-6.94 (m, 2H), 7.0-7.1 (m, 5H); 7.33-7.37 (m, 2H,) 9.13 (s, 1H,)

EXAMPLE 53

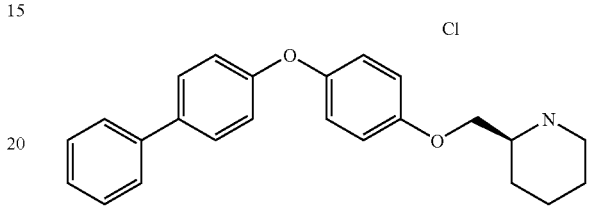

Step 1

4-(4-Methoxy-phenoxy)-biphenyl: To a solution of 4-methoxyphenol (3.99 g, 32.17 mmol) and 4-bromobiphenyl (5 g, 21.45 mmol) in anhydrous dioxane (40 mL) were added cesium carbonate (13.98 g, 42.9 mmol) and N,N-dimethylglycine.HCl (0.898 g, 6.4 mmol). The reaction mixture was flushed with nitrogen. Copper (I) iodide (0.408 g, 2.145 mmol) was added and the reaction mixture was stirred at 90° C. for 18 h under an atmosphere of nitrogen. The mixture was diluted with water (100 mL) and extracted with EtOAc (250 mL). Aqueous layer was re-extracted with EtOAc (150 mls). The organic layers were combined, dried over anhydrous $Na_2SO_4$, and concentrated to obtain the title product 7.84 g.

Step 2

4-(Biphenyl-4-yloxy)-phenol: To a solution of 4-(4-methoxy-phenoxy)-biphenyl (3.2 g, 11.6 mmol) in anhydrous dichloromethane (60 mL) at −78° C. was added borontribromide (1M solution in dichloromethane) (7.52 g, 30 mmol) over a period of 15 min. The reaction mixture was stirred at −78° C. for 1 h, warmed to rt and stirred at rt for 1 h. The mixture was cooled to 0-5° C. Cold water (125 mL) was added over a period of 10 min and the mixture was extracted with dichloromethane (250 mL). The organic layer was dried over anhydrous $Na_2SO_4$. The crude mixture was purified by silica gel flash chromatography to obtain the title product (375 mg, 12%).

Step 3

(S)-2-[4-(Biphenyl-4-yloxy)-phenoxymethyl]-piperidine hydrochloride: A mixture of (S)-hexahydro-[1,2,3]oxathiazolo[3,4-a]pyridine 1,1-dioxide (125 mg, 0.70 mmol), 4-(biphenyl-4-yloxy)-phenol (142 mg, 0.54 mmol), and potassium carbonate (150 mg, 1.1 mmol) in DMF (2.5 mL) was heated for 18 h at 65° C. The ambient mixture's pH was adjusted to 1 with an aqueous 20% $H_2SO_4$ solution and stirred at ambient temperature for about 20 h. The reaction solution's pH was adjusted to 12-14 with 5N NaOH, and extracted with EtOAc (2×18 mL). The organic layers were combined, dried over anhydrous $Na_2SO_4$, and concentrated to an oil. The oil was treated with 2M HCl in ether to give the title product as a solid (57 mg, 20%): MS; m/z 360 (MH)$^+$; LCMS (UV) 90%; $^1$H NMR (400 MHz, DMSO-d$_6$) δ 1.5-1.9 (m, 6H), 2.89-2.94 (m, 1H), 3.27 (d, 1H, J=12 Hz), 3.46-3.5 (m, 1H), 4.09-4.13 (dd, 1H J1=6.8 Hz, J2=10.4 Hz), 4.18-4.22 (dd, 1H J1=4 Hz, J2=10.8 Hz)), 7.0-7.02 (m, 2H), 7.081 (s, 3H); 7.32-7.3 (m, 1H,) 7.43-7.47 (m, 3H), 7.61-7.67 (m, 4H), 9.0-9.15 (m, 2H) (m, 1H), 3.47-3.50 (m, 1H), 4.11-4.15 (dd, 1H J1=6.8 Hz, J2=10.4 Hz), 4.19-4.23 (dd, 1H J1=4 Hz, J2=10.8 Hz)), 7.06-7.15 (m, 6H), 7.71 (d, 2H J=8.8 Hz); 9.11 (s, 2H).

EXAMPLE 54

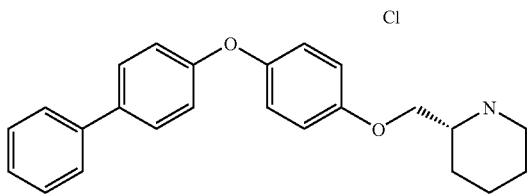

Step 1

(R)-2-[4-(Biphenyl-4-yloxy)-phenoxymethyl]-piperidine hydrochloride: A mixture of (R)-Hexahydro-[1,2,3]oxathiazolo[3,4-a]pyridine 1,1-dioxide (125 mg, 0.705 mmol), 4-(Biphenyl-4-yloxy)-phenol (142 mg, 0.543 mmol), and potassium carbonate (150 mg, 1.1 mmol) in DMF (2.5 mL) was heated for 18 h at 65° C. The ambient mixture's pH was adjusted to 1 with an aqueous 20% $H_2SO_4$ solution and stirred at ambient temperature for about 20 h. The reaction solution's pH was adjusted to 12-14 with 5N NaOH, and extracted with EtOAc (2×18 mL). The organic layers were combined, dried over anhydrous $Na_2SO_4$, and concentrated to an oil. The oil was treated with 2M HCl in ether to give the desired product as a solid (97 mg, 35%): MS; m/z 360 (MH)$^+$; LCMS (UV) 89% HPLC 81.5%; $^1$H NMR (400 MHz, DMSO-$d_6$) δ 1.53-1.9 (m, 6H), 2.93-2.98 (m, 1H), 3.27 (d, 1H, J=12.8 Hz), 3.47-3.50 (m, 1H), 4.07-4.11 (dd, 1H J1=7.2 Hz, J2=10.4 Hz), 4.18-4.21 (dd, 1H J1=3.6 Hz, J2=10.8 Hz)), 7.0-7.08 (m, 5H), 7.32-7.36 (m, 1H); 7.43-7.47 (m, 2H), 7.61-7.66 (m, 4H), 8.88-8.95 (m, 1H), 9.01-9.05 (m, 1H)

EXAMPLE 55

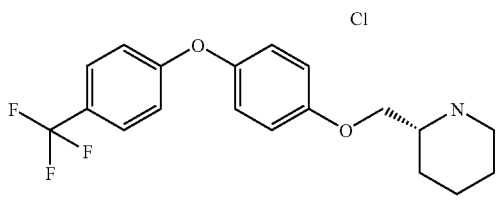

Step 1

(R)-2-[4-(4-Trifluoromethyl-phenoxy)-phenoxymethyl]-piperidine hydrochloride: A mixture of (R)-hexahydro-[1,2,3]oxathiazolo[3,4-a]pyridine 1,1-dioxide (125 mg, 0.705 mmol), 4-(4-trifluoromethyl-phenoxy)-phenol (138 mg, 0.543 mmol), and potassium carbonate (150 mg, 1.1 mmol) in DMF (2.5 mL) was heated for 18 h at 65° C. The ambient mixture's pH was adjusted to 1 with an aqueous 20% $H_2SO_4$ solution and stirred at ambient temperature for about 20 h. The reaction solution's pH was adjusted to 12-14 with 5N NaOH, and extracted with EtOAc (2×18 mL). The organic layers were combined, dried over anhydrous $Na_2SO_4$, and concentrated to an oil. The oil was treated with 2M HCl in ether to give the desired product as a solid (68 mg, 25%): MS; m/z 352 (MH)$^+$; LCMS (UV) 99%; $^1$H NMR (400 MHz, DMSO-$d_6$) δ 1.53-1.89 (m, 6H), 2.90-2.96 (m, 1H), 3.25-3.28

EXAMPLE 56

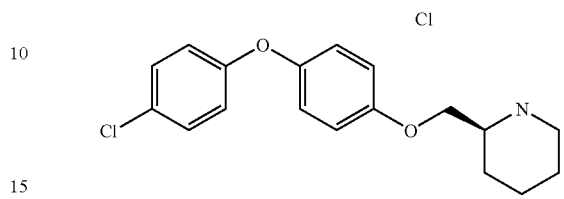

(S)-2-[4-(4-Chloro-phenoxy)-phenoxymethyl]-piperidine hydrochloride: A mixture of (S)-hexahydro-[1,2,3]oxathiazolo[3,4-a]pyridine 1,1-dioxide (83 mg, 0.47 mmol), 4-(4-chloro-phenoxy)-phenol (80 mg, 0.36 mmol), and potassium carbonate (99 mg, 0.72 mmol) in DMF (2.5 mL) was heated for 18 h at 65° C. The ambient mixture's pH was adjusted to 1 with an aqueous 20% $H_2SO_4$ solution and stirred at ambient temperature for about 20 h. The reaction solution's pH was adjusted to 12-14 with 5N NaOH, and extracted with EtOAc (2×18 mL). The organic layers were combined, dried over anhydrous $Na_2SO_4$, and concentrated to an oil. The oil was treated with 2M HCl in ether to give the desired product as a white solid (22 mg, 13%): MS; m/z 318 (MH)$^+$; LCMS (UV) 99% HPLC 99.5%; $^1$H NMR (400 MHz, DMSO-$d_6$) δ 1.50-1.88 (m, 6H), 2.90-2.97 (m, 1H), 3.25 (d, 1H, J=12.8 Hz), 3.42-3.47 (m, 1H), 4.09-4.13 (dd, 1H J1=7.2 Hz, J2=10.4 Hz), 4.17-4.21 (dd, 1H J1=4 Hz, J2=10.8 Hz)), 6.93-6.96 (m, 2H), 7.06-7.08 (m, 4H); 7.39-7.41 (m, 2H,) 9.155 (s, 2H)

EXAMPLE 57

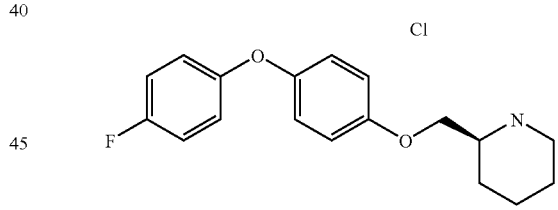

(S)-2-[4-(4-Fluoro-phenoxy)-phenoxymethyl]-piperidine hydrochloride: A mixture of (S)-hexahydro-[1,2,3]oxathiazolo[3,4-a]pyridine 1,1-dioxide (125 mg, 0.7 mmol), 4-(4-fluoro-phenoxy)-phenol (110 mg, 0.54 mmol), and potassium carbonate (150 mg, 1.1 mmol) in DMF (2.5 mL) was heated for 18 h at 65° C. The ambient mixture's pH was adjusted to 1 with an aqueous 20% $H_2SO_4$ solution and stirred at ambient temperature for about 20 h. The reaction solution's pH was adjusted to 12-14 with 5N NaOH, and extracted with EtOAc (2×18 mL). The organic layers were combined, dried over anhydrous $Na_2SO_4$, and concentrated to an oil. The oil was treated with 2M HCl in ether to give the title product as a solid (95 mg, 40%): MS; m/z 302 (MH)$^+$; LCMS (UV) 99%; $^1$H NMR (400 MHz, DMSO-$d_6$) δ 1.52-1.85 (m, 6H), 2.90-2.95 (m, 1H), 3.26 (d, 1H, J=12 Hz), 3.42-3.47 (m, 1H), 4.08-4.12 (dd, 1H J1=6.8 Hz, J2=10.4 Hz), 4.16-4.19 (dd, 1H J1=4 Hz, J2=10.8 Hz)), 6.96-7.06 (m, 5H), 7.17-7.22 (m, 2H) 9.15 (s, 2H).

EXAMPLE 58

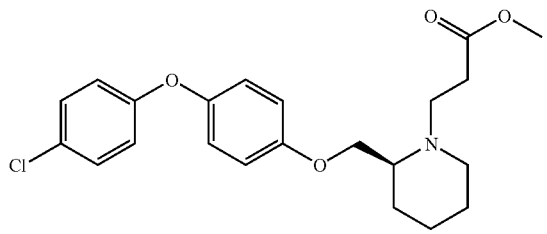

3-{(S)-2-[4-(4-Chloro-phenoxy)-phenoxymethyl]-piperidin-1-yl}-propionic acid methyl ester: A solution of (S)-2-[4-(4-chloro-phenoxy)-phenoxymethyl]-piperidine hydrochloride (218 mg, 0.615 mmol), methyl 3-bromopropionate (128 mg, 0.769 mmol), and triethylamine (124 mg, 1.23 mmol) in dichloromethane (2.5 mL) was heated for 18 h at 30° C. The mixture was diluted with 5 mls of water and extracted with dichloromethane (8 mL). The aqueous layer was re-extracted with ethyl acetate (8 mL). The combined organic layers were dried over anhy. $Na_2SO_4$ and the solvent was removed in vacuo to obtain the crude mixture, which was purified by silica gel flash chromatography to obtain the product (62 mg, 25%): $^1$H NMR (400 MHz, $CDCl_3$); δ 1.48-1.77 (m, 6H), 2.22-2.36 (m, 1H), 2.52-2.57 (m, 2H), 2.68-2.71 (m, 1H), 2.84-2.97 (m, 2H), 3.09-3.16 (m, 1H), 3.66 (s, 3H), 3.91-3.94 (dd, 1H J1=4.4 Hz, J2=10.0 Hz), 4.02-4.06 (dd, 1H J1=5.2 Hz, J2=10.0 Hz), 6.86-6.96 (m, 5H), 7.23-7.26 (m, 3H)

EXAMPLE 59

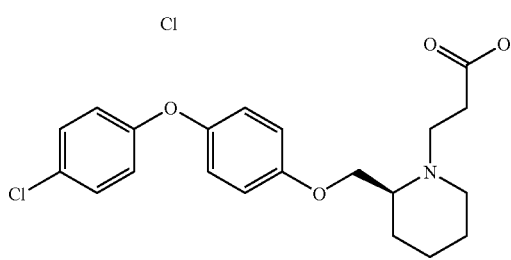

Step 1

3-{(S)-2-[4-(4-Chloro-phenoxy)-phenoxymethyl]-piperidin-1-yl}-propionic acid hydrochloride: To the product from Example 58 (25 mg, 0.0612 mmol) in 1,4-dioxane (1 mL) was added 12N HCl (0.8 mL) and the resulting mixture was stirred at 55° C. for 5 h. The solvent was removed in vacuo to obtain the product as a solid. The oil was triturated with diethyl ether (4 mL) to obtain the title product as a white solid. (19 mg, 73%): MS; m/z 390 (M+H): LCMS (UV) 90%; $^1$H NMR (400 MHz, DMSO-$d_6$) δ 1.5-1.54 (m, 1H), 1.77-1.79 (m, 4H), 1.95-1.98 (m, 1H) 2.79-2.84 (m, 2H), 3.05-3.1 (m, 1H), 3.37-3.47 (m, 3H), 3.64-3.69 (m, 1H), 4.27-4.29 (m, 2H), 6.94 (d, 2H, J=9.2 Hz), 7.04-7.06 (m, 4H), 7.4 (d, 2H J=8.8 Hz)

EXAMPLE 60

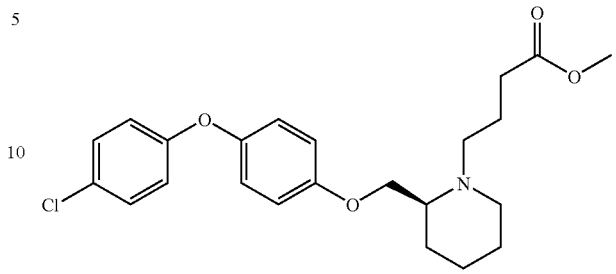

4-{(S)-2-[4-(4-Chloro-phenoxy)-phenoxymethyl]-piperidin-1-yl}-butyric acid methyl ester: A solution of (S)-2-[4-(4-chloro-phenoxy)-phenoxymethyl]-piperidine hydrochloride (218 mg, 0.615 mmol), methyl 4-bromobutyrate (139 mg, 0.769 mmol), and triethylamine (124 mg, 1.23 mmol) in dichloromethane (2.5 mL) was heated for 18 h at 30° C. The mixture was diluted with 5 mls of water and extracted with dichloromethane (8 mL). The aqueous layer was re-extracted with ethyl acetate (8 mL). The combined organic layers were dried over anhy. $Na_2SO_4$ and the solvent was removed in vacuo to obtain the crude mixture, which was purified by silica gel flash chromatography to obtain the title product (87 mg, 34%): $^1$H NMR (400 MHz, $CDCl_3$) δ 1.52-1.86 (m, 6H), 2.11-2.12 (m, 1H), 2.21-2.2 (m, 1H), 2.27-2.33 (m, 3H), 2.49-2.56 (m, 1H), 2.66-2.70 (m, 1H), 2.74-2.81 (m, 1H), 2.86-2.91 (m, 1H) 3.64 (s, 3H), 3.91-3.94 (dd, 1H J1=4.4 Hz, J2=10 Hz), 4.0-4.03 (dd, 1H J1=4.4 Hz, J2=10 Hz) 6.86-6.89 (m, 4H), 6.94-6.96 (m, 2H), 7.23-7.25 (m, 2H); MS

EXAMPLE 61

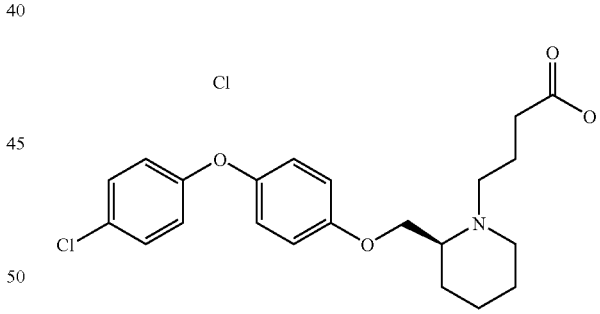

4-{(S)-2-[4-(4-Chloro-phenoxy)-phenoxymethyl]-piperidin-1-yl}-butyric acid hydrochloride: To the product from Example 60 (37 mg, 0.0885 mmol) in 1,4-dioxane (1.5 mL) was added 12N HCl (1 mL) and the resulting mixture was stirred at 55° C. for 5 h. The solvent was removed in vacuo to obtain the product as a solid. The oil was triturated with diethyl ether (4 mL) to obtain the product as a creamish red solid. (39 mg, 99%): MS; m/z 404 (M+H): LCMS (UV) 94%; $^1$H NMR (400 MHz, DMSO-$d_6$) δ 1.54-1.57 (m, 1H), 1.80-1.96 (m, 5H), 2.32-2.36 (m, 2H), 3.12-3.22 (m, 3H), 3.37-3.41 (m, 3H), 3.60-3.64 (m, 1H), 4.25-4.35 (m, 2H), 6.94 (d, 2H, J=6.8 Hz), 7.06 (s, 4H), 7.4 (d, 2H, J=6.4 Hz), 10.15 (s, 1H), 12.3 (s, 1H).

EXAMPLE 62

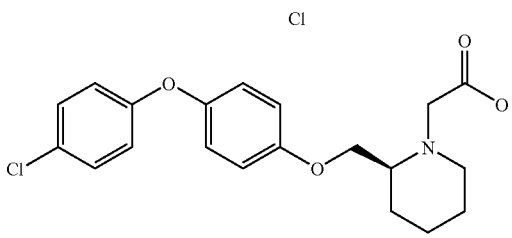

Step 1

{(S)-2-[4-(4-Chloro-phenoxy)-phenoxymethyl]-piperidin-1-yl}-acetic acid tert-butyl ester: A solution of (S)-2-[4-(4-chloro-phenoxy)-phenoxymethyl]-piperidine hydrochloride (218 mg, 0.615 mmol), t-butylbromoacetate (150 mg, 0.769 mmol), and triethylamine (124 mg, 1.23 mmol) in dichloromethane (2.5 mL) was heated for 18 h at 30° C. The mixture was diluted with 5 mls of water and extracted with dichloromethane (8 mL). The aqueous layer was re-extracted with ethyl acetate (8 mL). The combined organic layers were dried over anhy. $Na_2SO_4$ and the solvent was removed in vacuo to obtain the crude mixture, which was purified by silica gel flash chromatography to obtain the title product (125 mg, 47%).

Step 2

{(S)-2-[4-(4-Chloro-phenoxy)-phenoxymethyl]-piperidin-1-yl}-acetic acid hydrochloride: To the product from step 1 (55 mg, 0.127 mmol) in 1,4-dioxane (2 mL) was added 12N HCl (1.7 mL) and the resulting mixture was stirred at 55° C. for 5 h. The solvent was removed in vacuo to obtain the product as a solid. The oil was triturated with diethyl ether (4 mL) to obtain the title product as a white solid (27 mg, 52%): MS; m/z 374 (M−H): LCMS (UV) 94%; $^1$H NMR (400 MHz, DMSO-$d_6$) δ 1.49-1.54 (m, 1H), 1.74-1.83 (m, 4H), 1.93-1.96 (m, 1H), 3.30-3.36 (m, 2H), 3.44-3.47 (m, 1H), 3.82-3.84 (m, 1H), 4.02-4.06 (m, 1H), 4.17-4.20 (m, 2H), 4.29-4.33 (dd, 1H J1=6.8 Hz, J2=10.8 Hz), 6.93-6.95 (m, 2H) 6.95-6.98 (m, 2H), 7.00-7.07 (m, 2H), 7.39-7.41 (m, 2H).

EXAMPLE 63

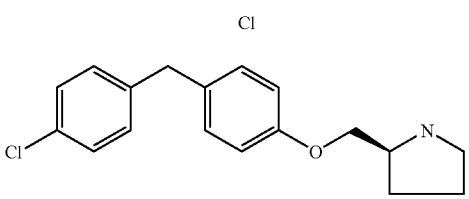

Step 1

(S)-2-[4-(4-Chloro-phenoxy)-phenoxymethyl]-1-[1,2,4]oxadiazol-5-ylmethyl-piperidine: A mixture of (S)-2-[4-(4-chloro-phenoxy)-phenoxymethyl]-piperidine hydrochloride (218 mg, 0.615 mmol), 3-(chloromethyl)-1,2,4-oxadiazole (47 mg, 0.393 mmol), and potassium carbonate (87 mg, 0.629 mmol) in DMF (2.5 mL) was heated for 18 h at rt. The solvent was removed in vacuo to obtain the crude mixture, which was purified by silica gel flash chromatography to obtain the title product (65 mg, 51%): MS; m/z 400 (M+H):: LCMS (UV) 93%.

Step 2

(S)-2-[4-(4-Chloro-phenoxy)-phenoxymethyl]-1-[1,2,4]oxadiazol-5-ylmethyl-piperidine hydrochloride: To the product from step 1 (60 mg, 0.15 mmol) was added 2M HCl in diethyl ether (6 mL) and the resulting mixture was stirred at rt for 0.5 h. The solvent was removed in vacuo to obtain the title product as a solid (56 mg, 82%). MS; m/z 400 (M+H): LCMS (UV) 95%; $^1$H NMR (400 MHz, DMSO-$d_6$) δ 1.5-2.04 (m, 6H), 3.2-3.25 (m, 1H), 3.43-3.5 (m, 1H), 3.63-3.68 (m, 1H), 4.4 (s, 2H), 4.73 (s, 2H), 6.94 (d, 2H J=9.2 Hz), 7.06 (s, 4H) 7.4 (d, 2H J=8.8 Hz), 9.91 (s, 1H)

EXAMPLE 64

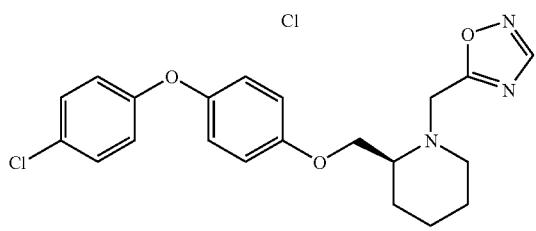

Step 1

(S)-2-[4-(4-Chloro-benzyl)-phenoxymethyl]-pyrrolidine-1-carboxylic acid tert-butyl ester: To a solution of 4-(4-chlorobenzyl)-phenol (3.08 g, 14 mmol) in DMF (30 mL) at 0-5° C. was added 60% NaH (1.05 g, 26 mmol) at 0-5° C. The reaction mixture was stirred at rt for 15 min at 0-5° C. A solution of (S)-2-(Toluene-4-sulfonyloxymethyl)-pyrrolidine-1-carboxylic acid tert-butyl ester (5 g, 14 mmol) in DMF (20 mL) was added to the above mixture at 0-5° C. The reaction mixture was warmed to it and then heated at 90° C. for 15 h. The mixture was concentrated, diluted with saturated aq $NaHCO_3$ and extracted with ethyl acetate. The aqueous layer was re-extracted with ethylacetate. The combined organic layers were dried over anhy. $MgSO_4$ and the solvent was removed in vacuo to obtain the crude mixture, which was purified by silica gel flash chromatography to obtain the title product (1.66 g, 30%).

Step 2

(S)-2-[4-(4-Chloro-benzyl)-phenoxymethyl]-pyrrolidine hydrochloride: To the product from step 1 (1.64 g, 4.1 mmol) was added 4M HCl in dioxane (45 mL) and the resulting mixture was stirred at rt for 5 h. The solvent was removed in vacuo to obtain the title product (1.38 g, 99%) $^1$H NMR (400 MHz, DMSO-$d_6$) δ 1.67-2.15 (m, 5H), 3.17-3.21 (m, 2H), 3.88 (s, 2H), 4.07-4.12 (dd, 1H J1=8.4 Hz, J2=10.8 Hz), 4.18-4.22 (dd, 1H J1=3.6 Hz, J2=10.8 Hz), 6.91 (d, 2H, J=8.8 Hz), 7.16 (d, 2H, J=8.8 Hz), 7.22 (d, 2H, J=8.8 Hz); 7.33 (d, 2H, J=8.8 Hz)

EXAMPLE 65

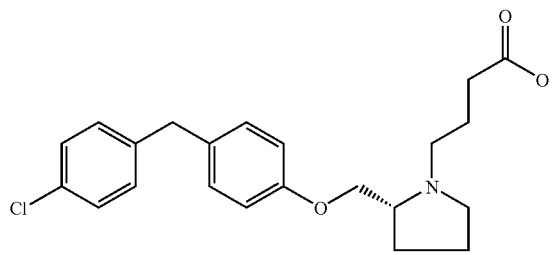

Step 1

(R)-2-[4-(4-Chloro-benzyl)-phenoxymethyl]-pyrrolidine-1-carboxylic acid tert-butyl ester: To a solution of 4-(4-chlorobenzyl)-phenol (1.1 g, 5 mmol) in DMF (15 mL) at 0-5° C. was added 60% NaH (0.4 g, 10 mmol) at 0-5° C. The reaction mixture was stirred at rt for 15 min at 0-5° C. A solution of (R)-2-(toluene-4-sulfonyloxymethyl)-pyrrolidine-1-carboxylic acid tert-butyl ester (2.14 g, 6 mmol) in DMF (5 mL) was added to the above mixture at 0-5° C. The reaction mixture was warmed to it and then heated at 90° C. for 15 h. The mixture was concentrated, diluted with saturated aq NaHCO$_3$ and extracted with ethyl acetate. The aqueous layer was re-extracted with ethylacetate. The combined organic layers were dried over anhy. MgSO$_4$ and the solvent was removed in vacuo to obtain the crude mixture, which was purified by silica gel flash chromatography to obtain the title product (1.58 g, 78%).

Step 2

(R)-2-[4-(4-Chloro-benzyl)-phenoxymethyl]-pyrrolidine hydrochloride: To the product from step 4 (1.58 g, 4 mmol) was added 4M HCl in dioxane (30 mL) and the resulting mixture was stirred at rt for 5 h. The solvent was removed in vacuo to obtain the title product (1.37 g, 99%).

Step 3

4-{(R)-2-[4-(4-Chloro-benzyl)-phenoxymethyl]-pyrrolidin-1-yl}-butyric acid methyl ester: A mixture of (R)-2-[4-(4-chloro-benzyl)-phenoxymethyl]-pyrrolidine hydrochloride (1.37 g, 4 mmol), methyl 4-bromobutyrate (916 mg, 5 mmol), and potassium carbonate (1.12 g, 8 mmol) in DMF (15 mL) was stirred for 60 h at rt. The solvent was removed in vacuo to obtain the crude mixture. The mixture was diluted with 30 mL of water and extracted with ethylacetate (130 mL). The aqueous layer was re-extracted with ethyl acetate (2×100 mL). The combined organic layers were dried over anhy. Na$_2$SO$_4$ and the solvent was removed in vacuo to obtain the crude mixture, which was purified by silica gel flash chromatography to obtain the title product (570 mg, 35%).

Step 4

4-{(R)-2-[4-(4-Chloro-benzyl)-phenoxymethyl]-pyrrolidin-1-yl}-butyic acid: A slurry of 4-{(R)-2-[4-(4-chloro-benzyl)-phenoxymethyl]-piperidin-1-yl}-butyric acid methyl ester (570 mg, 1.42 mmol) in 4:1 methanol:water (6 mL) was stirred at 50° C. for 18 h. The solvent was removed in vacuo. The mixture was diluted with water (25 mL), brought to pH 7 with 2N HCl and extracted with ethyl acetate (100 mL). The aqueous layer was re-extracted with ethyl acetate (1×80 mL). The combined organic layers were dried over anhy. Na$_2$SO$_4$ and the solvent was removed in vacuo to obtain the title product as a white solid (424 mg, 77%); HPLC 99.2%; $^1$H NMR (400 MHz, DMSO-d$_6$) δ 1.55-1.70 (m, 5H), 1.89-1.94 (m, 1H), 2.17-2.26 (m, 3H), 2.33-2.38 (m, 1H), 2.77-2.87 (m, 2H), 3.02-3.07 (m, 1H), 3.70-3.74 (dd, 1H J1=6.4 Hz, J2=10.8 Hz), 3.84-3.88 (m, 1H), 3.856 (s, 2H), 6.84 (d, 2H, J=8.8 Hz), 7.11 (d, 2H, J=8.8 Hz), 7.22 (d, 2H, J=8.4 Hz); 7.32 (d, 2H, J=8.4 Hz)

EXAMPLE 66

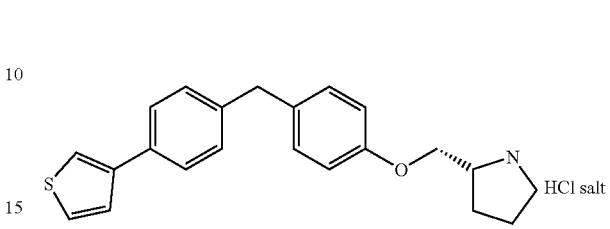

Step 1

(4-iodophenyl)-(4-methoxyphenyl)-methanone: Nitrobenzene (45 ml) was cooled in an ice-bath and treated portionwise with aluminum chloride (13.5 g, 101 mmol, 1.15 eq.) and followed by 4-iodobenzoic acid chloride (25 g, 94 mmol, 1.07 eq.) in nitrobenzene (25 ml) at a maximum of 10° C. The mixture was stirred at 0° C. for 10 minutes, where upon anisole (9.5 g, 88 mmol, 1 eq.) was added dropwise in such a manner that the temperature didn't excess 10° C. The solution then was left to warm to room temperature overnight. The yellow suspension was poured into ice-water (750 ml). The precipitate was collected by filtration and washed with water and then dissolved in dichloromethane (2 L), which was washed NaHCO$_3$ (aq.) (150 ml×2), dried over MgSO$_4$. Evaporation of solvent under reduced pressure to provide the title product in (26.7 g, 90%), $^1$H NMR (400 MHz, CDCl$_3$) δ 3.89 (s, 3H), 6.96 (d, J=8.4 Hz, 2H), 7.48 (d, J=8.0 Hz, 2H), 7.79 (d, J=8.4 Hz, 2H), 7.84 (d, J=8.0 Hz, 2H);

Step 2;

(4-iodophenyl)-(4-methoxyphenyl)-methane: To a suspension of (4-iodophenyl)-4-(methoxyphenyl-methanone (26.7 g, 79 mmol) in trifluoroacetic acid (90 ml) was added triethylsilane (30 ml, 187 mmol, 2.37 eq.) dropwise by a syringe at 0° C. The mixture was allowed to warm to room temperature with stirring overnight. After the reaction was complete (monitored by TLC analysis), the volatile material was removed on a rotary evaporator. The residue was dissolved in EtOAc (100 ml) and then washed with NaHCO$_3$ aq. (300 ml×2). The aqueous layers were extracted with EtOAc (100 ml). The combined organics was washed with 6 N HCl (50 ml×2) and dried over anhydrous MgSO$_4$. Removal of solvent gave 40 g of product, which contains silyl residue. Thus obtained product was forward to the next step without any further purification; $^1$H NMR (400 MHz, CDCl$_3$) δ 3.78 (s, 3H), 3.85 (s, 2H), 6.82 (d, J=8.8 Hz, 2H), 6.92 (d, J=8.4 Hz, 2H), 7.07 (d, J=8.4 Hz, 2H), 7.58 (d, J=8.8 Hz, 2H).

Step 3:

4-(4-iodobenzyl)-phenol: To a solution of 4-iodophenyl)-(4-methoxyphenyl)-methane (40 g,) in dichloromethane (150 ml) at −78° C. was added dropwise BBr$_3$ (158 ml, 1M solution in dichloromethane) by a syringe, keeping the temperature of the reaction mixture below −65° C. After the addition was complete, the reaction mixture was allowed to warm to room temperature, at which time the starting material was consumed. The mixture was poured into ice-water (1 L). Organic layer was separated and the aqueous layer was extracted with dichloromethane (100 ml×2). The combined organic layers were washed with NaHCO$_3$ (200 ml×2) followed by brine (100 ml), dried over MgSO₄. Evaporation of solvent under reduced pressure gave the crude product (33.8 g), which was triturated with hexane. The solid was filtered and washed with hexane. After drying, the title product was obtained (22.3 g, 91%) over the last two steps; $^1$H NMR (400 MHz, CDCl₃) δ 3.84 (s, 2H), 4.68 (s, 1H), 6.74 (d, J=8.4 Hz, 2H), 6.90 (d, J=8.8 Hz, 2H), 7.0 (d, J=8.8 Hz, 2H), 7.58 (d, J=8.4 Hz, 2H);

Step 4:

4-(4-Thiophen-3-yl-benzyl)-phenol: To a mixture of 4-(4-iodobenzyl)-phenol (12.4 g, 40 mmol), boronic acid (6.15 g, 48 mmol, 1.2 eq.), 10 wt. % Palladium on charcoal (2.12 g, 2 mmol, 0.05 eq.), potassium carbonate (16.6 g, 120 mmol, 3 eq.) was added isopropyl alcohol (200 ml) and water (40 ml). The mixture was bubbled with Ar for 10 min before it was stirred at 85° C. under Ar overnight. After cooling to room temperature, the reaction mixture was passed through a plug of celite (20 g) and washed with EtOAc thoroughly. The organics were evaporated under reduced pressure to give a residue, which was triturated with water. Thus obtained solid was washed with water thoroughly. After drying in the air, the solid was washed with hexane (50 ml×2) to give the desired product as an off-white solid (10.6 g, 99.5% yield); $^1$H NMR (400 MHz, CDCl₃) δ 3.93 (s, 2H), 4.68 (s, 1H), 6.76 (d, J=8.4 Hz, 2H), 7.08 (d, J=8.8 Hz, 2H), 7.19 (d, J=8.8 Hz, 2H), 7.36 (m, 2H), 7.40 (m, 1H), 7.50 (d, J=8.4 Hz, 2H);

Step 5.

(R)-2-(Toluene-4-sulfonyloxymethyl)-pyrrolidine-1-carboxylic acid tert-butyl ester: To a solution of (R)-2-hydroxymethyl-pyrrolidine-1-carboxylic acid tert-butyl ester (10.43 g, 52 mmol, 1 eq.) in pyridine (50 ml) was added p-toluenesulfonyl chloride (10.5 g, 55 mmol, 1.06 eq.) in one portion at 0° C. The resulting mixture was stirred at rt overnight. And then poured into ice-water (250 ml). The mixture was extracted with EtOAc (50 ml×3). The combined EtOAc layers was washed with water (50 ml) followed by 1N HCl (75 ml×4) and NaHCO₃ aq. (75 ml), dried over MgSO₄. Evaporation of solvent under reduced pressure gave the desired product as colorless oil (18 g, 100% yield); $^1$H NMR (400 MHz, CDCl₃) δ 1.28-1.39 (m, 9H), 1.60-1.90 (m, 4H), 2.42 (s, 3H), 3.20 (m, 2H), 3.83 (m, 1H), 4.0 (m, 2H), 7.48 (d, J=8.0 Hz, 2H), 7.77 (d, J=8.0 Hz, 2H);

Step 6:

(R)-2-[4-(4-Thiophen-3-yl-benzyl)-phenoxymethyl]pyrrolidine hydrochloric acid salt: To a mixture of 4-(4-Thiophen-3-yl-benzyl)-phenol (9 g, 33.8 mmol, 1 eq.) and (R)-2-(toluene-4-sulfonyloxymethyl)-pyrrolidine-1-carboxylic acid tert-butyl ester (12.6 g, 35.5 mmol, 1.05 eq.) in DMF (80 ml) was added sodium hydride (60% in mineral oil, 1.62 g, 40 mmol, 1.2 eq.) at 0° C. in one portion. The mixture was stirred at 85° C. overnight. Since (R)-2-(Toluene-4-sulfonyloxymethyl)-pyrrolidine-1-carboxylic acid tert-butyl ester was consumed with about 15% of 4-(4-thiophen-3-yl-benzyl)-phenol remaining (by TLC and $^1$H NMR analysis), 1.23 g of additional of (R)-2-(toluene-4-sulfonyloxymethyl)-pyrrolidine-1-carboxylic acid tert-butyl ester (3.46 mmol, 0.1 eq.) was added and the mixture was stirred for overnight. After cooling to room temperature, the mixture was poured into NaHCO₃ aq. (500 ml). The mixture was extracted with EtOAc (150 ml×3). The combined EtOAc layers were washed with water (50 ml×3), dried over anhydrous MgSO₄. Evaporation of solvent under reduced pressure gave the crude product as oil (15 g), of which $^1$H NMR indicated existence of 13% of starting 4-(4-thiophen-3-yl-benzyl)-phenol. Then the crude product thus obtained was treated with 4N HCl in dioxane (40 ml) overnight to form a solid, which was suspended in THF (3.5 L) and stirred at room temperature overnight. The solid was filtered off and washed with ether. After drying on a vacuum line at 65° C. overnight, 7 g of desired product was obtained as off-white solid. The mother liquid (THF) was evaporated under reduced pressure to 500 ml and the suspension was collected by filtration and washed with ether to give 2.5 g of product; m.p. 187.6~188.3° C.; LC-MS. 99% purity; HPLC: 99% purity; ee: 99%, determined by chiral HPLC; Elemental analysis (C₂₂H₂₅ClNOS): Calculated (%): C, 68.29; H, 6.51; N, 3.62; S, 8.29. Found (%): C, 67.97; H, 6.36; N, 3.49; S, 8.36. $^1$H NMR (400 MHz, DMSO-d₆) δ 1.70 (m, 1H), 1.90 (m 2H), 2.1 (m, 1H), 3.2 (m, 2H), 3.86 (m, 1H), 3.89 (S, 2H), 4.08 (dd, J=8.0 J2=10.4 Hz, 1H), 4.20 (dd, J1=3.6 Hz, J2=10.8 Hz, 1H), 6.92 (d, J=8.8 Hz, 2H), 7.19 (d, J=8.8 Hz, 2H), 7.23 (d, J=8.0 Hz, 2H), 7.51 (dd, J=1.6, 4.8 Hz, 1H), 7.62 (m, 3H), 7.79 (d, J=1.6, 3.2 Hz, 1H).

EXAMPLE 67

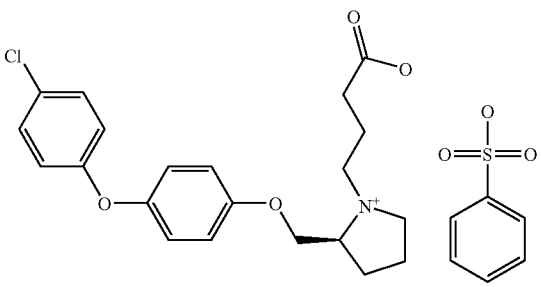

4-{(S)-2-[4-(4-chloro-phenoxy)-phenoxymethyl]-pyrrolidin-1-yl}-butyric acid phenylsulfonic acid salt: 500 mg of 4-{(S)-2-[4-(4-chloro-phenoxy)-phenoxymethyl]-pyrrolidin-1-yl}-butyric acid was dissolved in ether (120 ml). To the solution was added dropwise the solution of benzenesulfonic acid (240 mg, 1.2 eq.) in ether (4 ml). The mixture was stirred at rt for 2 h. Ether was removed to about 50 ml. The white solid was collected by filtration and washed with ether and dried on a vacuum line at 70° C. over weekend to provide the title product (595 mg, 63%); $^1$H NMR (400 MHz, DMSO-d₆) δ 1.80~2.05 (m, 5H), 2.25 (m, 1H), 2.37 (t, J=7.2 Hz, 2H), 3.17 (m, 2H), 3.44 (m, 1H), 3.62 (m, 1H), 3.94 (m, 1H), 4.15 (t, J=8.4 HZ, 1H), 4.30 (dd, J=3.2, 10.8 Hz, 1H), 6.94 (d, J=9.2 Hz, 2H), 7.06 (s, 4H), 7.31 (m, 3H), 7.41 (d, J=9.2 Hz, 2H), 7.60 (m, 2H). HPLC purity: 99%; MS?

EXAMPLE 68

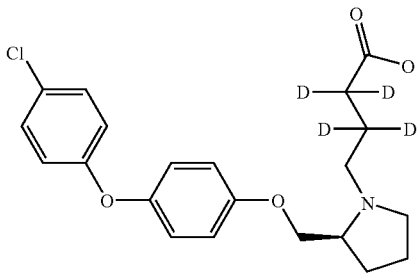

Step 1:

Succinic anhydride-d₄: To succinic acid-d₄ (1 g, 8.1 mmol, 1 eq.) in THF (200 ml) was added triethylamine (1.2 ml, 8.2 mmol, 1 eq.) followed by thiphosgene (260 mg, 1.2 mmol, 0.15 eq.). The resulting mixture was stirred at room temperature for 3 h. Then precipitate was filtered off and washed with ether. The combined organic solution was evaporated to dryness to give a residue. Thus obtained crude product was dissolved in THF (30 ml) and forward to the next step without further purification.

Step 2:

4-{(S)-2-[4-(4-Chloro-phenyoxy)-phenoxymethyl]-pyrrolidin-1-yl}-4-oxo-butyric acid (d4): To the solution of succinic anhydride-d₄ in THF prepared above was added a solution of (S)-2-[4-(4-chloro-phenoxy)-phenoxymethyl]pyrrolidine HCl salt (1.2 g, 3.95 mmol, 2.4 eq.) in THF (20 ml) at 0° C. After the addition was complete, the reaction mixture was allowed to warm to room temperature over night. 6 N HCl (excess) was added and then the mixture was stirred for 1 h before extracted with ethyl acetate (3×25 ml). The combined organic layers were dried and evaporated to dryness. The crude product was purified by chromatography on silica gel using dichloromethane and methanol (from 100:1 to 25:1) as eluent to give the title product (535 mg, 14% yield).

Step 3:

Methyl 4-{(S)-2-[4-(4-chloro-phenoxy)-phenoxymethyl]-pyrrolidin-1-yl}-4-oxo-butyrate (d4): To a solution of 4-{(S)-2-[4-(4-chloro-phenoxy)-phenoxymethyl]-pyrrolidin-1-yl}-4-oxo-butyric acid (d4) (500 mg, 1.2 mmol, 1 eq.) in a mixture of methanol (6 ml) and benzene (5 ml) was added dropwise TMSCHN₂ (2 M in hexane, 3 ml, 6 mmol, 3 eq.) with stirring. The mixture was stirred until the starting acid was consumed by indication of yellow color persists). Then volatile material was removed under reduced pressure. The crude product thus obtained was forwarded to the next step without further purification.

Step 4:

Methyl 4-{(S)-2-[4-(4-chloro-phenoxy)-phenoxymethyl]-pyrrolidin-1-yl}-butyrate (d4): To a solution of methyl 4-{(S)-2-[4-(4-chloro-phenoxy)-phenoxymethyl]-pyrrolidin-1-yl}-4-oxo-butyrate (d4) (500 mg, 1 mmol, 1 eq.) in THF (14 ml) was added BH₃ (1M in THF, 2 ml, 2 mmol, 2 eq.). The mixture was stirred under reflux overnight. After cooling to ambient temperature, THF was removed and the crude product was purified by chromatography on silica gel using dichloromethane as eluent to give the title product (200 mg, 49% yield).

Step 5:

4-{(S)-2-[4-(4-chloro-phenoxy)-phenoxymethyl]-pyrrolidin-1-yl}-butyric acid (D4) To a solution of methyl 4-{(S)-2-[4-(4-chloro-phenoxy)-phenoxymethyl]-pyrrolidin-1-yl}-butyrate (D4) (200 mg, 0.49 mmol, 1 eq.) in methanol (4 ml) was added a solution of NaOH (80 mg, 2 mmol, 4 eq.) in water (1 ml). The mixture was stirred at room temperature overnight. The volatile material was removed and the residue was added water followed by 2N HCl to pH=4. The mixture was extracted with dichloromethane (3×20 ml). The combined organic layers were dried over anhydrous MgSO₄. Removal of solvent gave a residue (210 mg), which was purified by chromatography on silica gel using dichloromethane/methanol (20:1 then 15:1) as eluent to give the title product as a solid (86 mg, 45% yield); ¹H NMR (400 MHz, DMSO-d₆) δ 1.81~2.20 (m, 4H), 3.09 (m, 2H), 3.37 (m, 1H), 3.58 (m, 1H), 3.44 (m, 1H), 4.17~4.26 (m, 2H), 6.92~6.95 (m, 2H), 7.06 (s, 4H), 7.39~7.41 (m, 2H); MS (APCI), 394 (M+1, 100), 396 (M+1, 31); LCMS (UV, ESI), m/z 394 (M+1), 396 (M+1), 92% purity.

EXAMPLE 69

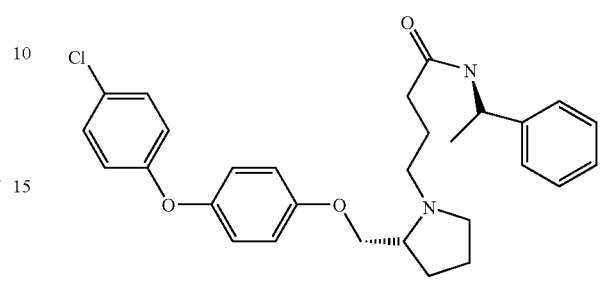

4-{(R)-2-[4-(4-chloro-phenoxy)-phenoxymethyl]-pyrrolidin-1-yl}-N—[(R)-1-phenylethyl]-butyramide: To a suspension of 4-{(R)-2-[4-(4-chloro-phenoxy)-phenoxymethyl]-pyrrolidin-1-yl}-butyric acid HCl salt (220 mg, 0.5 mmol, 1 eq.) in dichloromethane (5 ml) was added PyBrOP (280 mg, 0.6 mmol, 1.2 eq.), DIPEA (200 mg, 1.5 mmol, 3 eq.) and (R)-1-phenyl ethylamine (80 mg, 0.6 mmol 1.2 eq.). The mixture was stirred at room temperature overnight. The volatile material was removed under reduced pressure and the residue was purified by preparative TLC using dichloromethane/MeOH (15:1) as mobile phase (twice) followed by a column chromatography on silica gel using dichloromethane/MeOH (15:1) as eluent to give the desired product (12 mg, 5%); LCMS (UV, ESI), m/z 493 (M); HPLC: 99%.

EXAMPLE 70

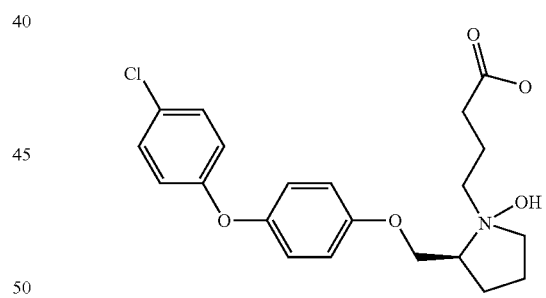

4-{(S)-2-[4-(4-Chloro-phenoxy)-phenoxymethyl]-1-hydroxy-pyrrolidin-1-yl}-butyric acid: To a solution of 4-{(S)-2-[4-(4-chloro-phenoxy)-phenoxymethyl]-pyrrolidin-1-yl}-butyric acid (95 mg, 0.33 mmol, 1 eq.) in dichloromethane (5 ml) was added mCPBA (660 mg, 2.9 mmol, 8.9 eq.). The mixture was shaken at a shaker overnight. Volatile material was removed under reduced pressure and the crude material was purified by chromatography on silica gel using ethyl acetate followed by dichloromethane/MeOH (151) as eluent to give the title product (13.5 mg, 14%); ¹H NMR (400 MHz, DMSO-d₆) δ 1.81~2.67 (m, 8H), 3.57~3.67 (m, 2H), 3.71~3.75 (m, 1H), 3.88 (m, 1H), 4.06~4.08 (m, 1H), 4.14~4.17 (m, 1H), 4.53~4.58 (dd, J1=8.0 Hz, J2=11.6 Hz, 1H), 6.92~6.97 (m, 2H), 7.04 (s, 4H), 7.37~7.40 (m, 2H); LCMS (UV, ESI), 407 (M+1), 87% purity.

EXAMPLE 71

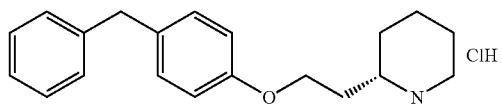

Step 1

(S)-2-[(4-Benzylphenoxy)ethyl]-piperidine-1-carboxylic acid tert-butyl ester: To a solution of (S)—N-Boc-piperidine-2-ethanol (1.00 g, 4.36 mmol), 4-hydroxydiphenylmethane (0.884 g, 4.79 mmol), and triphenylphosphine (1.26 g, 4.80 mmol) in anhydrous tetrahydrofuran (40 mL) at 0° C. under an atmosphere of nitrogen was added diisopropyl azodicarboxylate (0.92 ml, 4.80 mmol), and the resulting mixture was stirred at ambient temperature for about 20 h. The clear, yellow solution was concentrated in vacuo. The crude liquid was purified by silica gel flash chromatography to obtain the title compound as a clear, yellow oil (1.20 g, 70%): $^1$H NMR (400 MHz; CDCl$_3$) δ 7.35 (m, 2H), 7.17 (m, 3H), 7.07 (d, 2H, J=8.8 Hz), 6.79 (d, 2H, J=8.8 Hz), 4.46 (m, 1H), 3.97 (m, 5H), 2.80 (br t, 1H, J=13.2 Hz), 2.12 (m, 1H), 1.85 (m, 1H), 1.60 (m, 5H), 1.40 (m, 10H). MS, m/z 418 (M+Na)$^+$.

Step 2

(S)-2-[(4-Benzylphenoxy)ethyl]-piperidine hydrochloride: A solution of the product (1.18 g, 2.98 mmol) from step 1 in 4N HCl in dioxane (7.45 mL) was stirred at ambient temperature for about 30 min and then concentrated in vacuo. The residue was triturated with ether and dried in a 55° C. vacuum oven to afford the desired product as a white solid (0.897 g, 91%): $^1$H NMR ((400 NM; DMSO-d6): δ 8.98 (br s, 2H), 7.27 (m, 2H), 7.17 (m, 5H), 6.86 (d, 2H, J=8.8 Hz), 4.06 (m, 2H), 3.87 (s, 2H), 3.10 (m, 2H), 2.85 (t 1H), 2.16 (m, 1H), 1.91 (m, 2H), 1.60 (m, 5H). MS; m/z 296 (MH$^+$).

EXAMPLE 72

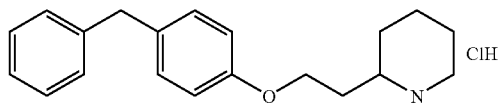

Step 1

(+/−)-2-[(4-Benzylphenoxy)ethyl]-piperidine-1-carboxylic acid tert-butyl ester: To a solution of (+/−)—N-Boc-piperidine-2-ethanol (1.50 g, 6.54 mmol), 4-hydroxydiphenylmethane (1.33 g, 7.20 mmol), and triphenylphosphine (2.36 g, 8.99 mmol) in anhydrous tetrahydrofuran (75 mL) at 0° C. under an atmosphere of nitrogen was added diisopropyl azodicarboxylate (1.74 ml, 8.99 mmol), and the resulting mixture was stirred at ambient temperature for about 20 h. Reaction was diluted with hexane and white solid was removed by filtration. The filtrate was washed with H$_2$O, dried over anhydrous MgSO$_4$, concentrated in vacuo, and purified by silica gel flash chromatography to obtain the Boc protected piperidine as a white solid (0.965 g, 37%): $^1$H NMR (400 MHz, CDCl$_3$): δ 7.27 (m, 2H), 7.17 (m, 3H), 7.07 (d, 2H, J=8.8 Hz), 6.79 (d, 2H, J=8.4 Hz), 4.46 (m, 1H), 3.97 (m, 5H), 2.80 (br t, 1H, J=12.8 Hz), 2.21 (m, 1H), 1.85 (m, 1H), 1.58 (m, 5H), 1.40 (m, 10H). MS; m/z 418 (M+Na)$^+$.

Step 2

(+/−)-2-[(4-Benzylphenoxy)ethyl]-piperidine hydrochloride: A solution of the product (0.951 g, 2.40 mmol) in step 1 in 4N HCl in dioxane (6.0 mL) was stirred at ambient temperature for about 40 min and then concentrated in vacuo. The residue was triturated with ether and dried in a 55° C. vacuum oven to afford the title product as a white solid (0.741 g, 93%): $^1$H NMR (400 MHz, DMSO-d6): δ 8.86 (br s, 2H), 7.27 (m, 2H), 7.17 (m, 5H), 6.86 (d, 2H, J=8.8 Hz), 4.05 (m, 2H), 3.87 (s, 2H), 3.22 (m, 2H), 2.86 (dt, 1H, J1=12.4 Hz, J2=2.8 Hz), 2.08 (m, 1H), 1.92 (m, 2H), 1.58 (m, 5H); MS; m/z 296 (MH$^+$).

EXAMPLE 9

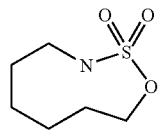

Procedure A

Step 1

Hexahydro-[1,2,3]oxathiazolo[3,4-a]pyridine 1-oxide: To a 0° C. solution of racemic 2-piperidinemethanol (0.900 g, 7.81 mmol), imidazole (2.09 g, 31.2 mmol), and triethylamine (2.39 mL, 17.2 mmol) in dichloromethane (93 mL) was added a solution of thionyl chloride (0.642 mL, 8.83 mmol) in dichloromethane (23 mL) over a 13 min period. After stirring at ambient temperature for 1.2 h, the reaction was partitioned with H$_2$O and the aqueous layer was extracted with dichloromethane (2×50 mL). The combined organic layer was washed with H$_2$O then brine, dried over Na$_2$SO$_4$, and concentrated in vacuo to give an orange liquid. Flash column chromatography purification (silica gel, 40% EtOAc in hexane) afforded the oxide as a clear, colorless liquid (1.11 g, 88%) which is a mixture of diasteriomers.

Step 2

Hexahydro-[1,2,3]oxathiazolo[3,4-a]pyridine 1,1-dioxide: To a 0° C. solution of the product (0.300, 1.86 mmol) in step 1 in anhydrous acetonitrile (4.6 mL) was added sodium (meta)periodate (0.436 g, 2.04 mmol), followed by ruthenium(III) chloride hydrate (3.90 mg, 0.0186 mmol), and then H$_2$O (4.6 mL). The mixture was stirred at 0° C. for 5 min and at ambient temperature for 10 min, then diluted with saturated NaHCO$_3$ (20 mL) and dichloromethane (20 mL). The aqueous layer was extracted with additional dichloromethane (2×10 mL). The combined organic layer was dried over Na$_2$SO$_4$, concentrated in vacuo, and purified by flash column chromatography (silica gel, 2% EtOAc in dichloromethane) to afforded the title product as a clear, colorless oil (0.165 g, 50%); $^1$H NMR (400 MHz, CDCl$_3$) δ 4.58 (dd, J1=7.6 Hz, J2=5.6 Hz, 1H), 4.19 (dd, J1=8.0 Hz, J2=9.8 Hz, 1H), 3.56 (m, 1H), 3.46 (m, 1H), 2.77 (m, 1H), 1.95-1.80 (m, 3H), 1.70-1.55 (m, 1H), 1.50-1.29 (m, 2H).

Procedure B

Step 1

Hexahydro-[1,2,3]oxathiazolo[3,4-a]pyridine 1,1-dioxide: To a −78° C. hazy solution under a nitrogen atmosphere of racemic 2-piperidinemethanol (0.576 g, 5.00 mmol) and triethylamine (1.42 mL, 10.0 mmol) in anhydrous dichloromethane (30 mL) was added a solution of sulfuryl chloride (0.41 mL, 5.06 mmol) in anhydrous dichloromethane (30 mL) and the reaction was stirred for around 18 h from −78° C. to ambient temperature. The clear, yellow solution was washed with 1.0N HCl (2×25 mL) and brine (25 mL), dried over $Na_2SO_4$, concentrated in vacuo to a dark yellow oil, and purified by flash column chromatography (silica gel, ether) to afford the title product as a clear yellow oil (0.342 g, 39%). The proton NMR was identical to the desired product in procedure A, step 2.

EXAMPLE 73

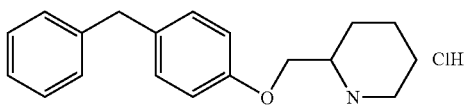

Step 1

(+/−)-2-[(4-Benzylphenoxy)methyl]-piperidine: A solution of 1,1-dioxo-2-oxa-1-thia-7a-azaperhydronoindene (0.300 g, 1.69 mmol), 4-hydroxydiphenylmethane (0.311 g, 1.69 mmol), and potassium carbonate (0.467 g, 3.38 mmol) in DMF (3.38 mL) at 40° C. under an atmosphere of nitrogen was heated for 18 h and then at 60° C. for 3.5 h. The ambient mixture's pH was adjusted to 1 with an aqueous 20% $H_2SO_4$ solution and stirred at ambient temperature for about 20 h. After the reaction solution's pH was adjusted to 14 with 5N NaOH, the white precipitate was collected and dried in a vacuum oven to give a white solid (1.03 g). The aqueous filtrate was extracted with EtOAc. The organic layer was dried over anhydrous $Na_2SO_4$ and concentrated in vacuo to give a yellow oil. TLC analysis of both the solid and oil showed the same major spot that was stained by Ninhydrin. The solid and oil were combined and purified by silica gel flash chromatography to obtain the title product as a clear, colorless oil (0.106 g, 22%). $^1$H NMR (400 MHz, $CDCl_3$): δ 7.27 (m, 2H), 7.17 (m, 3H), 7.08 (d, 2H, J=8.8 Hz), 6.82 (d, 2H, J=8.8 Hz), 3.91 (s, 2H), 3.85 (m, 1H), 3.77 (m, 1H), 3.10 (br d, 1H, J=12 Hz), 2.95 (m, 1H), 2.68 (dt, 1H, J2=11.6 Hz, J2=2.8 Hz), 2.22 (br s, 1H), 1.83 (m, 1H), 1.43 (m, 2H), 1.25 (m, 1H).

Step 2

(+/−)-2-[(4-Benzylphenoxy)methyl]-piperidine hydrochloride: A mixture of the product (0.090 g, 0.320 mmol) in step 1 in 4N HCl in dioxane was stirred for 5 min at ambient temperature and then diluted with ether. The precipitate was collected by filtration, washed with ether, and dried in vacuo to afford the title product as a white solid (0.084 g, 82%): $^1$H NMR (400 MHz, DMSO-$d_6$): δ 9.15 (br s, 2H), 7.28 (m, 2H), 7.18 (m, 5H), 6.93 (d, 2H, J=8.4 Hz), 4.11 (m, 2H), 3.88 (s, 2H), 3.43 (m, 1H) 3.23 (br d, 1H, J=12.8 Hz), 2.89 (br t, 1H, J=10.8 Hz), 1.67 (m, 6H). MS; m/z 282 (MH)$^+$.

EXAMPLE 74

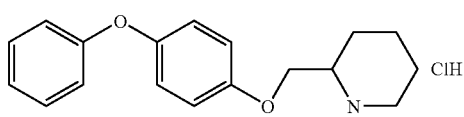

(+/−)-2-[(4-phenoxyphenoxy)methyl]-piperidine hydrochloride: A solution of 1,1-dioxo-2-oxa-1-thia-7a-azaperhydronoindene (0.400 g, 2.26 mmol), 4-phenoxyphenol (0.315 g, 1.69 mmol), and potassium carbonate (0.467 g, 3.38 mmol) in DMF (3.38 mL) at 40° C. under an atmosphere of nitrogen was heated for 18 h and then at 66° C. for 3.5 h. The ambient mixture's pH was adjusted to 1 with an aqueous 20% $H_2SO_4$ solution and stirred at ambient temperature for about 20 h. The reaction solution's pH was adjusted to 14 with 5N NaOH, diluted with $H_2O$ (20 mL), and extracted with EtOAc (3×10 mL). The organic layer was washed with $H_2O$ (2×10 mL), brine (10 mL), dried over anhydrous $Na_2SO_4$, and concentrated to an oil. The oil was treated with 2M HCl in ether to give the title product as a white solid (0.295 g, 54%): $^1$H NMR (400 MHz, DMSO-$d_6$): δ 9.09 (br s, 2H), 7.35 (m, 2H), 7.05 (m, 5H), 6.93 (d, 2H, J=7.6 Hz), 4.15 (m, 2H), 3.46 (br s, 1H), 3.26 (br d, 1H, J=12.4 Hz), 2.86 (m, 1H), 1.69 (m, 6H). MS; m/z 284 (MH)$^+$.

EXAMPLE 75

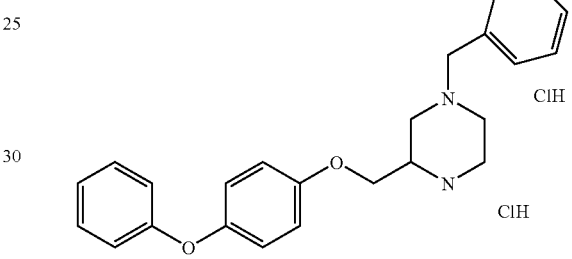

Step 1

5-Benzyl-hexahydro-2-oxa-1-thia-5,7a-diaza-indene 1-oxide: The compound was synthesized according to Procedure A, Step 1 by the addition of a solution of thionyl chloride (0.80 mL, 11.0 mmol) in dichloromethane (29 mL) to a solution of racemic 4-N-benzyl-2-hydroxymethylpiperidine (2.00 g, 9.70 mmol), imidazole (2.59 g, 38.2 mmol), and triethylamine (2.99 mL, 21.4 mmol) in dichloromethane (116 mL) to give a crude yellow oil. Flash chromatography purification (silica gel, 40% EtOAc in hexane) gave the title product as a diastereomer mixture (1.82 g, 74%).

Step 2

5-Benzyl-hexahydro-2-oxa-1-thia-5,7a-diaza-indene 1,1-dioxide mmol): The compound was synthesized according to Procedure A, Step 2 from the product (1.80 g, 7.13 mmol) in step 1, anhydrous acetonitrile (4.6 mL), sodium (meta)periodate (1.67 g, 7.82 mmol), ruthenium(III) chloride hydrate (15 mg, 0.072 and $H_2O$ (12 mL) to give a crude brown oil. Flash chromatography purification (silica gel, 40% EtOAc in hexane) gave the title product as a white solid (1.15 g, 60%); $^1$H NMR (400 MHz, $CDCl_3$): δ 7.32 (m, 5H), 4.52 (dd, 1H, J1=7.6 Hz, J2=6.4 Hz), 4.26 (dd, 1H, J1=9.2 Hz, J2=8.0 Hz), 3.81 (m, 1H), 3.64 (d, 1H, J=13.2 Hz), 3.55 (d, 1H, J=12.8 Hz), 3.44 (dt, 1H, J1=12.0 Hz, J2=3.2 Hz), 3.12 (dt, 1H, J1=12.0 Hz, J2=3.2 Hz), 2.88 (dd, 1H, J1=11.2 Hz, J2=3.2 Hz), 2.81 (dt, 1H, J1=11.6 Hz, J2=3.2 Hz), 2.46 (m, 1H), 2.24 (dd, 1H, J1=11.2 Hz, J2=8.8 Hz).

Step 3

1-Benzyl-3-(4-phenoxymethyl)-piperazine dihydrochloride: A solution of the product (0.606 g, 2.26 mmol) in step 2,4- phenoxyphenol (0.315 g, 1.69 mmol), and potassium carbonate (0.467 g, 3.38 mmol) in DMF (3.38 mL) at 60° C. under an atmosphere of nitrogen was heated for 6 h. The ambient mixture's pH was adjusted to 1 with an aqueous 20% $H_2SO_4$ solution and stirred at ambient temperature for about 20 h. The reaction mixture was basified to pH 12 with 5N NaOH, diluted with $H_2O$, and extracted with EtOAc. The combined organic layer was washed with $H_2O$ then brine, dried over anhydrous $Na_2SO_4$, and concentrated in vacuo to give a yellow semi-solid. The semi-solid was triturated with 2.0 M HCl in ether to give an impure off white solid. The solid was diluted with $H_2O$, basified with 5N NaOH, and extracted with EtOAc. The organic layer was washed with $H_2O$ then brine, dried over anhydrous $Na_2SO_4$, concentrated in vacuo, and purified by flash chromatography (silica gel, 5% MeOH in dichloromethane) to give a yellow oil. The oil was triturated with 2.0 M HCl in ether to afford the title product as a tan solid (0.249 g, 33%): $^1$H NMR (400 MHz, $CD_3OD$): δ 7.65 (br s, 2H), 7.52 (br s, 3H), 7.31 (t, 2H, J=8.0 Hz), 7.06 (m, 3H), 6.98 (m, 2H), 6.91 (d, 2H, J=7.6 Hz), 4.52 (s, 2H), 4.26 (m, 3H), 3.66 (m, 6H). MS; m/z 375 $(MH)^+$.

EXAMPLE 76

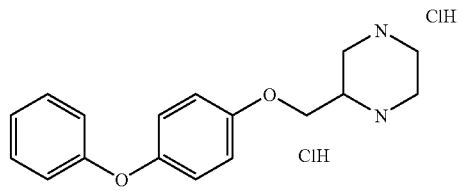

3-(4-Phenoxymethyl)-piperazine dihydrochloride: A mixture of 1-Benzyl-3-(4-phenoxymethyl)-piperazine dihydrochloride (0.190, 0.427 mmol) and palladium hydroxide on activated carbon (19 mg) in anhydrous MeOH (3 mL) was hydrogenated at ambient temperature at 60 psi for 24 h. The mixture was filtered through a celite bed, and the filtrate was concentrated in vacuo to a tan solid. The solid was triturated with 2.0 M HCl in ether and dried to give the title product as a tan solid (70 mg, 46%): $^1$H NMR (400 MHz, $CD_3OD$): δ 7.31 (m, 2H), 7.07 (m, 3H), 6.99 (d, 2H, J=9.6 Hz), 6.92 (d, 2H, J=8.0 Hz), 4.37 (dd, 1H, J=10.8 Hz, J=3.6 Hz), 4.29 (dd, 1H, J=10.8 Hz, J=5.6 Hz), 4.14 (m, 1H), 3.79 (m, 3H), 3.56 (m, 3H). MS; m/z 285 $(MH)^+$.

EXAMPLE 77

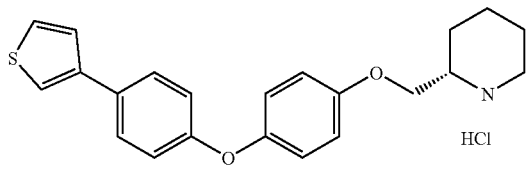

Step 1

(S)-2-[4-(-Thiophen-3-yl-phenoxy)-phenoxymethyl]-piperidine-1-carboxylic acid tert-butyl ester: A mixture of 4-(thiophen-3-yl)phenol (0.176 g, 1.00 mmol), (S)-2-(4-iodophenoxymethyl)piperidine-1-carboxylic acid tert-butyl ester (0.334 g, 0.800 mmol), N,N-dimethylglycine hydrochloride (0.0112 g, 0.800 mmol), cesium carbonate (0.547 g, 1.68 mmol), and copper(1) iodide (0.0057 g, 0.030 mmol) in anhydrous 1,4-dioxane (3.6 mL) was refluxed under an atmosphere of nitrogen for 2 d. The ambient greenish brown mixture was diluted with $H_2O$ (100 mL) and extracted with EtOAc (3×25 mL). The combined EtOAc layers were washed with $H_2O$ (2×25 mL) then brine (25 mL), dried over anhydrous sodium sulfate, and concentrated in vacuo to a brown semi solid. The crude solid was purified by flash column chromatography (silica gel, 15% EtOAc in hexane) to give the Boc protected amine as a clear, yellow oil (0.103 g, 28%): $^1$H NMR (400 MHz, $CDCl_3$): δ 7.52 (d, 2H, J=8.8 Hz), 7.32 (m, 3H), 6.96 (m, 4H), 6.90 (d, 2H, J=9.2 Hz), 4.58 (m, 1H), 4.02 (m, 3H), 2.84 (t, 1H, J=12.8 Hz), 1.90 (m, 1H), 1.47 (m, 16H).

Step 2

(S)-2-[4-(-Thiophen-3-yl-phenoxy)-phenoxymethyl]-piperidine hydrochloride: A solution of the product (0.090 g, 0.193 mmol) in step 2 in 2N HCl in $Et_2O$ (3 mL, 6.0 mmol) was stirred at ambient temperature for 2 h in a sealed vial to give a white mixture. The mixture was concentrating in vacuo, triturated with anhydrous ether, and concentrated in vacuo to give the desired product as a tan solid (0.055 g, 71%): %): $^1$H NMR (400 MHz, $CD_3OD$): δ 7.61 (d, 2H, J=8.4 Hz), 7.53 (m, 1H), 7.45 (m, 1H), 7.40 (dd, 1H, J1=4.8 Hz, J2=1.6 Hz), 7.03 (m, 4H), 6.95 (d, 2H, J=9.2 Hz), 4.23 (dd, 1H, J1=10.8 Hz, J2=3.6 Hz), 4.05 (dd, 1H, J1=10.8 Hz, J2=7.2 Hz), 3.50 (m, 2H), 3.08 (t, 1H, J=12.8 Hz), 2.02 (m, 3H), 1.70 (m, 3H). MS; m/z 366 $(MH)^+$.

EXAMPLE 78

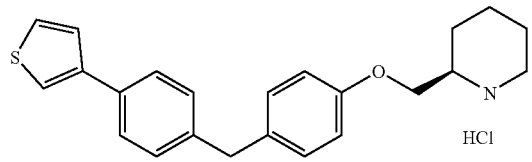

Step 1

3-(4-(4-Methoxy-benzyl)-phenyl]-thiophene: To a mixture of 1-(4-iodobenzyl)-4-methoxybenzene (0.300 g, 0.925 mmol), 2N aqueous $NaHCO_3$ solution (1.85 mL, 3.7 mmol), and 3-thiopheneboronic acid (0.237 g, 1.85 mmol) in a solution of toluene/EtOH (17.6/0.8 mL) at ambient temperature under an atmosphere of nitrogen was added tetrakis(triphenylphosphine)palladium(0) (0.107 g, 0.093 mmol). The mixture was refluxed for 18 h, cooled to ambient temperature, and diluted with $H_2O$ (30 mL). After extracting with EtOAc (3×25 mL) and filtering the EtOAc through a silica gel bed, the organic layer was washed with brine (25 mL), dried over anhydrous sodium sulfate, concentrated in vacuo, and purified by flash column chromatography (70% hexane in dichloromethane) to afford the title product as a white solid (0.125 g, 48%): $^1$H NMR (400 MHz, $CDCl_3$): δ 7.50 (d, 2H, J=8.4 Hz), 7.40 (t, 1H, J=2.0 Hz), 7.36 (d, 2H, J=2.4 Hz), 7.20 (d, 2H, J=8.4 Hz), 7.12 (d, 2H, J=8.8 Hz), 6.84 (d, 2H, J=8.8 Hz), 3.94 (s, 2H), 3.78 (s, 3H).

Step 2

4-(4-Thiophen-3-ylbenzyl)phenol: To a solution of the product (2.00 g, 7.12 mmol) in step 1 in dichloromethane (64 mL) at −78° C. under an atmosphere of nitrogen was added a solution of 1.0M boron tribromide in dichloromethane (2.03 mL, 21.5 mmol) in dichloromethane (20 mL) over a 3 m period. The solution was maintained at −78° C. for 1 hour and then stirred at ambient temperature for 2 h. The solution was pour into ice water (300 mL) and extracted with EtOAc (3×100 mL). The organic layer was washed with brine (100 mL), dried over anhydrous sodium sulfate, concentrated in vacuo, and purified by flash column chromatography (15% EtOAc in hexane) to give the title product as a white solid (1.19 g, 63%): $^1$H NMR (400 MHz, CDCl$_3$): δ 7.51 (d, 21-L J=8.0 Hz), 7.40 (m, 1H), 7.36 (d, 2H, J=2.4 Hz), 7.19 (d, 2H, J=8.8 Hz), 7.07 (d, 2H, J=8.8 Hz), 6.76 (d, 2H, J=8.8 Hz), 4.63 (br s, 1H), 3.92 (s, 2H).

Step 3

(R)-2-[4-(4-Thiophen-3-yl-benzyl)-phenoxymethyl]-piperidine hydrochloride: A solution of (R)-1,1-dioxo-2-oxa-1-thia-7a-azaperhydronoindene (0.585 g, 3.30 mmol), the product (0.879 g, 3.30 mmol) in step 2, and potassium carbonate (0.911 g, 6.59 mmol) in DMF (23 mL) under an atmosphere of nitrogen was heated for 18 h at 66° C. The ambient mixture's pH was adjusted to 1 with an aqueous 20% H$_2$SO$_4$ solution and stirred at ambient temperature for about 20 h. After the reaction solution's pH was adjusted to 12 with 5N NaOH, the white precipitate was collected, washed with H$_2$O, and dried in a vacuum oven to give a white solid (3.90 g). The solid was purified by silica gel flash chromatography (5-10% MeOH in dichloromethane) to give the free piperidine as a white solid (0.368 g, 31%). The solid was stirred in 2M HCl in ether (10 mL) at ambient temperature for 3 h. The white solid was collected by filtration, washed with ether, and dried at 50° C. in a vacuum over to give the title product as a white solid (0.299 g, 23%): $^1$H NMR (400 MHz, CDCl$_3$): δ 7.55 (m, 3H), 7.43 (m, 2H), 7.18 (m, 4H), 6.95 (d, 2H, J=8.8 Hz), 4.19 (dd, 1H, J1=10.8 Hz, J2=3.6 Hz), 4.01 (dd, 1H, J1=10.8 Hz, J2=7.2 Hz), 3.92 (s, 2H), 3.53 (s, 1H), 3.42 (d, 1H, J=12.8 Hz), 3.05 (m, 1H), 1.96 (m, 3H), 1.69 (m, 3H). MS; m/z 364 (MH)$^+$.

EXAMPLE 79

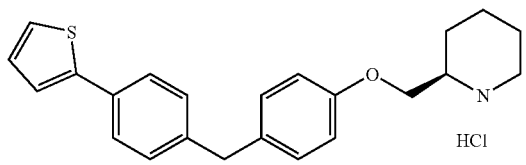

Step 1

3-(4-(4-Methoxy-benzyl)-phenyl]-thiophene: To a mixture of 1-(4-iodobenzyl)-4-methoxybenzene (0.300 g, 0.925 mmol), 2N aqueous NaHCO$_3$ solution (1.85 mL, 3.7 mmol), and 2-thiopheneboronic acid (0.237 g, 1.85 mmol) in a solution of toluene/EtOH (17.6/0.8 mL) at ambient temperature under an atmosphere of nitrogen was added tetrakis(triphenylphosphine)palladium(0) (0.107 g, 0.093 mmol). The procedure in Example 15, Step 1 was followed to give the title product as a white solid (2.06 g, 79%): $^1$H NMR (400 MHz, CDCl$_3$): δ 7.52 (d, 2H, J=8.4 Hz), 7.25 (m, 2H), 7.18 (d, 2H, J=8.4 Hz), 7.11 (d, 2H, J=8.8 Hz), 7.05 (m, 1H), 6.84 (d, 2H, J=8.8 Hz), 3.93 (s, 2H), 3.78 (s, 3H).

Step 2

4-(4-Thiophen-2-yl-benzyl)-phenol: To a solution of the product (0.500 g, 1.78 mmol) in step 1 in dichloromethane (16 mL) at −78° C. under an atmosphere of nitrogen was added a solution of boron tribromide (0.506 g 5.35 mmol) in dichloromethane (5 mL) over a 5 m period. The procedure in Example 15, Step 2 was followed to give the title product as a white solid (0.313 g, 66%): $^1$H NMR (400 MHz, CDCl$_3$): δ 7.53 (d, 2H, J=8.4 Hz), 7.25 (m, 3H), 7.17 (d, 2H, J=8.4 Hz), 7.06 (m, 2H), 6.76 (d, 2H, J=8.8 Hz), 4.60 (s, 1H), 3.92 (s, 2H).

Step 3

(R)-2-[4-(4-Thiophen-2-yl-benzyl)-phenoxymethyl]-piperidine hydrochloride: A solution of (R)-1,1-dioxo-2-oxa-1-thia-7a-azaperhydronoindene (0.935 g, 5.28 mmol), the product (1.30 g, 4.88 mmol) in step 2, and potassium carbonate (1.35 g, 9.75 mmol) in DMF (34 mL) under an atmosphere of nitrogen was heated for 18 h at 66° C. The procedure in Example 15, Step 2 was followed to give the title product as a white solid (670 g, 34%): $^1$H NMR (400 MHz, CD$_3$OD): δ 7.53 (d, 2H, J=8.4 Hz), 7.42 (d, 2H, J=4.4 Hz)), 7.18 (m, 4H), 6.50 (m, 1H), 6.95 (d, 2H, J=8.8 Hz), 4.19 (dd, 1H, J1=10.8 Hz, J2=3.6 Hz), 3.98 (dd, 1H, J1=10.8 Hz, J2=7.6 Hz), 3.92 (s, 2H), 3.54 (m, 1H), 3.42 (br d, 1H, J=12.8 Hz), 3.05 (m, 1H), 1.97 (m, 3H), 1.69 (m, 3H); MS; m/z 364 (MH)$^+$.

EXAMPLE 80

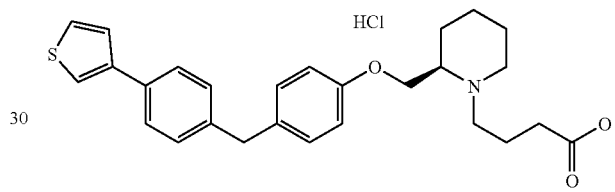

Step 1

4-{(R)-2-[4-(4-Thiophen-3-yl-benzyl)-phenoxymethyl]-piperidin-1-yl}-butyric acid Methyl ester: A mixture of (R)-2-[4-(4-thiophen-2-yl-benzyl)-phenoxymethyl]-piperidine hydrochloride (0.245 g, 0.613 mmol), ethyl 4-bromobutyate (0.102 mL, 0.705 mmol), and potassium carbonate (0.170 g, 1.23 mmol) in DMF (4 mL) was stirred sealed at ambient temperature for 18 h and than diluted with H$_2$O (40 mL). The aqueous mixture was extracted with EtOAc (3×20 mL), and the organic layer was washed with H$_2$O (2×10 mL) and brine (10 mL), and dried over N$_2$SO$_4$. The filtrate was concentrated in vacuo to a white solid. The crude solid was purified by silica gel flash chromatography to obtain the title product as a clear, yellow oil (0.168 g, 57%).

Step 2

4-{(R)-2-[4-(4-Thiophen-3-yl-benzyl)-phenoxymethyl]-piperidin-1-yl}-butyric acid hydrochloride: A two liquid phase solution of the product (0.150 g, 0.314 mmol) in step 1 and LiOHH$_2$O (0.153 g, 3.65 mmol) in H$_2$O (0.30 mL) and THF (2.5 mL) was stirred at ambient temperature for 48 h and then the pH was adjusted to around 6-7 with 1N HCl solution. After extracting the reaction with EtOAc (3×10 mL), the ordanic layer was dried over Na$_2$SO$_4$. The filtrate was concentrated in vacuo to give yellow semi-solid which was purified by flash chromatography to give a yellow oil. The oil was converted to the hydrochloride salt with 2N HCl in Et$_2$O to give the title product as an off white solid (0.030 g, 20%): $^1$H NMR (400 MHz, CD$_3$OD): δ 7.55 (m, 3H), 7.43 (m, 2H), 7.18 (m, 4H), 6.95 (d, 2H, J=8.4 Hz), 4.42 (dd, 1H, J1=11.2 Hz, J2=2.8 Hz), 4.02 (dd, 1H, J1=11.2 Hz, J2=4.0 Hz), 3.62 (s, 2H), 3.59 (m, 2H), 3.30 (m, 2H), 3.10 (m, 2H), 2.44 (m, 2H), 1.93 (m, 7H). 1.67 (m, 1H); MS; m/z 450 (MH)$^+$.

EXAMPLE 81

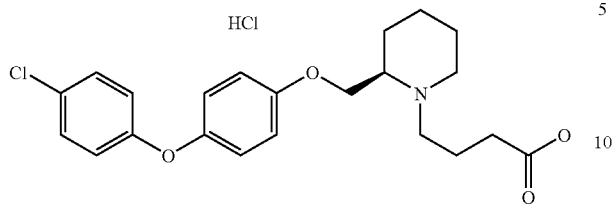

Step 1

(R)-2-[4-(4-Chloro-phenoxy)-phenoxymethyl]-piperidine: The desired piperidine was prepared by the procedure in Example 16, Step 3 from 4-(4-chloro-phenoxy)-phenol (0.951 g, 4.31 mmol), potassium carbonate (1.09 g, 7.90 mmol), (R)-1,1-dioxo-2-oxa-1-thia-7a-azaperhydronoindene (0.700 g, 3.95 mmol), and DMF (20 mL) as a tan solid (0.740 g, 53%): $^1$H NMR (400 MHz, CDCl$_3$): δ 7.24 (d, 2H, J=9.2 Hz), 6.94 (m, 2H), 6.87 (m, 4H), 3.89 (m, 1H), 3.79 (m, 1H), 3.13 (br d, 1H, J=11.6 Hz), 2.97 (m, 1H), 2.70 (dt, 1H, J1=12.0 Hz, J2=2.8 Hz), 2.12 (br s, 1H), 1.85 (m, 1H), 1.66 (m, 2H), 1.39 (m, 3H).

Step 2

4-{(R)-2-[4-(4-Chloro-phenoxy)-phenoxymethyl]-piperidin-1-yl}-butyric acid tert-butyl ester: To a mixture of the product (0.300 g, 0.944 mmol) in step 1, tert-butyl 4-bromobutryate (0.275 g, 1.23 mmol), and sodium carbonate (0.201 g, 1.90 mmol) in acetonitrile (3,8 mL) under an atmosphere of nitrogen was heated at 50° C. for around 18 h. To the reaction mixture was add more tert-butyl 4-bromobutryate (0.150 g, 0.622 mmol), and sodium carbonate (0.201 g, 1.90 mmol), and was heat another 24 h at 50° C. The mixture was diluted with H$_2$O (60 mL) and extracted with EtOAc (3×20 mL). The organic layer was washed with H$_2$O (2×20 mL) and brine (20 mL), and then dried over Na$_2$SO$_4$. The filtrate was concentrated in vacuo to give a clear yellow oil. The oil was purified by flash chromatography to give the tert-butyl ester as a clear tan oil (0.180 g, 41%): $^1$H NMR (CDCl$_3$): δ 7.25 (m, 2H), 6.91 (m, 6H), 4.02 (m, 1H), 3.94 (m, 1H), 2.91 (dt, 1H, J=11.6 Hz, J=4.0 Hz), 2.73 (m, 2H), 2.54 (m, 1H), 2.33 (m, 1H), 2.21 (dt, 2H, J1=7.6 Hz, J2=2.8 Hz), 1.78 (m, 4H), 1.60 (m, 3H), 1.42 (s, 9H), 1.35 (m, 1H).

Step 3

4-{(R)-2-[4-(4-Chloro-phenoxy)-phenoxymethyl]-piperidin-1-yl}-butyric acid hydrochloride: A solution of the product (0.183 g, 0.398 mmol) in step 2 m 2M HCl in Et$_2$O (3 mL, 6.00 mmol) was stirred at ambient temperature in a sealed vial for 18 h. The solution was concentrated in vacuo to a solid and the solid was triturated with Et$_2$O. The solid was dried in a 50° C. vacuum oven to give the title product as a white solid (0.121 g, 69%): $^1$H NMR (400 MHz, CD$_3$OD): δ 7.30 (d, 2H, J=8.8 Hz), 7.08 (d, 2H, J=8.8 Hz), 7.00 (d, 21-L J=9.2 Hz), 6.90 (d, 2H, J=9.2 Hz), 4.86 (br d, 1H, J=10 Hz), 4.12 (br d, 1H, J=11.2 Hz), 3.60 (m, 2H), 3.31 (m, 3H), 2.47 (br s, 2H), 1.98 (m, 7H), 1.70 (m, 1H). MS; m/z 403 (M)$^+$.

EXAMPLE 83

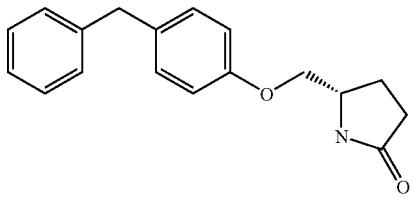

Step 1

(S) Toluene-4-sulfonic acid 5-oxo-pyrrolidin-2-ylmethyl ester: To a solution of (S)-5-(hydroxymethyl)-2-pyrrolidinone (230 mg, 2 mmol) in dry pyridine (3 mL) was added tosyl chloride (380 mg, 2 mmol) in pyridine (2 mL) drop by drop over 15 mm at 0° C. and under nitrogen. Reaction mixture was stirred at 0° C. for 2 h and at rt for 16 h. Pyridine was removed and residue was suspended in 3 mL of water. pH was adjusted to 9 with saturated aq. NaHCO$_3$ solution and product was extracted with EtOAc. Organic layer was washed with brine, dried over MgSO$_4$ and concentrated to give the title compound (98 mg, 18%).

Step 2

(S) 5-(4-Benzyl-phenoxymethyl)-pyrrolidin-2-one hydrochloride salt: To a solution of the product (67 mg, 0.25 mmol) from step 1 in anhydrous DMF (0.5 mL) was added 4-hydroxydiphenyl methane (46 mg, 0.25 mmol) in DMF (0.5 mL) and powdered K2CO3 (69 mg, 0.5 mmol). Reaction mixture was heated at 80° C. for 16 h under nitrogen. DMF was removed, residue was dissolved in EtOAc and washed with saturated aq. NaHCO3, 1N NaOH, water and brine. Then it was dried over MgSO$_4$ and concentrated to give off white solid. Off white solid was dissolved in 1 mL of MeOH and 2M HCl in ether was added until white solid precipitated out. Precipitate was collected by filtration, washed with ether and dried under vacuum to give the title compound (16.5 mg, 23%): MS; m/z 282.5 (M+H); $^1$H NMR (400 MHz, DMSO-d$_6$); δ 1.79-1.85 (m, 1H), 2.09-2.26 (m, 3H), 3.79-3.91 (m, 5H), 6.85 (dd, 2H, J1=6.4 Hz, J2=2.4 Hz), 7.12-7.21 (m, 5H), 7.25-7.29 (m, 2H), 7.80 (s, 1H); HPLC (UV); 90%.

EXAMPLE 84

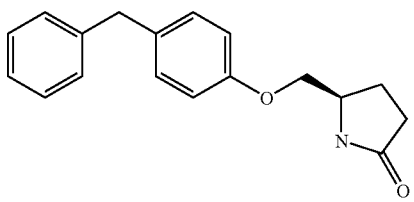

Step 1

(R) Toluene-4-sulfonic acid 5-oxo-pyrrolidin-2-ylmethyl ester: To a solution of R (−)-5-(hydroxymethyl)-2-pyrrolidinone (690 mg, 6 mmol) in dry pyridine (8 mL) was added tosyl chloride (1140 mg, 6 mmol) drop by drop over 20 min at 0° C. and under nitrogen. Reaction mixture was stirred at 0° C. for 2 h and at rt for 16 h. Pyridine was removed and residue was partioned between saturated aq. NaHCO3 and EtOAc.

Organic layer was removed, washed with water, brine, dried over MgSO4 and concentrated to give the title compound (254 mg, 16%).

Step 2

(R) 5-(4-Benzyl-phenoxymethyl)-pyrrolidin-2-one: To a solution of the product (135 mg, 0.5 mmol) from step 1 in anhydrous DMF (1 mL) was added 4-hydroxydiphenyl methane (92 mg, 0.5 mmol) in DMF (1 mL) and powdered K2CO3 (138 mg, 1 mmol). Reaction mixture was heated at 80° C. for 48 h under nitrogen. DMF was removed, residue was dissolved in EtOAc and washed with saturated aq. NaHCO3, 1N NaOH, water and brine. Then it was dried over MgSO$_4$ and concentrated to give off white solid. Off white solid was dissolved in 1 mL of MeOH and 2M HCl in ether was added until white solid precipitated out. Precipitated was collected by filtration, washed with ether and dried under vacuum to give the title compound (28 mg, 20%): MS; m/z 282.5 (M+H); $^1$H NMR (400 MHz, DMSO-d$_6$); δ 1.80-1.84 (m, 1H), 2.09-2.26 (m, 3H), 3.79-3.91 (m, 5H), 6.85 (dd, 2H, J1=6.8 Hz, J2=2 Hz), 7.12-7.20 (m, 5H), 7.25-7.29 (m, 2H), 7.80 (s, 1H) HPLC (ELSD); 99.7%.

EXAMPLE 85

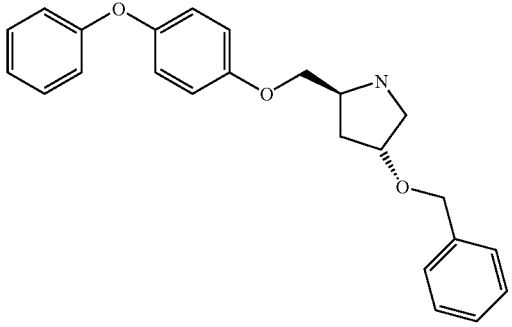

Step 1

(2S,4R)-4-Benzyloxy-2-hydroxymethyl-pyrrolidine-1-carboxylic acid tert-butyl ester: (2S,4R)-4-Benzyloxy-pyrrolidine-1,2-dicarboxylic acid 1-tert-butyl ester (960 mg, 3 mmol) in THF (5 mL) was cooled to 0° C. using ice-water bath. Then 1M solution of BH3 (6 mL, 6 mmol) in THF was added under nitrogen over period of 30 min. Reaction was stirred at 0° C. for 2 h and at rt for another 1 h. Reaction mixture was poured over ice water and product was extracted with EtOAc. Organic layers were combined, washed with water, brine, saturated sodium bicarbonate, dried over anhydrous MgSO$_4$ and concentrated to give the crude product. It was used in next step without purification (900 mg, 97%).

Step 2

(2S,4R)-4-Benzyloxy-2-(4-phenoxy-phenoxymethyl)-pyrrolidine-1-carboxylic acid tert-butyl ester: To a solution of (2S,4R)-4-benzyloxy-2-hydroxymethyl-pyrrolidine-1-carboxylic acid tert-butyl ester (900 mg, 2.93 mmol) in anhydrous THF (2 mL) was added 4-phenoxyphenyl (655 mg, 3.52 mmol) in THF) (2 mL) and triphenyl phosphine (997 mg, 3.8 mmol) in THF (1 mL). The resulting mixture was cooled to 0° C. using ice-water bath and purged with nitrogen. Diisopropyl azodicarboxylate (770 mg, 3.8 mmol) was dissolved in 3 mL of THF and added to above solution dropwise over a period of 20 min under nitrogen. Reaction then was heated at 70° C. for 16 h. THF was removed in vacuo and crude mixture was purified by silica gel flash chromatography (10% EtOAc/hexanes) to obtain the product. To a solution of the product (100 mg, 0.21 mmol) in dioxane (1 mL) was added 4M HCl in dioxane (5 mL) at rt and the resulting mixture was stirred for 2 h at that temperature. The solvent was removed in vacuo to obtain thick oil. The oil was neutralized with saturated sodium bicarbonate solution and product was extracted with EtOAc. Organic layers were combined and washed with 1N NaOH, water, brine, dried over anhydrous MgSO$_4$ and concentrated to give the crude product. The crude product was purified by silica gel flash chromatography (2% MeOH/dichloromethane) to obtain the title product (45 mg, 57%): MS; m/z 376.7 (M+H); $^1$H NMR (400 MHz, DMSO-d$_6$); δ 1.57-1.64 (m, 1H), 1.96-2.02 (m, 1H), 2.87-2.90 (m, 1H), 2.98-3.02 (m, 1H), 3.51-3.57 (m, 1H), 3.77-3.85 (m, 2H), 4.08-4.11 (m, 1H), 4.45 (s, 2H), 6.90-6.98 (m, 6H), 7.04-7.08 (m, 1H), 7.26-7.36 (m, 7H), 7.61-7.66 (m, 4H), 8.87 (s, 3H); HPLC (ELSD); 99%; Elemental analysis. Calc C, 76.77H, 6.71 N, 3.73. Found C, 76.66 H, 6.81 N, 3.92.

EXAMPLE 86

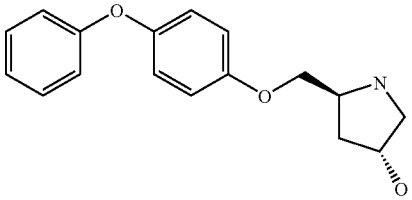

Step 1

(2S,4R)-4-Benzyloxy-2-hydroxymethyl-pyrrolidine-1-carboxylic acid tert-butyl ester: (2S,4R)-4-Benzyloxy-pyrrolidine-1,2-dicarboxylic acid 1-tert-butyl ester (960 mg, 3 mmol) in THF (5 mL) was cooled to 0° C. using ice-water bath. Then 1M solution of BH3 (6mL, 6 mmol) in THF was added under nitrogen over period of 30 min. Reaction was stirred at 0° C. for 2 h and at rt for another 1 h. Reaction mixture was poured over ice water and product was extracted with EtOAc. Organic layers were combined, washed with water, brine, saturated sodium bicarbonate, dried over anhydrous MgSO4 and concentrated to give the crude product. It was used in next step without purification (900 mg, 97%); MS; m/z 286.1 (M+H); $^1$H NMR (400 MHz, DMSO-4-d$_6$); δ 1.90 (m, 1H), 2.01 (m, 1H), 3.09 (m, 1H), 3.34 (m, 1H), 4.12 (m, 2H); 4.27 (m, 1H), 4.46 (m, 1H), 5.46 (br s, 2H), 6.92 (d, J=6.8 Hz, 2H), 7.02 (s, 4H), 7.08 (t, J=5.6 Hz, 1H), 7.35 (m, 2H), 9.09 (br s, 1H), 9.62 (br s, 3H);

Step 2

2S,4R)-4-Hydroxy-2-(4-phenoxy-phenoxymethyl)-pyrrolidine-1-carboxylic acid tert-butyl ester: To a solution of (2S,4R)-4-benzyloxy-2-hydroxymethyl-pyrrolidine-1-carboxylic acid tert-butyl ester (900 mg, 2.93 mmol) in anhydrous THF (2mL) was added 4-phenoxyphenyl (655 mg, 3.52 mmol) in THF) (2 mL) and triphenyl phosphine (997 mg, 3.8 mmol) in THF (1 mL). The resulting mixture was cooled to 0° C. using ice-water bath and purged with nitrogen. Diisopropyl azodicarboxylate (770 mg, 3.8 mmol) was dissolved in 3 mL of THF and added to above solution dropwise over a period of 20 min under nitrogen. Reaction then was heated at 70° C. for 16 h. THF was removed in vacuo and crude mixture was purified by silica gel flash chromatography (10% EtOAc/Hexane) to obtain the product.

Step 3

(3R,5S)-5-(4-Phenoxy-phenoxymethyl)-pyrrolidin-3-ol: Product from step 2 (100 mg, 0.21 mmol) in EtOH/THF (1 mL/2.5mL) was treated with 10% Pd on carbon (140 mg) over period of 3 days at room temperature under H2 balloon. Then reaction mixture was filtered through pad of Celite and concentrated.

EXAMPLE 87

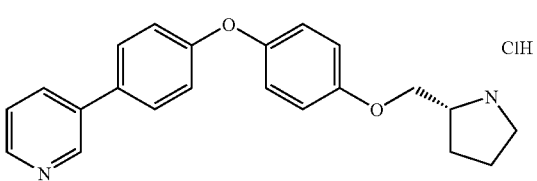

Step 1

3-(4-Benzyloxy-phenyl)-pyridine: To a solution of 4-benzyloxyphenylboronic acid (1.48 g, 6.5 mmol) in DME (10 mL) was added 3-iodo: pyridine (1.03 g, 5.0 mmol) in DME (8 mL), potassium carbonate (2.0 g, 15 mmol) in 1:1 mixture of EtOH:water (3 mL), palladium(II) acetate (56 mg 0.25 mmol), and triphenyl phosphine (202 mg, 1.0 mmol) in DME (2 mL). The resulting mixture was warmed up to 90° C. and stirred for 16 h at that temperature. After cooling to rt, reaction mixture was poured into ice-water 200 mL) and product was extracted with EtOAc, washed with brine, filtered through pad of Celite and concentrated to a yellow solid. The crude mixture was purified by silica gel flash chromatography (20% EtOAc/Hexane) to obtain the title product as yellow solid (1.2 g, 92%).

Step 2

4-Pyridin-3-yl-phenol: 3-(4-Benzyloxy-phenyl)-pyridine 1.15 g, 4.4 mmol) in EtOH/THF (10 mL/25 mL) was treated with 10% Pd on carbon (1.5 g) over period of 48 h at rt under H 2 balloon, Reaction mixture was filtered through Celite and concentrated to obtain the product (700 mg, 93%).

Step 3

(R)-2-[4-(4-Pyridin-3-yl-phenoxy)-phenoxymethyl]-pyrrolidine-1-carboxylic acid tert-butyl ester: To a solution of product from step 2 (114 mg, 0.66 mmol) in dioxane (2 mL) was added (R)-2-(4-iodo phenoxymethyl)-pyrrolidine-1-carboxylic acid tert-butyl ester (403 mg, 1.0 mmol) in dioxane (1.5 mL) and cesium carbonate (432 mg, 1.33 mmol). The vessel was purged with nitrogen for 15 min before N,N-dimethylglycine hydrochloride (9 mg, 0.06 mmol) in dioxane (0.5mL) and Cu(I) iodide (4 mg, 0.02 mmol) were added. The resulted mixture was stirred at 90° C. for 48 h. It was then diluted with EtOAc and water, organic layer was separate, washed with water, brine, dried over anhydrous MgSO$_4$ and concentrated in vacuo to yellow oil. The crude mixture was purified by silica gel flash chromatography (15% EtOAc/Hexane) to obtain the title product as yellow oil (142 µg, 48%).

Step 4

3-{4-[4-((R)-1-Pyrrolidin-2-ylmethoxy)-phenoxy]-phenyl}-pyridine hydrochloride salt: To a solution of the product from step 3 (100 mg, 0.22 mmol) in dioxane (1 mL) was added 4 M HCl in dioxane (5 mL) at rt and the resulting residue was triturated with ether and dried under vacuum to obtain the title product (79 mg, 95%): MS; m/z 347.7 (M°H); $^1$H NMR (400 MHz, DMSO-d$_6$); δ 1.72-1.77 (m, 1H), 1.90-2.00 (m, 2H), 2.11-2.15 (m, 1H), 3.21-3.24 (m, 2H), 3.89-3.91 (m, 1H), 4.15-4.19 (m, 2H), 7.05-7.13 (m, 6H), 7.83-7.86 (m, 2H), 7.94 (dd, 2H, J1=5.2 Hz, J2=8 Hz), 8.63 (d, 1H, J=7.6 Hz), 8.77 (dd, 1H, J1=5.2 Hz, J2=1.2 Hz), 9.13 (d, 2H, J=2 Hz), 9.67 (br, 3H); HPLC (UV); 97%.

EXAMPLE 88

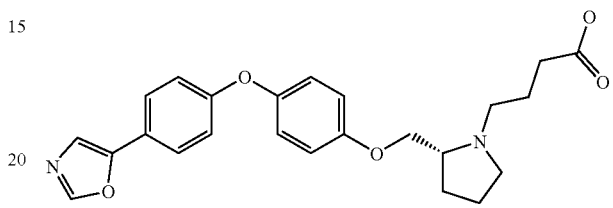

Step 1

(5-{4-[-4-((R)-1-Pyrrolidin-2-ylmethoxy)-phenoxy]-phenyl}-oxazole: To a solution of 5 (4-bromophenyl)-1,3-oxazole (224 mg 1.0 mmol) in dioxane (2mL) was added (R)-2-(4-hydroxy-phenoxymethyl)-pyrrolidine-1-carboxylic acid tert-butyl ester (440 mg, 1.5 µmmol) in dioxane (2 mL) and cesium carbonate (651 mg, 2.0 mmol), The vessel was purged with nitrogen for 15 min before N,N-dimethylglycine hydrochloride (12.5 mg, 0.09 mmol in dioxane (1 mL) and Cu(I) iodide (6 mg, 0.03 mmol) were added. The resulted mixture was stirred at 85° C. for 16 h. It was then diluted with EtOAc and water, organic layer was separated, washed with water, brine dried over anhydrous MgS(O)4 and concentrated in vacuo to yellow oil. The crude mixture was purified by silica gel flash chromatography (10% EtOAc/Hexane) before treating it with 4M HCl in dioxane (5 mL) at rt for 1 h. Solvent was removed in vacuo, residue was triturated with ether and dried under vacuum to give the title product as white solid (280 mg, 75%).

Step 2

4-{(R)-2-[4-(4-Oxazol-5-yl-phenoxy)-phenoxymethyl]-pyrrolidin-1-yl}-butyric acid methyl ester: To a solution of (5-{4-[4-((R)-1-pyrrolidin-2-ylmethoxy)-phenoxy]-phenyl}-oxazole (150 mg, 0.4 mmol) in anhydrous dichloromethane (0.5mL) was added methyl-4-bromobutyrate (80 mg, 0.44 mmol) in dichloromethane (0.5 mL) and triethylamine (81 mg, 0.8 mmol. The resulting mixture was purged with nitrogen and stirred at rt for 16 h. dichloromethane was removed in vacuo and crude mixture was partioned between EtOAc and water. EtOAc layer was removed, washed with brine, dried over anhydrous MgSO4 and concentrated. The crude mixture was purified by silica gel flash chromatography 3 (40% EtOAc/hexane) to obtain the title product as yellow oil (95 mg, 55%).

Step 3

4-{(R)-2-[4-(4-Oxazol-5-yl-phenoxy)-phenoxymethyl]-pyrrolidin-1-yl} butyric acid: To a solution of the product (90 mg, 0.21 mmol) from step 2 in 4:1 mixture of MeOH/water (2 mL) was added 2M solution of NaOH (124 uL 0.25 mmol). Reaction mixture was heated at 50° C. for 16 h. Solvent was removed in vacuo, residue was dissolved in water and pH was adjusted to 4-5 with 1M HCl solution. Then product was extracted with EtOAc, washed with water, brine, dried over anhydrous MgSO₄ and concentrated to give the title compound (9.5 mg, 11%): MS; m/z 423.8 (M+H); ¹H NMR (400 MHz, DMSO-d₆); δ 1.20-1.30 (m, 2H), 1.82-2.25 (m, 6H), 2.73 (t, 2H, J=7.2 Hz), 3.17 (br, 2H), 3.75 (br, 1H), 4.21-4.27 (m, 2H), 7.01 (dd, 2H, J1=6.8 Hz. J2=2.4 Hz), 7.07-7.08 (m, 4H), 7.59 (s, 1H), 7.71 (dd, 2H, J1=6.8 Hz, J2=2.4 Hz), 8.41 (s, 1H); HPLC (UV); 86%.

EXAMPLE 89

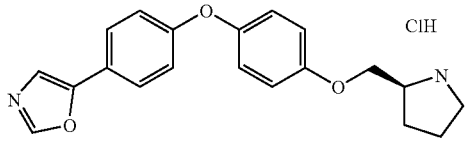

Step 1

(S)-2-(4-Benzyloxy-phenoxymethyl)-pyrrolidine-1-carboxylic acid tert-butyl ester: To a slurry of NaH (562 mg, 8.44 mmol, 60% dispersion in mineral oil) in anhydrous DMF (5 mL) at 0° C. was added p-benzyloxy phenol (1.41 g, 7.0 mmol) in anhydrous DMF (5 mL) dropwise over 30 min under N₂ atmosphere. The resulting slurry was stirred at 0° C. for 30 minutes, warmed to ambient temperature and stirred for 1 h before a solution of (S)-2-(Toluene-4-sulfonyloxymethyl)-pyrrolidine-1-carboxylic acid tert-butyl ester (2.5 g, 7.0 mmol) in DMF (10 mL) was added dropwise over 30 min at 0° C. The subsequent mixture was stirred at 85° C. 16 h. The reaction mixture was poured over ice-water, precipitated yellow solid was removed by filtration, washed with water and dried under reduced pressure. The crude product was crystallized from ether/hexane to obtain the title compound (1.2 g, 44%).

Step 2

(S)-2-(4-Hydroxy-phenoxymethyl)-pyrrolidine-1-carboxylic acid tert-butyl ester: Product from step 1 (1.2 g, 3.13 mmol) in EtOH/THF (10 mL/25 mL) was treated with 10% Pd on carbon (1.0 g) over period of 16 h at rt under H2 balloon. Reaction Mixture was filtered through Celite and concentrated under reduced pressure. The crude mixture was purified by silica gel flash chromatography (20% EtOAc/Hexane) to obtain the title product (645 mg, 70%).

Step 3

5-{4-[4-((S)-1-Pyrrolidin-2-ylmethoxy)-phenoxy]-phenyl}-oxazole: To a solution of 5-(4-bromophenyl)-1,3-oxazole (224 mg, 1.0 mmol) in dioxane (2 mL) was added (S)-2-(4-Hydroxy-phenoxymethyl)-pyrrolidine-1-carboxylic acid tert-butyl ester (440 mg, 1.5 mmol) in dioxane (2 mL) and cesium carbonate (651 mg, 2.0 mmol). The vessel was purged with nitrogen for 15 min before N,N-dimethylglycine hydrochloride (12.5 mg, 0.09 mmol) in dioxane (1 mL) and Cu(I) iodide (6 mg, 0.03 mmol) were added. The resulted mixture was stirred it 85° C. for 16 h. It was then diluted with EtOAc and water, organic layer was separated, washed with water, brine, dried over anhydrous MgSO4 and concentrated in vacuo to dark brownish oil. The crude mixture was purified by silica gel flash chromatography (10% EtOAc/Hexane) before treating it with 4M HCl in dioxane (5 mL) at rt for 1 h. Solvent was removed in residue was triturated with ether and dried under vacuum to give the product, as white solid (336 mg, 90%): MS; m/z 337.4 M+H), ¹H NMR (400 MHz, DMSO-d₆); δ 1.71-2.15 (m, 4H), 3.18-3.25 (m, 2H), 3.88-3.91 (m, 1H), 4.12-4.17 (m, 1H), 4.23-4.27 (m, 1H), 7.00-7.10 (m, 6H), 7.59 (s, 1H), 7.71 (dd, 2H, J1=6.8 Hz, J2=2.4 Hz, 8.41 (s, 1H), 9.04 (br, 1H), 9.6 (br, 1H); HPLC (UV); 99%

EXAMPLE 90

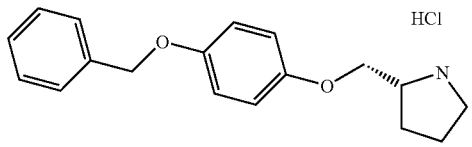

Step 1

(R)-2-(4-Benzyloxy-phenoxymethyl)-pyrrolidine-1-carboxylic acid tert-butyl ester: To a 250 mL round bottomed flask which contained a suspension of NaH (1 g, 24 mmol) in DMF (100 mL) was added p-benzyloxy phenol (4 g, 20 mmol) at 0° C., The mixture was allowed to warm to rt and stir at rt for 30 min then cooled to 0° C. To this reaction mixture was added (R)-2-(toluene-4-sulfonyloxymethyl)-pyrrolidine-1-carboxylic acid tert-butyl ester (7.1 g, 20 mmol) at 0° C. The resulting mixture was allowed warm to rt and stir at rt for 30 min and then was heated to 95° C. for 5 h. After cooling to rt, the mixture was poured into 500 mL ice-water solution and this solution was allowed to stir at 0° C. for 30 min. The solid formed was filtered out, dried through air to provide the crude which was further purified by recrystallization with ether-hexane to afford the title product (5 g, 65%); LCMS; 100%, ESI⁺, Calcd: 383.49 m/z. Found: 284.4, (M+1-boc). ¹H NMR (400 MHz, CDCl₃); δ 1.47 (s, 9H), 1.79-2.10 (m, 4H), 3.26-3.45 (m, 2H), 3.66-3.91 (m, 1H), 4.01-4.19 (m 2H), 5.01 (s, 2H), 6.83-6.91 (m, 4H), 7.28-7.44 (m, 5H):

Step 2:

(R)-2-(4-Benzyloxy-phenoxymethyl)-pyrrolidine hydrogen chloride salt: To a 20 mL vial which contained a solution of the product from step 1 (40 mg, 0.1 mmol) in dioxane (0.5 mL) was added HCl (4 N in dioxane 2 mL) at 0° C. The mixture was allowed to warm to rt and stir at rt for 16 h. The solvent was removed and the crude was purified by recrystallization with MeOH-ether to yield the title product (27 mg, 90%); LCMS; 95% ESI⁺, Calcd: 238.4 m/z. Found: 284.4 (M+1) m/z. ¹H NMR (400 MHz, DMSO-d₆); δ 1.68-1.76 (m, 1H), 1.86-2.04 (m, 2H), 2.07-2.14 (m, 1H), 3.20 (br, 2H), 3.87 (br, 1H), 4.05 (dd, J1=10.4 Hz, J2=8.4 Hz, 1H), 4.18 (dd, J/=10.4 Hz, J2=3.6 Hz, 1H), 5.05 (s, 2H), 6.91-6.99 (m, 4H), 7.30-7.44 (m, 5H):

EXAMPLE 91

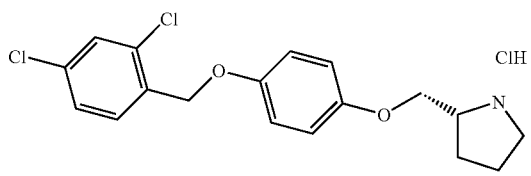

Step 1

(R)-2-(4-Hydroxy-phenoxymethyl)-pyrrolidine-1-carboxylic acid tert-butyl ester: To a 250 mL round bottomed flask which contained a suspension of Pd—C (10% wt 3 g) in EtOH (70 mL) and THF (30 mL) was added (R)-2-(4-benzyloxy-phenoxymethyl)-pyrrolidine-1-carboxylic acid tert-butyl ester (3.5 g, 9 mmol). The stirred solution was flushed with a H2 balloon. This process was repeated 3 times. The resulting solution was stirred at rt under hydrogen atmosphere overnight. The reaction mixture was then filtered, washed with THF (30 ml), EtOH (25 ml) and dried in vacuo to provide the crude product which was further purified by recrystallization with ether-EtOAc-hexane to yield the title product, (2.5, 90%); MS; APCI$^+$, Calcd: 293.5. Found m/z: 294.2 (M+1). $^1$H NMR (400 MHz, CDCl$_3$); δ 1.47 (s, 9H), 1.80-2.10 (m, 4H), 3.40 (br, 2H), 3.69-3.89 (m, 1H), 4.00-4.18 (m 2H), 6.71-6.76 (m, 4H).

Step 2

(R)-2-[4-(2,4-Dichloro-benzyloxy)-phenoxymethyl]-pyrrolidine-1-carboxylic acid tert-butyl ester: To a 25 mL vial which contained a solution of the product from step 1 (150 mg, 0.5 mmol) and 2,4-dichloro-benzyl chloride (180 mg, 0.8 mmol) in anhydrous DMF (15 mL) was added dry Cs$_2$CO$_3$ (150 mg, 0.75 mmol) at rt. The reaction mixture which resulted was allowed to stir at rt for 7 d. The mixture was poured onto 50 mL ice-water solution and extracted with EtOAc (3×30 mL) allowed). The combined organic layers were washed with water (30 mL) and brine (30 mL) and dried over anhy. Na$_2$SO$_4$. The solvent was removed under vacuo to obtain the crude product which was purified by silica gel flash chromatography to afford the title product (130 mg, 55%); $^1$H NMR (400 MHz, CDCl$_3$); δ 1.47 (s, 9H), 1.80-2.10 (m, 4H), 3.26-3.45 (m, 2H), 3.69-3.91 (m, 1H), 4.01-4.18 (m, 2H), 5.07 (s, 2H), 6.84-6.90 (m, 4H), 7.25-7.28 (m, 1H), 7.41 (d, J=2.0 Hz, 1H), 7.49 (d, J=8.4 Hz, 1H), Step 3

(R)-2-[4-(2,4-Dichloro-benzyloxy)-phenoxymethyl]-pyrrolidine hydrogen chloride salt; To a 25 mL vial which contained a solution of the product from step 2 (120 mg, 0.26 mmol) in MeOH (2 mL) was added HCl (2 N in ether, 4 mL) at 0° C. The mixture was allowed to warm to rt and stir at rt for 24 h. The ether (10 mL) was added to the mixture and the solid which formed was filtered out to provide the crude which was further purified by recrystallization with MeOH-ether to yield the title product, (104 mg, 95%); LCMS; 100% APCI$^+$, Calcd: 352.3. Found m/z 352.3 (M). $^1$H NMR (400 MHz, DMSO-d$_6$); δ 1.68-1.75 (m, 1H), 1.84-2.02 (m, 2H), 2.07-2.16 (m, 1H), 3.13-3.26 (m, 2H), 3.80-3.90 (m, 1H), 4.05-4.10 (m, 1H), 4.18 (dd, J1=10.4 Hz, J2=3.6 Hz, 1H), 5.09 (s, 2H), 6.94-7.01 (m, 4H), 7.48 (dd, J1=8.0 Hz, J2=2.0 Hz, 1H), 7.60 (d, J=8.4 Hz, 1H), 7.68 (d, 1H, J=2.0 Hz):

EXAMPLE 92

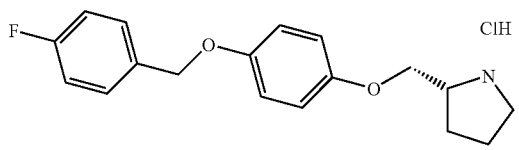

Step 1

(R)-2-[4-(4-Fluoro-benzyloxy)-phenoxymethyl]-pyrrolidine-1-carboxylic acid tert-butyl ester: Followed the same procedure as that of step 2 in Example 91 with the use of (R)-2-(4-hydroxy-phenoxymethyl)-pyrrolidine-1-carboxylic acid tert-butyl ester (150 mg, 0.5 mmol) and 4-fluoro-benzyl bromide (150 mg, 0.75 mmol) to afford the title product (100 mg, 50% yield); LCMS, 100% APCI$^+$, Calcd. 401.48. Found: 402.34 m/z (M+1). $^1$H NMR (400 MHz, CDCl$_3$); δ 1.47 (s, 9H), 1.80-2.10 (m, 4H), 3.39 (br, 2H), 3.70-3.90 (m, 1H), 4.02-4.19 (m, 2H), 4.97 (s, 2H), 6.82-6.89 (m, 2H), 7.06 (t, J=8.0 Hz, 2H), 7.23-7.28 (m, 2H), 7.35-7.42 (m, 2H).

Step 2

(R)-2-[4-(4-Fluoro-benzyloxy)-phenoxymethyl]-pyrrolidine Hydrogen chloride salt: Followed the same procedure as that of step 3 in Example 91 with the use of (R)-2-[4-(4-fluoro-benzyloxy)-phenoxymethyl]-pyrrolidine-1-carboxylic acid tert-butyl ester (80 mg, 0.2 mmol) to yield the title product (55 mg, 75% yield); LCMS; 100% APCI$^+$, Calcd: 301.36. Found m/z: 301.3 (M). $^1$H NMR (400 MHz, DMSO-d$_6$); δ 1.68-1.75 (m, 1H), 1.86-2.04 (m, 2H), 2.07-2.14 (m, 1H), 3.17-3.23 (m, 2H), 3.84-3.87 (m, 1H), 4.03 (dd, J1=10.4 Hz, J2=8.4 Hz, 1H), 4.17 (dd, J1=10.4 Hz, J2=3.6 Hz, 1H), 5.03 (s, 2H), 6.91-6.98 (m, 4H), 7.18-7.23 (m, 2H), 7.46-7.49 (m, 2H):

EXAMPLE 93

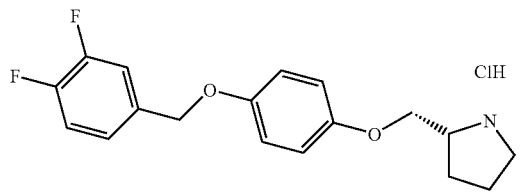

Step 1

(R)-2-[4-(3,4-Difluoro-benzyloxy)-phenoxymethyl]-pyrrolidine-1-carboxylic acid tert-butyl ester: Followed the same procedure as that of step 2 in Example 91 with the use of (R)-2-(4-hydroxy-phenoxymethyl)-pyrrolidine-1-carboxylic acid tert-butyl ester (150 mg, 0.5 mmol) and 3,4-difluoro-benzyl bromide (145 mg, 0.6 mmol) to afford the title product, (120 mg, 55% yield); LCMS, 100% APCI$^+$, Calcd; 419.5. Found m/z: 421.4 (M+2). $^1$H NMR (400 MHz, CDCl$_3$); δ 1.47 (s, 9H), 1.80-2.09 (m, 4H), 3.28-3.46 (m, 2H), 3.69-3.91 (m, 1H), 4.02-4.18 (m 2H), 4.95 (s, 2H), 6.84-6.88 (m, 4H), 7.55-7.28 (m, 3H).

Step 2

(R)-2-[4-(3,4-Difluoro-benzyloxy)-phenoxymethyl]-pyrrolidine Hydrogen chloride salt: Followed the same procedure as that of step 3 in Example 91 with the use of (R)-2-[4-(3,4-difluoro-benzyloxy)-phenoxymethyl]-pyrrolidine-1-carboxylic acid tert-butyl ester (105 mg, 0.25 mmol) to yield the title product (65 mg, 75% yield); LCMS, 98% ESI, Calcd: 319.50. Found m/z: 320.5 (M+1). $^1$H NMR (400 MHz, DMSO-d$_6$); δ 1.68-1.76 (m, 1H), 1.86-2.00 (m, 2H), 2.07-2.14 (m, 1H), 3.18-3.24 (m, 2H), 3.86 (br, 1H), 4.03 (dd, J1=10.8 Hz, J2=8.4 Hz, 1H), 4.18 (dd, J/=10.8 Hz, J2=3.6 Hz, 1H), 5.05 (s, 2H), 6.92-6.99 (m, 4H), 7.25-7.30 (m, 1H), 7.42-7.53 (m, 2H):

EXAMPLE 94

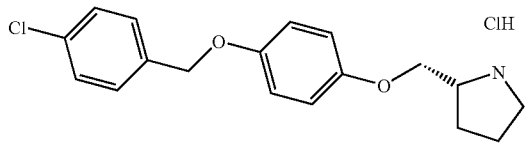

Step 1

(R)-2-[4-(4-Chloro-benzyloxy)-phenoxymethyl]-pyrrolidine-1-carboxylic acid tert-butyl ester: Followed the same procedure as that of step 2 in Example 91 with the use of (R)-2-(4-hydroxy-phenoxymethyl)-pyrrolidine-1-carboxylic acid tert-butyl ester (150 mg, 0.5 mmol) and 4-chlorobenzyl bromide (125 mg, 0.6 mmol) to afford the title product (120 mg, 58% yield); LCMS; 100% APCI+, Calcd: 417.94. Found m/z: 418.23 (M). $^1$H NMR (400 MHz, CDCl$_3$); δ 1.47 (s, 9H), 1.80-2.09 (m, 4H), 3.28-3.43 (m, 2H), 3.69-3.91 (m, 1H), 4.02-4.18 (m 2H), 4.97 (s, 2H), 6.86 (s, 4H), 7.35 (s, 4H).

Step 2

(R)-2-[4-(4-Chloro-benzyloxy)-phenoxymethyl]-pyrrolidine Hydrogen chloride salt: Followed the same procedure as that of step 3 in Example 91 with the use of (R)-2-[4-(4-chloro-benzyloxy)-phenoxymethyl]-pyrrolidine-1-carboxylic acid tert-butyl ester (105 mg, 0.25 mmol) to yield title product, (60 mg, 70% yield); LCMS; 99% APCI+, Calcd: 317.8. Found m/z: 318.2 (M). $^1$H NMR (400 MHz, DMSO-d$_6$); δ 1.68-1.75 (m, 1H), 1.84-2.02 (m, 2H), 2.07-2.14 (m, 1H), 3.20 (br, 2H), 3.86 (br, 1H), 4.05 (dd, J1=10.4 Hz, J2=8.0 Hz, 1H), 4.17 (dd, J1=10.4 Hz, J2=3.6 Hz, 1H), 5.06 (s, 2H), 6.91-6.98 (m, 4H), 7.39-7.4 (s, 4H):

EXAMPLE 95

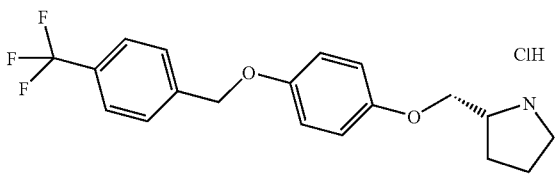

Step 1

(R)-2-[4-(4-Trifluoromethyl-benzyloxy)-phenoxymethyl]-pyrrolidine-1-carboxylic acid tert-butyl ester: Followed the same procedure as that of step 2 in Example 91 with the use of (R)-2-(4-hydroxy-phenoxymethyl)-pyrrolidine-1-carboxylic acid tert-butyl ester (150 mg, 0.5 mmol) and 4-trifluoromethyl-benzyl bromide (145 mg, 0.6 mmol) to afford title product (135 mg, 60% yield); LCMS; 100% APCI+, Calcd: +451.49. Found m/z: 452.3 (M+1). $^1$H NMR (400 MHz, CDCl$_3$); δ 1.47 (s, 9H), 1.80-2.09 (m, 4H), 3.28-3.46 (m, 2H), 3.69-3.91 (m, 1H), 4.02-4.18 (m 2H), 5.07 (s, 2H), 6.87 (s, 4H), 7.53 (d, J=8.4 Hz, 2H), 7.63 (d, J=8.0 Hz, 2H).

Step 2

(R)-2-[4-(4-Trifluoromethyl-benzyloxy)-phenoxymethyl]-pyrrolidine Hydrogen chloride salt: Followed the same procedure as that of step 3 in Example 91 with the use of (R)-2-[4-(4-trifluoromethyl-benzyloxy)-phenoxymethyl]-pyrrolidine-1-carboxylic acid tert-butyl ester (113 mg, 0.25 mmol) to yield the title product (90 mg, 90% yield); LCMS; 100% APCI+, Calcd: 351.37. Found m/z: 352.21 (M+1). $^1$H NMR (400 MHz, DMSO-d$_6$); δ 1.68-1.76 (m, 1H), 1.85-2.02 (m, 2H), 2.06-2.14 (m, 1H), 3.14-3.40 (m, 2H), 3.81-3.89 (m, 1H), 4.06 (dd, J1=10.4 Hz, J2=8.4 Hz, 1H), 4.17 (dd, J1=10.4 Hz, J2=3.6 Hz, 1H), 5.18 (s, 2H), 6.93-7.00 (m, 4H), 7.65 (d, J=8.0 Hz, 2H), 7.76 (d, J=8.4 Hz, 2H):EXAMPLE 102

EXAMPLE 96

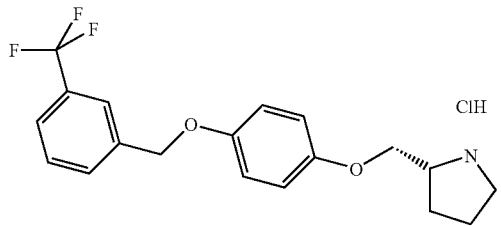

Step 1

(R)-2-[4-(3-Trifluoromethyl-benzyloxy)-phenoxymethyl]-pyrrolidine-1-carboxylic acid tert-butyl ester: Followed the same procedure as that of step 2 in Example 91 with the use of (R)-2-(4-hydroxy-phenoxymethyl)-pyrrolidine-1-carboxylic acid tert-butyl ester (150 mg, 0.5 mmol) and 3-trifluoromethyl-benzyl bromide (145 mg, 0.6 mmol) to afford the title product (120 mg, 55% yield); LCMS; 100% APCI+, Calcd: 451.49. Found m/z: 452.27 (M+1). $^1$H NMR (400 MHz, CDCl$_3$); δ 1.47 (s, 9H), 1.80-2.09 (m, 4H), 3.26-3.44 (m, 2H), 3.69-3.91 (m, 1H), 4.02-4.18 (m 2H), 5.05 (s, 2H), 6.88 (s, 4H), 7.49 (t, J=7.6 Hz, 1H), 7.57-7.62 (m, 2H), 7.70 (s, 1H).

Step 2

(R)-2-[4-(3-Trifluoromethyl-benzyloxy)-phenoxymethyl]-pyrrolidine Hydrogen chloride salt: Followed the same procedure as that of step 3 in Example 91 with the use of (R)-2-[4-(3-trifluoromethyl-benzyloxy)-phenoxymethyl]-pyrrolidine-1-carboxylic acid tert-butyl ester (113 mg, 0.25 mmol) to yield the title product (83 mg, 80% yield); LCMS; 100% APCI+, Calcd: 351.37. Found m/z: 352.22 (M+1). $^1$H NMR (400 MHz, DMSO-d$_6$); δ 1.66-1.75 (m, 1H), 1.84-2.02 (m, 2H), 2.04-2.15 (m, 1H), 3.14-3.24 (m, 2H), 3.81-3.89 (m, 1H), 4.03 (dd, 1H, J1=10.4 Hz, J2=8.4 Hz), 4.17 (dd, 1H, J1=10.4 Hz, J2=3.6 Hz), 5.17 (s, 2H), 6.93-7.01 (m, 4H), 7.09 (d, J=8.0 Hz, 1H), 7.63 (t, J=7.6 Hz, 1H), 7.74 (d, J=7.6 Hz, 1H), 7.79 (s, 1H):

EXAMPLE 97

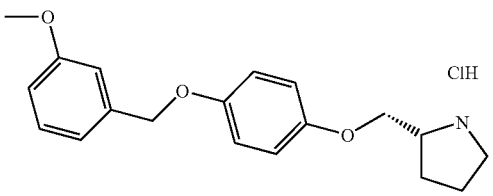

Step 1

(R)-2-[4-(3-Methoxy-benzyloxy)-phenoxymethyl]-pyrrolidine-1-carboxylic acid tert-butyl ester: Followed the same procedure as that of step 2 in Example 91 with the use of (R)-2-(4-hydroxy-phenoxymethyl)-pyrrolidine-1-carboxylic acid tert-butyl ester (150 mg, 0.5 mmol) and 3-methoxy-benzyl bromide (120 mg, 0.6 mmol) to afford the title product (110 mg, 53% yield); LCMS; 100% APCI$^+$, Calcd: 413.56. Found m/z: 414.29 (M+1). $^1$H NMR (400 MHz, CDCl$_3$); δ 1.47 (s, 9H), 1.80-2.09 (m, 4H), 3.28-3.46 (m, 2H), 3.69-3.91 (m, 1H), 3.82 (s, 3H), 4.02-4.18 (m 2H), 4.99 (s, 2H), 6.82-6.90 (m, 5H), 6.96-7.05 (m, 2H), 7.26-7.30 (m, 1H).

Step 2

(R)-2-[4-(3-Methoxy-benzyloxy)-phenoxymethyl]-pyrrolidine Hydrogen chloride salt: Followed the same procedure as that of step 3 in Example 91 with the use of (R)-2-[4-(3-methoxy-benzyloxy)-phenoxymethyl]-pyrrolidine-1-carboxylic acid tert-butyl ester (103 mg, 0.25 mmol) to yield the title product (60 mg, 80% yield); LCMS; 91% APCI$^+$, Calcd. 313.4. Found m/z: 314.1 (M+1). $^1$H NMR (400 MHz, DMSO-d$_6$); δ 1.65-1.75 (m, 1H), 1.84-2.02 (m, 2H), 2.06-2.15 (m, 1H), 3.14-3.24 (m, 2H), 3.75 (s, 3H), 3.98-4.19 (m, 2H), 5.03 (s, 2H), 6.69-7.00 (m, 7H), 7.29 (t, J=8.0 Hz, 1H):

EXAMPLE 98

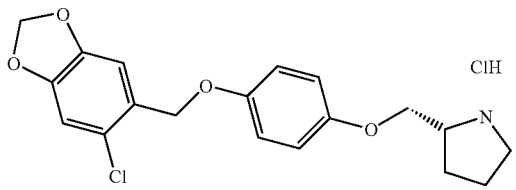

Step 1

(R)-2-[4-(6-Chloro-benzo[1,3]dioxol-5-ylmethoxy)phenoxymethyl]pyrrolidine-1-carboxylic acid tert-butyl ester: Followed the same procedure as that of step 2 in Example 91 with the use of (R)-2-(4-hydroxy-phenoxymethyl)-pyrrolidine-1-carboxylic acid tert-butyl ester (150 mg, 0.5 mmol) and 5-chloro-6-chloromethyl-benzo[1,3]dioxole (125 mg, 0.6 mmol) to afford the title product (80 mg, 40% yield).

Step 2

(R)-2-[4-(6-Chloro-benzo[1,3]dioxol-5-ylmethoxy)phenoxymethyl]pyrrolidine Hydrogen chloride salt: Followed the same procedure as that of step 3 in Example 91 with the use of (R)-2-[4-(6-chloro-benzo[1,3]dioxol-5-ylmethoxy) phenoxymethyl]pyrrolidine-1-carboxylic acid tert-butyl ester (70 mg, 0.15 mmol) to yield the title product (20 mg, 35% yield); LCMS; 72% APCI$^+$, Calcd: 361.83. Found m/z: 362.09 (M). $^1$H NMR (400 MHz, DMSO-d$_6$); δ 1.65-1.78 (m, 1H), 1.82-2.02 (m, 2H), 2.03-2.13 (m, 1H), 3.14-3.24 (m, 2H), 3.78-3.91 (m, 3H), 3.98-4.19 (m, 2H), 4.98 (s, 2H), 6.07-6.10 (m, 2H), 6.93-7.00 (m, 2H), 7.12-7.14 (m, 2H):

EXAMPLE 99

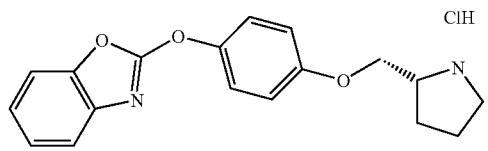

Step 1

(R)-2-[4-(Benzooxazol-2-yloxy)-phenoxymethyl]-pyrrolidine-1-carboxylic acid tert-butyl ester: To a 25 mL vial which contained a suspension of -(4-hydroxy-phenoxymethyl)-pyrrolidine-1-carboxylic acid tert-butyl ester (293 mg, 1 mmol) and dry Cs$_2$CO$_3$ (400 mg, 1.2 mmol) in anhydrous acetone (15 mL) was added 2-chloro-benzooxazole (154 mg, 1 mmol) at rt. The reaction mixture which resulted was allowed to stir at rt for 72 h. The mixture was poured onto 100 mL ice-water solution and this solution was allowed to stir at 0° C. for 1 h. The solid formed was filtered out, dried through air to provide the title product (300 mg, 75%); LCMS; 88% APCI$^+$, Calcd: 410.50. Found m/z: 411.28 (M+1). $^1$H NMR (400 MHz, CDCl$_3$); δ 1.48 (s, 9H), 1.78-2.01 (m, 4H), 3.28-3.46 (m, 2H), 3.73-3.97 (m, 1H), 4.08-4.21 (m 2H), 6.93-7.02 (m, 2H), 7.18-7.33 (m, 4H), 7.41 (d, J=7.2 Hz, 1H), 7.50 (d, J=7.2 Hz, 1H)

Step 2

(R)-2-[4-(Benzooxazol-2-yloxy)-phenoxymethyl]-pyrrolidine Hydrogen chloride salt: To a 20 mL vial which contained a solution of (R)-2-[4-(benzooxazol-2-yloxy)-phenoxymethyl]-pyrrolidine-1-carboxylic acid tert-butyl ester (40 mg, 0.1 mmol) in dioxane (0.5 mL) was added HCl (4 N in dioxane 2 mL) at 0° C. The mixture was allowed to warm to rt and stir at rt for 16 h. Removal of the solvent yielded the title product (28 mg, 80%); LCMS; 75% ESI$^+$, Calcd: 310.4. Found m/z: 311.4 (M+1). $^1$H NMR (400 MHz, DMSO-d$_6$); δ 1.68-1.75 (m, 1H), 1.85-2.03 (m, 2H), 2.06-2.13 (m, 1H), 3.14-3.26 (m, 2H), 3.79-3.89 (m, 1H), 3.98-4.03 (m, 1H), 4.12 (dd, J/=10.4 Hz, J2=3.6 Hz, 1H), 6.69-6.72 (m, 2H), 6.78-6.83 (m, 2H), 7.05-7.16 (m, 3H), 7.25-7.30 (m, 1H).

EXAMPLE 100

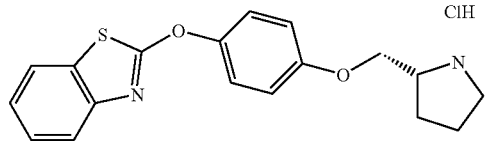

Step 1

(R)-2-[4-(Benzothiazol-2-yloxy)-phenoxymethyl]-pyrrolidine-1-carboxylic acid tert-butyl ester: Followed the same procedure as that of step 1 in Example 99 with the use of (R)-2-(4-hydroxy-phenoxymethyl)-pyrrolidine-1-carboxylic acid tert-butyl ester (293 mg, 1 mmol) and 2-chloro-benzothiazole (169 mg, 1 mmol) to afford the title product (305 mg, 75% yield); LCMS, 100% APCI$^+$, Calcd: 426.50. Found m/z: 427.26 (M+1). $^1$H NMR (400 MHz, DMSO-d$_6$); δ 1.41 (s, 9H), 1.78-2.13 (m, 4H), 3.24-3.36 (m, 2H), 3.89-4.12 (m, 3H), 7.08 (d, J=9.2 Hz, 2H), 7.31 (t, J=8.4 Hz, 1H), 7.37 (d, J=9.2 Hz, 2H), 7.42 (t, J=8.0 Hz, 1H), 7.67 (d, J=8.0 Hz, 1H), 7.91 (d, J=8.0 Hz, 1H).

Step 2

(R)-2-[4-(Benzothiazol-2-yloxy)-phenoxymethyl]-pyrrolidine-Hydrogen chloride salt: Followed the same procedure as that of step 2 in Example 99 with the use of (R)-2-[4-(benzothiazol-2-yloxy)-phenoxymethyl]-pyrrolidine-1-carboxylic acid tert-butyl ester (40 mg, 0.1 mmol) to yield the title product (30 mg, 85% yield); LCMS; 86% APCI$^+$, Calcd: 326.40. Found m/z: 327.2 (M+1). $^1$H NMR (400 MHz, DMSO-d$_6$); δ 1.70-1.80 (m, 1H), 1.89-2.05 (m, 2H), 2.09-

2.19 (m, 1H), 3.15-3.28 (m, 2H), 3.85-3.89 (m, 1H), 4.16-4.20 (m, 1H), 4.31 (dd, J1=10.4 Hz, J2=3.6 Hz, 1H), 7.12 (d, J=8.8 Hz, 2H), 7.32 (t, J=8.0 Hz, 1H), 7.41-7.45 (m, 3H), 7.67 (d, J=7.6 Hz, 1H), 7.92 (d, J=7.6 Hz, 1H):

EXAMPLE 101

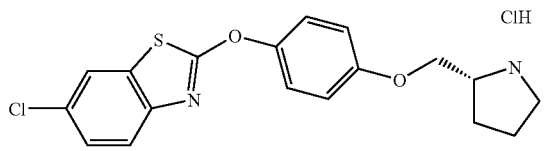

Step 1

(R)-2-[4-(6-Chloro-benzothiazol-2-yloxy)-phenoxymethyl]-pyrrolidine-1-carboxylic acid tert-butyl ester: Followed the same procedure as that of step 1 in Example 99 with the use of (R)-2-(4-hydroxy-phenoxymethyl)-pyrrolidine-1-carboxylic acid tert-butyl ester ((147 mg, 0.5 mmol) and 2,6-dichloro-benzothiazole (102 mg, 0.5 mmol) to yield the title product (172 mg, 75% yield); $^1$H NMR (400 MHz, DMSO-$d_6$); δ 1.41 (s, 9H), 1.75-2.04 (m, 4H), 3.24-3.35 (m, 2H), 3.89-4.12 (m, 3H), 7.08 (d, J=9.2 Hz, 2H), 7.38 (d, J=9.2 Hz, 2H), 7.45 (dd, J1=8.8 Hz, J2=2.0 Hz, 1H), 7.68 (d, J=8.8 Hz, 1H), 8.07 (d, J=2.0 Hz, 1H).

Step 2

(R)-2-[4-(6-Chloro-benzothiazol-2-yloxy)-phenoxymethyl]-pyrrolidine-Hydrogen chloride salt: Followed the same procedure as that of step 2 in Example 99 with the use of (R)-2-[4-(6-chloro-benzothiazol-2-yloxy)-phenoxymethyl]-pyrrolidine-1-carboxylic acid tert-butyl ester (150 mg, 0.32 mmol) to yield the title product, (115 mg, 90% yield); LCMS; 98% ESI$^+$, Calcd: 360.87. Found m/z: 361.3 (M+1). $^1$H NMR (400 MHz, DMSO-$d_6$); δ 1.73-1.80 (m, 1H), 1.89-2.05 (m, 2H), 2.09-2.19 (m, 1H), 3.19-3.27 (m, 2H), 3.89-3.96 (m, 1H), 4.13-4.18 (m, 1H), 4.31 (dd, J1=10.4 Hz, J2=3.6 Hz, 1H), 7.01-7.14 (m, 2H), 7.42-7.48 (m, 3H), 7.67 (d, J=8.4 Hz, 1H), 8.09 (d, J=2.4 Hz, 1H):

EXAMPLE 102

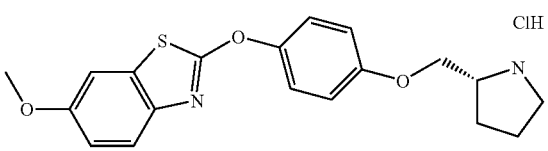

Step 1

(R)-2-[4-(6-Methoxy-benzothiazol-2-yloxy)-phenoxymethyl]-pyrrolidine-1-carboxylic acid tert-butyl ester: Followed the same procedure as that of step 1 in Example 99 with the use of (R)-2-(4-hydroxy-phenoxymethyl)-pyrrolidine-1-carboxylic acid tert-butyl ester ((147 mg, 0.5 mmol) and 2-chloro-6-methoxy-benzothiazole (100 mg, 0.5 mmol) to afford the title product (185 mg, 77% yield); $^1$H NMR (400 MHz, CDCl$_3$); δ 1.46 (s, 9H), 1.80-2.10 (m, 4H), 3.28-3.46 (m, 2H), 3.70-3.98 (m, 1H), 3.84 (s, 3H), 4.01-4.20 (m, 2H), 6.72-6.82 (m, 4H), 6.92-6.99 (m, 2H), 7.62 (d, J=8.8 Hz, 1H).

Step 2

(R)-2-[4-(6-Methoxy-benzothiazol-2-yloxy)-phenoxymethyl]-pyrrolidine-Hydrogen chloride salt: Followed the same procedure as that of step 2 in Example 99 with the use of (R)-2-[4-(6-methoxy-benzothiazol-2-yloxy)-phenoxymethyl]-pyrrolidine-1-carboxylic acid tert-butyl ester; (91 mg, 0.2 mmol) to yield the title product, (60 mg, 85% yield); LCMS; 92% ESI$^+$, Calcd: 356.5. Found m/z: 357.7 (M+1). $^1$H NMR (400 MHz, DMSO-$d_6$); δ 1.65-1.80 (m, 1H), 1.82-2.04 (m, 2H), 2.05-2.19 (m, 1H), 3.12-3.28 (m, 2H), 3.78 (s, 3H), 3.79-4.32 (m, 3H), 6.68-6.73 (m, 2H), 6.79-6.84 (m, 2H), 7.09-7.12 (m, 1H), 7.38-7.42 (m, 1H), 7.53-7.58 (m, 1H):

EXAMPLE 103

Step 1

2-Chloro-1-(2-trimethylsilanyl-ethoxymethyl)-1H-benzoimidazole. To a 25 mL vial which contained a suspension of NaH (140 mg, 60% in mineral oil, 3.5 mmol) in anhydrous DMF (10 mL) was added 2-chloro-1H-benzoimidazole (460 mg, 3 mmol) at 0° C. The reaction mixture which resulted was allowed to warm to rt and stir at rt for 30 min then was cooled to 0° C. and (2-Chloromethoxy-ethyl) trimethyl-silane was added to this mixture at 0° C. After warming to rt, the mixture was allowed to stir at rt for 16 h. and then was poured onto 100 mL ice-water solution. This solution was extracted with EtOAc (3×30 mL). The combined organic layers were washed with water (2×30 mL) and brine (20 mL). and dried over anhy. Na$_2$SO$_4$. The solvent was removed in vacuo to obtain the crude product, which was purified by silica gel flash chromatography to afford the title product (660 mg, 80%); $^1$H NMR (400 MHz, CDCl$_3$); δ 0.03 (s, 9H), 0.89-0.97 (m, 2H), 3.56-3.64 (m, 2H), 5.57 (s, 2H), 7.26-7.35 (m, 2H), 7.45-7.48 (m, 1H), 7.69-7.72 (m, 1H).

Step 2

(R)-2-{4-[1-(2-Trimethylsilanyl-ethoxymethyl)-1H-benzoimidazol-2-yloxy]-phenoxymethyl}-pyrrolidine-1-carboxylic acid tert-butyl ester To a 25 mL vial which contained a suspension of —(R)-2-(4-hydroxy-phenoxymethyl)-pyrrolidine-1-carboxylic acid tert-butyl ester (293 mg, 1 mmol) and dry Cs$_2$CO$_3$ (400 mg, 1.2 mmol) in anhydrous DMF (15 mL) was added the product from step 1 (330 mg, 1.2 mmol) at rt. The reaction mixture which resulted was allowed to stir at rt for 72 h. The mixture was poured onto 100 mL ice-water solution and this solution was allowed to stir at 0° C. for 1 h. The solid formed was filtered out, dried through air to provide the title product (275 mg, 50%); $^1$H NMR (400 MHz, CDCl$_3$); δ 0.03 (s, 9H), 1.50-1.57 (m, 5H), 1.82-2.14 (m, 3H), 2.20 (s, 2H), 3.44 (br, 2H), 3.70-4.25 (m, 3H), 6.76-6.85 (m, 4H), 6.99-7.03 (m, 2H), 7.22-7.29 (m, 2H).

Step 3

(R)-2-[4-(1H-Benzoimidazol-2-yloxy)-phenoxymethyl]-pyrrolidine-1-carboxylic acid tert-butyl ester: To a 20 mL vial which contained a solution of the product from step 2 (220 mg, 0.4 mmol) in THF (8 mL) was added tetrabutylammonium fluoride (2 mL, excess) at 0° C. The mixture was allowed to warm to rt and stir at rt for 24 h and then was poured onto 20 mL ice-water solution. This solution was extracted with EtOAc (3×20 mL). The combined organic layers were washed with water (2×20 mL) and brine (20 mL). and dried over anhy. Na₂SO₄. The solvent was removed in vacuo to obtain the crude product which was purified by silica gel flash chromatography to afford the title product (103 mg, 70%).

Step 4

2-[4-((R)-1-Pyrrolidin-2-ylmethoxy)-phenoxy]-1H-benzoimidazole Hydrogen chloride salt: To a 20 mL vial which contained a solution of the product from step 3 (21 mg, 0.05 mmol) in dioxane (1 mL) was added HCl (4 N in dioxane, 2 mL) at 0° C. The mixture was allowed to warm to rt and stirred at rt for 16 h. The solvent was reduced to 1 mL and ether (15 mL) was added to this vial. The resulting solid was filtered out and dried in vacuo to yield the title product (15 mg, 90%); LCMS); 87%, ESI⁺, Calcd. 309.4. Found m/z 310.5 (M+1). ¹H NMR (400 MHz, DMSO-d₆); δ 1.66-1.79 (m, 1H), 1.84-2.05 (m, 2H), 2.05-2.18 (m, 1H), 3.17-3.28 (m, 2H), 3.97-4.07 (m, 1H), 4.11-4.18 (m, 1H), 4.29 (dd, J1=10.4 Hz, J2=3.2 Hz, 1H), 6.69-6.73 (m, 1H), 6.80-6.83 (m, 1H), 7.06-7.11 (m, 3H), 7.33-7.38 (m, 3H):

EXAMPLE 104

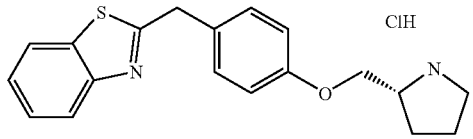

Step 1

4-Benzothiazol-2-ylmethyl-phenol: To a 50 mL press resistant vial which contained 2-amino-benzenethiol (1252 mg, 10 mmol) was added 4-(hydroxy-phenyl)-acetic acid (1522 mg, 10 mmol) at rt. The tube was sealed and the mixture was heated to 150° C. and stirred at 150° C. for 16 h. After cooling to rt, the mixture was poured onto 100 mL EtOAc and then washed with aq. HCl (2N, 2×30 mL), water (2×50 mL) and brine (50 mL) and dried over anhy. Na₂SO₄. The solvent was removed in vacuo to obtain the crude product which was purified by recrystallization with acetone-EtOAc-hexane to afford the title product (1500 mg, 63%); LCMS; 100% APCI⁺, Calcd: 241.3. Found m/z: 242.1 (M+1). ¹H NMR (400 MHz, CDCl₃); δ 4.36 (s, 2H), 6.78 (d, J=8.8, 2H), 7.20 (d, J=8.8, 2H), 7.34 (t, J=8.0, 1H), 7.45 (t, J=8.0, 1H), 7.80 (d, J=8.0, 1H), 7.99 (d, J=8.0, 1H).

Step 2

(R)-2-(4-Benzothiazol-2-ylmethyl-phenoxymethyl)-pyrrolidine-1-carboxylic acid tert-butyl ester: To a 25 mL vial which contained a suspension of NaH (60% in mineral oil, 60 mg, 1.5 mmol) in DMF (10 mL) was added the product from step 1 (241 mg, 1 mmol) at 0° C. The mixture was allowed to warm to rt and stir at rt for 30 min then cooled to 0° C. To this reaction mixture was added (R)-2-(toluene-4-sulfonyloxymethyl)-pyrrolidine-1-carboxylic acid tert-butyl ester (355 mg, 1 mmol) at 0° C. The resulting mixture was allowed warm to rt and stir at rt for 30 min and then was heated to 95° C. and stirred at 95° C. for 16 h. After cooling to rt, the mixture was poured onto 200 mL ice-water solution and this solution was allowed to stir at 0° C. for 30 min. The solid which formed was filtered out, dried through air to afford the title product (320 mg, 70%); ¹H NMR (400 MHz, CDCl₃); δ 1.47 (s, 9H), 1.81-2.11 (m, 4H), 3.32-3.47 (m, 2H), 3.70-4.20 (m, 3H), 4.37 (s, 2H), 6.84-6.97 (m, 4H), 7.33 (t J=7.6, 1H), 7.45 (t, J=7.6, 1H), 7.78 (d, J=8.0, 1H), 7.98 (d, J=8.4, 1H).

Step 3

2-[4-((R)-1-Pyrrolidin-2-ylmethoxy)-benzyl]-benzothiazole-hydrogen chloride salt: To a 20 mL vial which contained a solution of the product from step 2 (170 mg, 0.4 mmol) in dioxane (1 mL) was added HCl (4 N in dioxane, 2 mL) at 0° C. The mixture was allowed to warm to rt and stir at rt for 16 h. The solvent was reduced to 1 mL and ether (15 mL) was added to this vial. The resulting solid was filtered out and dried in vacuo to yield the title product, (120 mg, 80%); LCMS; 98% ESI⁺, Calcd: 324.5. Found m/z: 326.1 (M+2). ¹H NMR (400 MHz, DMSO-d₆); δ 1.66-1.79 (m, 1H), 1.84-2.05 (m, 2H), 2.05-2.16 (m, 1H), 3.15-3.27 (m, 2H), 3.82-3.97 (m, 1H), 4.13-4.16 (m, 1H), 4.24 (dd, J1=10.4 Hz, J2=3.2 Hz, 1H), 4.62 (s, 2H), 6.98 (d, J=8.4, 2H), 7.35 (d, J=8.4, 2H), 7.39 (d, J=7.6, 1H), 7.48 (t, J=7.2, 1H), 7.94 (d, J=8.4, 1H), 8.01 (d, J=8.0, 1H),

EXAMPLE 105

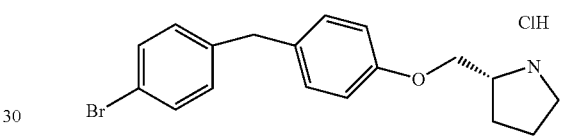

Step 1

(4-Bromo-phenyl)-(4-methoxy-phenyl)-methanone: To a solution of 4-bromo-benzoyl chloride (3.3 g, 15 mmol) and AlCl₃ (2.6 g, 20 mmol) in nitrobenzene (20 mL) was added a solution of methoxy-benzene (1.5 g, 14.5 mmol) in nitrobenzene (5 mL) slowly at 0° C. The resulting mixture was allowed to warm to rt and stir at rt for 16 h. The mixture was poured onto 150 mL ice-water solution and extracted with CH₂Cl₂ (5×100 mL). The combined organic layers were washed with water (2×100 mL) and brine (50 mL). and dried over anhy. Na₂SO₄. The solvent was removed in vacuo to obtain the crude product which was purified by recrystallization from cyclohexane to yield the title product (4.0 g, 91%) as a solid; ¹H NMR (500 MHz, CDCl₃); δ 3.90 (s, 3H), 6.97 (d, J=8.5, 2H), 7.63 (d, J=2.0, 4H), 7.79 (d, J=9.0, 2H).

Step 2

4-Methoxy(4-bromo-benzyl)-benzene: To a solution of the product from step 1 (0.5 g, 1.6 mmol) in TFA (1 mL) was added triethylsilane (0.5 mL, 25 mmol) at 0° C. The resulting mixture was allowed to warm to rt and stir at rt for 16 h. The mixture was poured onto 30 mL ice-water solution, neutralized with aq NaOH (2N) to pH=6-7, and then extracted with EtOAc (2×20 mL). The combined organic layers were washed with water (5×20 mL) and brine (20 mL). and dried over anhy. Na₂SO₄. The solvent was removed in vacuo to obtain the crude product which was purified by silica gel flash chromatography to afford the title product (0.45 g, 85%) as a solid; ¹H NMR (400 MHz, CDCl₃); δ 3.78 (s, 3H), 3.87 (s, 2H), 6.82 (d, J=8.8, 2H), 7.04 (d, J=8.8, 2H), 7.07 (d, J=8.8, 2H), 7.98 (d, J=8.4, 2H).

Step 3

4-(4-Bromo-benzyl)-phenol: To a solution of the product from step 2 (0.4 g, 1.4 mmol) from Step 2 in CH₂Cl₂ (150 mL)

was added BBr₃ (5 mL, 40 mmol; 1 M in CH₂Cl₂) at −78° C. The resulting mixture was allowed to warm to rt and stir at rt for 6 h. The mixture was poured onto 50 mL ice-water solution and extracted with CH₂Cl₂ (3×20 mL). The combined organic layers were washed with water (3×20 mL) and brine (20 mL). and dried over anhy. Na₂SO₄. The solvent was removed in vacuo to obtain the crude product which was purified by silica gel flash chromatography to provide the title product as a white solid (270 mg, 65%); LCMS; 90%, ESI⁻, (Calcd: 263.1. Found m/z: 263.0, (M). ¹H NMR (400 MHz, CDCl₃); δ 3.85 (s, 2H), 4.61 (s, 1H), 6.75 (d, J=8.4, 2H), 7.02 (d, J=8.4, 2H), 7.03 (d, J=8.8, 2H), 7.39 (d, J=8.4, 2H).

Step 4

(R)-2-[4-(4-Bromo-benzyl)-phenoxymethyl]-pyrrolidine-1-carboxylic acid tert-butyl ester: To a 25 mL vial which contained a suspension of NaH (60% in mineral oil, 30 mg, 0.75 mmol) in DMF (5 mL) was added the product from step 3 (132 mg, 0.5 mmol) at 0° C. The mixture was allowed to warm to rt and stir at rt for 30 min then cooled to 0° C. To this reaction mixture was added (R)-2-(toluene-4-sulfonyloxymethyl)-pyrrolidine-1-carboxylic acid tert-butyl ester (180 mg, 0.5 mmol) at 0° C. The resulting mixture was allowed warm to rt and stir at rt for 30 mm and then was heated to 90° C. and stirred at for 90° C. 16 h. After cooling to rt, the mixture was poured onto 100 mL ice-water solution and this solution was allowed to stir at 0° C. for 30 min. The solid formed was filtered out, dried through air to afford the title product (155 mg, 71%); ¹H NMR (400 MHz, CDCl₃); δ 1.47 (s, 9H), 1.79-2.18 (m, 4H), 3.28-3.44 (m, 2H), 3.70-3.92 (m, 1H), 3.86 (s, 2H), 4.02-4.19 (m, 2H), 6.82-6.88 (m, 2H), 7.05-7.08 (m, 4H), 7.38 (d, J=8.4 Hz, 2H):

Step 5

(R)-2-[4-(4-Bromo-benzyl)-phenoxymethyl]-pyrrolidine hydrogen chloride salt: To a 20 mL vial which contained a solution the product from step 4 (130 mg, 0.3 mmol) in dioxane was added HCl (4 N in dioxane, 2 mL) at 0° C. The mixture was allowed to warm to rt and stirred at rt for 16 h. The solvent was reduced to 1 mL and ether (15 mL) was added to this vial. the resulting solid was filtered out and dried in vacuo to yield the title product as a hydrogen chloride salt (80 mg, 80%); LCMS; 99%, ESI⁺, (Calcd: 346.3, Found m/z: 347.6, (M+1), 348.1, (M+2). ¹H NMR (400 MHz, DMSO-d₆); δ 1.68-1.76 (m, 1H), 1.86-2.02 (m, 2H), 2.07-2.14 (m, 1H), 3.15-3.24 (m, 2H), 3.86 (s, 2H), 3.83-3.92 (m, 1H), 4.02-4.07 (m, 1H), 4.21 (dd, J1=10.4 Hz, J2=3.6 Hz, 1H), 6.91 (d, J=8.8 Hz, 2H), 7.15-7.18 (m, 4H), 7.46 (d, J=8.4 Hz, 2H):

EXAMPLE 106

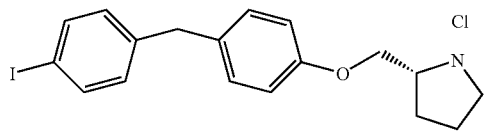

Step 1

(4-Iodo-phenyl)-(4-methoxy-phenyl)-methanone: To a solution of 4-iodo-benzoyl chloride (5 g, 15 mmol) and AlCl₃ (2.6 g, 20 mmol) in nitrobenzene (20 mL) was added a solution of methoxy-benzene (1.5 g, 14.5 mmol) in nitrobenzene (5 mL) slowly at 0° C. The resulting mixture was allowed to warm to rt and stir at rt for 16 h. The mixture was poured onto 150 mL ice-water solution and extracted with CH₂Cl₂ (5×100 mL). The combined organic layers were washed with water (2×100 mL) and brine (50 mL) and dried over anhy. Na₂SO₄. The solvent was removed in vacuo to provide the crude product, which was purified by recrystallization from cyclohexane to yield the title product (4.8 g, 88%); MS, APCI⁺ (Calcd: 338.15. Found m/z: 339.35, M+1). ¹H NMR (400 MHz, CDCl₃); δ 3.89 (s, 3H), 6.96 (d, J=8.8, 2H), 7.47 (d, J=8.4, 2H), 7.79 (d, J=9.2, 2H), 7.83 (d, J=8.4, 2H).

Step 2

4-Methoxy(4-odo-benzyl)-benzene: To a solution of the product from step 1 (4.7 g, 14 mmol) in TFA (15 mL) was added triethylsilane (4 mL, 25 mmol) at 0° C. The resulting mixture was allowed to warm to rt and stir at rt for 16 h. The mixture was poured onto 200 mL ice-water solution, neutralized with aq NaOH (2N) to pH=6-7, and then extracted with EtOAc (3×100 mL). The combined organic layers were washed with water (2×100 mL) and brine (50 mL), and dried over anhy. Na₂SO₄. The solvent was removed under vacuo to obtain the crude product which was purified by silica gel flash chromatography to afford the title product (4.2 g, 93%); ¹H NMR (400 MHz, CDCl₃); δ 3.78 (s, 3H), 3.85 (s, 2H), 6.83 (d, J=8.8, 2H), 6.92 (d, J=8.4, 2H), 7.06 (d, J=8.8, 2H), 7.59 (d, J=8.4, 2H).

Step 3

4-(4-Iodo-benzyl)-phenol: To a solution the product from step 2 (4.2 g, 13 mmol) in CH₂Cl₂ (150 mL) was added BBr₃ (40 mL, 40 mmol; 1 M in CH₂Cl₂) at −78° C. The resulting mixture was allowed to warm to rt and stir at rt for 6 h. The mixture was poured onto 150 mL ice-water solution and extracted with CH₂Cl₂ (3×100 mL). The combined organic layers were washed with water (2×100 mL) and brine (50 mL). and dried over anhy. Na₂SO₄. The solvent was removed under vacuo to obtain the crude product which was purified by recrystallization from acetone-EtOAc-hexane to provide the desired product (3.7 g, 92%); LCMS; 99%, ESI⁻, Calcd: 310.2. Found m/z: 309.1, (M−1). ¹H NMR (400 MHz, CDCl₃); δ 3.84 (s, 2H), 3.63 (s, 1H), 6.75 (d, J=8.8, 2H), 6.91 (d, J=8.4, 2H), 7.01 (d, J=8.0, 2H), 7.59 (d, J=8.4, 2H).

Step 4

(R)-2-[4-(4-Iodo-benzyl)-phenoxymethyl]-pyrrolidine-1-carboxylic acid tert-butyl ester: To a 25 mL vial which contained a suspension of NaH (60% in mineral oil, 60 mg, 1.5 mmol) in DMF (10 mL) was the product from step 3 (310 mg, 1 mmol) at 0° C. The mixture was allowed to warm to rt and stir at rt for 30 min then cooled to 0° C. To this reaction mixture was added (R)-2-(toluene-4-sulfonyloxymethyl)-pyrrolidine-1-carboxylic acid tert-butyl ester (355 mg, 1 mmol) at 0° C. The resulting mixture was allowed warm to rt and stir at rt for 30 min and then was heated to 90° C. and stirred at 90° C. for 16 h. After cooling to rt, the mixture was poured onto 200 mL ice-water solution and this solution was allowed to stir at 0° C. for 30 min. The solid which formed was filtered out, dried through air to afford the title product (290 mg, 59%); ¹H NMR (400 MHz, CDCl₃); δ 1.47 (s, 9H), 1.79-2.08 (m, 4H), 3.26-3.46 (m, 2H), 3.70-3.93 (m, 1H), 3.85 (s, 2H), 4.02-4.19 (m, 2H), 6.82-6.88 (m, 2H), 6.91 (d, J=7.6 Hz, 2H), 7.04 (d, J=8.0 Hz, 2H), 7.58 (d, J=8.0 Hz, 2H):

Step 5

(R)-2-[4-(4-Iodo-benzyl)-phenoxymethyl]-pyrrolidine Hydrogen chloride salt. 5. To a 20 mL vial which contained a solution of the product from step 4 (200 mg, 0.4 mmol) in dioxane was added HCl (4 N in dioxane, 2 mL) at 0° C. The mixture was allowed to warm to rt and stir at rt for 16 h. The solvent was reduced to 1 mL and ether (15 mL) was added to this vial. The resulting solid was filtered out and dried under vacuo to yield the title product (150 mg, 95%); LCMS; APCI+ 99%, Calcd: 393.3. Found m/z: 392.3 (M−1). ¹H NMR (400 MHz, DMSO-$d_6$); δ 1.68-1.77 (m, 1H), 1.86-2.04 (m, 2H), 2.05-2.16 (m, 1H), 3.14-3.23 (m, 2H), 3.84 (s, 2H), 3.83-3.89 (m, 1H), 4.07-4.11 (m, 1H), 4.20 (dd, J1=10.4 Hz, J2=3.6 Hz, 1H), 6.90 (d, J=8.8 Hz, 2H), 7.01 (d, J=8.0 Hz, 2H), 7.15 (d, J=8.8 Hz, 2H), 7.63 (d, J=8.4 Hz, 2H):

EXAMPLE 107

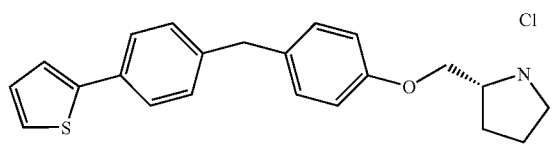

Step 1

(R)-2-[4-(2-Thiophen-benzyl)-phenoxymethyl]-pyrrolidine 1-carboxylic acid tert-butyl ester: To a 20 mL pressure resistant vial which contained a suspension of (R)-2-[4-(4-iodobenzyl)phenoxymethyl]-pyrrolidine-1-carboxylic acid tert-butyl ester (100 mg, 0.2 mmol), thiophene-2-boronic acid (52 mg, 0.4 mmol), palladium(II) acetate (10 mg, 0.05 mmol) and triphenyl phosphine (30 mg, 0.1 mmol) in DME (5 mL) was added potassium carbonate (100 mg, 0.7 mmol), ethanol (0.05 mL) and water (0.05 mL) at rt. The tube was sealed and the mixture was allowed to warm to rt and stir at rt for 30 min and then was heated to 98° C. and stirred at 98° C. for 16 h. After cooling to rt, the mixture was poured onto 200 mL ice-water solution and then extracted with EtOAc (3×30 mL). The combined organic layers were washed with water (2×30 mL) and brine (20 mL) and dried over anhy. $Na_2SO_4$. The solvent was removed in vacuo to obtain the crude product, which was purified by silica gel flash chromatography to afford desired product (68 mg, 75% yield); LCMS; 100%, APCI+, Calcd: 449.6. Found m/z: 449.6, M). ¹H NMR (400 MHz, CDCl₃); δ 1.46 (s, 9H), 1.79-2.08 (m, 4H), 3.27-3.44 (m, 2H), 3.70-3.95 (m, 1H), 3.92 (s, 2H), 4.03-4.18 (m, 2H), 6.91 (d, J=8.0 Hz, 2H), 7.09-7.11 (m, 1H), 7.16 (d, J=8.8 Hz, 2H), 7.26 (d, J=8.4 Hz, 2H), 7.39-7.42 (m, 2H), 7.58 (d, J=8.4 Hz, 2H):

Step 2

(R)-2-[4-(Benzothiazol-2-yloxy)-phenoxymethyl]-pyrrolidine-Hydrogen chloride salt: To a 20 mL vial which contained a solution of the product from step 1 (65 mg, 0.15 mmol) in dioxane was added HCl (4 N in dioxane 2 mL) at 0° C. The mixture was allowed to warm to rt and stir at rt for 16 h. The solvent was reduced to 1 mL and ether (15 mL) was added to this vial. The resulting solid was filtered out and dried under vacuo to yield the title product (40 mg, 85% yield); LCMS; 99%, APCI+, Calcd: 349.5. Found: 349.5, M) m/z. ¹H NMR (400 MHz, DMSO-$d_6$); δ 1.68-1.75 (m, 1H), 1.86-2.02 (m, 2H), 2.06-2.15 (m, 1H), 3.16-3.23 (m, 2H), 3.83-3.91 (m, 1H), 3.90 (s, 2H), 4.03-4.09 (m, 1H), 4.21 (dd, J1=10.8 Hz, J2=3.6 Hz, 1H), 6.92 (d, J=8.4 Hz, 2H), 7.10-7.13 (m, 1H), 7.19 (d, J=8.8 Hz, 2H), 7.23 (d, J=8.8 Hz, 2H), 7.45 (dd, J1=3.6 Hz, J2=1.2 Hz, 1H), 7.51 (dd, J1=5.2 Hz, J2=1.2 Hz, 1H), 7.56 (d, J=8.0 Hz, 2H):

EXAMPLE 108

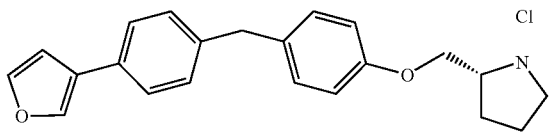

Step 1

(R)-2-[4-(3-Furan-benzyl)-phenoxymethyl]-pyrrolidine 1-carboxylic acid tert-butyl ester: Same procedure as that of step 1 in Example 107 with the use of (R)-2-[4-(4-iodobenzyl)phenoxymethyl]-pyrrolidine-1-carboxylic acid tert-butyl ester (100 mg, 0.2 mmol) and furan-3-boronic acid (50 mg, 0.4 mmol) to afford the title product (70 mg, 70% yield); LCMS; 83%, APCI+, Calcd: 433.6. Found m/z: 433.6, M). ¹H NMR (400 MHz, CDCl₃); δ 1.48 (s, 9H), 1.79-2.08 (m, 4H), 3.27-3.45 (m, 2H), 3.69-3.98 (m, 1H), 3.92 (s, 2H), 4.03-4.20 (m, 2H), 6.66-6.67 (m, 1H), 6.84-6.87 (m, 2H), 7.01-7.15 (m, 2H), 7.17 (d, J=8.0 Hz, 2H), 7.39 (d, J=8.0 Hz, 2H), 7.44-7.46 (m, 1H), 7.68-7.69 (m, 1H):

Step 2

(R)-2-[4-(3-Furan-benzyl)-phenoxymethyl]-pyrrolidine hydrogen chloride salt: Same procedure as that of step 2 in Example 107 with the use of (R)-2-[4-(3-furan-benzyl)-phenoxymethyl]-pyrrolidine 1-carboxylic acid tert-butyl ester (65 mg, 0.15 mmol) to yield the title product (32 mg, 70% yield); LCMS; 99%, APCI+, Calcd: 333.4. Found m/z: 333.4, (M). ¹H NMR (400 MHz, DMSO-$d_6$); δ 1.66-1.76 (m, 1H), 1.84-2.02 (m, 2H), 2.07-2.17 (m, 1H), 3.13-3.26 (m, 2H), 3.83-3.93 (m, 1H), 3.89 (s, 2H), 4.05-4.10 (m, 1H), 4.21 (dd, J1=10.8 Hz, J2=3.6 Hz, 1H), 6.90-6.93 (m, 2H), 7.17-7.24 (m, 4H), 7.52 (t J=4.0 Hz, 2H), 7.61-7.63 (m, 1H), 7.71-7.72 (m, 1H), 8.11 (s, 1H):

EXAMPLE 109

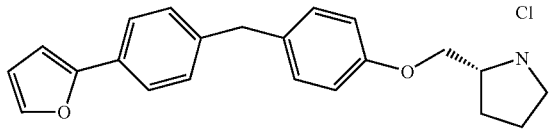

Step 1

(R)-2-[4-(2-Furan-benzyl)-phenoxymethyl]-pyrrolidine-1-carboxylic acid tert-butyl ester: Same procedure as that of step 1 in Example 107 with the use of (R)-2-[4-(4-iodobenzyl)phenoxymethyl]-pyrrolidine-1-carboxylic acid tert-butyl ester (100 mg, 0.2 mmol) and furan-2-boronic acid (50 mg, 0.4 mmol) to afford the title product (80 mg, 85% yield); MS: APCI+, Calcd: 433.6. found m/z; 434.6 M+1). ¹H NMR (400 MHz, CDCl₃); δ 1.46 (s, 9H), 1.80-2.08 (m, 4H), 3.27-3.44 (m, 2H), 3.70-3.95 (m, 1H), 3.92 (s, 2H), 4.02-4.19 (m, 2H), 6.44-6.46 (m, 1H), 6.59 (d, J=3.6 Hz, 1H), 6.85 (d, J=8.0 Hz, 2H), 7.09 (d, J=8.0 Hz, 2H),), 7.18 (d, J=8.0 Hz, 2H), 7.43-7.45 (m, 1H, 7.58 (d, J=8.4 Hz, 2H).

Step 2

(R)-2-[4-(2-Furan-benzyl)-phenoxymethyl]-pyrrolidine hydrogen chloride salt: Same procedure as that of step 2 in Example 107 with the use of (R)-2-[4-(2-furan-benzyl)-phenoxymethyl]-pyrrolidine 1-carboxylic acid tert-butyl ester (65 mg, 0.15 mmol) to yield the title product (52 mg, 90% yield); LCMS; 99%, APCI⁺, Calcd. 333.4. Found m/z: 333.4, M). ¹H NMR (400 MHz, DMSO-d₆); δ 1.68-1.76 (m, 1H), 1.86-2.02 (m, 2H), 2.06-2.15 (m, 1H), 3.16-3.24 (m, 2H), 3.82-3.90 (m, 1H), 3.90 (s, 2H), 4.05-4.10 (m, 1H), 4.21 (dd, J1=10.4 Hz, J2=3.6 Hz, 1H), 6.57 (q, J=2.0 Hz, 1H), 6.87 (d, J=3.6 Hz, 1H), 6.92 (d, J=8.8 Hz, 2H), 7.20 (d, J=8.8 Hz, 2H), 7.24 (d, J=8.0 Hz, 2H), 7.61 (d, J=8.0 Hz, 2H), 7.71-7.72 (m, 1H).

EXAMPLE 110

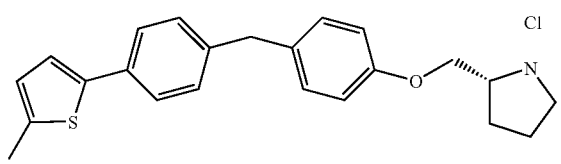

Step 1

(R)-2-{4-[4-(5-methyl-thiophen-2-yl)-benzyl]-phenoxymethyl}-pyrrolidine-1-carboxylic acid tert-butyl ester Same procedure as that of step 1 in Example 107 with the use of (R)-2-[4-(4-iodo-benzyl)phenoxymethyl]-pyrrolidine-1-carboxylic acid tert-butyl ester 4 (200 mg, 0.4 mmol), 5-methylthiophene-2-boronic acid (110 mg, 0.8 mmol) to afford the title product (150 mg, 76% yield); MS: ESI⁺, Calcd: 463.5. found m/z: 364.5 (M+1-boc). ¹H NMR (400 MHz, CDCl₃); δ 1.46 (s, 9H), 1.80-2.06 (m, 4H), 2.49 (s, 3H), 3.27-3.45 (m, 2H), 3.70-3.92 (m, 1H), 3.91 (s, 2H), 4.04-4.18 (m, 2H), 6.70 (dd, J1=3.6 Hz, J2=1.2 Hz, 1H), 6.85 (d, J=7.6 Hz, 2H), 7.05 (d, J=3.6 Hz, 1H), 7.09 (d, J=8.4 Hz, 2H),), 7.14 (d, J=8.0 Hz, 2H), 7.45 (d, J=8.4 Hz, 2H).

Step 2

(R)-2-{4-[4-(5-methyl-thiophen-2-yl)-benzyl]-phenoxymethyl}-pyrrolidine hydrogen chloroide salt: Same procedure as that of step 2 in Example 107 with the use of (R)-2-{4-[4-(5-methyl-thiophen-2-yl)-benzyl]-phenoxymethyl}-pyrrolidine-1-carboxylic acid tert-butyl ester (90 mg, 0.2 mmol) to yield the title product (70 mg, 85% yield); LCMS; 100%, APCI⁺(Calcd: 363.5. Found m/z: 364.5, M+1). ¹H NMR (400 MHz, DMSO-d₆); δ 1.67-1.75 (m, 1H), 1.86-2.03 (m, 2H), 2.06-2.16 (m, 1H), 2.45 (s, 3H), 3.15-3.25 (m, 2H), 3.83-3.91 (m, 1H), 3.88 (s, 2H), 4.04-4.08 (m, 1H), 4.21 (dd, J1=10.8 Hz, J2=3.6 Hz, 1H), 6.79 (dd, J=4.0 Hz, J2=1.2 Hz, 1H), 6.91 (d, J=8.8 Hz, 2H), 7.18-7.23 (m, 5H), 7.47 (d, J=8.4 Hz, 2H).

EXAMPLE 111

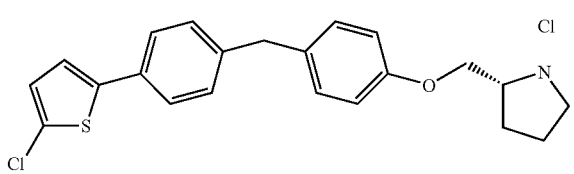

Step 1

(R)-2-{4-[4-(5-chloro-thiophen-2-yl)-benzyl]-phenoxymethyl}-pyrrolidine-1-carboxylic acid tert-butyl ester: Same procedure as that of step 1 in Example 107 with the use of (R)-2-[4-(4-iodo-benzyl)phenoxymethyl]-pyrrolidine-1-carboxylic acid tert-butyl ester (200 mg, 0.4 mmol), 5-chlorothiophene-2-boronic acid (135 mg, 0.8 mmol) to afford the title product (150 mg, 70% yield); MS ESI⁺, Calcd: 483.9. found m/z: 384.3 M-boc). ¹H NMR (400 MHz, CDCl₃); δ 1.46 (s, 9H), 1.80-2.00 (m, 4H), 3.28-3.45 (m, 2H), 3.70-3.92 (m, 1H), 3.91 (s, 2H), 4.03-4.18 (m, 2H), 6.82-6.88 (m, 2H), 6.6 (d, J=3.6 Hz, 1H), 7.01 (d, J=3.6 Hz, 1H), 7.08 (d, J=8.4 Hz, 2H),), 7.16 (d, J=8.0 Hz, 2H), 7.41 (d, J=8.4 Hz, 2H).

Step 2

(R)-2-{4-[4-(5-chloro-thiophen-2-yl)-benzyl]-phenoxymethyl}-pyrrolidine hydrogen chloroide salt: Same procedure as that of step 2 in Example 107 with the use of (R)-2-{4-[4-(5-chloro-thiophen-2-yl)-benzyl]-phenoxymethyl}-pyrrolidine-1-carboxylic acid tert-butyl ester (100 mg, 0.2 mmol) to yield the title product (85 mg, 90% yield); LCMS; 90%, APCI⁺Calcd: 383.9. Found m/z: 384.4, (M+1). ¹H NMR (400 MHz, DMSO-d₆); δ 1.67-1.76 (m, 1H), 1.86-2.02 (m, 2H), 2.06-2.16 (m, 1H), 3.15-3.25 (m, 2H), 3.83-3.92 (m, 1H), 3.90 (s, 2H), 4.03-4.08 (m, 1H), 4.21 (dd, J/=10.8 Hz, J2=3.6 Hz, 1H), 6.91 (d, J=9.2 Hz, 2H), 7.14 (d, J=4.0 Hz, 1H), 7.19 (d, J=8.4 Hz, 2H), 7.24 (d, J=8.4 Hz, 2H), 7.33 (d, J=3.6 Hz, 1H), 7.52 (d, J=8.4 Hz, 2H).

EXAMPLE 112

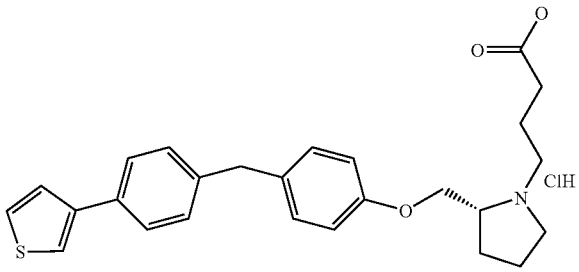

Step 1:

4-{(R)-2-[4-(4-Thiophen-3-yl-benzyl)-phenoxymethyl]-pyrrolidin-1-yl}-butyric acid methyl ester: To a 20 mL vial which contained a suspension of (R)-2-[4-(3-thiophen-benzyl)-phenoxymethyl]-pyrrolidine Hydrogen chloride salt (200 mg, 0.6 mmol) and K₂CO₃ (180 mg, 2 mmol) in DMF (10 mL) was added 4-bromo-butyric acid methyl ester (200 mg, 0.9 mmol) at rt. The mixture was allowed to stir at rt for 48 h and then was poured onto 30 mL ice-water solution and extracted with EtOAc (3×30 mL). The combined organic layers were washed with water (2×30 mL) and brine (20 mL) and dried over anhy. Na₂SO₄. The solvent was removed in vacuo to obtain the crude product which was purified by silica gel flash chromatography to afford desired product (175 mg, 75%); MS: APCI⁺Calcd: 449.6. Found m/z: 450.6 (M+1). ¹H NMR (400 MHz, CDCl₃); δ 1.62-2.01 (m, 5H), 2.19-2.49 (m, 4H), 2.79-2.91 (m, 2H), 3.10-3.19 (m, 1H), 3.64 (s, 3H), 3.75-3.79 (m, 1H), 3.88-3.93 (m, 2H), 3.93 (s, 2H), 6.83 (d, J=8.4 Hz, 2H), 7.10 (d, J=8.8 Hz, 2H), 7.20 (d, J=8.4 Hz, 2H), 7.36 (d, J=2.0 Hz, 2H),), 7.40 (t, J=2.0 Hz, 1H), 7.51 (d, J=8.4 Hz, 2H).

Step 2:

4-{(R)-2-[4-(4-Thiophen-3-yl-benzyl)-phenoxymethyl]-pyrrolidin-1-yl}-butyric acid hydrogen chloride salt: To a 20 mL vial which contained a solution of the product from step 1 (155 mg, 0.35 mmol) in HCl (4 N in dioxane 4 mL) was added water (0.5 mL) at 0° C. The mixture was allowed to warm to rt and stir at rt for 24 h. The solvent was removed to yield the crude which was purified by recrystallization from THF-ether to afford the title product (125 mg, 75%); LCMS; 100%, APCI+, Calcd: 435.6. Found m/z: 436.5, (M+1). $^1$H NMR (400 MHz, DMSO-$d_6$); δ 1.74-2.08 (m, 5H), 2.15-2.26 (m, 1H), 2.31-2.40 (m, 2H), 3.05-3.20 (m, 2H), 3.40-3.49 (m, 1H), 3.53-3.63 (m, 1H), 3.83-3.93 (m, 1H), 3.90 (s, 2H), 4.15-4.19 (m, 1H), 4.27 (dd, J1=10.8 Hz, J2=3.6 Hz, 1H), 6.93 (d, J=8.8 Hz, 2H), 7.20 (d, J=8.8 Hz, 2H), 7.23 (d, J=8.4 Hz, 2H), 7.51 (dd, J1=4.8 Hz, J2=1.6 Hz, 1H), 7.60-7.63 (m, 3H), 7.79 (dd, J=2.8 Hz, J2=1.2 Hz, 1H):

EXAMPLE 113

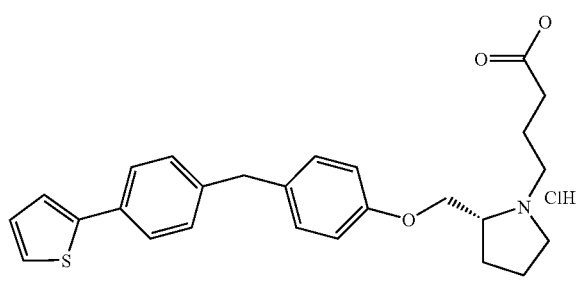

Step 1

4-{(R)-2-[4-(4-Thiophen-2-yl-benzyl)-phenoxymethyl]-pyrrolidin-1-yl}-butyric acid methyl ester: Same procedure as that of step 1 in Example 112 with the use of (R)-2-[4-(2-thiophen-benzyl)-phenoxymethyl]-pyrrolidine hydrogen chloride salt (200 mg, 0.6 mmol) and 4-bromo-butyric acid methyl ester (200 mg, 0.9 mmol) to afford the title product (150 mg, 70% yield); MS: APCI+Calcd: 435.6. Found m/z: 435.6, (M). $^1$H NMR (400 MHz, CDCl$_3$); δ 1.62-2.01 (m, 5H), 2.20-2.48 (m, 4H), 2.79-2.92 (m, 2H), 3.10-3.18 (m, 1H), 3.64 (s, 3H), 3.72-3.76 (m, 1H), 3.88-3.91 (m, 2H), 3.90 (s, 2H), 6.83 (d, J=8.8 Hz, 2H), 7.05-7.07 (m, 1H), 7.10 (d, J=8.8 Hz, 2H), 7.18 (d, J=8.4 Hz, 2H),), 7.23-7.27 (m, 2H), 7.52 (d, J=8.4 Hz, 2H).

Step 2

4-{(R)-2-[4-(4-Thiophen-2-yl-benzyl)-phenoxymethyl]-pyrrolidin-1-yl}-butyric acid hydrogen chloride salt. Same procedure as that of step 2 in Example 112 with the use of 4-{(R)-2-[4-(4-thiophen-2-yl-benzyl)-phenoxymethyl]-pyrrolidin-1-yl}-butyric acid methyl ester to yield the title product (145 mg, 88% yield); LCMS; 100%, APCI+, Calcd: 435.6. Found m/z: 436.5, M+1). $^1$H NMR (400 MHz, DMSO-$d_6$); δ 1.74-2.09 (m, 5H), 2.16-2.27 (m, 1H), 2.31-2.40 (m, 2H), 3.05-3.20 (m, 2H), 3.40-3.50 (m, 1H), 3.53-3.65 (m, 1H), 3.83-3.95 (m, 1H), 3.90 (s, 2H), 4.16-4.20 (m, 1H), 4.27 (dd, J1=10.8 Hz, J2=3.6 Hz, 1H), 6.94 (d, J=8.8 Hz, 2H), 7.10-7.13 (m, 1H), 7.20 (d, J=8.8 Hz, 2H), 7.23 (d, J=8.0 Hz, 2H), 7.43-7.45 (m, 1H), 7.51 (dd, J1=5.2 Hz, J2=1.2 Hz, 1H), 7.56 (d, J=8.0 Hz, 2H),

EXAMPLE 114

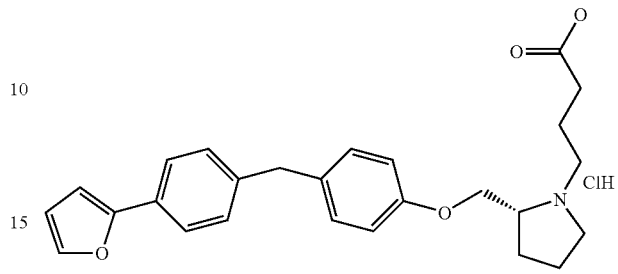

Step 1

4-{(R)-2-[4-(4-furan-2-yl-benzyl)-phenoxymethyl]-pyrrolidin-1-yl}-butyric acid methyl ester: Same procedure as that of step 1 in Example 112 with the use of ((R)-2-[4-(2-furan-benzyl)-phenoxymethyl]-pyrrolidine hydrogen chloride salt (40 mg, 0.1 mmol) and 4-bromo-butyric acid methyl ester (30 mg, 0.15 mmol) to afford the title product (35 mg, 65% yield); $^1$H NMR (400 MHz, CDCl$_3$); δ 1.65-2.05 (m, 5H), 2.19-2.48 (m, 4H), 2.80-2.91 (m, 2H), 3.10-3.18 (m, 1H), 3.64 (s, 3H), 3.72-3.75 (m, 1H), 3.86-3.92 (m, 2H), 3.92 (s, 2H), 6.82 (d, J=8.8 Hz, 2H), 7.09 (d, J=8.4 Hz, 2H), 7.18 (d, J=8.4 Hz, 2H), 7.21 (d, J=1.2 Hz, 1H), 7.31 (d, J=0.8 Hz, 1H), 7.44 (J=1.2 Hz, 1H), 7.58 (d, J=8.0 Hz, 2H).

Step 2

4-{(R)-2-[4-(4-furan-2-yl-benzyl)-phenoxymethyl]-pyrrolidin-1-yl}-butyric acid hydrogen chloride salt: Same procedure as that of step 2 in Example 112 with the use of 4-{(R)-2-[4-(4-furan-2-yl-benzyl)-phenoxymethyl]-pyrrolidin-1-yl}-butyric acid methyl ester (20 mg 0.04 mmol) to yield the title product (18 mg, 90% yield); LCMS; 98%, APCI+, Calcd: 419.5. Found m/z: 420.4, (M+1). $^1$H NMR (400 MHz, DMSO-$d_6$); δ 1.74-2.27 (m, 6H), 2.33-2.38 (m, 2H), 3.05-3.20 (m, 2H), 3.40-3.65 (m, 2H), 3.83-3.93 (m, 1H), 3.90 (s, 2H), 4.10-4.20 (m, 1H), 4.21-4.30 (m, 1H), 6.56-6.59 (m, 1H), 6.89-6.98 (m, 3H), 7.14-7.27 (m, 5H), >7.5-7.72 (m, 2H):

EXAMPLE 115

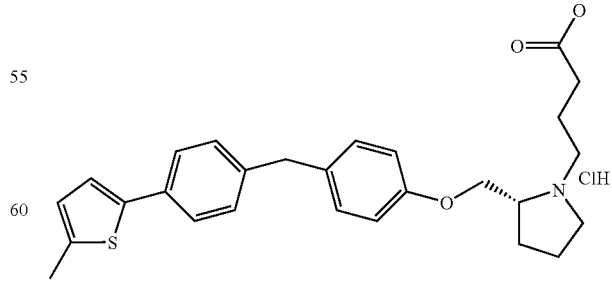

Step 1

(R)-2-{4-[4-(5-methyl-thiophen-2-yl)-benzyl]-phenoxymethyl}-pyrrolidin-1-yl}-butyric acid methyl ester: Same procedure as that of step 1 in Example 112 with the use of (R)-2-{4-[4-(5-methyl-thiophen-2-yl)-benzyl]-phenoxymethyl}-pyrrolidine hydrogen chloroide salt (40 mg, 0.1 mmol) and 4-bromo-butyric acid methyl ester (30 mg, 0.15 mmol) to afford the title product (30 mg, 65% yield); $^1$H NMR (400 MHz, CDCl$_3$); δ 1.63-2.03 (m, 5H), 2.19-2.48 (m, 4H), 2.49 (s, 3H), 2.79-2.91 (m, 2H), 3.10-3.19 (m, 1H), 3.64 (s, 3H), 3.70-3.77 (m, 1H), 3.85-3.92 (m, 2H), 3.91 (s, 2H), 6.70 (dd, J=7.6 Hz, J2=1.2 Hz, 1H), 6.82 (d, J=8.8 Hz, 2H), 7.05 (d, J=3.2 Hz, 1H), 7.09 (d, J=8.4 Hz, 2H), 7.14 (d, J=8.4 Hz, 2H), 7.45 (J=8.4 Hz, 2H).

Step 2

(R)-2-{4-[4-(5-methyl-thiophen-2-yl)-benzyl]-phenoxymethyl}-pyrrolidin-1-yl}-butyric acid hydrogen chloride salt: Same procedure as that of step 2 in Example 112 with the use of (R)-2-{4-[4-(5-methyl-thiophen-2-yl)-benzyl]-phenoxymethyl}-pyrrolidin-1-yl}-butyric acid methyl ester (20 mg, 0.04 mmol) to yield the title product, (18 mg, 90% yield); LCMS; 85%, ESI$^+$, Calcd: 449.6. Found m/z: 450.4, M+1). $^1$H NMR (400 MHz, DMSO-d$_6$); δ 1.74-2.09 (m, 5H), 2.13-2.26 (m, 1H), 2.31-2.39 (m, 2H), 2.45 (s, 3H), 3.05-3.19 (m, 2H), 3.38-3.49 (m, 1H), 3.53-3.64 (m, 1H), 3.86-3.94 (m, 1H), 3.89 (s, 2H), 4.09-4.17 (m, 1H), 4.20-4.30 (m, 1H), 6.79 (dd, J1=3.6 Hz, J2=1.2 Hz, 1H), 6.93 (d, J=8.4 Hz, 2H), 7.18-7.23 (m, 5H), 7.47 (d, J=8.4 Hz, 2H).

EXAMPLE 116

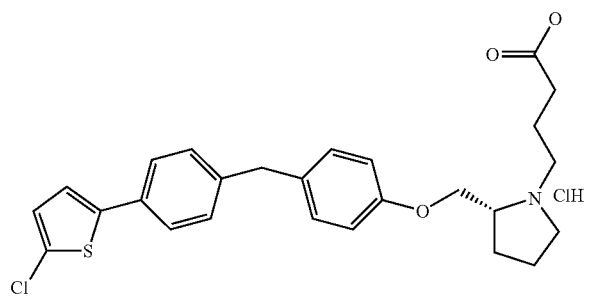

Step 1

(R)-2-{4-[4-(5-chloro-thiophen-2-yl)-benzyl]-phenoxymethyl}-pyrrolidin-1-yl}-butyric acid methyl ester: Same procedure as that of step 1 in Example 112 with the use of (R)-2-{4-[4-(5-chloro-thiophen-2-yl)-benzyl]-phenoxymethyl}-pyrrolidine hydrogen chloroide salt (40 mg, 0.1 mmol) and 4-bromo-butyric acid methyl ester (30 mg, 0.15 mmol) to afford the title product (30 mg, 65% yield); $^1$H NMR (400 MHz, CDCl$_3$); δ 1.63-2.03 (m, 5H), 2.19-2.48 (m, 4H), 2.79-2.91 (m, 2H), 3.10-3.18 (m, 1H), 3.64 (s, 3H), 3.72-3.77 (m, 1H), 3.86-3.92 (m, 2H), 3.91 (s, 2H), 6.82 (d, J=8.8 Hz, 2H), 6.86 (d, J=4.0 Hz, 1H), 7.01 (d, J=3.6 Hz, 1H), 7.09 (d, J=8.4 Hz, 2H), 7.17 (d, J=8.0 Hz, 2H), 7.41 (J=8.4 Hz, 2H).

Step 2

(R)-2-{4-[4-(5-chloro-thiophen-2-yl)-benzyl]-phenoxymethyl}-pyrrolidin-1-yl}-butyric hydrogen chloride salt: Same procedure as that of step 2 in Example 112 with the use of (R)-2-{4-[4-(5-chloro-thiophen-2-yl)-benzyl]-phenoxymethyl}-pyrrolidin-1-yl}-butyric acid methyl ester (20 mg, 0.04 mmol) to yield the title product, (13 mg, 80% yield); LCMS; 85%, APCI$^+$, Calcd: 470.0. Found m/z: 470.6 (M+1). $^1$H NMR (400 MHz, DMSO-d$_6$); δ 1.74-2.09 (m, 5H), 2.16-2.27 (m, 1H), 2.31-2.39 (m, 2H), 3.05-3.19 (m, 2H), 3.38-3.50 (m, 1H), 3.53-3.65 (m, 1H), 3.83-3.90 (m, 1H), 3.90 (s, 2H), 4.15-4.20 (m, 1H), 4.26 (dd, J1=10.4 Hz, J2=3.2 Hz, 1H), 6.93 (d, J=8.4 Hz, 2H), 7.14 (d, J=4.0 Hz, 1H), 7.19 (d, J=8.8 Hz, 2H), 7.24 (d, J=8.4 Hz, 2H), 7.33 (d, J=4.0 Hz, 1H), 7.51 (d, J=8.4 Hz, 2H), EXAMPLE 124

EXAMPLE 117

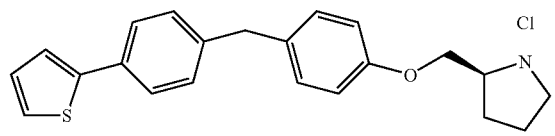

Step 1

(S)-2-[4-(2-Thiophen-benzyl)-phenoxymethyl]-pyrrolidine 1-carboxylic acid tert-butyl ester: Same procedure as that of step 1 in Example 107 with the use of (S)-2-[4-(4-iodo-benzyl)phenoxymethyl]-pyrrolidine-1-carboxylic acid tert-butyl ester (100 mg, 2 mmol), thiophene-2-boronic acid (520 mg, 4 mmol) to afford the title product (730 mg, 75% yield); $^1$H NMR (400 MHz, CDCl$_3$); δ 1.46 (s, 9H), 1.79-2.08 (m, 4H), 3.27-3.44 (m, 2H), 3.70-3.95 (m, 1H), 3.92 (s, 2H), 4.03-4.18 (m, 2H), 6.91 (d, J=8.0 Hz, 2H), 7.09-7.11 (m, 1H), 7.16 (d, J=8.8 Hz, 2H), 7.26 (d, J=8.4 Hz, 2H), 7.39-7.42 (m, 2H), 7.58 (d, J=8.4 Hz, 2H):

Step 2

(S)-2-[4-(Benzothiazol-2-yloxy)-phenoxymethyl]-pyrrolidine-hydrogen chloride salt: Same procedure as that of step 2 in Example 107 with the use of (S)-2-[4-(2-thiophen-benzyl)-phenoxymethyl]-pyrrolidine 1-carboxylic acid tert-butyl ester (720 mg, 1.6 mmol) to yield the title product (515 mg, 90% yield); LCMS; 98%, ESI$^+$, Calcd: 349.5. Found m/z: 351.3, M+2). $^1$H NMR (400 MHz, DMSO-d$_6$); δ 1.68-1.75 (m, 1H), 1.86-2.02 (m, 2H), 2.06-2.15 (m, 1H), 3.16-3.23 (m, 2H), 3.83-3.91 (m, 1H), 3.90 (s, 2H), 4.03-4.09 (m, 1H), 4.21 (dd, J1=10.8 Hz, J2=3.6 Hz, 1H), 6.92 (d, J=8.8 Hz, 2H), 7.10-7.13 (m, 1H), 7.19 (d, J=8.8 Hz, 2H), 7.23 (d, J=8.8 Hz, 2H), 7.44 (dd, J1=3.6 Hz, J2=1.2 Hz, 1H), 7.51 (dd, J1=5.2 Hz, J2=1.2 Hz, 1H), 7.56 (d, J=8.0 Hz, 2H).

EXAMPLE 118

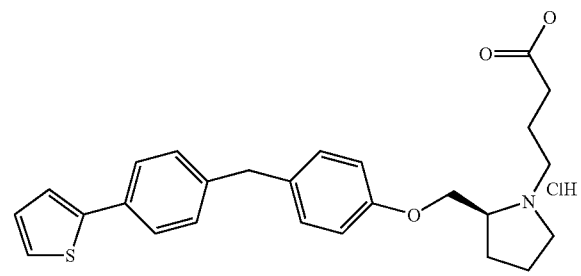

Step 1

Same procedure as that of step 1 in Example 112 with the use of (S)-2-[4-(2-thiophen-benzyl)-phenoxymethyl]-pyrrolidine hydrogen chloride salt (500 mg, 1.3 mmol) and 4-bromo-butyric acid methyl ester (360 mg, 2 mmol) to afford the title product (520 mg, 70% yield); $^1$H NMR (400 MHz, CDCl₃); δ 1.62-2.01 (m, 5H), 2.20-2.48 (m, 4H), 2.79-2.92 (m, 2H), 3.10-3.18 (m, 1H), 3.64 (s, 3H), 3.72-3.76 (m, 1H), 3.88-3.91 (m, 2H), 3.90 (s, 2H), 6.83 (d, J=8.8 Hz, 2H), 7.05-7.07 (m, 1H), 7.10 (d, J=8.8 Hz, 2H), 7.18 (d, J=8.4 Hz, 2H),), 7.23-7.27 (m, 2H), 7.52 (d, J=8.4 Hz, 2H).

Step 2

Same procedure as that of step 2 in Example 112 with the use of 4-{(S)-2-[(Z)-1-prop-2-en-(E)-ylidene-5-(4-thiophen-2-yl-phenyl)-pent-2-enyloxymethyl]-pyrrolidin-1-yl}-butyric acid methyl ester to yield the title product (450 mg, 80% yield); LCMS; 95%, ESI⁺, Calcd: 435.6. Found m/z: 436.6 μM+1). ¹H NMR (400 MHz, DMSO-d₆); δ 1.74-2.09 (m, 5H), 2.16-2.27 (m, 1H), 2.31-2.40 (m, 2H), 3.05-3.20 (m, 2H), 3.40-3.50 (m, 1H), 3.53-3.65 (m, 1H), 3.83-3.95 (m, 1H), 3.90 (s, 2H), 4.16-4.20 (m, 1H), 4.27 (dd, 1H, J1=10.8 Hz, J2=3.6 Hz), 6.94 (d, J=8.8 Hz, 2H), 7.10-7.13 (m, 1H), 7.20 (d, J=8.8 Hz, 2H), 7.23 (d, J=8.0 Hz, 2H), 7.45 (dd, J1=3.6 Hz, J2=1.2 Hz, 1H), 7.51 (dd, J1=5.2 Hz, J2=1.2 Hz, 1H), 7.56 (d, J=8.0 Hz, 2H).

EXAMPLE 119

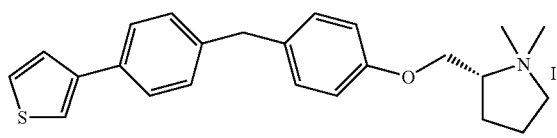

(R)-1,1-Dimethyl-2-[4-(4-thiophen-3-yl-benzyl)-phenoxymethyl]-pyrrolidine iodide salt: To a solution of Example 66 (100 mg, 0.25 mmol) in DMF (2 mL) was added K₂CO₃ (50 mg, 3.5 mmol) and then MeI (1 mL, 10 mmol) at 0° C. The resulting mixture was allowed to warm to rt and stir at rt for 2 h. The mixture was poured onto 50 mL ice-water solution and stirred for 30 min. The solid which formed was filtered, washed with water (2×30 mL), and then dried over air to provide the title product) (85 mg, 75%); LCMS; 99%, ESI⁺ Calcd. 378.5.6. found m/z: 379.5 (M+1). ¹H NMR (400 MHz, DMSO-d₆); δ 1.94-2.12 (m, 3H), 2.25-2.36 (m, 1H), 2.98 (s, 3H), 3.25 (s, 3H), 3.55-3.70 (m, 2H), 3.90 (s, 2H), 4.05-4.10 (m, 1H), 4.25-4.40 (m, 2H), 6.96 (d, J=8.8 Hz, 2H), 7.22 (d, J=9.2 Hz, 2H), 7.24 (d, J=8.8 Hz, 2H), 7.51 (dd, J1=5.2 Hz, J2=1.2 Hz, 1H), 7.61-7.63 (m, 3H), 7.80 (dd, J1=2.8 Hz, J2=1.2 Hz, 1H).

EXAMPLE 120

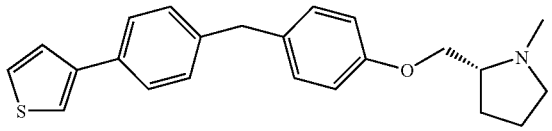

(R)-1-Methyl-2-[4-(4-thiophen-3-yl-benzyl)-phenoxymethyl]-pyrrolidine: Followed the same procedure as that of step 3 in Example 119 with the exception of using 50 mg (0.3 mmol) MeI rather than 1 mL MeI to yield the title product (65 mg, 70%); LCMS; 98%, APCI⁺Calcd: 363.5. found: 364.4 m/z (M+1). ¹H NMR (400 MHz, DMSO-d₆); δ 1.51-1.70 (m, 3H), 1.88-1.99 (m, 1H), 2.13-2.20 (m, 1H), 2.34 (s, 3H), 2.34-2.55 (m, 1H), 2.91-2.96 (m, 1H), 3.74-3.79 (m, 1H), 3.88 (s, 2H), 3.90-3.94 (m, 1H), 6.85 (d, J=8.4 Hz, 2H), 7.14 (d, J=8.8 Hz, 2H), 7.23 (d, J=8.4 Hz, 2H), 7.51 (dd, 1H, J1=5.2 Hz, J2=1.2 Hz), 7.60-7.62 (m, 3H), 7.79 (dd, 1H, J=2.8 Hz, 1.2 Hz):

EXAMPLE 121

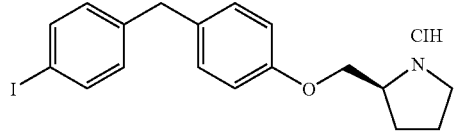

(S)-2-[4-(4-Iodo-benzyl)-phenoxymethyl]-pyrrolidine: To a 20 mL vial which contained a solution of (S)-2-(4-iodo-phenoxymethyl)-pyrrolidine-1-carboxylic acid tert-butyl ester (50 mg, 0.1 mmol) in dioxane (1 mL) was added HCl (4 N in dioxane, 2 mL) at 0° C. The mixture was allowed to warm to rt and stir at rt for 16 h. The solvent was reduced to 1 mL and ether (15 mL) was added to this vial. The resulting solid was filtered out and dried under vacuo to yield the title product (35 mg, 85%); LCMS; 95%, ESI⁺ Calcd: 393.3. found: 394.8. m/z (M+1). ¹H NMR (400 MHz, DMSO-d₆); ¹H NMR (400 MHz, DMSO-d₆); δ 1.68-1.77 (m, 1H), 1.86-2.04 (m, 2H), 2.05-2.16 (m, 1H), 3.14-3.23 (m, 2H), 3.84 (s, 2H), 3.83-3.89 (m, 1H), 4.07-4.11 (m, 1H), 4.20 (dd, J1=10.4 Hz, J2=3.6 Hz, 1H), 6.90 (d, J=8.8 Hz, 2H), 7.01 (d, J=8.0 Hz, 2H), 7.15 (d, J=8.8 Hz, 2H), 7.63 (d, J=8.4 Hz, 2H):

EXAMPLE 122

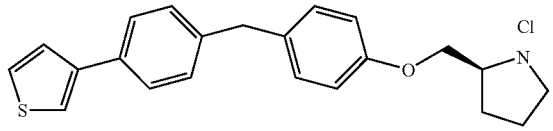

Step 1

(S)-2-[4-(3-thiophen-benzyl)-phenoxymethyl]-pyrrolidine 1-carboxylic acid tert-butyl ester: Followed the same procedure as that of step 1 in Example 107 with the use of (S)-2-[4-(4-iodo-benzyl)phenoxymethyl]-pyrrolidine-1-carboxylic acid tert-butyl ester (2000 mg, 4 mmol), thiophene-3-boronic acid (1200 mg, 8 mmol) to afford the title product, (1300 mg, 74%); ¹H NMR (400 MHz, CDCl₃); δ 1.47 (s, 9H), 1.79-2.08 (m, 4H), 3.26-3.44 (m, 2H), 3.70-3.95 (m, 1H), 3.93 (s, 2H), 4.03-4.18 (m, 2H), 6.82-6.88 (m, 2H), 7.10 (d, J=8.0 Hz, 2H), 7.19 (d, J=8.0 Hz, 2H), 7.35-7.41 (m, 3H), 7.50 (d, J=8.0 Hz, 2H):

Step 2

(S)-2-[4-(3-Thiophen-benzyl)-phenoxymethyl]-pyrrolidine hydrogen chloride salt: Followed the same procedure as that of step 2 in Example 107 with the use of (S)-2-[4-(3-thiophen-benzyl)-phenoxymethyl]-pyrrolidine 1-carboxylic acid tert-butyl ester (1300 mg, 3 mmol) to yield the title product, (980 mg, 90%); LCMS; 98%, ESI⁺, Calcd: 349.5. Found m/z: 350.4 m/z; (M+1). ¹H NMR (400 MHz, DMSO-d₆); δ 1.66-1.76 (m, 1H), 1.86-2.02 (m, 2H), 2.07-2.16 (m, 1H), 3.15-3.24 (m, 2H), 3.83-3.93 (m, 1H), 3.90 (s, 2H), 4.04-4.09 (m, 1H), 4.21 (dd, J1=10.8 Hz, J2=3.6 Hz, 1H), 6.92 (d, J=8.4 Hz, 2H), 7.20 (d, J=8.4 Hz, 2H), 7.22 (d, J=8.0 Hz, 2H), 7.51 (dd, J1=4.8 Hz, J2=1.6 Hz, 1H,), 7.60-7.63 (m, 3H), 7.79 (dd, J/=2.8 Hz, J2=1.2 Hz, 1H):

EXAMPLE 123

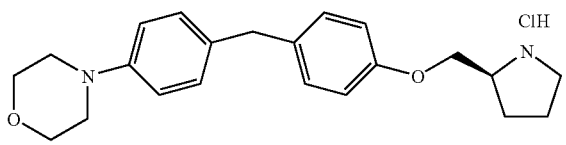

Step 1

(S)-2-[4-(4-Morpholin-4-yl-benzyl)-phenoxymethyl]-pyrrolidine-1-carboxylic acid tert-butyl ester: To a 25 mL vial which contained a suspension of (S)-2-(4-iodo-phenoxymethyl)-pyrrolidine-1-carboxylic acid tert-butyl ester (250 mg, 0.5 mmol), morpholine (45 mg, 0.5 mmol), $Pd_2(dba)_3$ (15 mg, 0.5 eq) and tri-tert-butyl-phosphine (31 mg, 1.5 eq) in toluene (5 mL) was added sodium tert-butoxide (47 mg, 0.5 mmol) at 0° C. and flashed with argon. The mixture was allowed to warm to rt and stir at rt for 48 h. The mixture was poured onto 100 mL ice-water solution and then extracted with EtOAc (3×30 mL). The combined organic layers were washed with water (2×30 mL), brine (20 mL) and dried over anhy. $Na_2SO_4$. The solvent was removed under vacuo to obtain the crude product which was purified by silica gel flash chromatography to afford the title product (120 mg, 50%); $^1H$ NMR (400 MHz, $CDCl_3$); δ 1.47 (s, 9H), 1.79-2.08 (m, 4H), 3.08-3.13 (m, 4H), 3.26-3.44 (m, 2H), 3.70-3.95 (m, 7H), 4.03-4.18 (m, 2H), 6.84 (d, J=8.8 Hz, 4H), 7.05-7.11 (m, 4H):

Step 2

4-{4-[4-((S)-1-Pyrrolidin-2-ylmethoxy)-benzyl]-phenyl}-morpholine: To a 20 mL vial which contained a solution of (S)-2-[4-(4-morpholin-4-yl-benzyl)-phenoxymethyl]-pyrrolidine-1-carboxylic acid tert-butyl ester (100 mg, 0.2 mmol) in dioxane (1 mL) was added HCl (4 N in dioxane, 2 mL) at 0° C. The mixture was allowed to warm to rt and stir at rt for 16 h. The solvent was reduced to 1 mL and ether (15 mL) was added to this vial. the resulting solid was filtered out and dried under vacuo to yield the title product (70 mg, 80%); LCMS; 90%, $ESI^+$ Calcd: 352.5. found m/z: 353.7 (M+1). $^1H$ NMR (400 NM, DMSO-$d_6$); δ 1.66-1.76 (m, 1H), 1.84-2.02 (m, 2H), 2.04-2.14 (m, 1H), 3.05-3.24 (m, 4H), 3.73-4.12 (m, 10H), 4.19 (dd, J1=10.8 Hz, J2=3.6 Hz, 1H), 6.91 (d, J=8.4 Hz, 2H), 7.20 (m, 6H):

EXAMPLE 124

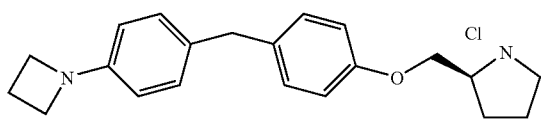

Step 1

(S)-2-[4-(4-Azetidin-1-yl-benzyl)-phenoxymethyl]-pyrrolidine-1-carboxylic acid tert-butyl ester: Followed the same procedure as that of step 1 in Example 123 with the use of (S)-2-(4-iodo-phenoxymethyl)-pyrrolidine-1-carboxylic acid tert-butyl ester (250 mg, 0.5 mmol) and azetidine (45 mg, 0.5 mmol) to afford the title product, (100 mg, 50%); $^1H$ NMR (400 MHz, $CDCl_3$); δ 1.46 (s, 9H), 1.79-2.08 (m, 4H), 2.29-2.37 (m, 2H), 3.27-3.43 (m, 2H), 3.68-3.93 (m, 7H), 4.04-4.20 (m, 2H), 6.38 (d, J=8.4 Hz, 2H), 6.82 (d, J=8.8 Hz, 2H), 7.00 (d, J=8.0 Hz, 2H), 7.06 (d, J=7.6 Hz, 2H).

Step 2

(S)-2-[4-(4-Azetidin-1-yl-benzyl)-phenoxymethyl]-pyrrolidine hydrogen chloride salt: Followed the same procedure as that of step 2 in Example 123 with the use of (S)-2-[4-(4-azetidin-1-yl-benzyl)-phenoxymethyl]-pyrrolidine-1-carboxylic acid tert-butyl ester (85 mg, 0.2 mmol) to yield the title product, (60 mg, 85%); LCMS; 93%, $APCI^+$, Calcd: 322.5. Found m/z: 323.8, (M+1). $^1H$ NMR (400 MHz, DMSO-$d_6$); δ 1.66-1.76 (m, 1H), 1.84-2.14 (m, 4H), 3.15-3.28 (m, 4H), 3.72-3.78 (m, 2H), 3.82-3.91 (m, 1H), 3.85 (s, 2H), 4.08-4.12 (m, 1H), 4.21 (dd, J1=10.4 Hz, J2=3.6 Hz, 1H), 6.90 (d, J=8.8 Hz, 2H), 7.16 (d, J=8.4 Hz, 2H), 7.00-7.25 (m, 4H).

EXAMPLE 125

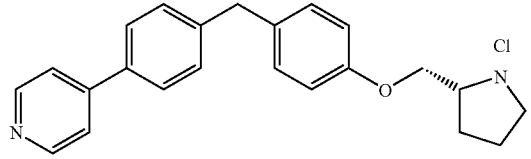

Step 1:

(R)-2-[4-(4-Pyridin-4-yl-benzyl)-phenoxymethyl]-pyrrolidine-1-carboxylic acid tert-butyl ester: To a 20 mL press resistant vial which contained a suspension of (R)-2-[4-(4-iodo-benzyl)phenoxymethyl]-pyrrolidine-1-carboxylic acid tert-butyl ester (200 mg, 0.4 mmol), pyridine-4-boronic acid (110 mg, 0.8 mmol), palladium(II) acetate (10 mg, 0.05 mmol) and triphenyl phosphine (30 mg, 0.1 mmol) in DME (5 mL) was added potassium carbonate (100 mg, 0.7 mmol), ethanol (0.05 mL) and water (0.05 mL) at rt. The tube was sealed and the mixture was allowed to warm to rt and stir at rt for 30 min and then was heated to 98° C. and stirred at 98° C. for 16 h. After cooled to rt, the mixture was poured onto 200 mL ice-water solution and then extracted with EtOAc (3×30 mL). The combined organic layers were washed with water (2×30 mL) and brine (20 mL). and dried over anhy. $Na_2SO_4$. The solvent was removed in vacuo to obtain the crude product which was purified by silica gel flash chromatography to afford the title product (100 mg, 60%); $^1H$ NMR (400 MHz, $CDCl_3$); δ 1.47 (s, 9H), 1.79-2.08 (m, 4H), 3.27-3.44 (m, 2H), 3.70-3.96 (m, 1H), 3.97 (s, 2H), 4.04-4.20 (m, 2H), 6.82-6.86 (m, 2H), 7.11 (d, J=8.8 Hz, 2H), 7.29 (d, J=8.4 Hz, 2H), 7.48 (d, J=6.0 Hz, 2H), 7.56 (d, J=8.4 Hz, 2H), 8.63 (d, J=6.0 Hz, 2H):

Step 2:

4-{4-[4-(R)-1-Pyrrolidin-2-ylmethoxy)-benzyl]-phenyl}-pyridine hydrogen chloride salt: To a 20 mL vial which contained a solution of (R)-2-[4-(4-Pyridin-4-yl-benzyl)-phenoxymethyl]-pyrrolidine-1-carboxylic acid tert-butyl ester (65 mg, 0.15 mmol) in dioxane (1 mL) was added HCl (4 N in dioxane 2 mL) at 0° C. The mixture was allowed to warm to rt and stir at rt for 16 h. The solvent was reduced to 1 mL and ether (15 mL) was added to this vial. the resulting solid was filtered out and dried in vacuo to yield the title product (35 mg, 80%); LCMS; 97%, $APCI^+$, Calcd: 344.5. Found m/z:

345.8 (M+1). ¹H NMR (500 MHz, DMSO-d₆); δ 1.66-1.76 (m, 1H), 1.84-2.02 (m, 2H), 2.06-2.15 (m, 1H), 3.14-3.26 (m, 2H), 3.87 (br, 1H), 4.00 (s, 2H), 4.09-4.19 (m, 1H), 4.21 (dd, J1=11.0, J2=4.0, 1H), 6.93 (d, J=8.5 Hz, 2H), 7.23 (d, J=8.5 Hz, 2H), 7.45 (d, J=8.0 Hz, 2H), 7.94 (d, J=8.5 Hz, 2H), 8.27 (d, J=6.0 Hz, 2H), 8.89 (d, J=6.0 Hz, 2H):

EXAMPLE 126

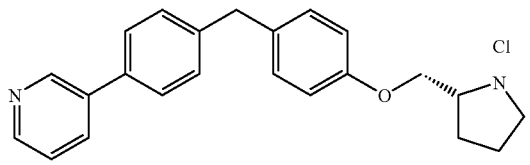

Step 1

(R)-2-[4-(4-Pyridin-3-yl-benzyl)-phenoxymethyl]-pyrrolidine-1-carboxylic acid tert-butyl ester: Followed the same procedure as that of step 1 in Example 125 with the use of pyridine-4-boronic acid (110 mg, 0.8 mmol) to afford the title product (100 mg, 60%); ¹H NMR (400 MHz, CDCl₃); δ 1.47 (s, 9H), 1.79-2.08 (m, 4H), 3.28-3.46 (m, 2H), 3.70-3.97 (m, 1H), 3.97 (s, 2H), 4.04-4.20 (m, 2H), 6.82-6.90 (m, 2H), 7.12 (d, J=8.4 Hz, 2H), 7.28 (d, J=8.0 Hz, 2H), 7.33-7.37 (m, 1H), 7.42-7.59 (m, 2H), 7.64-7.70 (m, 1H), 7.84-7.87 (m, 1H), 8.57 (dd, J1=4.8 Hz, J2=2.0 Hz, 1H):

Step 2

3-{4-[4-((R)-1-Pyrrolidin-2-ylmethoxy)-benzyl]-phenyl}-pyridine: Followed the same procedure as that of step 2 in Example 125 with the use of (R)-2-[4-(4-Pyridin-3-yl-benzyl)-phenoxymethyl]-pyrrolidine-1-carboxylic acid tert-butyl ester to yield title product (35 mg, 80%); LCMS; 90%, ESI⁺, Calcd: 344.5. Found m/z: 345.7, (M+1). ¹H NMR (400 MHz, DMSO-d₆); δ 1.66-1.76 (m, 1H), 1.84-2.02 (m, 2H), 2.05-2.16 (m, 1H), 3.15-3.26 (m, 2H), 3.87 (br, 1H), 3.96 (s, 2H), 4.07-4.12 (m, 1H), 4.19-4.23 (m, 1H), 6.93 (d, J=8.0 Hz, 2H), 7.22 (d, J=8.0 Hz, 2H), 7.38 (d, J=8.0 Hz, 2H), 7.73 (d, J=7.6 Hz, 2H), 7.75-7.83 (m, 1H), 8.42-8.49 (m, 1H), 8.69-8.74 (m, 1H), 9.05 (s, 1H):

EXAMPLE 127

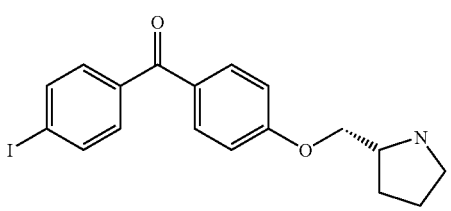

Step 1

(4-Iodo-phenyl)-(4-hydroxy-phenyl)-methanone: To a solution of (4-iodo-phenyl)-(4-methoxy-phenyl)-methanone (1.7 g, 5 mmol in CH₂Cl₂ (20 mL) was added BBr₃ (15 mL, 15 mmol; 1 M in CH₂Cl₂) at −78° C. The resulting mixture was allowed to warm to rt and stir at rt for 6 h. The mixture was poured onto 50 mL ice-water solution and extracted with CH₂Cl₂ (3×30 mL). The combined organic layers were washed with water (2×30 mL) and brine (20 mL) and dried over anhy. Na₂SO₄. The solvent was removed in vacuo to obtain the crude product which was purified by recrystallization from acetone-EtOAc-hexane to provide the title product (1.4 g, 85%) which was directly used for the next step.

Step 2

(R)-2-[4-(4-Iodo-benzoyl)-phenoxymethyl]-pyrrolidine-1-carboxylic acid tert-butyl ester: To a 25 mL vial which contained a suspension of NaH (60% in mineral oil, 60 mg, 1.5 mmol) in DMF (10 mL) was added the product from step 1 (324 mg, 1 mmol) at 0° C. The mixture was allowed to warm to rt and stir at rt for 30 min then cooled to 0° C. To this reaction mixture was added (R)-2-(toluene-4-sulfonyloxymethyl)-pyrrolidine-1-carboxylic acid tert-butyl ester (400 mg, 1.1 mmol) at 0° C. The resulting mixture was allowed warm to rt and stir at rt for 30 min and then was heated to 95° C. and stirred at 95° C. for 16 h. After cooling to rt, the mixture was poured onto 100 mL ice-water solution and this solution was allowed to stir at 0° C. for 30 min. The solid which formed was filtered out, dried through air to afford the title product (280 mg, 60%); ¹H NMR (400 MHz, CDCl₃); δ 1.47 (s, 9H), 1.82-2.11 (m, 4H), 3.30-3.48 (m, 2H), 3.85-4.05 (m, 1H), 4.07-4.30 (m, 2H), 6.96-7.25 (m, 2H), 7.47 (d, J=8.4 Hz, 2H), 7.77 (d, J=8.8 Hz, 2H), 7.83 (d, J=8.4 Hz, 2H):

Step 3

(4-Iodo-phenyl)-[4-((R)-1-pyrrolidin-2-ylmethoxy)-phenyl]-methanone: To a 20 mL vial which contained a solution of the product from step 2 (25 mg, 0.05 mmol) in dioxane (1 mL) was added HCl (4 N in dioxane, 2 mL) at 0° C. The mixture was allowed to warm to rt and stir at rt for 16 h. The solvent was reduced to 1 mL and ether (15 mL) was added to this vial. The resulting solid was filtered out and dried under vacuo to yield the title product (16 mg, 80%); LCMS; 100% ESI⁺Calcd: 407.3. found m/z: 408.5 (M+1). ¹H NMR (500 NM, DMSO-d₆); δ 1.71-1.80 (m, 1H), 1.82-2.06 (m, 2H), 2.10-2.20. (m, 1H), 3.16-3.30 (m, 2H), 3.90-4.00 (m, 1H), 4.23-4.27 (m, 1H), 4.38 (dd, J1=10.0 Hz, J2=2.5 Hz, 1H), 7.14 (d, J=8.5 Hz, 2H), 7.46 (d, J=7.5 Hz, 2H), 7.78 (d, J=9.0 Hz, 2H), 7.95 (d, J=8.0 Hz, 2H):

EXAMPLE 128

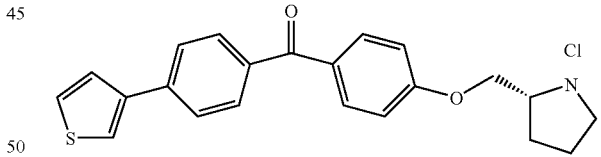

Step 1

(R)-2-[4-(4-Thiophen-3-yl-benzoyl)-phenoxymethyl]-pyrrolidine-1-carboxylic acid tert-butyl ester: To a 25 mL press resistant vial which contained a suspension of (R)-2-[4-(4-Iodo-benzoyl)-phenoxymethyl]-pyrrolidine-1-carboxylic acid tert-butyl ester (250 mg, 0.5 mmol), thiophene-3-boronic acid (130 mg, 1 mmol), palladium(II) acetate (20 mg, 0.1 mmol) and triphenyl phosphine (60 mg, 0.25 mmol) in DME (10 mL) was added potassium carbonate (500 mg, 3 mmol), ethanol (1 mL) and water (1 mL) at rt. The tube was sealed and the mixture was allowed to stir at rt for 30 min and then was heated to 98° C. and stirred at 98° C. for 16 h. After cooling to rt, the mixture was poured onto 200 mL ice-water solution and then extracted with EtOAc (3×30 mL). The combined organic layers were washed with water (2×30 mL) and brine (20 mL). and dried over anhy. Na$_2$SO$_4$. The solvent was removed in vacuo to obtain the crude product which was purified by silica gel flash chromatography to afford title product, (130 mg, 60%); $^1$H NMR (400 MHz, CDCl$_3$); δ 1.48 (s, 9H), 1.81-2.10 (m, 4H), 3.30-3.48 (m, 2H), 3.87-4.10 (m, 1H), 4.10-4.30 (m, 2H), 6.98-7. (m, 2H), 7.42-7.48 (m, 2H), 7.58-7.60 (m, 1H), 7.70 (d, J=8.4 Hz, 2H), 7.80-7.84 (m, 4H):

Step 2:

[4-((R)-1-Pyrrolidin-2-ylmethoxy)-phenyl]-(4-thiophen-3-yl-phenyl)-methanone, hydrogen chloride salt: To a 20 mL vial which contained a solution of the product from step 1 (50 mg, 0.1 mmol) in dioxane (2 mL) was added HCl (4 N in dioxane, 2 mL) at 0° C. The mixture was allowed to warm to rt and stir at rt for 16 h. The solvent was reduced to 1 mL and ether (15 mL) was added to this vial. The resulting solid was filtered out and dried under vacuo to yield the title product (30 mg, 80%); LCMS; 98% ESI$^+$ Calcd: 363.5. found m/z: 364.7 (M+1). $^1$H NMR (400 MHz, DMSO-d$_6$); δ 1.91-2.31 (m, 4H), 3.26-3.40 (m, 2H), 4.05-4.10 (m, 1H), 4.20-4.25 (m, 1H), 4.46 (dd, J1=10.8 Hz, J2=3.6 Hz, 1H), 7.16 (d, J=9.2 Hz, 2H), 7.53-7.57 (m, 2H), 7.78-7.87 (m, 7H):

EXAMPLE 129

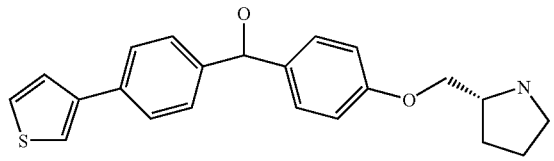

[4-(R)-1-Pyrrolidin-2-ylmethoxy)-phenyl]-(4-thiophen-3-yl-phenyl)-methanol: To a 25 mL vial which contained a solution of [4-((R)-1-Pyrrolidin-2-ylmethoxy)-phenyl]-(4-thiophen-3-yl-phenyl)-methanone, hydrogen chloride salt (15 mg, 0.04 mmol) in EtOH (2 mL) were added NaBH$_4$ (8 mg, 0.2 mmol) at 0° C. The reaction mixture was allowed to warm to rt and stir at rt for 16 h then was poured onto 15 mL ice-water solution and this solution was extracted with EtOAc (3×10 mL). The combined organic layers were washed with water (2×10 mL), brine (10 mL) and dried over anhydrous Na$_2$SO$_4$. The solvent was removed under vacuo to obtain the crude product which was purified by silica gel flash chromatography to afford the title product (20 mg, 65%); LCMS; 75% ESI$^+$ Calcd: 365.5. found m/z: 367.1 (M+2); $^1$H NMR (400 MHz, CD$_3$OD-d$_4$); δ 1.39-2.05 (m, 4H), 2.90-3.05 (m, 3H), 3.45-3.55 (m, 1H), 3.88-3.92 (m, 1H), 4.00 (dd, J1=9.6 Hz, J2=4.8 Hz, 1H), 5.74 (s, 1H), 6.90 (d, J=8.8 Hz, 2H), 7.29 (d, J=8.8 Hz, 2H), 7.37 (d, J=8.8 Hz, 2H), 7.42-7.46 (m, 2H), 7.7.56-7.59 (m, 1H), 7.60 (d, J=8.4 Hz, 2H),:

EXAMPLE 130

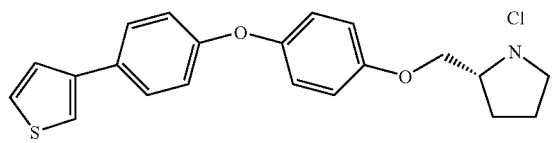

Step 1

4-Thiophen-3-yl-phenol: To a 25 mL press resistant vial which contained a suspension of 4-iodo-phenol (220 mg, 1 mmol), thiophene-3-boronic acid (128 mg, 1 mmol), palladium(II) acetate (20 mg, 0.1 mmol) and triphenyl phosphine (60 mg, 0.25 mmol) in DME (10 mL) was added potassium carbonate (400 mg, 2.5 mmol), ethanol (0.25 mL) and water (0.25 mL) at rt. The tube was sealed and the mixture was allowed to stir at rt for 30 min and then was heated to 98° C. and stirred at 98° C. for 16 h. After cooling to rt, the mixture was poured onto 200 mL ice-water solution and then extracted with EtOAc (3×30 mL). The combined organic layers were washed with water (2×30 mL) and brine (20 mL). and dried over anhy. Na$_2$SO$_4$. The solvent was removed in vacuo to obtain the crude product which was purified by silica gel flash chromatography to afford the title product (130 mg, 70%); $^1$H NMR (400 MHz, CDCl$_3$); 4.70 (s, 1H), 6.65 (d, J=6.8 Hz, 2H), 7.31-7.3 (m, 3H), 7.48 (d, J=6.8 Hz, 2H).

Step 2

(R)-2-(4-Iodo-phenoxymethyl)-pyrrolidine-1-carboxylic acid tert-butyl ester: To a 250 mL flask which contained a suspension of NaH (60% in mineral oil, 500 mg, 12 mmol) in DMF (50 mL) was added 4-iodo-phenol (2200 mg, 10 mmol), at 0° C. The mixture was allowed to warm to rt and stir at rt for 30 min then cooled to 0° C. To this reaction mixture was added (R)-2-(toluene-4-sulfonyloxymethyl)-pyrrolidine-1-carboxylic acid tert-butyl ester (3600 mg, 10 mmol) at 0° C. The resulting mixture was allowed warm to rt and stir at rt for 30 min and then was heated to 95° C. and stirred at 95° C. for 16 h. After cooling to rt, the mixture was poured onto 2000 mL ice-water solution and this solution was allowed to stir at 0° C. for 30 min. The solid which formed was filtered out, dried through air to afford the title product (2480 mg, 60%); $^1$H NMR (400 MHz, CDCl$_3$); δ 1.47 (s, 9H), 1.81-2.07 (m, 4H), 3.27-3.48 (m, 2H), 3.70-3.95 (m, 1H), 4.00-4.19 (m, 2H), 6.66-6.69. (m, 2H), 7.53 (d, J=8.4 Hz, 2H):

Step 3

(R)-2-[4-(4-Thiophen-3-yl-phenoxy)-phenoxymethyl]-pyrrolidine-1-carboxylic acid tert-butyl ester: To a 25 mL pressure resistant vial which contained a solution of the product from step 1 (44 mg, 0.25 mmol) and the product from step 2 (130 mg, 0.33 mmol) in anhydrous dioxane (4 mL) were added cesium carbonate (300 mg, 1.5 mmol) and N,N-dimethylglycine.HCl (25 mg, 0.66 mmol) at rt. The reaction mixture was flushed with argon and copper (I) iodide (14 mg, 0.06 mmol) was added. The vial was sealed and the reaction mixture was stirred at 98° C. for 72 h. After cooling to rt, the mixture was poured onto 50 mL ice-water solution and this solution was extracted with EtOAc (3×20 mL). The combined organic layers were washed with water (2×20 mL), brine (20 mL) and dried over anhydrous Na$_2$SO$_4$. The solvent was removed in vacuo to obtain the crude product which was purified by silica gel flash chromatography to afford the title product (80 mg, 70%); LCMS; 100%, APCI$^+$ Calcd: 451.6. found m/z: 451.6 (M); $^1$H NMR (400 MHz, CDCl$_3$); δ 1.48 (s, 9H), 1.81-2.09 (m, 4H), 3.27-3.48 (m, 2H), 3.70-3.97 (m, 1H), 4.02-4.21 (m, 2H), 6.88-7.05. (m, 6H), 7.32-7.38 (m, 3H), 7.52 (d, J=8.8 Hz, 2H):

Step 4

(R)-2-[4-(4-Thiophen-3-yl-phenoxy)-phenoxymethyl]-pyrrolidine-1-hydrogen chloride salt 7a. To a 20 mL vial which contained a solution of the product from step 3 (25 mg, 0.06 mmol) in dioxane (1 mL) was added HCl (4 N in dioxane, 2 mL) at 0° C. The mixture was allowed to warm to rt and stir at rt for 16 h. The solvent was reduced to 1 mL and ether (15 mL)

was added to this vial. The resulting solid was filtered out and dried in vacuo to yield the title product (18 mg, 85%); LCMS; 100%, APCI⁺Calcd: 351.5. found m/z: 351.5 (M); ¹H NMR (400 MHz, DMSO-d₆); δ 1.68-1.77 (m, 1H), 1.86-2.04 (m, 2H), 2.04-2.18 (m, 1H), 3.18-3.26 (m, 2H), 3.90 (br, 1H), 4.09-4.13 (m, 1H), 4.23-4.27 (m, 1H), 6.96 (d, J=8.4, 2H), 7.02-7.08 (m, 4H), 7.51 (d, J=4.4, 1H), 7.60-7.63 (m, 1H), 7.70 (d, J=8.4, 2H), 7.78 (s, 1H):

EXAMPLE 131

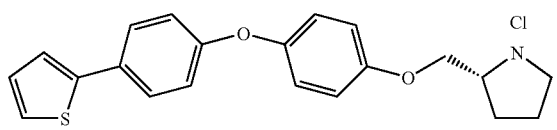

Step 1

4-Thiophen-2-yl-phenol: Same procedure as that of step 1 in Example . . . with the use of 4-iodo-phenol (220 mg, 1 mmol) and thiophene-2-boronic acid (128 mg, 1 mmol) to yield the title product, (130 mg, 70%); ¹H NMR (400 MHz, CDCl₃); 4.73 (s, 1H), 6.85 (d, J=6.8 Hz, 2H), 7.05 (t J=4.0 Hz, 1H), 7.18-7.06 (m, 2H), 7.49 (d, J=6.8 Hz, 2H)

Step 2

(R)-2-[4-(4-thiophen-2-yl-phenoxy)-phenoxymethyl]-pyrrolidine-1-carboxylic acid tert-butyl ester: To a 25 mL pressure resistant vial which contained a solution of the product from step 1 (44 mg, 0.25 mmol) and (R)-2-(4-iodo-phenoxymethyl)-pyrrolidine-1-carboxylic acid tert-butyl ester (130 mg, 0.33 mmol) in anhydrous dioxane (4 mL) were added cesium carbonate (300 mg, 1.5 mmol) and N,N-dimethylglycine.HCl (25 mg, 0.66 mmol) at rt. The reaction mixture was flushed with argon and copper (I) iodide (14 mg, 0.06 mmol) was added. The vial was sealed and the reaction mixture was stirred at 98° C. for After cooling to rt, the mixture was poured onto 50 mL ice-water solution and this solution was extracted with EtOAc (3×20 mL). The combined organic layers were washed with water (2×20 mL), brine (20 mL) and dried over anhydrous Na₂SO₄. The solvent was removed in vacuo to obtain the crude product which was purified by silica gel flash chromatography to afford the title product (70 mg, 60%); LCMS; 100%, APCI⁺Calcd: 451.6 m/z, found: 451.6 m/z (M).

Step 3

(R)-2-[4-(4-Thiophen-2-yl-phenoxy)-phenoxymethyl]-pyrrolidine-1-hydrogen chloride salt: To a 20 mL vial which contained a solution of the product from step 3 (25 mg, 0.06 mmol) in dioxane (1 mL) was added HCl (4 N in dioxane, 2 mL) at 0° C. The mixture was allowed to warm to rt and stir at rt for 16 h. The solvent was reduced to 1 mL and ether (15 mL) was added to this vial. The resulting solid was filtered out and dried in vacuo to yield the title product (20 mg, 90%); LCMS; 93%, APCI⁺Calcd: 351.5. found m/z: 351.5 (M). ¹H NMR (400 MHz, DMSO-d₆); δ 1.68-1.78 (m, 1H), 1.84-2.04 (m, 2H), 2.05-2.18 (m, 1H), 3.15-3.26 (m, 2H), 3.90 (br, 1H), 4.09-4.15 (m, 1H), 4.20-4.27 (m, 1H), 6.84 (d, J=8.4, 1H), 6.96 (d, J=8.4, 2H), 7.02-7.12 (m, 4H), 7.42 (m, 1H), 7.51 (d, J=4.8, 1H), 7.63 (d, J=8.4, 2H):

EXAMPLE 132

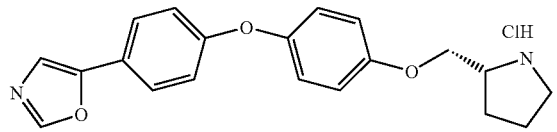

Step 1

(R)-2-[4-(4-Oxazol-5-y-phenoxy)-phenoxymethyl]-pyrrolidine-1-carboxylic acid tert-butyl ester: To a 25 mL pressure resistant vial which contained a solution of (R)-2-(4-hydroxy-phenoxymethyl)-pyrrolidine-1-carboxylic acid tert-butyl ester (147 mg, 0.5 mmol) and 5-(4-bromo-phenyl)-oxazole (170 mg, 0.75 mmol) in anhydrous dioxane (4 mL) were added cesium carbonate (300 mg, 1.5 mmol) and N,N-dimethylglycine.HCl (25 mg, 0.66 mmol) at rt. The reaction mixture was flushed with argon and Copper (I) iodide (14 mg, 0.06 mmol) was added. The vial was sealed and the reaction mixture was stirred at 98° C. for 72 h. After cooling to rt, the mixture was poured onto 50 mL ice-water solution and this solution was extracted with EtOAc (3×20 mL). The combined organic layers were washed with water (2×20 mL), brine (20 mL) and dried over anhydrous Na₂SO₄. The solvent was removed in vacuo to obtain the crude product which was purified by silica gel flash chromatography to afford title product (145 mg, 65%).

Step 2

5-{4-[4((R)-1-Pyrrolidin-2-ylmethoxy)-phenoxy]-phenyl}-oxazole, hydrogen chloride salt: To a 20 mL vial which contained a solution of the product from step 1(75 mg, 0.15 mmol) in dioxane (2 mL) was added HCl (4 N in dioxane, 2 mL) at 0° C. The mixture was allowed to warm to rt and stir at rt for 16 h. The solvent was reduced to 1 mL and ether (15 mL) was added to this vial. The resulting solid was filtered out and dried in vacuo to yield the title product (58 mg, 80% yield); LCMS; 99% APCI⁺Calcd: 336.4. found m/z: 336.4 (M). ¹H NMR (400 MHz, DMSO-d₆); δ 1.66-1.79 (m, 1H), 1.84-2.05 (m, 2H), 2.05-2.16 (m, 1H), 3.17-3.28 (m, 2H), 3.77-3.97 (m, 1H), 4.11-4.18 (m, 1H), 4.25 (dd, J1=10.4 Hz, J2=3.2 Hz, 1H), 6.69-6.83 (m, 1H), 7.06-7.11 (m, 4H), 7.60 (s, 1H), 7.71 (d, J=8.8 Hz, 2H), 8.41 (s, 2H)

EXAMPLE 133

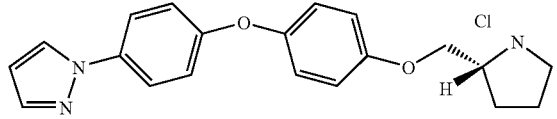

Step 1:

(R)-2-[4-(4-Pyrazol-1-yl-phenoxy)-phenoxymethyl]-pyrrolidine-1-carboxylic acid tert-butyl ester: Followed the same procedure as that of step 1 in Example 133 with the use of (R)-2-(4-hydroxy-phenoxymethyl)-pyrrolidine-1-carboxylic acid tert-butyl ester (147 mg, 0.5 mmol) and 1-(4-iodo-phenyl)-1H-pyrazole (203 mg, 0.75 mmol) to afford the title product (140 mg, 60% yield).

Step 2

1-{4-[4-((R)-1-Pyrrolidin-2-ylmethoxy)-phenoxy]-phenyl}-1H-pyrazole, hydrogen chloride salt: Followed the same procedure as that of step 2 in Example 133 with the use of (R)-2-[4-(4-pyrazol-1-yl-phenoxy)-phenoxymethyl]-pyrrolidine-1-carboxylic acid tert-butyl ester (135 mg, 0.26 mmol) to yield title product (100 mg, 70% yield); LCMS; 99%, ESI+ Calcd: 335.4. found m/z: 336.5 (M+1). $^1$H NMR (400 MHz, DMSO-d$_6$); δ 1.68-1.79 (m, 1H), 1.86-2.04 (m, 2H), 2.08-2.18 (m, 1H), 3.16-3.27 (m, 2H), 3.84-3.96 (m, 1H), 4.11-4.16 (m, 1H), 4.25 (dd, J1=10.8 Hz, J2=3.2 Hz, 1H), 6.53 (s, 1H), 7.03-7.10 (m, 6H), 7.71 (s, 1H), 7.81 (d, J=8.8 Hz, 2H), 8.42 (s, 1H)

EXAMPLE 134

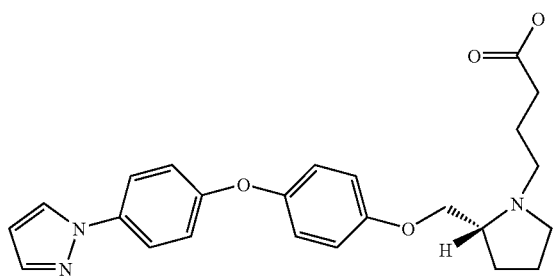

Step 1:

4-{(R)-2-[4-(4-Pyrazol-1-yl-phenoxy)-phenoxymethyl]-pyrrolidin-1-yl}-butyric acid methyl ester: To a 20 mL vial which contained a suspension of 1-{4-[4-((R)-1-pyrrolidin-2-ylmethoxy)-phenoxy]-phenyl}-1H-pyrazole, hydrogen chloride salt (80 mg, 0.2 mmol) and K$_2$CO$_3$ (80 mg, 1 mmol) in DMF (7 mL) was added 4-bromo-butyric acid methyl ester (60 mg, 0.3 mmol) at rt. The mixture was allowed to stir at rt for 48 h and then was poured onto 20 mL ice-water solution and extracted with EtOAc (3×20 mL). The combined organic layers were washed with water (2×20 mL) and brine (20 mL) and dried over anhy. Na$_2$SO$_4$. The solvent was removed in vacuo to obtain the crude product which was purified by silica gel flash chromatography to afford the title product (60 mg, 60%).

Step 2:

4-{(R)-2-[4-(4-Pyrazol-1-yl-phenoxy)-phenoxymethyl]-pyrrolidin-1-yl}-butyric acid: To a 20 mL vial which contained a solution of the product from step 1 (40 mg, 0.1 mmol) in HCl (4 N in dioxane 2 mL) was added water (0.3 mL) at 0° C. The mixture was allowed to warm to rt and stir at rt for 24 h. The solvent was removed to yield the crude, which was purified by recrystallization from THF-ether to afford the title product (25 mg, 75%); LCMS; 94%, ESI−, Calcd: 421.5. Found m/z: 420.6 (M-1). $^1$H NMR (400 MHz, DMSO-d$_6$); δ 1.74-2.09 (m, 5H), 2.16-2.25 (m, 1H), 2.31-2.40 (m, 2H), 3.03 (br, 2H), 3.45-3.80 (m, 3H), 4.16-4.20 (m, 1H), 4.20-4.23 (m, 1H), 6.52 (t, J=2.0 Hz, 1H), 6.87 (s, 1H), 7.04-7.06 (m, 5H), 7.71 (d, J=1.6 Hz, 1H), 7.80 (d, J=9.2 Hz, 2H), 8.42 (d, J=2.4 Hz, 1H):

EXAMPLE 135

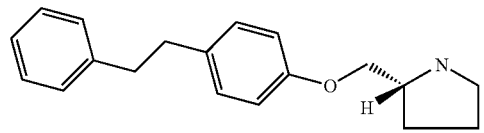

(R)-2-(4-Phenethyl-phenoxymethyl)-pyrrolidine: To a solution of R)-2-(4-phenylacetyl-phenoxymethyl)-pyrrolidine-1-carboxylic acid tert-butyl ester (40 mg, 0.16 mmol) in TFA (1.0 mL) was added triethylsilane (0.2 mL, 0.9 mmol) at 0° C. The resulting mixture was allowed to warm to rt and stir at rt for 16 h. The mixture was poured onto 20 mL ice-water solution, neutralized with aq NaOH (2N) to pH=6-7, and then extracted with EtOAc (3×20 mL). The combined organic layers were washed with water (2×20 mL) and brine (20 mL) and dried over anhy. Na$_2$SO$_4$. The solvent was removed in vacuo to obtain the crude product which was purified by silica gel flash chromatography to afford the title product (25 mg, 82%); LCMS; 99%, ESI+, Calcd: 281.4. Found m/z: 282.6 M+1). $^1$H NMR (400 MHz, CDCl$_3$,); δ 1.54-1.61 (m, 1H), 1.74-1.84 (m, 2H), 1.90-1.99 (m, 1H), 2.84-3.07 (m, 6H), 3.49-3.52 (m, 1H), 3.83-3.92 (m, 2H), 6.82 (d, J=8.8 Hz, 2H), 7.07 (d, J=8.8 Hz, 2H), 7.16-7.20 (m, 3H)-7.34 (m, 2H).

EXAMPLE 136

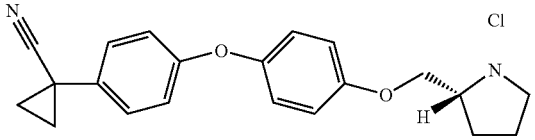

Step 1

1-(4-Bromo-phenyl)-cyclopropanecarbonitrile: To a 100 mL round bottom flask which contained a solution of 1,2-dibromo-ethane (6.6 g, 35 mmol) and 4-bromo-phenyl)-acetonitrile (4.5 g, 25 mmol) in toluene (20 mL) were added aq NaOH (50%, 20 mL) and tetrabutylammonium bromide (1.6 g, 5 mmol) at rt. The reaction mixture was vigorously stirred at rt for 24 h then was poured onto 450 mL ice-water solution and this solution was extracted with EtOAc (3×130 mL). The combined organic layers were washed with water (2×150 mL), brine (150 mL) and dried over anhydrous Na$_2$SO$_4$. The solvent was removed under vacuo to obtain the crude product which was purified by silica gel flash chromatography to afford the desired product (3.5 g, 70%); $^1$H NMR (400 MHz, CDCl$_3$); δ 1.36-1.40 (m, 2H), 1.73-1.76 (m, 2H), 7.17 (d, J=8.8 Hz, 2H), 7.47 (d, J=8.8 Hz, 2H).

Step 2:

(R)-2-{4-[4-(1-Cyano-cyclopropyl)-phenoxy]-phenoxymethyl}-pyrrolidine-1-carboxylic acid tert-butyl ester: To a 25 mL press resistant vial which contained a solution of (R)-2-(4-Hydroxy-phenoxymethyl)-pyrrolidine-1-carboxylic acid tert-butyl ester 2 (293 mg, 1 mmol) and the product from step 1 (340 mg, 1.5 mmol) in anhydrous dioxane (8 mL) were added cesium carbonate (450 mg, 2.5 mmol) and N,N-dimethylglycine.HCl (40 mg, 0.0.24 mmol) at rt. The reaction mixture was flushed with argon and copper (I) iodide (20 mg, 0.1 mmol) was added. The vial was sealed and the reaction mixture was stirred at 98° C. for 72 h. After cooled to rt, the mixture was poured onto 100 mL ice-water solution and this solution was extracted with EtOAc (3×30 mL). The combined organic layers were washed with water (2×30 mL), brine (30 mL) and dried over anhydrous Na₂SO₄. The solvent was removed under vacuo to obtain the crude product which was purified by silica gel flash chromatography to yield the title product, (260 mg, 75%); LCMS; 93%, ESI⁺ Calcd: 434.5. found m/z: 335.6 (M+1-boc). ¹H NMR (400 MHz, CDCl₃); δ 1.33-1.39 (m, 2H), 1.47 (s, 9H), 1.66-1.68 (m, 2H), 1.81-2.10 (m, 4H), 3.30-3.45 (m, 2H), 3.75-4.21 (m, 3H), 6.90 (d, J=9.2 Hz, 2H), 6.91-6.94 (m, 2H), 7.23 (d, J=8.4 Hz, 2H), 7.24-7.27 (m, 2H)

Step 3

1-{4-[4-(R)-1-Pyrrolidin-2-ylmethoxy)-phenoxy]-phenyl}-cyclopropanecarbonitrile hydrogen chloride salt: To a 20 mL vial which contained a solution of the product from step 2 (30 mg, 0.07 mmol) in dioxane (1 mL) was added HCl (4 N in dioxane, 1 mL) at 0° C. The mixture was allowed to warm to rt and stir at rt for 16 h. The solvent was reduced to 0.5 mL and ether (10 mL) was added to this vial. The resulting solid was filtered out and dried under vacuo to yield the title product, (17 mg, 85%); LCMS; 90%, ESI⁺ Calcd: 334.4, found m/z: 335.7 (M+1). ¹H NMR (400 MHz, DMSO-d₆) δ 1.41-1.44 (m, 2H), 1.64-1.68 (m, 3H), 1.86-1.95 (m, 1H), 2.05-2.37 (m, 4H), 3.98-4.15 (m, 2H), 4.30-4.35 (m, 1H), 6.90-6.93 (m, 2H), 6.98-7.04 (m, 4H), 7.29-7.36 (m, 2H)

EXAMPLE 137

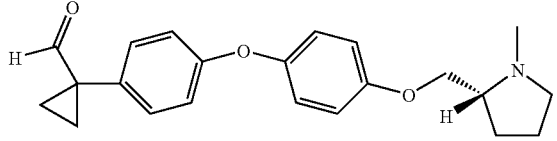

1-{4-[4-(R)-1-Methyl-pyrrolidin-2-ylmethoxy)-phenoxy]-phenyl}-cyclopropanecarbaldehyde: To a 25 mL vial which contained a solution of (R)-2-{4-[4-(1-Cyano-cyclopropyl)-phenoxy]-phenoxymethyl}-pyrrolidine-1-carboxylic acid tert-butyl ester 3 (110 mg, 0.25 mmol) in anhydrous toluene (2 mL) were added DIBAL (0.5 mL 1M in hexane)) at −78° C. under the atmosphere of argon. The reaction mixture was allowed to warm to rt and stir at rt for 0.5 h. After cooled to ° C., 0.5 mL HCl was added to the mixture, the mixture was stirred for 10 min and then was neutralized with the addition of sat. NaHCO₃ solution. This mixture was extracted with EtOAc (3×30 mL). The combined organic layers were washed with water (2×30 mL), brine (30 mL) and dried over anhydrous Na₂SO₄. The solvent was removed under vacuo to obtain the crude product which was purified by silica gel flash chromatography to afford the title product, (50 mg, 65%); LCMS; 95%, APCI⁺ Calcd: 351.5. found m/z: 353.1 (M+1). ¹H NMR (400 MHz, CDCl₃); δ 1.36-1.39 (m, 2H), 1.54-1.56 (m, 2H), 1.70-2.10 (m, 4H), 2.26-2.33 (m, 1H), 2.48 (s, 3H), 2.60-2.70 (m, 1H), 3.09-3.13 (m, 1H), 3.85-3.99 (m, 2H), 6.88-6.93 (m, 4H), 6.95-6.99 (m, 2H), 7.20-7.30 (m, 2H) 9.22 (s, 1H),

EXAMPLE 138

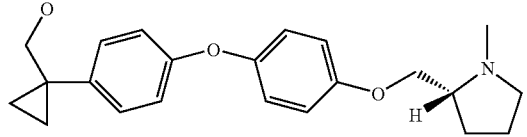

1-{4-[4-(R)-1-Methyl-pyrrolidin-2-ylmethoxy)-phenoxy]-phenyl}-cyclopropyl)methanol: To a 25 mL vial which contained a solution of product 1-{4-[4-((R)-1-Methyl-pyrrolidin-2-ylmethoxy)-phenoxy]-phenyl}-cyclopropanecarbaldehyde 5 (30 mg, 0.1 mmol) in EtOH (2 mL) were added NaBH₄ (8 mg, 0.2 mL) at 0° C. The reaction mixture was allowed to warm to rt and stir at rt for 16 h then was poured onto 20 mL ice-water solution and this solution was extracted with EtOAc (3×10 mL). The combined organic layers were washed with water (2×10 mL), brine (10 mL) and dried over anhydrous Na₂SO₄. The solvent was removed under vacuo to obtain the crude product which was purified by silica gel flash chromatography to afford the title product, (20 mg, 65%); LCMS; 85%, ESI⁺ Calcd: 353.5. found m/z: 354.8 (M+1). ¹H NMR (400 MHz, CDCl₃); δ 0.82-0.84 (m, 4H), 1.25-1.26 (m, 1H), 1.65-2.10 (m, 4H), 2.26-2.31 (m, 1H), 2.48 (s, 3H), 2.60-2.67 (m, 1H), 3.09-3.13 (m, 1H), 3.64 (s, 2H), 3.84-3.99 (m, 2H), 6.86-6.90 (m, 4H), 6.94-6.97 (m, 2H), 7.27-7.30 (m, 2H)

EXAMPLE 139

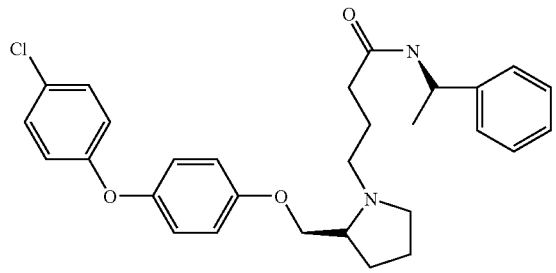

4-{(S)-2-[4-(4-Chloro-phenoxy)-phenoxymethyl]-pyrrolidin-1-yl}-N—[(R)-1-phenylethyl]-butyramide: To a suspension of 4-{(S)-2-[4-(4-chloro-phenyoxy)-phenoxymethyl]-pyrrolidin-1-yl}-butyric acid HCl salt (220 mg, 0.5 mmol, 1 eq.) in dichloromethane (5 ml) was added PyBrOP (280 mg, 0.6 mmol, 1.2 eq.), DIPEA (200 mg, 1.5 mmol, 3 eq.) and (R)-1-phenyl ethylamine (80 mg, 0.6 mmol 1.2 eq.). The mixture was stirred at room temperature for 24 h. The mixture was poured onto 30 mL ice-water solution and this solution was extracted with EtOAc (3×30 mL). The combined organic layers were washed with water (2×30 mL), brine (30 mL) and dried over anhy. Na₂SO₄. The solvent was removed in vacuo to provide the crude product which was purified by silica gel flash chromatography to afford the title product (68 mg, 25%); LCMS; 95%; APCI⁺, Calcd 493.05. Found m/z 493.2 (M). ¹H NMR (400 MHz, CDCL₃); δ 1.47 (d, J=5.6 Hz, 3H), 1.52-2.01 (m, 6H), 2.21-2.59 (m, 4H), 2.79-2.98 (m, 2H), 3.12-3.23 (m, 1H), 3.68-3.89 (m, 2H), 5.10-5.17 (m, 1H), 6.81 (d, J=9.2 Hz, 2H), 6.86 (d, J=9.2 Hz, 2H), 6.92 (d, J=9.2 Hz, 2H), 7.22-7.26 (m, 5H), 7.29 (d, J=4.4 Hz, 2H).

EXAMPLE 140

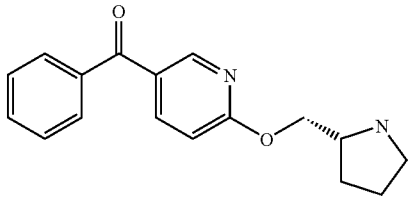

Step 1:

6-Chloro-nicotinoyl chloride: 6-Chloro-nicotinic acid (11.0 g, 6.34 mmol) was dissolved in 10 mL thionyl chloride and the resulting mixture was refluxed for 3 h. The excess thionyl chloride was removed under reduced pressure to give the title compound (11.0 g, 89%).

Step 2:

(6-Chloro-pyridin-3-yl)-phenyl-methanone To a solution of product from step 1 (320 mg, 1.82 mmol) in 10 mL anhydrous benzene was added $AlCl_3$ (683 mg, 5.12 mmol) and the reaction mixture was refluxed for 1.5 h. The mixture was cooled and poured into EtOAc and water, and the organic layer was dried over anhydrous $MgSO_4$ and the solvent was removed in vacuo to obtain the title compound as a pale yellow solid. (348 mg, 88%).

Step 3:

(R)-2-(5-Benzoyl-pyridin-2-yloxymethyl)-pyrrolidine-1-carboxylic acid tert-butyl ester: To (R) Boc-prolinol (653 mg, 3.25 mmol) in 5 ml anhy. DMF was added NaH (162 mg, 60% dispersion in oil, 4.05 mmol). After the mixture was stirred at rt for 40 min, product from step 2 (470 mg, 2.16 mmol) in 5 ml anhy.DMF was added dropwise over 5 min. The mixture was stirred at rt for 48 h. The mixture was poured into EtOAc and water, the organic layer dried over anhy. $MgSO_4$, and concentrated. Flash chromatography on silica gel using EtOAc/Hexane gave the title compound (343 mg, 41.5%).

Step 4:

Phenyl-[6-(R)-1-pyrrolidin-2-ylmethoxy)-pyridin-3-yl]-methanone: To a solution of product from step 3 (100 mg, 0.26 mmol) was treated with 5 ml of 4 N HCl in dioxane and stirred for 2 h. The solvent was removed in vacuo, triturated with ether to give the title compound as the hydrochloride salt (35 mg, 42%) MS; m/z 283 (M+H) 99% $^1H$ NMR (DMSO-$d_6$, 400 MHz) δ 1.78-2.22 (4H, m), 3.20 (2H, m), 3.98 (1H, m), 4.45-4.65 (2H, m), 7.05 (1H, d, J=8.8 Hz), 7.60 (2H, m), 7.69-7.76 (3H, m), 8.14 (1H, dd, J1=2.8 Hz, J2=8.8 Hz), 8.56 (1H, dd, J1=0.8 Hz, J2=2.4 Hz), 9.2 (1NH, s)

EXAMPLE 141

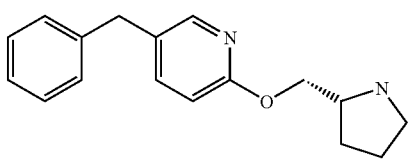

D000155839

Step 1

(R)-2-[5-(Hydroxy-phenyl-methyl)-pyridin-2-yloxymethyl]-pyrrolidine-1-carboxylic acid tert-butyl ester: Product from Example 140, step 3 (100 mg, 0.26 mmol) was dissolved in 3 ml EtOH, and $NaBH_4$ (7.5 mg, 0.196 mmol) in 1 ml $H_2O$ was added and the mixture stirred at rt for 2 h. The mixture was then quenched with 3N NaOH (5 mL) and ether was added to extract the compound, which was dried over anhy. $MgSO_4$ and concentrated to give a yellow oil (90.1 mg, 90.1%)

Step 2:

(R)-2-(5-Benzyl-pyridin-2-yloxymethyl)-pyrrolidine-1-carboxylic acid tert-butyl ester: To the product from step 2 (30 mg, 0.078 mmol) was added 10 mg Pd/C, 10% by wt, MeOH/AcOH (1.5 ml, 6:4) and stirred under $H_2$ ($H_2$ balloon, atm pr) for 6 h. 5 ml 10% NaOH was added to quench the reaction. EtOAc was added and the mixture was filtered and dried down to give the title compound (19 mg, 66%).

Step 3:

5-Benzyl-2-(R)-1-pyrrolidin-2-ylmethoxy)-pyridinehydrochloride salt: To the product from step 2 (10 mg, 0.027 mmol) was added 3 ml of 2N HCl in diethyl ether. The resulting mixture was stirred at rt for 2 h. The solvent was removed to give the title compound (8 mg, 96%). MS; m/z 269 (M+H) >90% $^1H$ NMR (DMSO-$d_6$, 400 MHz) δ 1.59-2.12 (4H, m), 3.21 (2H, m), 3.90 (2H, s), 4.31 (1H, m), 4.46 (1H, dd, J1=4.0 Hz, J2=11.6 Hz), 6.80 (1H, d, J=8.4 Hz), 7.17-7.31 (5H, m), 7.57 (1H, dd, J1=2.4 Hz, J2=8.4 Hz), 8.09 (1H, d, J=2.4 Hz), 8.93 (1NH, s), 9.48 (1NH, s)

EXAMPLE 142

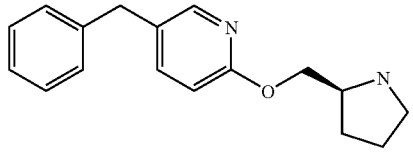

D000155840

Step 1

(S)-2-(5-Benzoyl-pyridin-2-yloxymethyl)-pyrrolidine-1-carboxylic acid tert-butyl ester: To a solution of N—BOC-L-prolinol (500 mg, 3.25 mmol) in anhydrous DMF (7 ml) was added NaH (124 mg, 60% dispersion in oil, 3.1 mmol) and stirred for 15 min at rt. A solution of product from Example 140, step 2 (364 mg, 1.68 mmol) in anhy.DMF (5 ml) was added dropwise over 5 min. The mixture was stirred at rt for 48 h. The mixture was poured into EtOAc and water, the organic layer dried over $MgSO_4$, and concentrated. Silica gel flash chromatography using EtOAc/hexanes gave the title compound (185 mg, 29%).

Step 2:

(S)-2-[5-(Hydroxy-phenyl-methyl)-pyridin-2-yloxymethyl]-pyrrolidine-1-carboxylic acid tert-butyl ester: The product from step 1 (100 mg, 0.26 mmol) was dissolved in 2 ml EtOH, and $NaBH_4$ (7.5 mg, 0.196 mmol) in 0.5 ml $H_2O$ was added and the mixture stirred at rt for 2 h. The mixture was then quenched with 3N NaOH, and 5 ml of ether was added to extract the compound, which was dried over $MgSO_4$ and concentrated to give yellow oil (79 mg, 90.1%).

Step 3:

(S)-2-(5-Benzyl-pyridin-2-yloxymethyl)-pyrrolidine-1-carboxylic acid tert-butyl ester: To product from step 2 (50 mg, 0.13 mM) was added Pd/C, 10% (40 mg, wt) in MeOH/AcOH (1.5 ml, 6:4) and stirred under H₂ (H2 balloon, atm pr) for 6 h. 10% NaOH (5 mL) was added to quench the reaction. EtOAc was added and the mixture was filtered and dried down to give the title compound (29 mg, 83%).

Step 4

5-Benzyl-2-((S)-1-pyrrolidin-2-ylmethoxy)-pyridine hydrochloride salt: To the product from step 3 (25 mg, 0.068 mmol) was added 2N HCl (3 mL) in diethyl ether. The resulting mixture was stirred at rt for 2 h. The solvent was removed to give the title compound (20 mg, 97%). MS; m/z 269 (M+H) >90%.¹H NMR (DMSO-d6, 400 MHz) δ 1.59-2.12 (4H, m), 3.19 (2H, m), 3.88 (2H, s), 4.34 (1H, d, J=8.0 Hz), 4.48 (1H, dd, J1=4.0 Hz, J2=11.6 Hz), 6.80 (1H, d, J=8.4 Hz), 7.17-7.30 (5H, m), 7.58 (1H, dd, J1=2.4 Hz, J2=8.4 Hz), 8.09 (1H, d, J=2.4 Hz), 8.93 (1NH, s), 9.49 (1NH, s).

EXAMPLE 143

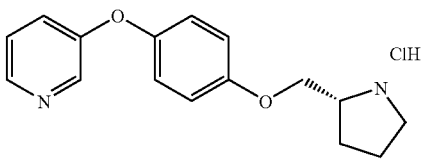

Step 1:

3-(4-Benzyloxy-phenoxy)-pyridine: To a solution of p-benzyloxyphenol (550 mg, 2.754 mmol), Cs₂CO₃ (1.795 g, 5.509 mmol), 3-iodo pyridine (850 mg, 4.14 mmol) in anhydrous dioxane (15 ml) under N₂ was added diglyme (38.42 mg, 0.275 mmol). After stirring for 10 min, CuI (19.38 mg, 0.102 mmol) was added and the reaction mixture was kept in a shaker at 85° C. overnight. The mixture was poured into EtOAc and water, the organic layer was dried over Na₂SO₄, and concentrated. Silica gel flash chromatography using EtOAc/Hexane gave the title compound (200 mg, 17%).

Step 2:

4-(Pyridin-3-yloxy)-phenol: The product from step 1 (130 mg, 0.469 mmol) was added to a vial containing THF (1 ml), EtOH (2.5 ml), 10% Pd/C (110 mg, 0.0469 mmol), charged with H₂ and left to stir under H₂ atmosphere overnight. The Pd/C was removed by filtering the reaction mixture through celite. The resulting solution was concentrated to give the title compound (97 mg, 100%).

Step 3:

3-[4-((R)-1-Pyrrolidin-2-ylmethoxy)-phenoxy]-pyridine: The product from step 2 (97 mg, 0.52 mmol) was added to a solution of NaH, (60% dispersion in oil, 41.6 mg, 1.04 mmol) in anhy. DMF (2.5 ml) at 0° C. The mixture was stirred at rt for 45 min, then cooled to −10° C. and N—BOC-L-Prolinol (184 mg, 0.52 mmol) in 2.5 ml anhy. DMF was added dropwise over 5 min. The mixture was stirred at 90° C. overnight. The mixture was poured into EtOAc and water, the organic layer dried over anhy. MgSO₄, and concentrated. Flash chromatography on silica gel using EtOAc/Hexane gave the boc protected compound (125 mg, 65%) To this was added 3 ml of 4N HCl in Dioxane. The resulting mixture was stirred at rt for 2 hrs. The solvent was removed and triturated with ether to give the title compound (40 mg, 43%) MS; m/z 271.24 (M+H) 99% ¹H NMR (DMSO, 400 MHz) δ1.71-2.15 (4H, m), 3.21 (2H, m), 3.91 (1H, m), 4.11-4.27 (2H, m), 6.96-7.11 (6H, m), 7.83 (1H, dd, J1=2.0 Hz, J2=8.4 Hz) 8.11 (1H, dd, J1=2.0 Hz, J2=5.6 Hz), 8.97 (1NH, s), 9.51 (1NH, s).

EXAMPLE 144

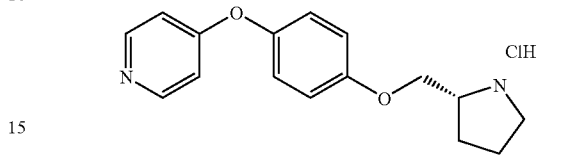

Step 1

4-(4-Benzyloxy-phenoxy)-pyridine: The same procedure from Example 143, step 1 was followed using p-benzyloxyphenol (500 mg, 2.5 mmol), Cs₂CO₃ (1.58 g, 4.85 mmol), 4-iodo pyridine (780 mg, 3.805 mmol), anhydrous dioxane (15 ml), diglyme (34 mg, 0.24 mmol), CuI (17 mg, 0.089 mmol) to give the title compound (600 mg, 57%).

Step 2:

4-(Pyridin-4-yloxy)-phenol: The same procedure from Example 143, step 2 was followed using the product from step 1 (306 mg, 0.905 mmol), THF (3 ml), EtOH (9 ml), 10% Pd/C (300 mg, 0.0905 mmol) to give the title compound (160 mg, 95%).

Step 3:

4-[4-((R)-1-Pyrrolidin-2-ylmethoxy)-phenoxy]-pyridine: The same procedure from Example 143, step 3 was followed using the product from step 2 (160 mg, 0.855 mmol), NaH, (60% dispersion in oil, 64 mg, 1.607 mmol), anhy. DMF (2.5 ml) N—BOC-L-prolinol (317 mg, 0.893 mmol) to give the Boc protected compound. To this was added 5 ml of 4N HCl in ether. The resulting mixture was stirred at rt for 2 h. The solvent was removed and triturated with ether to give the title compound (80 mg, 35%); MS; m/z 271.24 (M+H) 99%; ¹H NMR (DMSO-d6, 400 MHz) δ 1.72-2.16 (4H, m), 3.22 (2H, m), 3.91 (1H, m), 4.21-4.32 (2H, m), 7.17 (2H, d, J=9.6 Hz), 7.32 (2H, d, J=8.8 Hz), 7.41 (2H, d, J=6.8 Hz), 8.79 (2H, d, J=6.8 Hz), 9.26 (NH, s), 9.75 (NH, s).

EXAMPLE 145

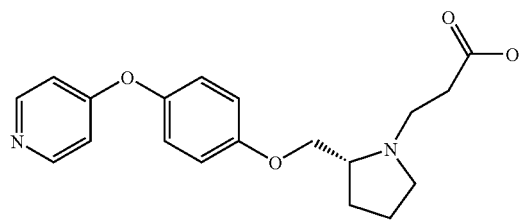

3-{(R)-2-[4-(Pyridin-4-yloxy)-phenoxymethyl]-pyrrolidin-1-yl}-propionic acid: The product from Example 144 (50 mg, 0.15 mmol) was treated with 20% NaOH (5 ml) and extracted with EtOAc, dried over Na₂SO₄ and dried down to give the free base. Dichloromethane (3 ml) and methyl acrylate (0.4 ml, 2.8 mmol) were added and the mixture was stirred at rt overnight. The reaction mixture was dried down to give an oil. Excess 4.0M HCl in dioxane was added and the mixture was stirred overnight at rt. The solvent was removed in vacuo to give the title compound. (15 mg, 23%); LC/MS; m/z 343 (M+H) 99% ¹H NMR (DMSO-d6, 400 MHz) δ 1.79-2.29 (4H, m), 2.89 (2H, m), 3.16 (1H, m), 3.56-3.71 (3H, m), 3.97 (1H, m) 4.34-4.51 (2H, m), 7.18 (2H, d, J=8.8 Hz), 7.33 (2H, d, J=9.6 Hz), 7.43 (2H, d, J=7.2 Hz), 8.80 (2H, d, J=7.2 Hz)

EXAMPLE 146

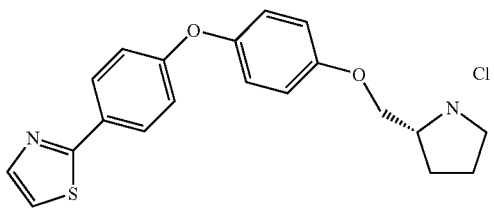

Step 1

2-(4-Methoxy-phenyl)-thiazole: To a solution of thiazole (3.0 g, 16 mmol) in THF (75 ml) was added n-BuLi (2.5 M in hexane, 11 ml, 27.3 mmol) at −78° C. dropwise, and stirred at −78° C. for 30 min. ZnCl₂ (10.7 g, 78.3 mmol) was added at −78° C. in portions. The resulting mixture was stirred at −78° C. for 30 min, and room temperature for 1.5 h. To this solution was added 4-bromoanisole (1.60 g, 8.5 mmol) and terakis (triphenylphosphine)-palladium (0). The reaction mixture was heated to 65° C. for 16 h. After the catalyst was filtered off, the filtrate was concentrated in vacuo. The residue was purified by a column chromatography on silica gel with 25% ethyl acetate in hexane to yield the title product (2 g, 67%); ¹H NMR (400 MHz, CDCl₃) δ 7.90 (d, J=9.2 Hz, 2H), 7.81 (d, J=3.2 Hz, 1H), 7.25 (d, J=3.2 Hz, 1H), 6.95 (d, J=9.2 Hz, 2H), 3.86 (s, 3H); MS (ESI⁺) 192 (M+1, 100).

Step 2

4-Thiazol-2-yl-phenol: To a solution of the product of step 1 (1.0 g, 5.23 mmol) in methylene chloride (25 ml) was slowly added boron tribromide (2.00 ml, 15.7 mmol) at −78° C., and stirred at −78° C. for 1 h. After it was stirred at room temperature for 16 h, the reaction mixture was poured into ice-water. The product was collected on a filter, washed with ether to yield the title product (0.84 g, 84%); ¹H NMR (400 MHz, CDCl₃) δ 7.85 (d, J=3.2 Hz, 1H), 7.79 (d, J=8.8 Hz, 2H), 7.67 (d, J=3.2 Hz, 1H), 6.88 (d, J=8.8 Hz, 2H); MS (ESI⁻) 176 (M−1, 100).

Step 3

(R)-2-[4-(4-Thiazol-2-yl-phenoxy)-phenoxymethyl]-pyrrolidine-1-carboxylic acid tert-butyl ester: A mixture of the product of step 2 (0.1 g, 0.56 mmol), the product of Example 130, step 2 (0.30 g, 0.73 mmol), N,N-dimethylglycine HCl salt (0.20 g, 1.46 mmol), copper(I) iodide (0.19 g, 1.01 mmol) and cesium carbonate (0.28 g, 0.85 mmol) in dioxane (2 ml) was heated 100° C. for 60 h under nitrogen. The solids were filtered off, and the filtrate was concentrated in vacuo. The residue was purified by a column chromatography on silica gel eluting with 25% EtOAc/hexanes to yield the title product (130 mg, 69%); ¹HNMR (400 MHz, CDCl₃) δ 7.88 (d, J=8.4 Hz, 2H), 7.84 (d, J=3.2 Hz, 1H), 7.30 (d, J=3.2 Hz, 1H), 7.24 (d, J=8.4 Hz, 2H), 7.10 (d, J=8 Hz, 2H), 6.86 (br d, J=8 Hz, 2H), 4.10 (br, 2H), 3.96 (s, 2H), 3.40 (br, 2H), 2.03-1.80 (m, 4H), 1.46 (s, 9H).

Step 4

2-{4-[4-(R)-1-Pyrrolidin-2-ylmethoxy)-phenoxy]-phenyl}-thiazole hydrochloride salt: A solution of the product of step 3 (90 mg, 0.21 mmol) in dioxane (2 ml) was added 4M HCl in dioxane (0.5 ml, 2.1 mmol), and stirred at room temperature for 4 h. After the solvent was removed, the crude material was triturated with ether to afford the title product (60 mg, 83%); ¹HNMR (400 MHz, CD₃OD) δ 7.90 (d, J=8.4 Hz, 2H), 7.82 (d, J=3.2 Hz, 1H), 7.55 (d, J=3.6 Hz, 1H), 7.07 (s, 4H), 7.00 (d, J=8.8 Hz, 2H), 4.22 (dd, J=10.4, 3.2, 1H), 4.14 (m, 1H), 4.04 (m, 1H), 3.38 (m, 2H), 2.28 (m, 1H), 2.14 (m, 2H), 1.92 (m, 1H); LC/MS (ESI⁺) 88%; m/z: 353 (M+1, 100).

EXAMPLE 147

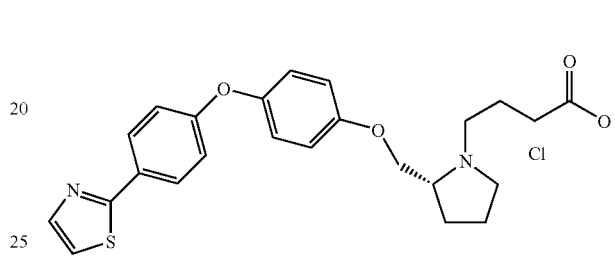

4-{(R)-2-[4-(4-Thiazol-2-yl-phenoxy)-phenoxymethyl]-pyrrolidin-1-yl}-butyric acid: A mixture of the product from Example 146 (0.3 g, 0.77 mmol), methyl 4-bromobutyrate (0.17 g, 0.93 mmol) and K₂CO₃ (powder) (0.21 g, 1.54 mmol) in DMF (5 mL) was stirred at room temperature for 18 h. After the DMF was removed, the residue was partitioned with methylene chloride and water, washed with brine. The combined organic phases were dried over anhydrous Na₂SO₄ and concentrated. The crude material was purified by a chromatography on silica gel eluting with 10% ethyl acetate in hexane to provide the ester. A solution of this ester and NaOH (62 mg, 1.54 mmol) in THF/water (1:1, 5 mL) was stirred at room temperature for 16 h. After the THF was removed, the aqueous solution was acidified with 10% HCl to pH=2, extracted with ethyl acetate. The combined organic phases were dried over Na₂SO₄ and concentrated. The crude material was recrystallized with CH₂Cl₂/ether to yield the title compound (120 mg, 33%); ¹H NMR (400 MHz, DMSO-d₆) δ 7.90 (d, J=8.8 Hz, 2H), 7.82 (d, J=3.2 Hz, 1H), 7.28 (d, J=3.2 Hz, 1H), 7.02 (d, J=8.8 Hz, 2H), 4.55 (m, 1H), 4.22 (m, 1H), 3.78-3.5 (m, 3H), 3.15 (m, 2H), 2.53 (m, 2H), 2.35-2.05 (m, 6H); LC/MS (ESI⁺) m/z: 93%.

EXAMPLE 148

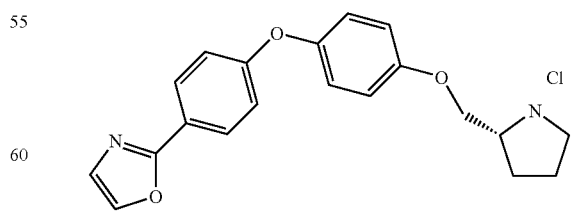

Step 1

2-(4-Methoxy-phenyl)-oxazole: The title compound (0.16 g, 33%) was prepared from oxazole (0.74 g, 10.7 mmol) and 4-bromoanisole (2.0 g, 10.7 mmol) using the procedure of Example 146, step 1; ¹HNMR (400 MHz, CDCl₃) δ 8.0 (d, J=9.2 Hz, 2H), 7.66 (d, J=1.2 Hz, 1H), 7.19 (d, J=0.8 Hz, 1H), 6.97 (d, J=8.8 Hz, 2H), 3.87 (s, 3H).

Step 2

4-Oxazol-2-yl-phenol: The title compound (0.52 g, 95%) was prepared from the product of step 1 (0.6 g, 3.4 mmol) and boron tribromide (1M in methylene chloride, 10.3 ml, 10.3 mmol) using the procedure of Example 146, step 2; ¹HNMR (400 MHz, DMSO-d₆) δ 8.1 (s, 1H), 7.81 (d, J=8.8 Hz, 2H), 7.30 (s, 1H), 6.92 (d, J=9.2 Hz, 2H), MS (APCI⁺) 162 (M+1, 100);

Step 3

(R)-2-[4-(4-Oxazol-2-yl-phenoxy)-phenoxymethyl]-pyrrolidine-1-carboxylic acid tert-butyl ester: The title compound (60 mg, 30%) was prepared from product of step 2 (0.1 g, 0.6 mmol) and (R)-2-(4-Iodo-phenoxymethyl)-pyrrolidine-1-carboxylic acid tert-butyl ester (0.38 g, 0.9 mmol) using the procedure of Example 146, step 3, ¹HNMR (400 MHz, CDCl₃) δ 7.96 (d, J=8.8 Hz, 2H), 7.67 (s, 1H), 7.20 (s, 1H), 6.92 (m, 6H), 4.13 (m, 2H), 3.86 (m, 1H), 3.41 (m, 2H), 2.07-1.78 (m, 4H), 1.48 (s, 9H)

Step 4

2-{4-[4-(R)-1-Pyrrolidin-2-ylmethoxy)-benzyl]-phenyl}-oxazole hydrochloride salt: The title compound (30 mg, 59%) was prepared from the product of step 3 (60 mg, 0.14 mmol) and 4M HCl in dioxane (0.35 ml, 1.4 mmol) using the procedure of Example 146, step 4, ¹HNMR (400 MHz, CD₃OD) δ 8.04 (s, 1H), 8.00 (d, J=8.8 Hz, 2H), 7.40 (s, 1H), 7.08 (s, 4H), 7.03 (d, J=8 Hz, 2H), 4.46 (m, 2H), 4.18-4.01 (m, 2H), 3.36 (m, 2H), 2.32 (m, 1H), 2.18 (m, 2H), 1.96 (m, 1H), LC/MS (ESI⁺) 91%, 337 (100, M+1).

EXAMPLE 149

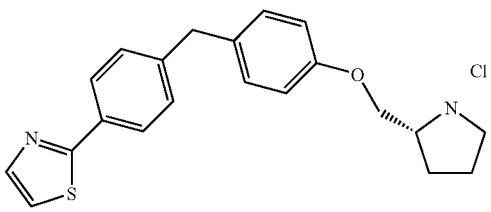

Step 1

(R)-2-[4-(4-Thiazol-2-yl-benzyl)-phenoxymethyl]-pyrrolidine-1-carboxylic acid tert-butyl ester: The title compound (90 mg, 99%) was prepared from thiazole (0.07 g, 0.8 mmol) and (R)-2-[4-(4-iodo-benzyl)-phenoxymethyl]-pyrrolidine-1-carboxylic acid tert-butyl ester (0.1 g, 0.2 mmol) using the procedure of Example 146, step 1, ¹HNMR (400 Hz, CDCl₃) δ 7.88 (d, J=8.4 Hz, 2H), 7.84 (d, J=3.2 Hz, 1H), 7.30 (d, J=3.2 Hz, 1H), 7.25 (d, J=8.4 Hz, 2H), 7.10 (d, J=8 Hz, 2H), 6.86 (br d, J=7.2 Hz, 2H), 4.10 (br, 2H), 3.96 (s, 2H), 3.9-3.75 (br, 2H), 3.40 (br, 2H), 2.03-1.84 (br, 4H), 1.46 (s, 9H) MS?

Step 2

2-{4-[4-((R)-1-Pyrrolidin-2-ylmethoxy)-benzyl]-phenyl}-thiazole hydrochloride salt: The title compound (60 mg, 83%) was prepared from the product of step 1 (0.09 g, 0.21 mmol) and 4M HCl in dioxane (0.5 ml, 2.1 mmol) using the procedure of Example 146, step 4; ¹HNMR (400 MHz, CD₃OD) δ 9.42 (br, 1H), 8.96 (br, 1H), 7.89 (d, J=3.6 Hz, 1H), 7.86 (d, J=8.4 Hz, 2H), 7.75 (d, J=3.6 Hz, 1H), 7.32 (d, J=8.4 Hz, 2H), 7.20 (d, J=8.8 Hz, 2H), 6.93 (d, J=8.8 Hz, 2H), 4.22 (dd, J=10.4, 3.6 Hz, 1H), 4.08 (m, 1H), 3.96 (s, 2H), 3.89 (m, 1H), 3.20 (m, 2H), 2.12 (m, 1H), 1.92 (m, 2H), 1.63 (m, 1H); LC/MS (APCI⁺) 99%, 351 (M+1, 100); HPLC 98.5%.

EXAMPLE 150

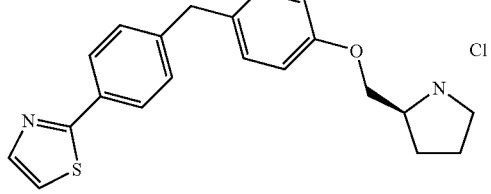

Step 1

(S)-2-[4-(4-Thiazol-2-yl-benzyl)-phenoxymethyl]-pyrrolidine-1-carboxylic acid tert-butyl ester: The title compound (200 mg, 86%) was prepared from thiazole (0.28 g, 3.2 mmol) and (S)-2-[4-(4-iodo-benzyl)-phenoxymethyl]-pyrrolidine-1-carboxylic acid tert-butyl ester (0.4 g, 0.8 mmol) using the procedure of Example 146, step 1; ¹HNMR (400 MHz, CDCl₃) δ 7.87 (d, J=8.4 Hz, 2H), 7.84 (d, J=3.2 Hz, 1H), 7.30 (d, J=3.6 Hz, 1H), 7.25 (d, J=8.4 Hz, 2H), 7.10 (d, J=8 Hz, 2H), 6.86 (br d, J=7.2 Hz, 2H), 4.10 (br, 2H), 3.96 (s, 2H), 3.9-3.75 (br, 2H), 3.40 (br, 2H), 2.03-1.84 (br, 4H), 1.46 (s, 9H); MS (ESI+) 451 (M+1, 100).

Step 2

2-{4-[4-((S)-1-Pyrrolidin-2-ylmethoxy)-benzyl]-phenyl}-thiazole hydrochloride salt: The title compound (60 mg, 83%) was prepared from the product of step 1 (0.09 g, 0.21 mmol) and 4M HCl in dioxane (0.5 ml, 2.1 mmol) using the procedure of Example 146, step 4, ¹HNMR (400 MHz, CD₃OD) δ 8.17 (d, J=4 Hz, 1H), 7.98 (d, J=3.6 Hz, 1H), 7.90 (d, J=8.4 Hz, 2H), 7.45 (d, J=8.4 Hz, 2H), 7.20 (d, J=8.8 Hz, 2H), 6.95 (d, J=8.8 Hz, 2H), 4.32 (dd, J=10.4, 3.6 Hz, 1H), 4.10 (m, 1H), 4.04 (s, 2H), 4.03 (m, 1H), 3.36 (m, 2H), 2.25 (m, 1H), 2.10 (m, 2H), 1.90 (m, 1H); LC/MS (APCI⁺) 93%, 351 (M+1, 100); HPLC 94%.

EXAMPLE 151

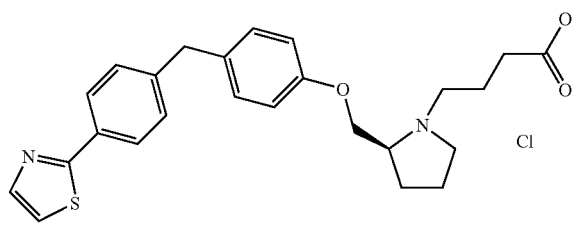

4-{(S)-2-[4-(4-Thiazol-2-yl-benzyl)-phenoxymethyl]-pyrrolidin-1-yl}-butyric acid hydrochloride salt: The title compound (56 mg, 42%) was prepared from the product of Example 150 (0.1 g, 0.28 mmol) and methyl bromobutyrate (0.062 g, 0.34 mmol) using the procedure of Example 147; ¹HNMR (400 MHz, CD₃OD) δ 8.07 (m, 1H), 7.90 (d, J=8 Hz, 1H), 7.85 (m, 2H), 7.42 (d, J=8.4 Hz, 2H), 7.20 (d, J=8.8 Hz, 2H), 6.98 (d, J=8.8 Hz, 2H), 4.32 (m, 1H), 4.20 (m, 1H), 4.10 (m, 1H), 4.04 (s, 2H), 3.95 (m, 1H), 3.65 (m, 3H), 3.36 (m, 2H), 2.50-2.00 (m, 6H); MS.?

EXAMPLE 152

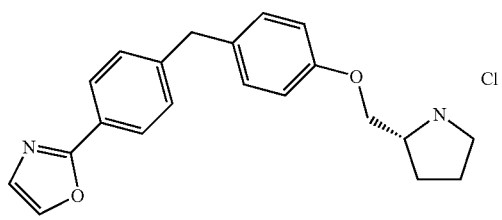

Step 1

(R)-2-[4-(4-Oxazol-2-yl-benzyl)-phenoxymethyl]-pyrrolidine-1-carboxylic acid tert-butyl ester: The title compound (20 mg, 23%) was prepared from oxazole (60 mg, 0.81 mmol) and (R)-2-[4-(4-iodo-benzyl)-phenoxymethyl]-pyrrolidine-1-carboxylic acid tert-butyl ester (0.1 g, 0.2 mmol) using the procedure of Example 146, step 1; ¹HNMR (400 MHz, CDCl₃) δ 7.95 (d, J=8.4 Hz, 2H), 7.68 (d, J=0.8 Hz, 1H), 7.26 (m, 2H), 7.21 (d, J=0.8 Hz, 1H), 7.10 (d, J=8 Hz, 2H), 6.86 (br d, J=7.2 Hz, 2H), 4.10 (br, 2H), 3.96 (s, 2H), 3.9-3.75 (br, 2H), 3.40 (br, 2H), 2.03-1.84 (br, 4H), 1.46 (s, 9H).

Step 2

2-{4-[4-(R)-1-Pyrrolidin-2-ylmethoxy)-benzyl]-phenyl}-oxazole: The title compound (15 mg, 80%) was prepared from the product of step 1 (20 mg, 0.05 mmol) and 4M HCl in dioxane (0.12 ml, 0.5 mmol) using the procedure of Example 146, step 4; ¹HNMR (400 MHz, CD₃OD) δ 8.0 (s, 1H), 7.93 (d, J=38.4 Hz, 2H), 7.34 (d, s, J=8.4 Hz, 3H), 7.19 (d, J=8.8 Hz, 2H), 6.95 (d, J=8.8 Hz, 2H), 4.32 (dd, J=10.4, 3.6 Hz, 1H), 4.10 (m, 1H), 4.32 (m, 2H), 4.10 (m, 1H), 3.94 (s, 2H), 3.36 (m, 2H), 2.25 (m, 1H), 2.10 (m, 2H), 1.90 (m, 1H); LC/MS (APCI⁺) 90%, 335 (M+1, 100).

EXAMPLE 153

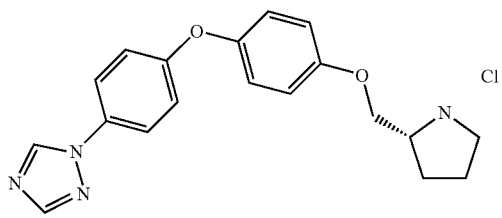

Step 1

(R)-2-[4-(4-[1,2,4]Triazol-1-yl-phenoxy)-phenoxymethyl]-pyrrolidine-1-carboxylic acid tert-butyl ester: The title compound (130 mg, 80%) was prepared from 4-[1,2,4]triazol-1-yl-phenol (0.7 g, 0.43 mmol) and (R)-2-(4-Iodo-phenoxymethyl)-pyrrolidine-1-carboxylic acid tert-butyl ester (0.23 g, 0.56 mmol) using the procedure of Example 146, step 3.

Step 2

1-{4-[4-(R)-1-Pyrrolidin-2-ylmethoxy)-phenoxy]-phenyl}-1H-[1,2,4]triazole hydrochloride salt: The title compound (80 mg, 80%) was prepared from the product of step 1 (130 mg, 0.30 mmol) and 4M HCl in dioxane (0.75 ml, 3 mmol) using the procedure of Example 146, step 4; ¹HNMR (400 MHz, CD₃OD) δ 10.15 (br, 1H), 9.80 (br, 1H), 7.82 (br, 2H), 7.00 (m, 8H), 4.12 (br, 2H), 4.01 (br, 1H), 3.36 (m, 2H), 2.18-1.96 (m, 4H); LC/MS (ESI+) 99%, 337 (100, M+1).

EXAMPLE 154

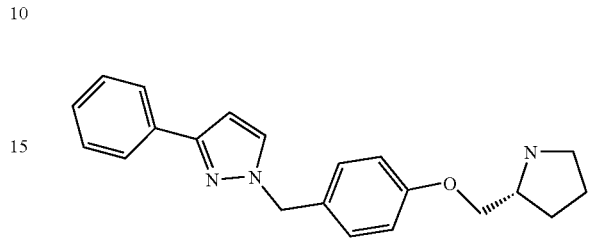

Step 1

1-(4-Methoxy-benzyl)-3-phenyl-1H-pyrazole: A mixture of 3-phenyl-1H-pyrazole (1.35 g, 9.36 mmol), 4-methoxybenzyl chloride (1.5 g, 9.7 mmol) and K₂CO₃ (3.3 g, 24.2 mmol) in methyl ethyl ketone was refluxed for 24 h. The salts were filtered off, and the solvent was removed in vacuo. The residue was purified by a column chromatography on silica gel to yield the title compound (2.2 g, 89%).

Step 2

4-(3-Phenyl-pyrazol-1-ylmethyl)-phenol: The title compound (1.0 g, 53%) was prepared from the product of step 1 (2.0 g, 7.6 mmol) and BBr₃ (1M in CH₂Cl₂, 23 mL, 23 mmol) using the procedure of Example 146, step 2.

Step 3

3-Phenyl-1-[4-((R)-1-pyrrolidin-2-ylmethoxy)-benzyl]-1H-pyrazole hydrochloride salt: To a mixture of NaH (60% in mineral oil, 36 mg, 1.65 mmol) in DMF (3 mL) was added a solution of the product of step 2 (0.3 g, 1.2 mmol) in DMF (1 mL) at 0° C. The resulting slurry was stirred at 0° C. for 30 minutes and at room temperature for 30 minutes before a solution of (R)-2-(toluene-4-sulfonyloxymethyl)-pyrrolidine-1-carboxylic acid tert-butyl ester (0.36 g, 1.5 mmol) in DMF (1 mL) was added. The mixture was stirred at 80° C. for 4 h. The reaction mixture was poured over ice and then concentrated under reduced pressure. The crude residue was extracted into ethyl acetate and sequentially washed with water, saturated aq. NaHCO₃, water and brine. The combined organic portions were dried over Na₂SO₄, filtered and concentrated in vacuo. The crude product was purified by a column chromatography on silica gel eluting with 10% ethyl acetate in hexane to afford the Boc-protected compound, which was dissolved in dioxane. To this solution was added 4M HCl in dioxane (0.5 ml, 2.2 mmol), and stirred at room temperature for 4 h. After the solvent was removed, the crude material was triturated with ether to afford the title compound (360 mg, 76%); ¹H NMR (400 MHz, CDCl₃) δ 7.88 (m, 3H), 7.65 (d, J=8.8 Hz, 2H), 7.42 (m, 2H), 7.35 (m, 1H), 7.08 (d, J=8.8 Hz, 1H), 6.72 (d, J=3 Hz, 1H), 4.45 (m, 1H), 4.34 (m, 1H), 4.01 (m, 1H), 3.41 (m, 2H), 2.25-1.98 (m, 4H); LC/MS (ESI+) m/z: 90%; 367 (M+1, 100).

EXAMPLE 155

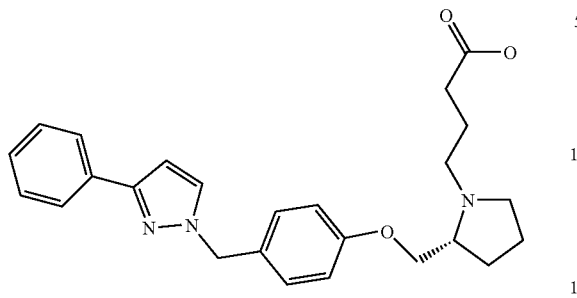

1-{(R)-2-[4-(3-Phenylpyrazol-yl methyl)phenoxymethyl] pyrrolidin-1-yl} butyric acid hydrochloride salt: The title compound (60 mg, 30%) was prepared from the Example 154 (0.15 g, 0.41 mmol) and 4-bromobutyrate (0.11 g, 0.49 mmol) using the procedure of Example 147; $^1$H NMR (400 MHz, DMSO-d$_6$) δ 7.85 (d, J=2 Hz, 1H), 7.77 (d, J=8.4 Hz, 2H), 7.38 (t, J=8 Hz, 2H), 7.27 (d, J=8 Hz, 3H), 6.98 (d, J=8.4 Hz, 2H), 6.72 (d, J=2 Hz, 1H), 5.30 (s, 2H), 4.43 (m, 1H), 4.30 (m, 2H), 3.84 (m, 1H), 3.57 (m, 4H), 3.14 (m, 1H), 2.38 (m, 2H), 2.25-1.98 (m, 4H); LC/MS (ESI+) m/z: 91%; 367 (M+1, 100).

EXAMPLE 156

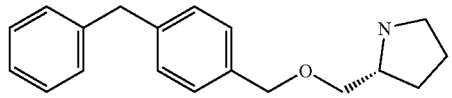

Step 1

4-Benzyl-benzoic acid ethyl ester: To a solution of 4-benzyl-benzoic acid (4.0 g, 18.8 mmol) in methylene chloride (11 mL) was added oxalyl chloride (3.6 g, 28.3 mmol) at room temperature, and stirred at room temperature for 3 h. After the solvent was removed, the acid chloride was dissolved in ethanol (20 mL) and triethylamine (5.7 g, 56.5 mmol) was added. The resulting reaction was stirred at room temperature for 16 h, and the ethanol was removed to obtain the title 9 (4.5 g, 98%)

Step 2

(4-Benzyl-phenyl)-methanol: To a solution of the product of step 1 (1 g, 4.2 mmol) in THF (20 mL) was added LiAlH$_4$ (0.32 g, 8.3 mmol) in portions, and stirred at room temperature for 16 h. The reaction was quenched with water followed by aqueous 15% NaOH. The solids were filtered off, and the filtrate was concentrated. The residue was purified by a column chromatography on silica gel to yield the title compound (0.6 g, 75%).

Step 3

(R)-2-(4-Benzyl-phenoxymethyl)-pyrrolidine hydrochloride salt: The title compound (200 mg, 40%) was prepared from the product of step 2 (0.3 g, 1.5 mmol) and (R)-2-(toluene-4-sulfonyloxymethyl)-pyrrolidine-1-carboxylic acid tert-butyl ester (0.65 g, 1.8 mmol) using the procedure of Example 154, step 3; $^1$H NMR (400 MHz, CD$_3$OD) δ 7.23 (m, 9H), 4.56 (s, 2H), 3.95 (s, 2H), 3.75 (m, 2H), 3.55 (m, 1H), 3.26 (m, 2H), 2.25-1.98 (m, 4H); LC/MS (ESI$^+$) m/z: 98%; 282 (M+1, 100).

EXAMPLE 157

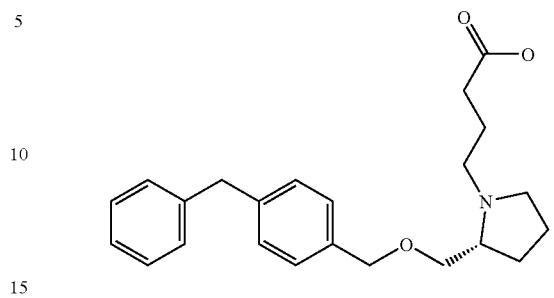

4-[(R)-2-(4-Benzyl-benzyloxymethyl)pyrrolidin-1-yl]butyric acid hydrochloride salt. The title compound (60 mg, 30%) was prepared from the product of step 3 (0.04 g, 0.12 mmol) and 4-bromobutyrate (0.03 g, 0.15 mmol) using the procedure of Example 147; $^1$H NMR (400 MHz, CD$_3$OD) δ 7.23 (m, 9H), 4.56 (d, J=2.8 Hz, 2H), 4.31 (m, 1H), 4.19 (m, 1H), 3.95 (s, 2H), 3.78-3.60 (m, 5H), 2.39 (t, J=6.8 Hz, 2H), 2.25-1.98 (m, 6H); LC/MS (ESI+) m/z: 94%; 368 (M+1, 100).

EXAMPLE 158

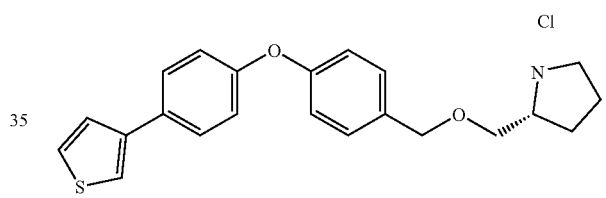

Step 1

4-(4-Iodo-phenoxy)-benzoic acid To a solution of 4-iodo-diphenyl ether (5 g, 11.8 mmol) was added n-BuLi (2.5 M in hexane, 4.7 mL, 11.8 mmol) at −78° C., and stirred at −78° C. for 30 min. Anhydrous CO$_2$ gas was bubbled into the reaction solution for 15 min. After warmed to room temperature, the carboxylic salt was collected on a filter, and then was suspended in ethyl acetate-water. After it was acidified with 4 N HCl to pH to ~1, the organic layer was separated, dried over Na$_2$SO$_4$, and concentrated to yield the title compound (3.7 g), which contained 25% of the diacid.

Step 2

4-(4-Iodo-phenoxy)-benzoic acid ethyl ester: The title compound (2.1 g, 53%) was prepared from the product of step 1 (3.7 g, 10.9 mmol) and oxalyl chloride (2.1 g, 16.3 mmol) using the procedure of Example 156, step 1.

Step 3

4-(4-Thiophen-3-yl-phenoxy)-benzoic acid ethyl ester; A mixture of the product of step 2 (0.5 g, 1.4 mmol), 3-thiophen-boronic acid (0.2 g, 1.4 mmol), K$_2$CO$_3$ (1.1 &, 8.1 mmol) and (Ph$_3$P)$_4$Pd (0.08 g, 0.07 mmol) in EtOH (10 mL) was heated to reflux for 24 h. After the solids were filtered off, the filtrate was concentrated to dryness. The residue was purified by a column chromatography on silica gel to yield the title compound (0.4 g, 91%).

Step 4

[4-(4-Thiophen-3-yl-phenoxy)-phenyl]-methanol: The title compound (300 mg, 99%) was prepared from the product of step 3 (0.35 g, 1.1 mmol) and LiAlH$_4$ (82 mg, 2.2 mmol) using the procedure of Example 156, step 2.

Step 5

(R)-2-[4-(4-Thiophen-3-yl-phenoxy)benzyloxymethyl]pyrrolidine hydrochloride salt: The title compound (90 mg, 65%) was prepared from the product of step 2 (0.1 g, 0.35 mmol) and (R)-2-(toluene-4-sulfonyloxymethyl)-pyrrolidine-1-carboxylic acid tert-butyl ester (0.15 g, 0.42 mmol) using the procedure of Example 154, step 3; $^1$HNMR (400 MHz, CD$_3$OD) δ 7.56 (d, J=8.8 Hz, 2H), 7.35 (m, 5H), 7.02 (d, J=8.4 Hz, 2H), 6.98 (d, J=8.8 Hz, 2H), 4.56 (dd, J=20, 12 Hz, 2H), 3.89 (m, 1H), 3.77 (m, 1H), 3.70 (m, 1H), 3.36 (m, 2H), 2.10-1.98 (m, 4H); LC/MS (ESI$^+$) m/z: 90%; 367 (M+1, 100).

EXAMPLE 159

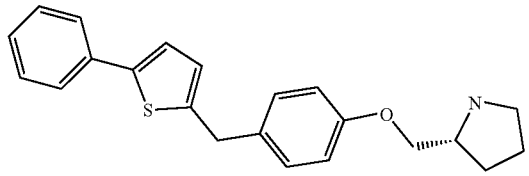

Step 1

5-Phenyl-thiophene-2-carbaldehyde: A mixture of 5-bromo-thiophene-2-carbaldehyde (2.0 g, 10.5 mmol), phenylboronic acid (17 g, 11 mmol), K$_2$CO$_3$ (8.7 g, 62.8 mmol) and 10% Pd/C (0.56 g) in isopropanol/H$_2$O (1:1, 40 mL) was refluxed for 5 h. The reaction mixture was filtered through a pad of Celite. After the isopropanol was removed, the product was collected on a filter, washed with hexane and dried in vacuo to yield the title compound (1.9 g, 82%).

Step 2

(4-Methoxy-phenyl)-(5-phenyl-thiophen-2-yl)-methanol: To a solution of 4-bromoanisole (0.6 g, 3.2 mmol) in THF was added n-BuLi (2.5M in hexane, 1.5 mL, 3.5 mmol) at −78° C., and continued to stir for 30 min. The product of step 1 (0.48 g, 2.6 mmol) was added. After it was stirred at −78° C. for 30 min, the reaction was allowed to warm to room temperature and stirred for an additional 1 h. The reaction was quenched with water, extracted with EtOAc, washed with brine and dried over Na$_2$SO$_4$. After the solvent was removed, the residue was purified by a column chromatography on silica gel to yield the title compound (0.6 g, 68%).

Step 3

2-(4-Methoxy-benzyl)-5-phenyl-thiophene: To a solution of the product of step 2 (0.6 g, 2.0 mmol) in TFA (5 mL) was added triethylsilane (2.4 g, 20.2 mmol) at 0° C., and stirred at room temperature for 4 h. The reaction mixture was poured into ice-water, extracted with EtOAc, washed with brine and dried over Na$_2$SO$_4$. After the solvent was removed, the residue was purified by a column chromatography on silica gel to yield the title compound (0.55 g, 98%).

Step 4

4-(5-Phenyl-thiophen-2-ylmethyl)-phenol: The title compound (480 mg, 99%) was prepared from the product of step 3 (0.50 g, 1.8 mmol) and BBr$_3$ (1.3 g, 5.3 mmol) using the procedure of Example 146, step 2.

Step 5

(R)-2-[4-(5-Phenyl-thiophen-2-ylmethyl)-phenoxymethyl]-pyrrolidine hydrochloride salt: The title compound (350 mg, 80%) was prepared from the product of step 4 (0.3 g, 1.1 mmol) and (R)-2-(toluene-4-sulfonyloxymethyl)-pyrrolidine-1-carboxylic acid tert-butyl ester (0.48 g, 1.4 mmol) using the procedure of Example 154, step 3; $^1$HNMR (400 MHz, CD$_3$OD) δ 7.50 (d, J=8.8 Hz, 2H), 7.29-7.20 (m, 5H), 7.08 (d, J=4 Hz, 1H), 6.98 (d, J=8.8 Hz, 2H), 6.77 (d, J=5.2 Hz, 1H), 4.34 (dd, J=7.2, 3.6 Hz, 1H), 4.12 (s, 2H), 4.01 (m, 2H), 3.35 (m, 2H), 2.25 (m, 1H), 2.11 (m, 2H), 1.98 (m, 1H); LC/MS (ESI+) m/z: 96%; 351 (M+1, 100).

EXAMPLE 160

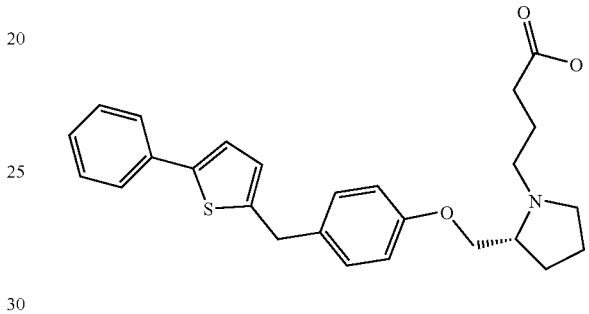

4-{(R)-2-[4-(5-Phenyl-thiophen-2-ylmethyl)-phenoxymethyl]-pyrrolidin-1-yl}-butyric acid: The title compound (60 mg, 36%) was prepared from the product of Example 159 (0.15 g, 0.39 mmol) and methyl 4-bromobutyrate (84 mg, 0.47 mmol) using the procedure of Example 147; $^1$HNMR (400 MHz, CD$_3$OD) δ 7.50 (d, J=8.8 Hz, 2H), 7.32 (t J=6 Hz, 2H), 7.24 (m, 3H), 7.18 (d, J=3.6 Hz, 1H), 6.98 (d, J=8.8 Hz, 2H), 6.77 (d, J=3.6 Hz, 1H), 4.36 (dd, J=7.2, 3.6 Hz, 1H), 4.18 (m, 1H), 4.10 (s, 2H), 4.00 (m, 1H), 3.71 (m, 1H), 3.55 (m, 1H), 3.25 (m, 2H), 2.50-2.30 (m, 4H), 2.19-1.98 (m, 4H), LC/MS (ESI+) m/z: 90%; 437 (M+1, 100).

EXAMPLE 161

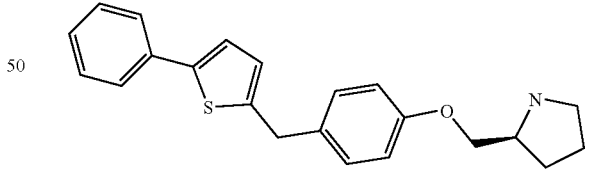

(S)-2-[4-(5-Phenyl-thiophen-2-ylmethyl)-phenoxymethyl]-pyrrolidine hydrochloride salt: The title compound (150 mg, 52%) was prepared from the product of Example 159, step 4 (0.3 g, 1.1 mmol) and (S)-2-(toluene-4-sulfonyloxymethyl)-pyrrolidine-1-carboxylic acid tert-butyl ester (0.48 g, 1.4 mmol) using the procedure of Example 140, step 3, $^1$HNMR (400 MHz, CD$_3$OD) δ 7.50 (d, J=8.4 Hz, 2H), 7.32 (t J=6 Hz, 2H), 7.24 (m, 3H), 7.17 (d, J=3.6 Hz, 1H), 6.98 (d, J=8.4 Hz, 2H), 6.77 (d, J=3.6 Hz, 1H), 4.34 (dd, J=7.2, 3.6 Hz, 1H), 4.12 (s, 2H), 4.01 (m, 2H), 3.35 (m, 2H), 2.25 (m, 1H), 2.11 (m, 2H), 1.98 (m, 1H); LC/MS (ESI+) m/z: 96%; 351 (M+1, 100).

EXAMPLE 162

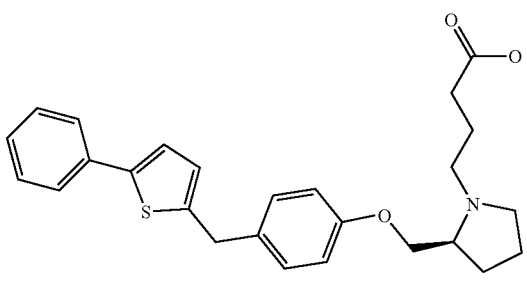

4-{(S)-2-[4-(5-Phenyl-thiophen-2-ylmethyl)-phenoxymethyl]-pyrrolidin-1-yl}-butyric acid: The title compound was prepared from the product of Example 161 (0.1 g, 0.26 mmol) and methyl 4-bromobutyrate (56 mg, 0.31 mmol) using the procedure of Example 147; $^1$HNMR (400 MHz, CDCl$_3$) δ 7.50 (d, J=8.8 Hz, 2H), 7.32 (t J=6 Hz, 2H), 7.24 (m, 3H), 7.18 (d, J=3.6 Hz, 1H), 6.98 (d, J=8.8 Hz, 2H), 6.77 (d, J=3.6 Hz, 1H), 4.36 (dd, J=7.2, 3.6 Hz, 1H), 4.20 (br, 1H), 4.10 (s, 2H), 3.71 (br, 1H), 3.05 (br, 2H), 2.44 (br, 2H), 2.19-1.98 (m, 9H); LC/MS (ESI+) m/z: 95%; 437 (M+1, 100).

EXAMPLE 163

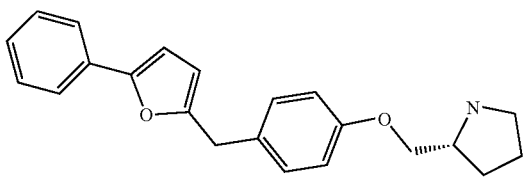

Step 1

5-Phenyl-furan-2-carbaldehyde; The title compound (2.0 g, 95%) was prepared from 5-bromo-2-furaldehyde (2.0 g, 11.4 mmol) and phenylboronic acid (1.5 g, 12 mmol) using the procedure of Example 159, step 1.

Step 2

(4-Methoxy-phenyl)-(5-phenyl-furan-2-yl)-methanol: The title compound was prepared from the product of step 1 and 4-bromoanisole using the procedure of Example 159, step 2

Step 3

2-(4-Methoxy-benzyl)-5-phenyl-furan: The title compound (940 mg, 99%) was prepared from the product of step 2 (1.0 g, 3.6 mmol) and triethylsilane (2.3 g, 21.4 mmol) using the procedure of Example 159, step 3.

Step 4

4-(5-Phenyl-furan-2-ylmethyl)-phenol: The title compound (280 mg, 99%) was prepared from the product of step 3 (0.3 g, 1.1 mmol) and BBr$_3$ (0.85 g, 3.4 mmol) using the procedure of Example 159, step 4.

Step 5

(R)-2-[4-(5-Phenyl-furan-2-yl methyl)-phenoxymethyl]-pyrrolidine: The title compound (80 mg, 50%) was prepared from the product of step 4 (0.1 g, 0.4 mmol) and (R)-2-(toluene-4-sulfonyloxymethyl)-pyrrolidine-1-carboxylic acid tert-butyl ester (0.17 g, 0.48 mmol) using the procedure of Example 154, step 3, $^1$HNMR (400 MHz, CD$_3$OD) δ 7.58 (d, J=8 Hz, 2H), 7.32 (t J=6 Hz, 2H), 7.26 (d, J=8 Hz, 2H), 7.19 (t, J=8 Hz, 1H), 7.17 (d, J=3.6 Hz, 1H), 6.98 (d, J=8.4 Hz, 2H), 6.63 (d, J=3.2 Hz, 1H), 6.09 (d, J=3.2 Hz, 1H), 4.32 (dd, J=7.2, 3.6 Hz, 1H), 4.08 (t, J=9.4 Hz, 1H), 4.01 (m, 1H), 3.98 (s, 2H), 3.35 (m, 2H), 2.25 (m, 1H), 2.11 (m, 2H), 1.98 (m, 1H); LC/MS (ESI+) m/z: 91%; 334 (M+1, 100).

EXAMPLE 164

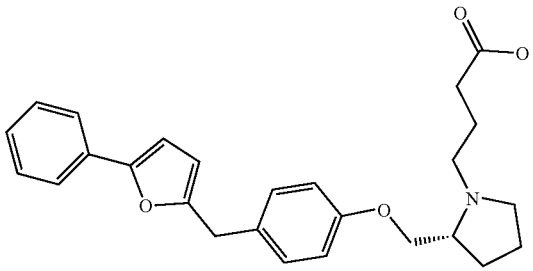

4-{(S)-2-[4-(5-Phenyl-thiophen-2-ylmethyl)-phenoxymethyl]-pyrrolidin-1-yl}-butyric acid: The title compound (20 mg, 45%) was prepared from the Example 156 (40 mg, 0.11 mmol) and methyl 4-bromobutyrate (24 mg, 0.13 mmol) using the procedure of Example 147; $^1$HNMR (400 MHz, CD$_3$OD) δ 7.58 (d, J=8 Hz, 2H), 7.32 (t, J=6 Hz, 2H), 7.26 (d, J=8 Hz, 2H), 7.19 (t, J=8 Hz, 1H), 7.17 (d, J=3.6 Hz, 1H), 6.98 (d, J=8.4 Hz, 2H), 6.63 (d, J=3.2 Hz, 1H), 6.09 (d, J=3.2 Hz, 1H), 4.32 (dd, J=7.2, 3.6 Hz, 1H), 4.08 (t, J=9.4 Hz, 1H), 4.01 (m, 1H), 3.98 (s, 2H), 3.71 (br, 3H), 3.05 (br, 2H), 2.44 (br, 2H), 2.19-1.98 (m, 6H); LC/MS (ESI+) m/z: 80%; 437 (M+1, 100).

EXAMPLE 165

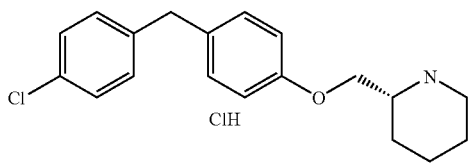

(S)-2-[4-(4-Chlorobenzyl)-phenoxymethyl]-piperidine hydrochloride: A solution of (R)-1,1-dioxo-2-oxa-1-thia-7a-azaperhydronoindene (0.750 g, 4.23 mmol), 4-(4-chlorobexzyl)phenol (0.926 g, 4.23 mmol), and potassium carbonate (1.17 g, 8.46 mmol) in DMF (60 mL) under an atmosphere of nitrogen was heated for 18 h at 70° C. The ambient mixture's pH was adjusted to 1 with an aqueous 20% H$_2$SO$_4$ solution (30 mL) and stirred at ambient temperature for about 20 h. After the reaction solution's pH was adjusted to 12 with 5N NaOH, the mixture was diluted with H$_2$O (250 mL) and extracted with EtOAc (3×75 mL). The organic layer was washed with H$_2$O (2×50 mL) and brine (50 mL), dried over magnesium sulfate, and concentrated in vacuo to give a brown oil. A solution of the product (0.252 g, 0.798 mmol) in 2.0M HCl in diethyl ether (2 mL) was stirred at ambient temperature for about 30 min and then concentrated in vacuo. The residue was triturated with ether and dried in a 55° C. vacuum oven for one hour to afford the desired product as a white solid (0.250 g, 89%): $^1$H NMR (400 MHz, DMSO): δ 1.48-1.68 (m, 3H), 1.76 (t 2H, J=14.8 Hz), 1.85 (d, 1H, J=12.8 Hz), 2.9 (d, 1H, J=9.2 Hz), 3.24 (d, 1H, J=12.4 Hz), 3.43 (s, 1H), 3.88 (s, 2H), 4.08 (dd, H, J=6.8 Hz, J=10.4 Hz), 4.15 (dd, 1H, J=4.4 Hz, J=10.4 Hz), 6.94 (d, 2H, J=8.4 Hz), 7.16 (d, 2H, J=8.8), 7.22 (d, 21-L J=8.4 Hz), 7.33 (d, 2H, J=8.4 Hz); MS: m/z 316 (NM)$^+$; LCMS (UV) 87%.

EXAMPLE 166

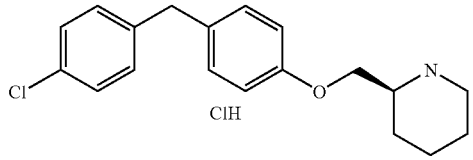

(R)-2-[4-(4-Chlorobenzyl)-phenoxymethyl]-piperidine hydrochloride: A solution of (S)-1,1-dioxo-2-oxa-1-thia-7a-azaperhydronoindene (0.750 g, 4.23 mmol), 4-(4-chlorobexzyl)phenol (0.926 g, 4.23 mmol), and potassium carbonate (1.17 g, 8.46 mmol) in DMF (60 mL) under an atmosphere of nitrogen was heated for 18 h at 70° C. The ambient mixture's pH was adjusted to 1 with an aqueous 20% H$_2$SO$_4$ solution (30 mL) and stirred at ambient temperature for about 20 h. After the reaction solution's pH was adjusted to 12 with 5N NaOH, the mixture was diluted with H$_2$O (250 mL) and extracted with EtOAc (3×75 mL). The organic layer was washed with H$_2$O (2×50 mL) and brine (50 mL), dried over anhydrous magnesium sulfate, concentrated in vacuo, and purified by flash column chromatography (5% MeOH in dichloromethane) to give the free amine as a dark yellow oil (0.263 g). A solution of the product (0.500 g, 1.58 mmol) in step 1 through purification by of silica gel flash chromatography, using 5% ethanol in dichloromethanne, was treated with 2.0M HCl in diethyl ether (2 mL) and stirred at ambient temperature for about 30 min and then concentrated in vacuo. The residue was triturated with ether and dried in a 55° C. vacuum oven for one hour to afford the desired product as a white solid (0.153 g, 28%): $^1$H NMR (400 MHz, DMSO): δ 1.48-1.66 (m, 3H), 1.77 (t, 2H, J=13.2 Hz), 1.85 (d, 1H, J=12.4 Hz), 2.9 (d, 1H, J=10.2 Hz), 3.24 (d, 1H, J=12.4 Hz), 3.44 (s, 1H), 3.88 (s, 2H), 4.07 (dd, 1H, J=7.2 Hz, J=10.4 Hz), 4.15 (dd, 1H, J=4.0 Hz, J=10.8 Hz), 6.94 (d, 2H, J=8.4 Hz), 7.16 (d, 2H, J=8.8 Hz), 7.22 (d, 2H, J=8.4 Hz), 7.33 (d, 2H, J=8.4 Hz); MS: m/z 316 (MH)$^+$; LCMS (UV) 95%; Elemental Analysis: Found (Theoretical): C, 63.82 (64.78), H, 6.46 (6.58) N, 4.13 (3.98).

EXAMPLE 167

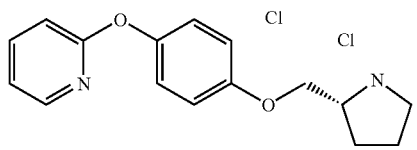

Step 1

(R)-2-(Toluene-4-sulfonyloxymethyl)-pyrrolidine-1-carboxylic acid tert-butyl ester: To a solution of (R)-Boc-prolinol (500 mg, 2.48 mmol) in pyridine (1.5 mL) was added tosyl chloride (565 mg, 2.96 mmol) in pyridine (1 mL) at 0° C., and the resulting mixture was stirred at 0° C. for 20 min. before allowing it to warm to rt. The mixture was stirred for 8 h at that temperature. The solvent was removed from the resulting suspension, and aq. 1N HCl was added to the crude product and extracted with EtOAc. Organic layer was washed with saturated aq. NaHCO$_3$ followed by water and brine. Organic layer was dried over anhy. Na$_2$SO$_4$ and the solvent was removed in vacuo to obtain the title product (800 mg, 91%) as a thick oil: MS; m/z 378 (M+Na); $^1$H NMR (400 MHz, CDCl$_3$); δ 1.38 (m, 9H), 1.79 (m, 2H), 1.93 (m, 2H), 2.44 (s, 3H), 3.26-3.32 (m, 3H), 3.88-3.97 (m, 2H), 4.07-4.14 (m, 2H), 7.34 (br s, 2H), 7.77 (d, 2H, J=8.0 Hz); HPLC (ELSD); 99%.

Step 2:

(R)-2-(4-Benzyloxy-phenoxymethyl)-pyrrolidine-1-carboxylic acid tert-butyl ester: To p-benzyloxyphenol (7.05 g, 35.2 mmol) was added to a solution of NaH (60% dispersion in oil, 1.70 g, 42.2 mmol) in anhy. DMF (70 mL) at 0° C. The mixture was stirred at ambient temperature for 30 min, then cooled to −10° C. and (R)-2-(Toluene-4-sulfonyloxymethyl)-pyrrolidine-1-carboxylic acid tert-butyl ester (12.5 g, 35.2 mmol) in anhy.DMF (20 mL) was added dropwise over 5 min. The mixture was stirred at 92° C. for 5 h and then ambient temperature overnight. The reaction mixture was poured into ice water and stirred for one h. The subsequent mixture was filtered and the organic portion was extracted into ether. The portion was dried over anhy. MgSO$_4$, and concentrated to afford the product (11.7 g, 86%).

Step 3: (R)-2-(4-Hydroxy-phenoxymethyl)-pyrrolidine-1-carboxylic acid tert-butyl ester: The product from step 2 (12.0 g, 31.3 mmol) was added to a round-bottom flask containing THF (100 mL), EtOH (200 mL) and 10% Pd/C (10.5 g). The flask was charged with H$_2$ and left to stir under H$_2$ atmosphere overnight. The Pd/C was removed by filtering the reaction mixture through celite. The resulting solution was concentrated to give the title compound. (6.00 g, 65%).

Step 4:

2-[4-((R)-1-Pyrrolidin-2-ylmethoxy)-phenoxy]-pyridine hydrochloride: To the product from step 3 (586 mg, 2.00 mmol), Cs$_2$CO$_3$ (1.30 g, 4.00 mmol), 2-iodo pyridine (615 mg, 3.00 mmol) in anhydrous dioxane (15 mL) under N$_2$ was added diglyme (27.9 mg, 0.20 mmol). After stirring for 10 min, CuI (14 mg, 0.07 mmol) was added and the reaction mixture was kept in a shaker at 85° C. overnight. The mixture was poured into EtOAc and water, the organic layer dried over Na$_2$SO$_4$, and concentrated. Silica gel flash chromatography using EtOAc/Hexane gave the title compound (680 mg, 92%). To this was added 25 mL of 4N HCl in Dioxane. The resulting mixture was stirred at ambient temperature overnight. The solvent was removed and triturated with ether to give the title compound (360 mg, 60%) MS; m/z 271.24 (M+H) 99% $^1$H NMR (DMSO, 400 MHz) δ 171-2.15 (4H, m), 3.21 (2H, m), 3.91 (1H, m), 4.11-4.27 (2H, m), 6.96-7.11 (6H, m), 7.83 (1H, dd, J=2.0 Hz, 8.4 Hz) 8.11 (1H, dd, J=2.0 Hz, 5.6 Hz), 8.97 (1NH, s), 9.51 (1NH, s).

EXAMPLE 168

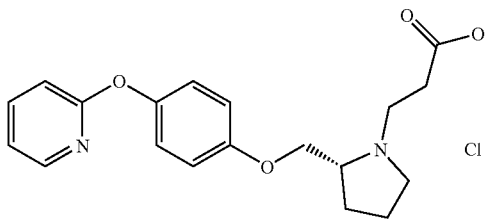

3-{2-[4-(Pyridin-2-yloxy)-phenoxymethyl]-pyrrolidin-1-yl}-propionic acid: The product from Example 167 (125 mg, 0.37 mmol) was treated with 20% NaOH (10 mL) and extracted with EtOAc, dried over Na₂SO₄ and dried down to give the free base. Dichloromethane (3 mL) and methyl acrylate (1 mL, 7 mmol) were added and the mixture was stirred at ambient temperature overnight. The reaction mixture was dried down to give oil. 4.0M HCl in dioxane was added and the mixture was stirred overnight at ambient temperature. The solvent was evaporated to give the title compound (61 mg, 57%); LC/MS; m/z 343 (M+H) 99%

EXAMPLE 169

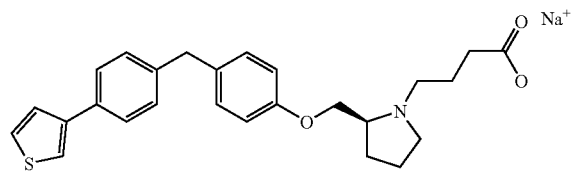

Step 1

4-{(S)-2-[4-(4-Thiophen-3-yl-benzyl)-phenoxymethyl]-pyrrolidin-1-yl}-butyric acid methyl ester: To the Example 122 (240 mg, 0.62 mmol) in anhydrous DMF (12 mL) was added 4-bromobutyric acid methyl ester (160 mg, 0.88 mmol) and K₂CO₃ (300 mg, 2.17 mmol). The subsequent mixture was stirred at ambient temperature overnight. The solvent was removed in vacuo and the crude residue was purified by silica gel flash chromatography using ethyl acetate/hexane (gradient system) to afford the title compound (128 mg, 45%).

Step 2

4-{(S)-2-[4-(4-Thiophen-3-yl-benzyl)-phenoxymethyl]-pyrrolidin-1-yl}-butyric acid sodium salt: To the product from step 1 (128 mg, 0.29 mmol) in methanol (5 mL) was added 1N NaOH (0.30 mL). The resulting solution was stirred at 58° C. for 5.5 h. The reaction mixture was concentrated in vacuo. The subsequent powder was washed with ether to afford the title compound (85 mg, 68%); LCMS; m/z: 436.9 (M+1); +H NMR (400 MHz, DMSO-d₆); δ 1.54-1.68 (m, 5H), 1.82-1.90 (m, 3H), 2.15-2.26 (m, 2H), 2.70-2.74 (m, 2H), 3.00-3.02 (m, 1H), 3.63-3.67 (m, 1H), 3.87-3.90 (m, 3H), 6.84 (d, J=8.8 Hz, 2H), 7.13 (d, J=8.8 Hz, 2H), 7.22 (d, J=8.0 Hz, 2H), 7.51 (dd, J1=5.2 Hz, J2=1.2 Hz, 1H), 7.60-7.62 (m, 3H), 7.78-7.79 (m, 1H):

EXAMPLE 170

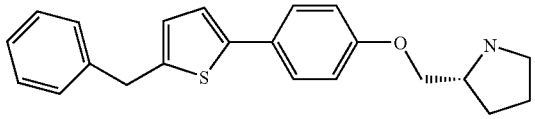

Step 1

5-(4-Methoxy-phenyl)-thiophene-2-carbaldehyde: The title compound was prepared from 5-bromo-thiophene-2-carbaldehyde (2.0 g, 10.5 mmol) and (4-methoxyphenyl) boronic acid (1.6 g, 11 mmol) using the procedure of Example 159, step 1 with 82% yield (1.9 g).

Step 2

[5-(4-Methoxy-phenyl)-thiophen-2-yl]-phenyl-methanol: The title compound was prepared from the product of step 1 (0.56 g, 2.55 mmol) and benzyl bromide (0.5 g, 3.2 mmol) using the procedure of Example 159, step 2 with 64% yield (0.6 g).

Step 3

2-Benzyl-5-(4-methoxy-phenyl)-thiophene: The title compound was prepared from the product of step 2 (0.6 g, 2.0 mmol) and triethylsilane (2.4 g, 20.2 mmol) using the procedure of Example 159, step 3 with 99% yield (0.55 g).

Step 4

4-(5-Benzyl-thiophen-2-yl)-phenol: The title compound was prepared from the product of step 3 (0.5 g, 1.8 mmol) and BBr₃ (1.34 g, 5.4 mmol) using the procedure of Example 159, step 4 with 99% yield (0.48 g).

Step 5

(R)-2-[4-(5-Benzyl-thiophen-2-yl)-phenoxymethyl]-pyrrolidine The title compound was prepared from the product of step 4 (0.3 g, 1.1 mmol) and (R)-2-(toluene-4-sulfonyloxymethyl)-pyrrolidine-1-carboxylic acid tert-butyl ester (0.5 g, 1.4 mmol) using the procedure of Example 159, step 5 with 85% yield (360 mg). ¹HNMR (CD₃OD) δ 7.53 (d, J=8 Hz, 2H), 7.33 (t, J=6 Hz, 2H), 7.22 (m, 3H), 7.18 (d, J=3.6 Hz, 1H), 6.96 (d, J=8.8 Hz, 2H), 6.78 (d, J=3.6 Hz, 1H), 4.33 (dd, J=7.2, 3.6 Hz, 1H), 4.10 (s, 2H), 4.01 (m, 2H), 3.98 (s, 2H), 3.35 (m, 2H), 2.26 (m, 1H), 2.10 (m, 2H), 1.90 (m, 1H), LC/MS (ESI+) m/z: 95%; 351 (M+1, 100).

EXAMPLE 171

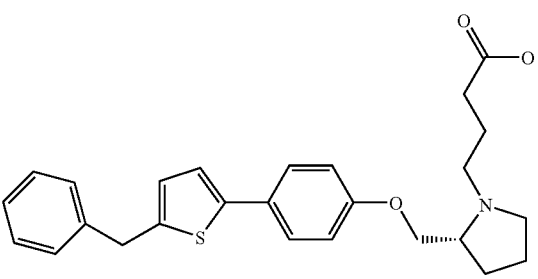

4-{(R)-2-[4-(5-Benzyl-thiophen-2-yl)-phenoxymethyl]-pyrrolidin-1-yl}-butyric acid: The title compound was prepared from the product of example 170 (150 mg, 0.39 mmol) and methyl 4-bromobutyrate (84 mg, 0.47 mmol) using the procedure of example 147 with 25% yield (40 mg). ¹HNMR (CD₃OD) 7.51 (d, J=8.8 Hz, 2H), 7.32-7.20 (m, 5H), 7.08 (d, J=3.6 Hz, 1H), 7.01 (d, J=8.8 Hz, 2H), 6.77 (d, J=3.6 Hz, 1H), 4.38 (dd, J=7.2, 3.6 Hz, 1H), 4.20 (m, 1H), 4.12 (s, 2H), 4.01 (m, 1H), 3.72 (m, 1H), 3.60 (m, 1H), 3.23 (m, 2H), 2.48 (m, 2H), 2.36 (m, 2H), 2.19-1.98 (m, 4H), LC/MS (ESI+) m/z: 90%; 437 (M+1, 100).

EXAMPLE 172

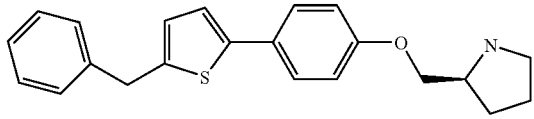

(S)-2-[4-(5-Benzyl-thiophen-2-yl)-phenoxymethyl]-pyrrolidine: The title compound was prepared from the product of example 170, step 4 (0.3 g, 1.1 mmol) and (S)-2-(toluene-4-sulfonyloxymethyl)-pyrrolidine-1-carboxylic acid tert-butyl ester (0.5 g, 1.4 mmol) using the procedure of Example 159, step 5 with 85% yield (360 mg). ¹HNMR (CD₃OD) 7.50 (d, J=8.8 Hz, 2H), 7.39-7.18 (d, J=3.6 Hz, 5H), 7.08 (d, J=3.6 Hz, 1H), 7.00 (d, J=8.8 Hz, 1H), 6.77 (d, J=3.6 Hz, 1H), 4.58 (m, 1H), 4.32 (m, 1H), 4.12 (s, 2H), 4.03 (m, 2H), 3.34 (m, 2H), 2.26 (m, 1H), 2.10 (m, 2H), 1.90 (m, 1H), LC/MS (ESI+) m/z: 99%; 351 (M+1, 100). Elemental analysis

EXAMPLE 173

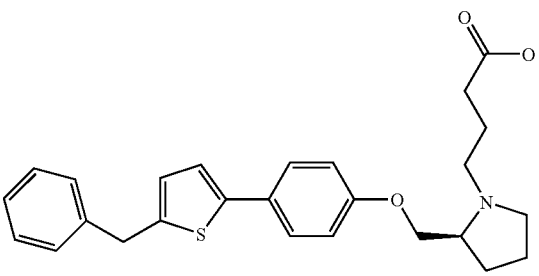

4-{(S)-2-[4-(5-Benzyl-thiophen-2-yl)-phenoxymethyl]-pyrrolidin-1-yl}-butyric acid: The title compound was prepared from the product of example 172 (100 mg, 0.22 mmol) and methyl 4-bromobutyrate (56 mg, 0.31 mmol) using the procedure of example 147 with 30% yield (30 mg). ¹HNMR (CD₃OD) 7.44 (br d, J=8 Hz, 2H), 7.32-7.20 (m, 5H), 7.01 (br d, J=3.6 Hz, 1H), 6.99 (br d, J=8 Hz, 2H), 6.73 (br d, J=3.6 Hz, 1H), 4.70 (br, 1H), 4.20 (br, 2H), 4.12 (s, 2H), 3.97 (br, 1H), 3.59 (br, 3H), 3.00 (br, 2H), 2.45 (br, 2H), 2.19-1.98 (br, 4H), LC/MS (ESI+) m/z: 92%; 437 (M+1, 100). Elemental analysis

EXAMPLE 174

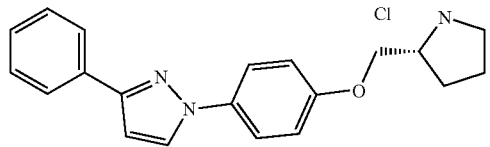

Step 1

1-(4-Methoxy-phenyl)-3-phenyl-1H-pyrazole To a solution of p-toluenesulfonyl-hydrazde (0.56 g, 3 mmol) in MeCN (10 mL) was added benzaldehyde (0.32 g, 3 mmol). After the mixture was stirred at room temperature for 3 h, a solution of 5 N NaOH (600 µl, 3 mmol) was added and the mixture was stirred for a further 20 min. N-Vinylimidazole (1.41 g, 15 mmol) was added, and the mixture was stirred at 50° C. for 48 h. The volatiles were removed in vacuo, and the residue was dissolved in a 1:1 mixture water-ethyl acetate. The organic layer was separated, dried over Na₂SO₄, and concentrated to yield the crude pyrazole product.

A mixture of the above pyrazole, 4-methoxyphenylboronic acid (0.91 g, 6 mmol), TEA (0.61 g, 6 mmol) and Cu(OAc)₂ (0.54 g, 3 mmol) in CH₂Cl₂ (25 mL) was stirred at room temperature for 48 h. The mixture was diluted with water-CH₂Cl₂ (1:1). The organic layer was separated, dried over Na₂SO₄, and concentrated. The crude product was purified by a column chromatography on silica gel to yield the title compound (0.60 g, 88%).

Step 2

4-(3-Phenyl-pyrazol-1-yl)-phenol The title compound was prepared from the product of step 1 (0.5 g, 2 mmol) and BBr₃ (1.5 g, 6 mmol) using the procedure of Example 146, step 2 with 42% (0.2 g).

Step 3

3-Phenyl-1-[4-((R)-1-pyrrolidin-2-ylmethoxy)-phenyl]-1H-pyrazole To a mixture of NaH (60% in mineral oil, 26 mg, 1.1-mmol) in DMF (2 mL) was added a solution of the product of step 2 (0.2 g, 0.85 mmol) in DMF (1 mL) at 0° C. The resulting slurry was stirred at 0° C. for 30 minutes and at room temperature for 30 minutes before a solution of (R)-2-(toluene-4-sulfonyloxymethyl)-pyrrolidine-1-carboxylic acid tert-butyl ester (0.32 g, 0.89 mmol) in DMF (1 mL) was added. The mixture was stirred at 80° C. for 4 h. The reaction mixture was poured over ice and then concentrated under reduced pressure. The crude residue was extracted into ethyl acetate and sequentially washed with water, saturated aq. NaHCO₃, water and brine. The combined organic portions were dried over Na₂SO₄, filtered and concentrated in vacu. The crude product was purified by a column chromatography on silica gel eluting with 10% ethyl acetate in hexane to afford the Boc-protected compound, which was dissolved in dioxane. To this solution was added 4M HCl in dioxane (0.5 ml, 2.2 mmol), and stirred at room temperature for 4 h. After the solvent was removed, the crude material was triturated with ether to afford the title compound (185 mg, 69%); ¹H NMR (400 MHz, CDCl₃) 7.90 (d, J=8.4 Hz, 2H), 7.84 (d, J=2.4 Hz, 1H), 7.64 (d, J=8.4 Hz, 2H), 7.45 (t, J=8 Hz, 1H), 7.34 (m, 1H), 7.08 (d, J=9.2 Hz, 2H), 6.72 (d, J=2.4 Hz, 1H), 4.40 (m, 1H), 4.34 (m, 1H), 4.01 (m, 1H), 3.45 (m, 2H), 2.25-1.98 (m, 4H); LC/MS (ESI+) m/z: 99%; 320 (M+1, 100).

EXAMPLE 175

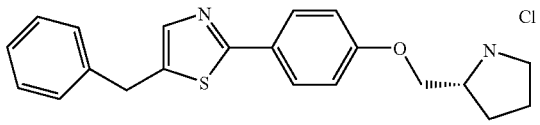

Step 1

2-(4-Methoxy-phenyl)-thiazole: The title compound was prepared from thiazole (2.0 g, 24 mmol) and 4-bromoanisole (3.0 g, 16 mmol) using the procedure of Example 146, step 1 with 67% yield (2.0 g).

Step 2

5-Benzyl-2-(4-methoxy-phenyl)-thiazole The title compound was prepared from the product of step 1 (1.0 g, 5.2 mmol) and benzylbromide (1.4 g, 7.8 mmol) using the procedure of Example 146, step 1 with 50% yield (0.74 g).

Step 3

4-(5-Benzyl-thiazol-2-yl)-phenol The title compound was prepared from the product of step 2 (0.4 g, 1.4 mmol) and BBr$_3$ (1M in CH$_2$Cl$_2$, 4.3 mL, 4.3 mmol) using the procedure of Example 146, step 2 with 79% yield (0.3 g). ?

Step 4

5-Benzyl-2-[4-((R)-1-pyrrolidin-2-ylmethoxy)-phenyl]-thiazole The title compound was prepared from the product of step 3 (0.1 g, 0.37 mmol) and (R)-2-(toluene-4-sulfonyloxymethyl)-pyrrolidine-1-carboxylic acid tert-butyl ester (0.15 g, 0.41 mmol) using the procedure of Example 146, step 3 with 50% yield (0.065 g). $^1$H NMR (400 MHz, CD$_3$OD) 7.92 (d, J=8 Hz, 2H), 7.85 (br, 1H), 7.35 (m, 5H), 7.20 (d, J=8.8 Hz, 2H), 4.76 (dd, J=10, 3.6 Hz, 1H), 4.12 (m, 1H), 4.29 (s, 2H), 4.24 (m, 1H), 4.08 (m, 1H), 3.36 (m, 2H), 2.25-1.98 (m, 4H); LC/MS (ESI+) m/z: 85%; 351 (M+1, 100).

EXAMPLE 176

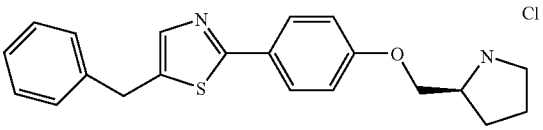

5-Benzyl-2-[4-((S)-1-pyrrolidin-2-ylmethoxy)-phenyl]-thiazole: The title compound was prepared from the product of example 175, step 3 (0.1 g, 0.37 mmol) and (S)-2-(toluene-4-sulfonyloxymethyl)-pyrrolidine-1-carboxylic acid tert-butyl ester (0.15 g, 0.41 mmol) using the procedure of example 154, step 3 with 50% yield (0.065 g). $^1$H NMR (400 MHz, CD$_3$OD) 7.87 (br, 3H), 7.35 (m, 5H), 7.20 (br, 2H), 4.76 (m, 1H), 4.12 (m, 1H), 4.29 (s, 2H), 4.24 (m, 1H), 4.08 (m, 1H), 3.36 (m, 2H), 2.25-1.98 (m, 4H); LC/MS (ESI+) m/z: 75%.

EXAMPLE 177

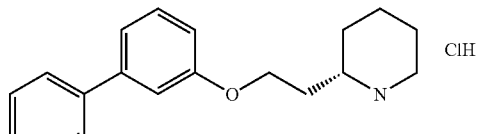

Step 1

(S)-2-[(4-Trifluoromethoxyphenoxy)ethyl]-piperidine-1-carboxylic acid tert-butyl ester: To a solution of (S)—N-Boc-piperidine-2-ethanol (0.300 g, 1.31 mmol), 3-phenylphenol (0.245 g, 1.44 mmol), and triphenylphosphine (0.412 g, 1.57 mmol) in anhydrous tetrahydrofuran (12 mL) at 0° C. under an atmosphere of nitrogen was added diisopropyl azodicarboxylate (0.30 ml, 1.57 mmol), and the resulting mixture was stirred at ambient temperature for about 20 h. The clear, yellow solution was concentrated in vacuo to a yellow oil. The crude oil was purified by silica gel flash chromatography to obtain the Boc protected piperidine as a clear, colorless oil (0.204 g, 41%): $^1$H NMR (400 MHz, CDCl$_3$): δ 7.58 (m, 2H), 7.42 (m, 2H), 7.34 (m, 2H), 7.16 (m, 1H), 7.10 (m, 1H), 6.86 (m, 1H), 4.51 (m, 1H), 4.01 (m, 3H), 2.83 (br t, 1H), 2.25 (m, 1H), 1.90 (m, 1H), 1.63 (m, 5H), 1.40 (m, 10H). MS; m/z 404 (M+Na$^+$).

Step 2

(S)-2-[(4-Trifluoromethoxyphenoxy)ethyl]-piperidine hydrochloride: A solution of the product (0.190 g, 0.498 mmol) in step 1 in 4N HCl in dioxane (1.25 mL) was stirred at ambient temperature for about 40 min and then concentrated in vacuo. The residue was triturated with ether and dried in a 55° C. vacuum oven to afford the title product as a white solid (0.123 g, 78%): $^1$H NMR (400 MHz, DMSO-d6): δ 9.00 (br s, 2H), 7.67 (m, 2H), 7.41 (m, 4H), 7.23 (m, 2H), 6.96 (m, 1H), 4.20 (m, 2H), 3.24 (m, 2H), 2.87 (dt 1H, J=12.4 Hz, J=3.2 Hz), 2.18 (m, 1H), 1.98 (m, 2H), 1.61 (m, 5H). MS; m/z 282 (MH$^+$).

EXAMPLE 178

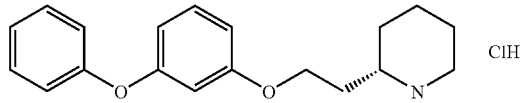

Step 1

(S)-2-[(3-Phenoxyphenoxy)ethyl]-piperidine-1-carboxylic acid tert-butyl ester: To a solution of (S)—N-Boc-piperidine-2-ethanol (0.300 g, 1.31 mmol), 3-phenoxyphenol (0.268 g, 1.44 mmol), and triphenylphosphine (0.412 g, 1.57 mmol) in anhydrous tetrahydrofuran (12 mL) at 0° C. under an atmosphere of nitrogen was added diisopropyl azodicarboxylate (0.30 ml, 1.57 mmol), and the resulting mixture was stirred at ambient temperature for about 20 h. The clear, yellow solution was concentrated in vacuo to a yellow oil. The crude oil was purified by silica gel flash chromatography to obtain the Boc protected piperidine as a clear, yellow oil (0.274 g, 53%): $^1$H NMR ((400MHz; CDCl$_3$): δ 7.32 (m, 2H), 7.20 (m, 1H), 7.09 (m, 1H), 7.01 (d, 2H, J=8.4 Hz), 6.59 (m, 2H), 6.53 (m, 1H), 4.46 (m, 1H), 3.95 (m, 3H), 2.78 (br t, 1H), 2.19 (m, 1H), 1.84 (m, 1H), 1.61 (m, 5H), 1.38 (m, 10H). MS; m/z 397 (MH)+.

Step 2

(S)-2-[(3-Phenoxyphenoxy)ethyl]-piperidine hydrochloride: A solution of the product (0.250 g, 0.629 mmol) from step 1 in 4N HCl in dioxane (1.57 mL) was stirred at ambient temperature for about 1 h and then concentrated in vacuo. The residue was triturated with ether and dried in a 55° C. vacuum oven to afford the desired product as a white solid (0.187 g, 89%): $^1$H NMR (400 MHz, DMSO-d6): δ 8.98 (br s, 2H), 7.40 (m, 2H), 7.28 (t, 1H, J=8.4 Hz), 7.15 (tt, 1H, J1=7.6 Hz, J2=1.2 Hz), 7.02 (m, 2H), 6.73 (ddd, 1H, J1=8.4 Hz, J2=2.4 Hz, J3=0.8 Hz), 6.57 (m, 2H), 4.09 (m, 2H), 3.21 (m, 2H), 2.85 (td, 1H, J1=12 Hz, J2=2.8 Hz), 2.13 (m, 1H), 1.93 (m, 2H), 1.59 (m, 5H). MS; m/z 298 (MH+).

Assays to determine potency of LTA4 hydrolase inhibitors:

(1) In vitro assay testing inhibitory activity against purified recombinant human LTA4 hydrolase. A human LTA4 hydrolase full-length cDNA clone (NM_000895) was purchased from OriGene Technologies (Rockville, Md.). The gene was amplified by polmerase chain reaction and transferred via pDONR201 into the bacterial expression vector pDEST17 by recombination (both plasmids from Invitrogen, Carlsbad, Calif.). The resulting construct was transformed into *Escherichia coli* BL21-AI (Invitrogen), and expression was induced by chemical induction with arabinose. The recombinant enzyme was purified by chromatography on an FPLC system (Amersham Biosciences, Uppsala, Sweden) using immobilized metal affinity chromatography (Ni-NTA Superflow, Qiagen, Hilden, Germany) and anion exchange chromatography (MonoQ HR 10/10, Amersham Biosciences).

The compounds of the invention were incubated in a series of dilutions with 200 nM of recombinant enzyme in assay buffer (100 mM Tris-HCl, 100 mM NaCl, 5 mg/ml fatty-acid free BSA, 10% DMSO, pH 8.0) for 10 min at room temperature to allow binding between LTA4 hydrolase and the inhibitors. LTA4 was prepared by alkaline hydrolysis of LTA4 methyl ester (Biomol, Plymouth Meeting, Pa., or Cayman Chemicals, Ann Arbor, Mich.). A solution of 10 μg of the ester was dried under a nitrogen stream and redissolved in 60 μl of a solution of 80% acetone and 20% 0.25 M NaOH. After incubation for 40 min at room temperature the resulting approximately 500 mM tock of LTA4 was kept at −80° C. for no more than a few days prior to use.

Immediately before the assay, LTA4 was diluted to a concentration of 10 μM in assay buffer (without DMSO) and added to the reaction mixture to a final concentration of 2 μM to initiate the enzyme reaction. After incubation for 120 sec at room temperature, the reaction was stopped by adding 2 volumes of chilled quenching buffer, containing acetonitril with 1% acetic acid and 225 nM $LTB_4$-$d_4$ (Biomol). The samples were then kept at 4° C. overnight to complete protein precipitation and centrifuged for 15 min at 1800 g. $LTB_4$ formed was measured by LC-MS/MS using $LTB_4$-$d_4$ as an internal standard and an external $LTB_4$ standard (Biomol) as reference. Based on the amounts of $LTB_4$ found at each inhibitor concentration, a dose-response curve was fitted to the data and an $IC_{50}$ value was calculated.

(2) Ex vivo assay testing inhibitory activity in human whole blood after stimulation with calcium ionophor.

Human blood was collected in heparin-containing Vacutainer tubes. For each sample, 200 μl of blood were dispensed into a pre-warmed plate and 188 μl of RPMI-1640 medium (Invitrogen) containing 20 μg/ml Indomethacin (Sigma, St. Louis, Mo.) were added. Then 4 μl of a series of compound dilutions (in DMSO) were added, followed by a 15 min incubation at 37° C. with gentle shaking. After that, blood samples were stimulated by adding Ionomycin (Calbiochem) to a final concentration of 20 μM. After another incubation at 37° C. for 30 min, samples were centrifuged for 5 min at 1800 g and 4° C. Supernatants were taken and $LTB_4$ concentrations were determined using a commercially available enzyme-linked immunosobentassay (R&D Systems, Minneapolis, Minn.) according to the manufacturer's instructions. Results obtained for different concentrations of hydrolase inhibitor were then used to fit a dose-response curve and calculate an $IC_{50}$ value.

The results of testing of representative species are shown below.

| Example # | AvgIC50 | hWBIC50 | Example # | AvgIC50 | hWBIC50 |
|---|---|---|---|---|---|
| 1 | A | A | 90 | A | A |
| 2 | A | ND | 91 | B | ND |
| 3 | A | A | 92 | A | ND |
| 4 | A | A | 93 | A | ND |
| 5 | A | A | 94 | A | ND |
| 6 | A | ND | 95 | A | ND |
| 7 | A | ND | 98 | B | ND |
| 8 | A | A | 97 | C | ND |
| 9 | A | A | 98 | C | ND |
| 10 | A | A | 99 | A | ND |
| 11 | A | ND | 100 | A | A |
| 12 | A | ND | 101 | A | ND |
| 13 | A | A | 102 | A | ND |
| 14 | A | ND | 103 | A | ND |
| 15 | A | ND | 104 | A | A |
| 16 | A | A | 105 | A | A |
| 17 | A | ND | 106 | A | A |
| 18 | A | ND | 107 | A | A |
| 19 | A | A | 108 | A | A |
| 20 | A | A | 109 | A | A |
| 21 | A | A | 110 | A | B |
| 22 | A | A | 111 | A | A |
| 23 | A | A | 112 | A | A |
| 24 | A | ND | 113 | A | A |
| 25 | A | ND | 114 | A | ND |
| 26 | A | ND | 115 | A | ND |
| 27 | ND | A | 116 | A | ND |
| 28 | A | ND | 117 | A | A |
| 29 | A | ND | 118 | A | ND |
| 30 | A | A | 121 | A | ND |
| 31 | A | ND | 122 | A | A |
| 32 | A | ND | 123 | 0 | ND |
| 33 | A | ND | 124 | B | ND |
| 34 | B | ND | 125 | B | ND |
| 35 | B | ND | 126 | B | ND |
| 36 | A | ND | 127 | B | ND |
| 37 | A | ND | 128 | B | B |
| 38 | A | ND | 129 | B | ND |
| 39 | A | A | 130 | B | A |
| 40 | ND | A | 131 | B | ND |
| 41 | A | ND | 132 | B | ND |
| 42 | A | A | 133 | B | A |
| 43 | A | ND | 134 | B | A |
| 44 | A | ND | 135 | B | B |
| 45 | A | ND | 136 | A | ND |
| 46 | B | ND | 137 | ND | ND |
| 47 | B | ND | 138 | ND | ND |
| 48 | A | A | 139 | A | ND |
| 49 | A | A | 140 | 0 | ND |
| 50 | A | A | 141 | A | ND |
| 51 | A | A | 142 | A | ND |
| 52 | A | A | 143 | A | ND |
| 53 | A | A | 144 | A | ND |
| 54 | A | A | 145 | A | ND |
| 55 | A | A | 146 | A | A |
| 56 | A | A | 147 | ND | A |
| 57 | A | A | 148 | A | ND |
| 58 | A | ND | 149 | A | ND |
| 59 | A | ND | 150 | A | ND |

-continued

| Example # | AvgIC50 | hWBIC50 | Example # | AvgIC50 | hWBIC50 |
|---|---|---|---|---|---|
| 60 | A | A | 151 | A | ND |
| 61 | A | A | 152 | A | ND |
| 62 | A | ND | 153 | A | ND |
| 63 | A | ND | 154 | ND | ND |
| 64 | A | A | 155 | 0 | ND |
| 65 | A | ND | 156 | A | ND |
| 66 | A | A | 157 | A | ND |
| 68 | A | ND | 158 | ND | ND |
| 69 | ND | ND | 159 | A | A |
| 70 | A | B | 160 | A | ND |
| 71 | A | ND | 161 | A | ND |
| 72 | A | ND | 162 | A | ND |
| 73 | A | A | 163 | A | ND |
| 74 | A | A | 164 | B | ND |
| 75 | A | ND | 165 | A | ND |
| 76 | A | ND | 166 | A | ND |
| 77 | A | A | 167 | ND | ND |
| 78 | A | ND | 168 | A | ND |
| 79 | A | ND | 169 | A | A |
| 80 | A | A | 170 | A | ND |
| 81 | A | ND | 171 | A | ND |
| 83 | A | ND | 172 | A | ND |
| 84 | A | ND | 173 | ND | ND |
| 85 | B | ND | 175 | ND | ND |
| 86 | A | ND | 176 | ND | ND |
| 87 | A | A | | | |
| 88 | A | A | | | |
| 89 | A | ND | | | |

A = <5 uM; B = 5-20 uM; C = 20-100 uM; ND = Not Determined; Q = the compound was tested and found to be an inhibitor but no IC50 was determined

We claim:

1. A compound of formula:

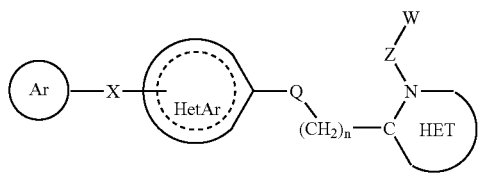

wherein

Ar is selected from the group consisting of
  phenyl; and
  phenyl substituted with from one to three substituents independently selected from the group consisting of halogen, loweralkyl, loweracyl, loweralkoxy, fluoroloweralkyl, fluoroloweralkoxy, hydroxy, hydroxy($C_1$-$C_4$)alkyl, formyl, formyl($C_1$-$C_4$)alkyl, cyano, cyano($C_1$-$C_4$)alkyl, benzyl, benzyloxy, phenyl, substituted phenyl, heteroaryl, heterocyclylalkyl, substituted heteroaryl, and nitro;

X is selected from the group consisting of direct bond, O, SO, S($O_2$), $NR^1$, $CH_2$, $CF_2$, $CH_2CH_2$, $CH_2NR^1$, $NR^1CH_2$, CH=CH, C=O, $CH_2$C=O, $CR^{1a}R^{1b}$, $OCR^{1a}R^{1b}$, $CR^{1a}R^{1b}$O; $SO_2NR^1$, $NR^1SO_2$, C(=O)$NR^1$ and $NR^1$C(=O);

$R^1$ is selected separately in each occurrence from the group consisting of H and lower alkyl;

$R^{1a}$ is selected from the group consisting of H, OH and lower alkyl;

$R^{1b}$ is selected from the group consisting of H and lower alkyl, or $R^{1a}$ and $R^{1b}$ taken together may form a 3-6 membered ring, which may optionally contain a heteroatom chosen from O, S, and N;

HetAr is a phenyl ring attached via a ring carbon to Q, further characterized in that Q and X cannot be on adjacent positions in said aryl ring;

Q is —O—;

n is an integer selected from 1-5;

HET is selected from the group consisting of
  pyrrolidine and
  pyrrolidine substituted with one or two substituents independently selected from the group consisting of halogen, hydroxyl, amino, carboxy, loweralkyl, loweracyl, loweralkoxy, N-oxide, fluoroloweralkyl, fluoroloweralkoxy, formyl, cyano, benzyl, benzyloxy, phenyl, heteroaryl and nitro; and taken together ZW is H or Z is $(CH_2)_{1-10}$, in which one or two ($CH_2$) may optionally be replaced by —O—, —$NR^1$—, —SO—, —S(O)$_2$—, —C(=O)— or —C=O(NH)—, provided that said —O—, —$NR^1$—, —SO—, —S(O)$_2$—, —C(=O)— or —C=O(NH)— are not at the point of attachment to HET and are separated by at least one —($CH_2$)—;

W is selected from the group consisting of acyl, hydroxyl, carboxyl, amino, —C(O)$NHR^4$, aminoacyl, —COOalkyl, —CHO, heterocyclyl, substituted aryl, substituted heterocyclyl, sulfonamide, —C(O)fluoroalkyl, —C(O)$CH_2$C(O)Oalkyl, —C(O)$CH_2$C(O)Ofluoroalkyl, —SH, —C(O)NH(OH), —C(O)N(OH)$R^4$, —N(OH)C(O)OH, —N(OH)C(O)$R^4$; and $R^4$ is selected from the group consisting of H, ($C_1$-$C_4$) alkyl, and phenyl($C_1$-$C_4$) alkyl;

with the provisos that;
  (a) when HET is (S)-pyrrolidine or rac-pyrrolidine Ar is phenyl or halo-substituted phenyl, and HetAr is p-phenylene, then the Z—W combination is other than H.

2. A compound according to claim 1 wherein the HetAr ring is para or meta phenylene of formula:

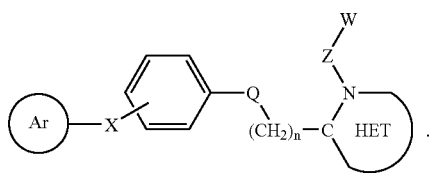

3. A compound according to claim 2 of formula:

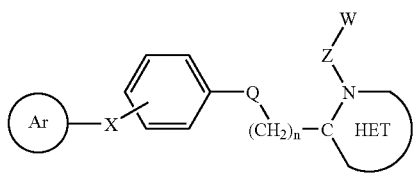

wherein

Ar is selected from the group consisting of
  phenyl; and
  phenyl substituted with from one to three substituents independently selected from the group consisting of halogen, loweralkyl, loweracyl, loweralkoxy, fluoroloweralkyl, fluoroloweralkoxy, formyl, cyano, benzyl, benzyloxy, phenyl, heteroaryl and nitro;

X is selected from the group consisting of direct bond, O, SO, S(O$_2$), NR$^1$, CH$_2$, CF$_2$, CH$_2$O, C=O and CH$_2$C=O;

R$^1$ is selected independently in each occurrence from the group consisting of H and lower alkyl;

n is an integer selected from 1-5;

HET is selected from the group consisting of
  pyrrolidine and
  pyrrolidine substituted with one or two substituents independently selected from the group consisting of halogen, loweralkyl, loweracyl, loweralkoxy, fluoroloweralkyl, fluoroloweralkoxy, formyl, cyano, benzyl, benzyloxy, phenyl, heteroaryl and nitro;

Z is (CH$_2$)$_{1-10}$; in which one or two (CH$_2$) may optionally be replaced by —O—, —NR$^1$—, —SO, —S(O)$_2$, —C(=O)— or —C=O(NH)—, provided that said —O—, —NR—, —SO—, —S(O)$_2$—, —C(=O)— or —C=O(NH)— are not at the point of attachment to HET and are separated by at least two —(CH$_2$)—;

W is selected from acyl, hydroxyl, carboxyl, amino, carboxamido, aminoacyl, —COOalkyl, —CHO, heterocyclyl, substituted aryl, and substituted heterocyclyl.

4. A compound according to claim 3 wherein X is selected from CH$_2$, O and NR$^1$.

5. A compound according to claim 3 wherein HET is (S) pyrrolidine, of the formula

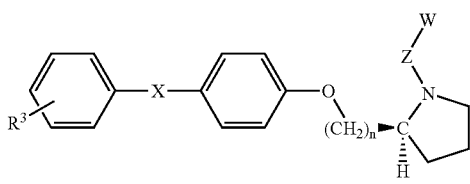

wherein
R$^3$ is chosen from halogen, CF$_3$, methyl, methoxy and CF$_3$O.

6. A compound according to claim 3 wherein HET is (S) pyrrolidine, of the formula

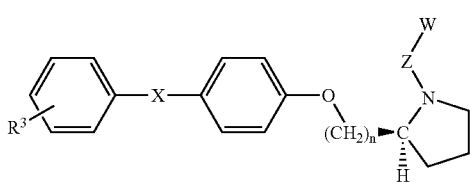

wherein X is O or CH$_2$.

7. A compound according to claim 3 wherein HET is (S) pyrrolidine, of the formula

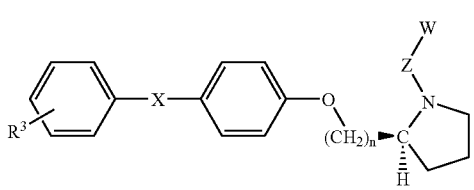

wherein n is 1 or 2.

8. A compound according to claim 3 wherein HET is (S) pyrrolidine, of the formula

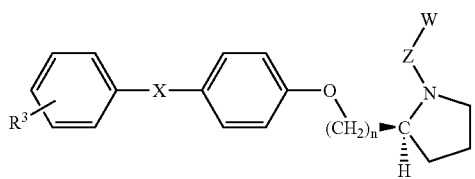

wherein Z is C$_1$-C$_4$ alkylene.

9. A compound according to claim 3 wherein HET is (S) pyrrolidine, of the formula

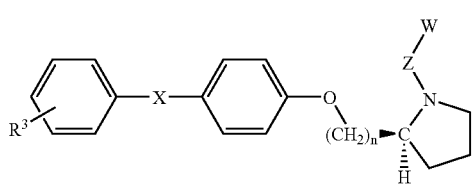

wherein W is COOH.

10. A compound according to claim 3 wherein HET is (S) pyrrolidine, of the formula

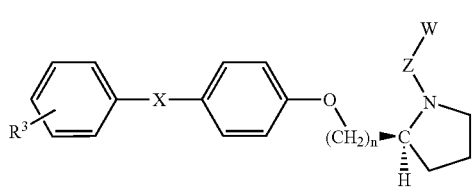

wherein
R$^3$ is chosen from halogen, CF$_3$, methyl, methoxy, CF$_3$O;
X is O or CH$_2$;
n is 1 or 2;
Z is C$_1$-C$_4$ alkylene and;
W is COOH.

11. A compound according to claim 3 wherein HET is pyrrolidine and the Z—W combination is other than H.

12. A compound according to claim 11 wherein HET-Z—W is selected from the group consisting of pyridinylmethylpyrrolidine, oxadiazolylmethylpyrrolidine, carboxyalkylpyrrolidine, and alkoxycarbonylalkylpyrrolidine.

13. A compound according to claim 12 wherein HET-Z—W is carboxyalkylpyrrolidine, of the formula:

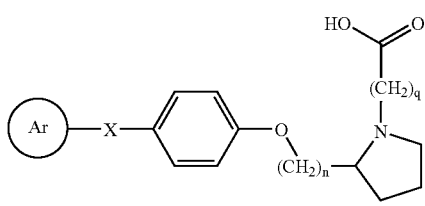

wherein q is an integer selected from 2-6.

14. A compound according to claim 12 wherein HET-Z—W is carboxyalkyl (S) pyrrolidine, of formula:

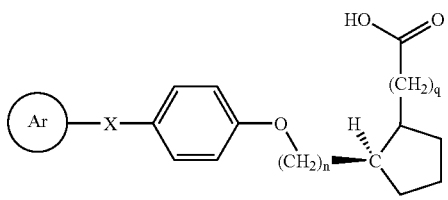

wherein q is an integer selected from 2-6.

15. A compound according to claim 3 wherein HET is (R) pyrrolidine of the formula:

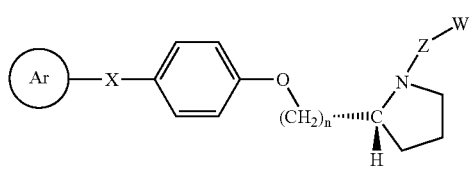

wherein
Ar is selected from the group consisting of
  phenyl; and
  phenyl substituted with from one to three substituents independently selected from the group consisting of halogen, loweralkyl, loweracyl, loweralkoxy, fluoroloweralkyl, fluoroloweralkoxy, hydroxy, hydroxy ($C_1$-$C_4$) alkyl, formyl, formyl($C_1$-$C_4$) alkyl, cyano, cyano($C_1$-$C_4$) alkyl, benzyl, benzyloxy, phenyl, substituted phenyl, heteroaryl, heterocyclylalkyl, substituted heteroaryl, and nitro;
X is selected from the group consisting of direct bond, O, SO, S($O_2$), $NR_1$, $CH_2$, $CF_2$, $CH_2CH_2$, $CH_2NH$, $NHCH_2$, CH=CH, C=O and $CH_2C$=O;
taken together ZW is H or
Z is $(CH_2)_{1-10}$; in which one or two ($CH_2$) may optionally be replaced by —O—, —$NR^1$—, —SO—, —S(O)$_2$—, —C(=O)— or —C=O(NH)—, provided that said —O—, —$NR^1$—, —SO—, —S(O)$_2$—, —C(=O)— or —C=O(NH)— are not at the point of attachment to HET and are separated by at least one —($CH_2$)—; and
W is selected from the group consisting of acyl, hydroxyl, carboxyl, amino, carboxamido, aminoacyl, —COOalkyl, —CHO, heterocyclyl, substituted aryl, substituted heterocyclyl.

16. A compound according to claim 15 wherein ZW is H, of the formula:

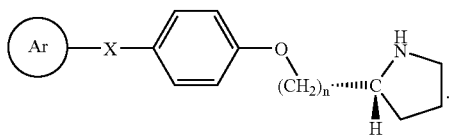

17. A compound according to claim 16 wherein X is selected from $CH_2$, O and $NR^1$.
18. A compound according to claim 17 wherein X is $CH_2$ or O, n is 1, and Ar is para-substituted phenyl.
19. A compound according to claim 18 wherein Ar is heteroarylphenyl.
20. A compound according to claim 3 wherein HET is (S) pyrrolidine, of the formula:

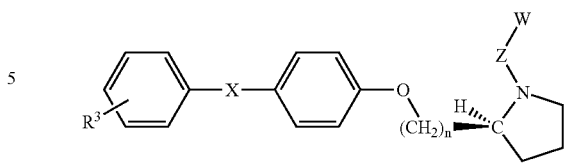

wherein
$R^3$ represents one to three residues independently selected from the group consisting of benzyl, benzyloxy, phenyl, heteroaryl and heteroaryl substituted with halogen, methyl, methoxy or trifluoromethoxy.

21. A compound according to claim 1 wherein Ar is

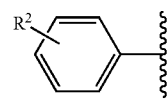

wherein the wavy line indicates the point of attachment to X and $R^2$ is chosen from hydrogen, halogen, trifluoromethyl, methyl, methoxy, thienyl, furanyl, and thienyl or furanyl substituted with halogen, trifluoromethyl, methyl or methoxy.

22. A pharmaceutical composition comprising a pharmaceutically acceptable carrier and a therapeutically effective amount of a compound according to claim 1.
23. A method for inhibiting leukotriene A4 hydrolase comprising contacting the LTA4H enzyme with a therapeutically effective amount of a compound according to claim 1.
24. A method for inhibiting leukotriene A4 hydrolase comprising contacting the LTA4H enzyme with a therapeutically effective amount of a compound according to claim 3.
25. A method for treating inflammation comprising administering to a mammal a therapeutically effective amount of a compound according to claim 1.
26. A method according to claim 25 wherein said inflammation is selected from allergic inflammation, acute inflammation and chronic inflammation.
27. A method for treating inflammation comprising administering to a mammal a therapeutically effective amount of a compound according to claim 1 and an inhibitor of 5-lipoxygenase activating protein (FLAP).
28. A method for treating inflammation comprising administering to a mammal a therapeutically effective amount of a compound according to claim 1 and a leukotriene B4 (LTB4) antagonist.
29. A compound according to claim 10, wherein the compound is:

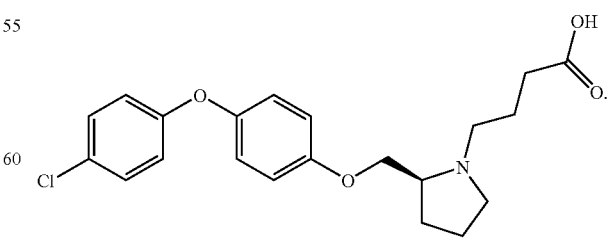

* * * * *

UNITED STATES PATENT AND TRADEMARK OFFICE
CERTIFICATE OF CORRECTION

| | |
|---|---|
| PATENT NO. | : 7,402,684 B2 |
| APPLICATION NO. | : 11/426287 |
| DATED | : July 22, 2008 |
| INVENTOR(S) | : Sandanayaka et al. |

Page 1 of 1

It is certified that error appears in the above-identified patent and that said Letters Patent is hereby corrected as shown below:

Col. 94, Line 14: Delete "EXAMPLE 9" and insert -- EXAMPLE 73 --

Col. 95, Line 13: Delete "EXAMPLE 73" and insert -- EXAMPLE 74 --

Col. 95, Line 58: Delete "EXAMPLE 74" and insert -- EXAMPLE 75 --

Col. 96, Line 20: Delete "EXAMPLE 75" and insert -- EXAMPLE 76 --

Col. 97, Line 24: Delete "EXAMPLE 76" and insert -- EXAMPLE 77 --

Col. 97, Line 50: Delete "EXAMPLE 77" and insert -- EXAMPLE 78 --

Col. 98, Line 30: Delete "EXAMPLE 78" and insert -- EXAMPLE 79 --

Col. 99, Line 38: Delete "EXAMPLE 79" and insert -- EXAMPLE 80 --

Col. 100, Line 22: Delete "EXAMPLE 80" and insert -- EXAMPLE 81 --

Col. 101, Line 1: Delete "EXAMPLE 81" and insert -- EXAMPLE 82 --

Claim 3, Col. 170, Line 54, In The Formula, Delete "Q" and insert -- O --

Signed and Sealed this

Thirtieth Day of September, 2008

JON W. DUDAS
*Director of the United States Patent and Trademark Office*